US012559555B2

(12) United States Patent
Song et al.

(10) Patent No.: US 12,559,555 B2
(45) Date of Patent: Feb. 24, 2026

(54) ANTI-LILRB4 ANTIBODIES AND DERIVATIVE PRODUCTS

(71) Applicant: IMMUNE-ONC THERAPEUTICS, INC., Palo Alto, CA (US)

(72) Inventors: An Song, Palo Alto, CA (US); Tao Huang, Mountain View, CA (US); Ryan Stafford, Foster City, CA (US); Maria Jose Costa, Palo Alto, CA (US); Kyu Hee Hong, Palo Alto, CA (US); Caroline Bonnans, San Francisco, CA (US); Jianhui Zhou, Redwood City, CA (US); Li Zhou, San Jose, CA (US); Ji Li, Foster City, CA (US); J. Paul Woodard, Palo Alto, CA (US); X. Charlene Liao, Palo Alto, CA (US)

(73) Assignee: IMMUNE-ONC THERAPEUTICS, INC.

( * ) Notice: Subject to any disclaimer, the term of this patent is extended or adjusted under 35 U.S.C. 154(b) by 748 days.

(21) Appl. No.: 17/905,943

(22) PCT Filed: Mar. 12, 2021

(86) PCT No.: PCT/US2021/022029

§ 371 (c)(1),
(2) Date: Sep. 9, 2022

(87) PCT Pub. No.: WO2021/183839

PCT Pub. Date: Sep. 16, 2021

(65) Prior Publication Data

US 2023/0340114 A1 Oct. 26, 2023

Related U.S. Application Data

(60) Provisional application No. 62/988,892, filed on Mar. 12, 2020.

(51) Int. Cl.

| | |
|---|---|
| ***C07K 16/28*** | (2006.01) |
| ***A61K 38/17*** | (2006.01) |
| ***A61K 39/395*** | (2006.01) |
| ***A61K 40/11*** | (2025.01) |
| ***A61K 40/24*** | (2025.01) |
| ***A61K 40/31*** | (2025.01) |
| ***A61K 40/42*** | (2025.01) |
| ***A61K 45/06*** | (2006.01) |
| ***A61P 35/02*** | (2006.01) |
| ***C07K 14/705*** | (2006.01) |

(Continued)

(52) U.S. Cl.

CPC ........ *C07K 16/2803* (2013.01); *A61K 38/177* (2013.01); *A61K 38/1774* (2013.01); *A61K 39/3955* (2013.01); *A61K 40/11* (2025.01); *A61K 40/24* (2025.01); *A61K 40/31* (2025.01); *A61K 40/4203* (2025.01); *A61K 45/06* (2013.01); *A61P 35/02* (2018.01); *C07K 14/7051* (2013.01); *C07K 14/70517* (2013.01); *C07K 14/70521* (2013.01); *C07K 14/70578* (2013.01); *C07K 16/2809* (2013.01); *C12N 5/0636* (2013.01); *A61K 2039/505* (2013.01); *A61K 2239/21* (2023.05); *A61K 2239/22* (2023.05); *A61K 2239/29* (2023.05); *C07K 2317/24* (2013.01); *C07K 2317/31* (2013.01); *C07K 2317/622* (2013.01); *C07K 2317/73* (2013.01); *C07K 2317/732* (2013.01); *C07K 2317/92* (2013.01); *C07K 2319/02* (2013.01); *C07K 2319/03* (2013.01); *C07K 2319/33* (2013.01)

(58) Field of Classification Search

CPC ............ C07K 16/2803; C07K 14/7051; C07K 14/70517; C07K 14/70521; C07K 14/70578; C07K 16/2809; C07K 2317/24; C07K 2317/31; C07K 2317/622; C07K 2317/73; C07K 2317/732; C07K 2317/92; C07K 2317/565; A61K 38/177; A61K 38/1774; A61K 39/3955; A61K 40/11; A61K 40/24; A61K 40/31; A61K 40/4203; A61K 45/06; A61K 2039/505; A61K 2239/21; A61K 2239/22; A61K 2239/29; A61K 39/001103; A61K 39/395; A61P 35/02; C12N 5/0636

See application file for complete search history.

(56) References Cited

U.S. PATENT DOCUMENTS 12,202,895 B2 * 1/2025 An .................. G01N 33/57426
2015/0110714 A1 4/2015 Suciu-Foca et al.

(Continued)

FOREIGN PATENT DOCUMENTS

JP 2018-510340 A 4/2018
JP 2022-500084 A 1/2022

(Continued)

OTHER PUBLICATIONS

The First Office Action for the counterpart JP application No. 2022-555069, issued on Feb. 21, 2025.

(Continued)

*Primary Examiner* — Shafiqul Haq
(74) *Attorney, Agent, or Firm* — Junhe Law Office P.C.; Yi Zhang

(57) ABSTRACT

The present disclosure provides anti-LILRB4 antibodies or antigen-binding fragments thereof, anti-LILRB4 chimeric antigen receptor protein, isolated polynucleotides encoding the same, pharmaceutical compositions comprising the same, and the uses thereof.

20 Claims, 48 Drawing Sheets

Specification includes a Sequence Listing.

(51) Int. Cl.

| | |
|---|---|
| ***C07K 14/725*** | (2006.01) |
| ***C12N 5/0783*** | (2010.01) |
| *A61K 39/00* | (2006.01) |

(56) References Cited

U.S. PATENT DOCUMENTS

| | | | |
|---|---|---|---|
| 2018/0086829 | A1 | 3/2018 | Zhang et al. |
| 2019/0241655 | A1 | 8/2019 | Cua et al. |

FOREIGN PATENT DOCUMENTS

| | | | |
|---|---|---|---|
| WO | 2008/094176 | A2 | 8/2008 |
| WO | 2009/155724 | A2 | 12/2009 |
| WO | 2018/089300 | A1 | 5/2018 |
| WO | 2018/148494 | A1 | 8/2018 |
| WO | 2019/005634 | A2 | 1/2019 |
| WO | 2020/056077 | A1 | 3/2020 |

OTHER PUBLICATIONS

The international search report of PCT application No. PCT/US2021/022029, issued on Feb. 3, 2022.
The Extended European Search Report for the corresponding European application, issued on Mar. 14, 2024.

* cited by examiner

| | H7K3m5 | VHVL | VLVH |
|---|---|---|---|
| EC50 | 0.3591 | ~ 7.550e+015 | 0.5330 |

| | H7K3m5 | VHVL | VLVH |
|---|---|---|---|
| EC50 | 0.5597 | 4.098 | 0.8864 |

| | H7K3m5 | VHVL | VLVH |
|---|---|---|---|
| EC50 | ~ 314.6 | 1.490 | 0.8958 |

| | H7K3m5 | VHVL | VLVH |
|---|---|---|---|
| EC50 | 0.01756 | 0.03918 | 0.02321 |

SEQUENCE LISTING

```
<160> NUMBER OF SEQ ID NOS: 124

<210> SEQ ID NO 1
<211> LENGTH: 120
<212> TYPE: PRT
<213> ORGANISM: Artificial Sequence
<220> FEATURE:
<223> OTHER INFORMATION: Synthetic

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Ser
            20                  25                  30

Tyr Trp Ile Ser Trp Val Arg Gln Ala Pro Gly Lys Gly Leu Glu Trp
        35                  40                  45

Ile Gly Ser Ile Asp Ser Gly Ser Val Gly Ile Thr Tyr Tyr Ala Thr
    50                  55                  60

Trp Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
```

-continued

```
                85                  90                  95

Tyr Cys Ala Arg His Gly Asp Asn Trp Ala Leu Asp Leu Trp Gly Gln
            100                 105                 110

Gly Thr Leu Val Thr Val Ser Ser
        115                 120


<210> SEQ ID NO 2
<211> LENGTH: 360
<212> TYPE: DNA
<213> ORGANISM: Artificial Sequence
<220> FEATURE:
<223> OTHER INFORMATION: Synthetic

<400> SEQUENCE: 2

gaggtgcagc tggtcgagtc cggaggcgga ctggtgcagc ctggaggatc cctgaggctg     60

tcctgcgccg cttccggctt ctccctgtcc tcctcctact ggatctcctg ggtgaggcag    120

gcccctggaa agggcctgga gtggatcggc tccatcgact ccggctccgt gggcatcacc    180

tactacgcca cctgggtgaa gggcaggttc accatctcca gggacaactc caagaacacc    240

ctgtacctgc agatgaactc cctgagggcc gaggacaccg ccgtgtacta ctgcgccagg    300

cacggcgata actgggctct ggacctgtgg ggacagggca cactggtgac cgtgtcctcc    360


<210> SEQ ID NO 3
<211> LENGTH: 110
<212> TYPE: PRT
<213> ORGANISM: Artificial Sequence
<220> FEATURE:
<223> OTHER INFORMATION: Synthetic

<400> SEQUENCE: 3

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Asn Ser Trp
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Gly Tyr Ile Arg Gly Asp
                85                  90                  95

Leu Asp Asn Val Phe Gly Gly Gly Thr Lys Val Glu Ile Lys
            100                 105                 110


<210> SEQ ID NO 4
<211> LENGTH: 330
<212> TYPE: DNA
<213> ORGANISM: Artificial Sequence
<220> FEATURE:
<223> OTHER INFORMATION: Synthetic

<400> SEQUENCE: 4

gacatccaga tgacccagtc cccttccacc ctgtccgctt ccgtgggcga cagggtgacc     60

atcacctgca gggccagcca gtccatcaac tcctggctgg cctggtacca gcagaagccc    120

ggcaaggccc ccaagctgct gatctacaag gcttccaccc tggcttccgg cgtgcctagc    180

aggttttccg gctccggctc cggcaccgag tttaccctga ccatctcctc cctgcagccc    240
```

-continued

```
gacgacttcg ccacctacta ctgccagcac ggctacatca ggggcgacct ggacaacgtg    300

tttggcggcg gcaccaaggt ggagatcaag                                     330


<210> SEQ ID NO 5
<211> LENGTH: 9
<212> TYPE: PRT
<213> ORGANISM: Artificial Sequence
<220> FEATURE:
<223> OTHER INFORMATION: Synthetic

<400> SEQUENCE: 5

Gly Phe Ser Leu Ser Ser Ser Tyr Trp
1               5


<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Ile Asp Ser Gly Ser Val Gly Ile Thr
1               5


<210> SEQ ID NO 7
<211> LENGTH: 11
<212> TYPE: PRT
<213> ORGANISM: Artificial Sequence
<220> FEATURE:
<223> OTHER INFORMATION: Synthetic

<400> SEQUENCE: 7

Ala Arg His Gly Asp Asn Trp Ala Leu Asp Leu
1               5                   10


<210> SEQ ID NO 8
<211> LENGTH: 6
<212> TYPE: PRT
<213> ORGANISM: Artificial Sequence
<220> FEATURE:
<223> OTHER INFORMATION: Synthetic

<400> SEQUENCE: 8

Gln Ser Ile Asn Ser Trp
1               5


<210> SEQ ID NO 9
<211> LENGTH: 7
<212> TYPE: PRT
<213> ORGANISM: Artificial Sequence
<220> FEATURE:
<223> OTHER INFORMATION: Synthetic

<400> SEQUENCE: 9

Lys Ala Ser Thr Leu Ala Ser
1               5


<210> SEQ ID NO 10
<211> LENGTH: 11
<212> TYPE: PRT
<213> ORGANISM: Artificial Sequence
<220> FEATURE:
<223> OTHER INFORMATION: Synthetic

<400> SEQUENCE: 10
```

His Gly Tyr Ile Arg Gly Asp Leu Asp Asn Val
1 5 10

<210> SEQ ID NO 11
<211> LENGTH: 120
<212> TYPE: PRT
<213> ORGANISM: Artificial Sequence
<220> FEATURE:
<223> OTHER INFORMATION: Synthetic

<400> SEQUENCE: 11

Glu Val Gln Leu Val Glu Ser Gly Gly Gly Leu Val Gln Pro Gly Gly
1 5 10 15

Ser Leu Arg Leu Ser Cys Ala Ala Ser Gly Phe Ser Leu Ser Ser Ser
20 25 30

Tyr Trp Ile Ser Trp Val Arg Gln Ala Pro Gly Lys Gly Leu Glu Trp
35 40 45

Ile Gly Ser Ile Asp Ser Gly Ser Val Gly Ile Thr Tyr Tyr Ala Thr
50 55 60

Trp Val Lys Gly Arg Phe Thr Ile Ser Arg Asp Asn Ser Lys Asn Thr
65 70 75 80

Leu Tyr Leu Gln Met Asn Ser Leu Arg Ala Glu Asp Thr Ala Val Tyr
85 90 95

Tyr Cys Ala Arg His Gly Asp Asn Val Ala Leu Asp Leu Trp Gly Gln
100 105 110

Gly Thr Leu Val Thr Val Ser Ser
115 120

<210> SEQ ID NO 12
<211> LENGTH: 11
<212> TYPE: PRT
<213> ORGANISM: Artificial Sequence
<220> FEATURE:
<223> OTHER INFORMATION: Synthetic

<400> SEQUENCE: 12

Ala Arg His Gly Asp Asn Val Ala Leu Asp Leu
1 5 10

<210> SEQ ID NO 13
<211> LENGTH: 120
<212> TYPE: PRT
<213> ORGANISM: Artificial Sequence
<220> FEATURE:
<223> OTHER INFORMATION: Synthetic

<400> SEQUENCE: 13

Glu Val Gln Leu Val Glu Ser Gly Gly Gly Leu Val Gln Pro Gly Gly
1 5 10 15

Ser Leu Arg Leu Ser Cys Ala Ala Ser Gly Phe Ser Leu Ser Ser Ser
20 25 30

Tyr Trp Ile Ser Trp Val Arg Gln Ala Pro Gly Lys Gly Leu Glu Trp
35 40 45

Ile Gly Ser Ile Asp Ser Gly Ser Val Gly Ile Thr Tyr Tyr Ala Thr
50 55 60

Trp Val Lys Gly Arg Phe Thr Ile Ser Arg Asp Asn Ser Lys Asn Thr
65 70 75 80

Leu Tyr Leu Gln Met Asn Ser Leu Arg Ala Glu Asp Thr Ala Val Tyr
85 90 95

Tyr Cys Ala Arg His Gly Asp Asn Tyr Ala Leu Asp Leu Trp Gly Gln

```
            100                 105                 110

Gly Thr Leu Val Thr Val Ser Ser
        115                 120


<210> SEQ ID NO 14
<211> LENGTH: 11
<212> TYPE: PRT
<213> ORGANISM: Artificial Sequence
<220> FEATURE:
<223> OTHER INFORMATION: Synthetic

<400> SEQUENCE: 14

Ala Arg His Gly Asp Asn Tyr Ala Leu Asp Leu
1               5                   10


<210> SEQ ID NO 15
<211> LENGTH: 120
<212> TYPE: PRT
<213> ORGANISM: Artificial Sequence
<220> FEATURE:
<223> OTHER INFORMATION: Synthetic

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Ser
            20                  25                  30

Tyr Trp Ile Ser Trp Val Arg Gln Ala Pro Gly Lys Gly Leu Glu Trp
        35                  40                  45

Ile Gly Ser Ile Asp Ser Gly Ser Val Gly Ile Thr Tyr Tyr Ala Thr
    50                  55                  60

Trp Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asp Asn Phe Ala Leu Asp Leu Trp Gly Gln
            100                 105                 110

Gly Thr Leu Val Thr Val Ser Ser
        115                 120


<210> SEQ ID NO 16
<211> LENGTH: 11
<212> TYPE: PRT
<213> ORGANISM: Artificial Sequence
<220> FEATURE:
<223> OTHER INFORMATION: Synthetic

<400> SEQUENCE: 16

Ala Arg His Gly Asp Asn Phe Ala Leu Asp Leu
1               5                   10


<210> SEQ ID NO 17
<211> LENGTH: 120
<212> TYPE: PRT
<213> ORGANISM: Artificial Sequence
<220> FEATURE:
<223> OTHER INFORMATION: Synthetic

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Ser
```

```
            20                  25                  30

Tyr Trp Ile Ser Trp Val Arg Gln Ala Pro Gly Lys Gly Leu Glu Trp
        35                  40                  45

Ile Gly Ser Ile Asp Ser Gly Ser Val Gly Ile Thr Tyr Tyr Ala Thr
    50                  55                  60

Trp Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asp Asn Gln Ala Leu Asp Leu Trp Gly Gln
            100                 105                 110

Gly Thr Leu Val Thr Val Ser Ser
        115                 120


<210> SEQ ID NO 18
<211> LENGTH: 11
<212> TYPE: PRT
<213> ORGANISM: Artificial Sequence
<220> FEATURE:
<223> OTHER INFORMATION: Synthetic

<400> SEQUENCE: 18

Ala Arg His Gly Asp Asn Gln Ala Leu Asp Leu
1               5                   10


<210> SEQ ID NO 19
<211> LENGTH: 110
<212> TYPE: PRT
<213> ORGANISM: Artificial Sequence
<220> FEATURE:
<223> OTHER INFORMATION: Synthetic

<400> SEQUENCE: 19

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Val Ser Trp
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Gly Tyr Ile Arg Gly Asp
                85                  90                  95

Leu Asp Asn Val Phe Gly Gly Gly Thr Lys Val Glu Ile Lys
            100                 105                 110


<210> SEQ ID NO 20
<211> LENGTH: 6
<212> TYPE: PRT
<213> ORGANISM: Artificial Sequence
<220> FEATURE:
<223> OTHER INFORMATION: Synthetic

<400> SEQUENCE: 20

Gln Ser Ile Val Ser Trp
1               5


<210> SEQ ID NO 21
```

<211> LENGTH: 110
<212> TYPE: PRT
<213> ORGANISM: Artificial Sequence
<220> FEATURE:
<223> OTHER INFORMATION: Synthetic

<400> SEQUENCE: 21

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Asp Ser Trp
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Gly Tyr Ile Arg Gly Asp
                85                  90                  95

Leu Asp Asn Val Phe Gly Gly Gly Thr Lys Val Glu Ile Lys
            100                 105                 110
```

<210> SEQ ID NO 22
<211> LENGTH: 6
<212> TYPE: PRT
<213> ORGANISM: Artificial Sequence
<220> FEATURE:
<223> OTHER INFORMATION: Synthetic

<400> SEQUENCE: 22

```
Gln Ser Ile Asp Ser Trp
1               5
```

<210> SEQ ID NO 23
<211> LENGTH: 110
<212> TYPE: PRT
<213> ORGANISM: Artificial Sequence
<220> FEATURE:
<223> OTHER INFORMATION: Synthetic

<400> SEQUENCE: 23

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Glu Ser Trp
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Gly Tyr Ile Arg Gly Asp
                85                  90                  95

Leu Asp Asn Val Phe Gly Gly Gly Thr Lys Val Glu Ile Lys
            100                 105                 110
```

<210> SEQ ID NO 24
<211> LENGTH: 6
<212> TYPE: PRT
<213> ORGANISM: Artificial Sequence
<220> FEATURE:

<223> OTHER INFORMATION: Synthetic

<400> SEQUENCE: 24

Gln Ser Ile Glu Ser Trp
1 5

<210> SEQ ID NO 25
<211> LENGTH: 110
<212> TYPE: PRT
<213> ORGANISM: Artificial Sequence
<220> FEATURE:
<223> OTHER INFORMATION: Synthetic

<400> SEQUENCE: 25

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Gln Ser Trp
20 25 30

Leu Ala Trp Tyr Gln Gln Lys Pro Gly Lys Ala Pro Lys Leu Leu Ile
35 40 45

Tyr Lys Ala Ser Thr Leu Ala Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln His Gly Tyr Ile Arg Gly Asp
85 90 95

Leu Asp Asn Val Phe Gly Gly Gly Thr Lys Val Glu Ile Lys
100 105 110

<210> SEQ ID NO 26
<211> LENGTH: 6
<212> TYPE: PRT
<213> ORGANISM: Artificial Sequence
<220> FEATURE:
<223> OTHER INFORMATION: Synthetic

<400> SEQUENCE: 26

Gln Ser Ile Gln Ser Trp
1 5

<210> SEQ ID NO 27
<211> LENGTH: 110
<212> TYPE: PRT
<213> ORGANISM: Artificial Sequence
<220> FEATURE:
<223> OTHER INFORMATION: Synthetic

<400> SEQUENCE: 27

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Ser Ser Trp
20 25 30

Leu Ala Trp Tyr Gln Gln Lys Pro Gly Lys Ala Pro Lys Leu Leu Ile
35 40 45

Tyr Lys Ala Ser Thr Leu Ala Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln His Gly Tyr Ile Arg Gly Asp
85 90 95

-continued

```
Leu Asp Asn Val Phe Gly Gly Gly Thr Lys Val Glu Ile Lys
            100                 105                 110


<210> SEQ ID NO 28
<211> LENGTH: 6
<212> TYPE: PRT
<213> ORGANISM: Artificial Sequence
<220> FEATURE:
<223> OTHER INFORMATION: Synthetic

<400> SEQUENCE: 28

Gln Ser Ile Ser Ser Trp
1               5


<210> SEQ ID NO 29
<211> LENGTH: 110
<212> TYPE: PRT
<213> ORGANISM: Artificial Sequence
<220> FEATURE:
<223> OTHER INFORMATION: Synthetic

<400> SEQUENCE: 29

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Thr Ser Trp
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Gly Tyr Ile Arg Gly Asp
                85                  90                  95

Leu Asp Asn Val Phe Gly Gly Gly Thr Lys Val Glu Ile Lys
            100                 105                 110


<210> SEQ ID NO 30
<211> LENGTH: 6
<212> TYPE: PRT
<213> ORGANISM: Artificial Sequence
<220> FEATURE:
<223> OTHER INFORMATION: Synthetic

<400> SEQUENCE: 30

Gln Ser Ile Thr Ser Trp
1               5


<210> SEQ ID NO 31
<211> LENGTH: 110
<212> TYPE: PRT
<213> ORGANISM: Artificial Sequence
<220> FEATURE:
<223> OTHER INFORMATION: Synthetic

<400> SEQUENCE: 31

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Asn Gln Trp
            20                  25                  30

Leu Ala Trp Tyr Gln Gln Lys Pro Gly Lys Ala Pro Lys Leu Leu Ile
        35                  40                  45
```

```
Tyr Lys Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Gly Tyr Ile Arg Gly Asp
                85                  90                  95

Leu Asp Asn Val Phe Gly Gly Gly Thr Lys Val Glu Ile Lys
            100                 105                 110
```

<210> SEQ ID NO 32
<211> LENGTH: 6
<212> TYPE: PRT
<213> ORGANISM: Artificial Sequence
<220> FEATURE:
<223> OTHER INFORMATION: Synthetic

<400> SEQUENCE: 32

```
Gln Ser Ile Asn Gln Trp
1               5
```

<210> SEQ ID NO 33
<211> LENGTH: 110
<212> TYPE: PRT
<213> ORGANISM: Artificial Sequence
<220> FEATURE:
<223> OTHER INFORMATION: Synthetic

<400> SEQUENCE: 33

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Asn Val Trp
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Gly Tyr Ile Arg Gly Asp
                85                  90                  95

Leu Asp Asn Val Phe Gly Gly Gly Thr Lys Val Glu Ile Lys
            100                 105                 110
```

<210> SEQ ID NO 34
<211> LENGTH: 6
<212> TYPE: PRT
<213> ORGANISM: Artificial Sequence
<220> FEATURE:
<223> OTHER INFORMATION: Synthetic

<400> SEQUENCE: 34

```
Gln Ser Ile Asn Val Trp
1               5
```

<210> SEQ ID NO 35
<211> LENGTH: 330
<212> TYPE: DNA
<213> ORGANISM: Artificial Sequence
<220> FEATURE:
<223> OTHER INFORMATION: Synthetic

<400> SEQUENCE: 35

```
gacatccaga tgacccagtc ccctagcaca ctgtccgcca gcgtgggcga tcgtgtgacc     60

atcacttgtc gggcttccca gagcatcagc agctggctgg cttggtatca gcagaagccc    120

ggcaaggccc ccaagctgct gatctacaag gcttccactt tagctagcgg cgtgccttct    180

cgtttctccg gatccggatc cggcaccgag ttcactttaa ccatcagctc tttacagccc    240

gacgacttcg ccacatacta ctgccagcac ggctacatcc ggggcgattt agacaatgtg    300

ttcggcggcg gcaccaaggt cgagatcaag                                     330


<210> SEQ ID NO 36
<211> LENGTH: 6
<212> TYPE: PRT
<213> ORGANISM: Artificial Sequence
<220> FEATURE:
<223> OTHER INFORMATION: Synthetic

<400> SEQUENCE: 36

Gln Ser Ile Ala Ser Trp
1               5


<210> SEQ ID NO 37
<211> LENGTH: 6
<212> TYPE: PRT
<213> ORGANISM: Artificial Sequence
<220> FEATURE:
<223> OTHER INFORMATION: Synthetic

<400> SEQUENCE: 37

Gln Ser Ile Cys Ser Trp
1               5


<210> SEQ ID NO 38
<211> LENGTH: 6
<212> TYPE: PRT
<213> ORGANISM: Artificial Sequence
<220> FEATURE:
<223> OTHER INFORMATION: Synthetic

<400> SEQUENCE: 38

Gln Ser Ile Phe Ser Trp
1               5


<210> SEQ ID NO 39
<211> LENGTH: 6
<212> TYPE: PRT
<213> ORGANISM: Artificial Sequence
<220> FEATURE:
<223> OTHER INFORMATION: Synthetic

<400> SEQUENCE: 39

Gln Ser Ile Gly Ser Trp
1               5


<210> SEQ ID NO 40
<211> LENGTH: 6
<212> TYPE: PRT
<213> ORGANISM: Artificial Sequence
<220> FEATURE:
<223> OTHER INFORMATION: Synthetic

<400> SEQUENCE: 40

Gln Ser Ile His Ser Trp
1               5


<210> SEQ ID NO 41
```

<211> LENGTH: 6
<212> TYPE: PRT
<213> ORGANISM: Artificial Sequence
<220> FEATURE:
<223> OTHER INFORMATION: Synthetic

<400> SEQUENCE: 41

Gln Ser Ile Ile Ser Trp
1               5

<210> SEQ ID NO 42
<211> LENGTH: 6
<212> TYPE: PRT
<213> ORGANISM: Artificial Sequence
<220> FEATURE:
<223> OTHER INFORMATION: Synthetic

<400> SEQUENCE: 42

Gln Ser Ile Lys Ser Trp
1               5

<210> SEQ ID NO 43
<211> LENGTH: 6
<212> TYPE: PRT
<213> ORGANISM: Artificial Sequence
<220> FEATURE:
<223> OTHER INFORMATION: Synthetic

<400> SEQUENCE: 43

Gln Ser Ile Leu Ser Trp
1               5

<210> SEQ ID NO 44
<211> LENGTH: 6
<212> TYPE: PRT
<213> ORGANISM: Artificial Sequence
<220> FEATURE:
<223> OTHER INFORMATION: Synthetic

<400> SEQUENCE: 44

Gln Ser Ile Met Ser Trp
1               5

<210> SEQ ID NO 45
<211> LENGTH: 6
<212> TYPE: PRT
<213> ORGANISM: Artificial Sequence
<220> FEATURE:
<223> OTHER INFORMATION: Synthetic

<400> SEQUENCE: 45

Gln Ser Ile Pro Ser Trp
1               5

<210> SEQ ID NO 46
<211> LENGTH: 6
<212> TYPE: PRT
<213> ORGANISM: Artificial Sequence
<220> FEATURE:
<223> OTHER INFORMATION: Synthetic

<400> SEQUENCE: 46

Gln Ser Ile Arg Ser Trp
1               5

<210> SEQ ID NO 47
<211> LENGTH: 6

<212> TYPE: PRT
<213> ORGANISM: Artificial Sequence
<220> FEATURE:
<223> OTHER INFORMATION: Synthetic

<400> SEQUENCE: 47

Gln Ser Ile Trp Ser Trp
1 5

<210> SEQ ID NO 48
<211> LENGTH: 6
<212> TYPE: PRT
<213> ORGANISM: Artificial Sequence
<220> FEATURE:
<223> OTHER INFORMATION: Synthetic

<400> SEQUENCE: 48

Gln Ser Ile Tyr Ser Trp
1 5

<210> SEQ ID NO 49
<211> LENGTH: 6
<212> TYPE: PRT
<213> ORGANISM: Artificial Sequence
<220> FEATURE:
<223> OTHER INFORMATION: Synthetic

<400> SEQUENCE: 49

Gln Ser Ile Asn Ala Trp
1 5

<210> SEQ ID NO 50
<211> LENGTH: 6
<212> TYPE: PRT
<213> ORGANISM: Artificial Sequence
<220> FEATURE:
<223> OTHER INFORMATION: Synthetic

<400> SEQUENCE: 50

Gln Ser Ile Asn Cys Trp
1 5

<210> SEQ ID NO 51
<211> LENGTH: 6
<212> TYPE: PRT
<213> ORGANISM: Artificial Sequence
<220> FEATURE:
<223> OTHER INFORMATION: Synthetic

<400> SEQUENCE: 51

Gln Ser Ile Asn Asp Trp
1 5

<210> SEQ ID NO 52
<211> LENGTH: 6
<212> TYPE: PRT
<213> ORGANISM: Artificial Sequence
<220> FEATURE:
<223> OTHER INFORMATION: Synthetic

<400> SEQUENCE: 52

Gln Ser Ile Asn Glu Trp
1 5

<210> SEQ ID NO 53
<211> LENGTH: 6
<212> TYPE: PRT

<213> ORGANISM: Artificial Sequence
<220> FEATURE:
<223> OTHER INFORMATION: Synthetic

<400> SEQUENCE: 53

Gln Ser Ile Asn Phe Trp
1               5

<210> SEQ ID NO 54
<211> LENGTH: 6
<212> TYPE: PRT
<213> ORGANISM: Artificial Sequence
<220> FEATURE:
<223> OTHER INFORMATION: Synthetic

<400> SEQUENCE: 54

Gln Ser Ile Asn Gly Trp
1               5

<210> SEQ ID NO 55
<211> LENGTH: 6
<212> TYPE: PRT
<213> ORGANISM: Artificial Sequence
<220> FEATURE:
<223> OTHER INFORMATION: Synthetic

<400> SEQUENCE: 55

Gln Ser Ile Asn His Trp
1               5

<210> SEQ ID NO 56
<211> LENGTH: 6
<212> TYPE: PRT
<213> ORGANISM: Artificial Sequence
<220> FEATURE:
<223> OTHER INFORMATION: Synthetic

<400> SEQUENCE: 56

Gln Ser Ile Asn Ile Trp
1               5

<210> SEQ ID NO 57
<211> LENGTH: 6
<212> TYPE: PRT
<213> ORGANISM: Artificial Sequence
<220> FEATURE:
<223> OTHER INFORMATION: Synthetic

<400> SEQUENCE: 57

Gln Ser Ile Asn Lys Trp
1               5

<210> SEQ ID NO 58
<211> LENGTH: 6
<212> TYPE: PRT
<213> ORGANISM: Artificial Sequence
<220> FEATURE:
<223> OTHER INFORMATION: Synthetic

<400> SEQUENCE: 58

Gln Ser Ile Asn Leu Trp
1               5

<210> SEQ ID NO 59
<211> LENGTH: 6
<212> TYPE: PRT
<213> ORGANISM: Artificial Sequence
<220> FEATURE:
<223> OTHER INFORMATION: Synthetic

<400> SEQUENCE: 59

Gln Ser Ile Asn Met Trp
1 5

<210> SEQ ID NO 60
<211> LENGTH: 6
<212> TYPE: PRT
<213> ORGANISM: Artificial Sequence
<220> FEATURE:
<223> OTHER INFORMATION: Synthetic

<400> SEQUENCE: 60

Gln Ser Ile Asn Asn Trp
1 5

<210> SEQ ID NO 61
<211> LENGTH: 6
<212> TYPE: PRT
<213> ORGANISM: Artificial Sequence
<220> FEATURE:
<223> OTHER INFORMATION: Synthetic

<400> SEQUENCE: 61

Gln Ser Ile Asn Pro Trp
1 5

<210> SEQ ID NO 62
<211> LENGTH: 6
<212> TYPE: PRT
<213> ORGANISM: Artificial Sequence
<220> FEATURE:
<223> OTHER INFORMATION: Synthetic

<400> SEQUENCE: 62

Gln Ser Ile Asn Arg Trp
1 5

<210> SEQ ID NO 63
<211> LENGTH: 6
<212> TYPE: PRT
<213> ORGANISM: Artificial Sequence
<220> FEATURE:
<223> OTHER INFORMATION: Synthetic

<400> SEQUENCE: 63

Gln Ser Ile Asn Thr Trp
1 5

<210> SEQ ID NO 64
<211> LENGTH: 6
<212> TYPE: PRT
<213> ORGANISM: Artificial Sequence
<220> FEATURE:
<223> OTHER INFORMATION: Synthetic

<400> SEQUENCE: 64

Gln Ser Ile Asn Trp Trp
1 5

<210> SEQ ID NO 65
<211> LENGTH: 6
<212> TYPE: PRT
<213> ORGANISM: Artificial Sequence
<220> FEATURE:

<223> OTHER INFORMATION: Synthetic

<400> SEQUENCE: 65

Gln Ser Ile Asn Tyr Trp
1 5

<210> SEQ ID NO 66
<211> LENGTH: 245
<212> TYPE: PRT
<213> ORGANISM: Artificial Sequence
<220> FEATURE:
<223> OTHER INFORMATION: Synthetic

<400> SEQUENCE: 66

Glu Val Gln Leu Val Glu Ser Gly Gly Gly Leu Val Gln Pro Gly Gly
1 5 10 15

Ser Leu Arg Leu Ser Cys Ala Ala Ser Gly Phe Ser Leu Ser Ser Ser
20 25 30

Tyr Trp Ile Ser Trp Val Arg Gln Ala Pro Gly Lys Gly Leu Glu Trp
35 40 45

Ile Gly Ser Ile Asp Ser Gly Ser Val Gly Ile Thr Tyr Tyr Ala Thr
50 55 60

Trp Val Lys Gly Arg Phe Thr Ile Ser Arg Asp Asn Ser Lys Asn Thr
65 70 75 80

Leu Tyr Leu Gln Met Asn Ser Leu Arg Ala Glu Asp Thr Ala Val Tyr
85 90 95

Tyr Cys Ala Arg His Gly Asp Asn Trp Ala Leu Asp Leu Trp Gly Gln
100 105 110

Gly Thr Leu Val Thr Val Ser Ser Gly Gly Gly Gly Ser Gly Gly Gly
115 120 125

Gly Ser Gly Gly Gly Gly Ser Asp Ile Gln Met Thr Gln Ser Pro Ser
130 135 140

Thr Leu Ser Ala Ser Val Gly Asp Arg Val Thr Ile Thr Cys Arg Ala
145 150 155 160

Ser Gln Ser Ile Ser Ser Trp Leu Ala Trp Tyr Gln Gln Lys Pro Gly
165 170 175

Lys Ala Pro Lys Leu Leu Ile Tyr Lys Ala Ser Thr Leu Ala Ser Gly
180 185 190

Val Pro Ser Arg Phe Ser Gly Ser Gly Ser Gly Thr Glu Phe Thr Leu
195 200 205

Thr Ile Ser Ser Leu Gln Pro Asp Asp Phe Ala Thr Tyr Tyr Cys Gln
210 215 220

His Gly Tyr Ile Arg Gly Asp Leu Asp Asn Val Phe Gly Gly Gly Thr
225 230 235 240

Lys Val Glu Ile Lys
245

<210> SEQ ID NO 67
<211> LENGTH: 813
<212> TYPE: DNA
<213> ORGANISM: Artificial Sequence
<220> FEATURE:
<223> OTHER INFORMATION: Synthetic

<400> SEQUENCE: 67
accggtgccg ccaccatggg ctggagctgc atcatcctgt tcctggtggc caccgctaca 60
ggcgtgcact ctgaggtgca gctggtggag agcggaggag gactggtgca gcctggaggc 120

```
tccctgagac tgtcttgtgc cgcttctggc tttagcctga gctcctctta ctggatctcc    180

tgggtgcgcc aggctccagg caagggactg gagtggatcg gctctatcga cagcggctcc    240

gtgggcatca cctactatgc cacatgggtg aagggccggt tcaccatcag cagggacaac    300

tccaagaata cactgtatct gcagatgaac tccctgcggg ccgaggatac agccgtgtac    360

tattgcgcca ggcacggcga caattgggct ctggatctgt ggggacaggg caccctggtg    420

acagtgagct ccggcggcgg cggctctgga ggaggaggca gcggcggagg aggctccgac    480

atccagatga cccagtctcc cagcacactg tccgcttctg tgggcgatag agtgaccatc    540

acatgtcgcg ccagccagtc catctctagc tggctggctt ggtaccagca gaagcccggc    600

aaggccccta agctgctgat ctataaggcc tctaccctgg ctagcggagt gccatcccgg    660

ttctctggca gcggctccgg aacagagttt accctgacaa tctcctctct gcagcccgac    720

gatttcgcca cctactattg ccagcacgga tacatcaggg gcgacctgga taacgtgttt    780

ggcggcggca ccaaggtgga gatcaagaga tct                                 813
```

```
<210> SEQ ID NO 68
<211> LENGTH: 245
<212> TYPE: PRT
<213> ORGANISM: Artificial Sequence
<220> FEATURE:
<223> OTHER INFORMATION: Synthetic

<400> SEQUENCE: 68

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Gly Tyr Ile Arg Gly Asp
                85                  90                  95

Leu Asp Asn Val Phe Gly Gly Gly Thr Lys Val Glu Ile Lys Gly Gly
            100                 105                 110

Gly Gly Ser Gly Gly Gly Gly Ser Gly Gly Gly Gly Ser Glu Val Gln
        115                 120                 125

Leu Val Glu Ser Gly Gly Gly Leu Val Gln Pro Gly Gly Ser Leu Arg
    130                 135                 140

Leu Ser Cys Ala Ala Ser Gly Phe Ser Leu Ser Ser Ser Tyr Trp Ile
145                 150                 155                 160

Ser Trp Val Arg Gln Ala Pro Gly Lys Gly Leu Glu Trp Ile Gly Ser
                165                 170                 175

Ile Asp Ser Gly Ser Val Gly Ile Thr Tyr Tyr Ala Thr Trp Val Lys
            180                 185                 190

Gly Arg Phe Thr Ile Ser Arg Asp Asn Ser Lys Asn Thr Leu Tyr Leu
        195                 200                 205

Gln Met Asn Ser Leu Arg Ala Glu Asp Thr Ala Val Tyr Tyr Cys Ala
    210                 215                 220

Arg His Gly Asp Asn Trp Ala Leu Asp Leu Trp Gly Gln Gly Thr Leu
225                 230                 235                 240
```

Val Thr Val Ser Ser
245

<210> SEQ ID NO 69
<211> LENGTH: 813
<212> TYPE: DNA
<213> ORGANISM: Artificial Sequence
<220> FEATURE:
<223> OTHER INFORMATION: Synthetic

<400> SEQUENCE: 69
accggtgccg ccaccatggg ctggagctgc atcatcctgt tcctggtggc caccgctaca 60
ggcgtgcact ccgacatcca gatgacccag tccccctcta cactgagcgc ctccgtgggc 120
gatagagtga ccatcacatg tcgcgcctct cagagcatca acagctggct ggcttggtac 180
cagcagaagc ccggcaaggc ccctaagctg ctgatctata aggcctctac cctggctagc 240
ggagtgccat cccggttctc cggctctggc agcggaacag agtttaccct gacaatcagc 300
tccctgcagc ccgacgattt cgccacctac tattgccagc acggatacat caggggcgac 360
ctggataacg tgttcggcgg cggcacaaag gtggagatca agggaggagg aggcagcggc 420
ggaggaggct ccggcggcgg cggctctgag gtgcagctgg tggagtccgg aggaggactg 480
gtgcagcctg gaggctctct gagactgagc tgtgccgcta gcggcttctc cctgtctagc 540
tcctactgga tctcttgggt gcgccaggct ccaggcaagg gactggagtg gatcggcagc 600
atcgactccg gctctgtggg catcacctac tatgccacat gggtgaaggg ccggtttacc 660
atctccaggg acaactctaa gaatacactg tatctgcaga tgaactctct gcgggccgag 720
gataccgccg tgtactattg cgccaggcac ggcgacaatt gggctctgga tctgtgggga 780
cagggcaccc tggtgacagt gtctagcaga tct 813

<210> SEQ ID NO 70
<211> LENGTH: 15
<212> TYPE: PRT
<213> ORGANISM: Artificial Sequence
<220> FEATURE:
<223> OTHER INFORMATION: Synthetic

<400> SEQUENCE: 70

Gly Gly Gly Gly Ser Gly Gly Gly Gly Ser Gly Gly Gly Gly Ser
1 5 10 15

<210> SEQ ID NO 71
<211> LENGTH: 21
<212> TYPE: PRT
<213> ORGANISM: Artificial Sequence
<220> FEATURE:
<223> OTHER INFORMATION: Synthetic

<400> SEQUENCE: 71

Ile Tyr Ile Trp Ala Pro Leu Ala Gly Thr Cys Gly Val Leu Leu Leu
1 5 10 15

Ser Leu Val Ile Thr
20

<210> SEQ ID NO 72
<211> LENGTH: 63
<212> TYPE: DNA
<213> ORGANISM: Artificial Sequence
<220> FEATURE:
<223> OTHER INFORMATION: Synthetic

<400> SEQUENCE: 72

-continued

```
atctacatct gggctccact ggcaggaacc tgtggcgtgc tgctgctgtc cctggtcatc     60

aca                                                                   63


<210> SEQ ID NO 73
<211> LENGTH: 27
<212> TYPE: PRT
<213> ORGANISM: Artificial Sequence
<220> FEATURE:
<223> OTHER INFORMATION: Synthetic

<400> SEQUENCE: 73

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25


<210> SEQ ID NO 74
<211> LENGTH: 81
<212> TYPE: DNA
<213> ORGANISM: Artificial Sequence
<220> FEATURE:
<223> OTHER INFORMATION: Synthetic

<400> SEQUENCE: 74

ttttgggtgc tggtggtggt tggtggagtc ctggcttgct atagcttgct agtaacagtg     60

gcctttatta ttttctgggt g                                               81


<210> SEQ ID NO 75
<211> LENGTH: 41
<212> TYPE: PRT
<213> ORGANISM: Artificial Sequence
<220> FEATURE:
<223> OTHER INFORMATION: Synthetic

<400> SEQUENCE: 75

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40


<210> SEQ ID NO 76
<211> LENGTH: 123
<212> TYPE: DNA
<213> ORGANISM: Artificial Sequence
<220> FEATURE:
<223> OTHER INFORMATION: Synthetic

<400> SEQUENCE: 76

aggagtaaga ggagcaggct cctgcacagt gactacatga acatgactcc ccgccgcccc     60

gggcccaccc gcaagcatta ccagccctat gccccaccac gcgacttcgc agcctatcgc    120

tcc                                                                  123


<210> SEQ ID NO 77
<211> LENGTH: 42
<212> TYPE: PRT
<213> ORGANISM: Artificial Sequence
<220> FEATURE:
<223> OTHER INFORMATION: Synthetic

<400> SEQUENCE: 77
```

Lys Arg Gly Arg Lys Lys Leu Leu Tyr Ile Phe Lys Gln Pro Phe Met
1 5 10 15

Arg Pro Val Gln Thr Thr Gln Glu Glu Asp Gly Cys Ser Cys Arg Phe
20 25 30

Pro Glu Glu Glu Glu Gly Gly Cys Glu Leu
35 40

<210> SEQ ID NO 78
<211> LENGTH: 126
<212> TYPE: DNA
<213> ORGANISM: Artificial Sequence
<220> FEATURE:
<223> OTHER INFORMATION: Synthetic

<400> SEQUENCE: 78
aaacggggca gaaagaaact cctgtatata ttcaaacaac catttatgag accagtacaa 60
actactcaag aggaagatgg ctgtagctgc cgatttccag aagaagaaga aggaggatgt 120
gaactg 126

<210> SEQ ID NO 79
<211> LENGTH: 113
<212> TYPE: PRT
<213> ORGANISM: Artificial Sequence
<220> FEATURE:
<223> OTHER INFORMATION: Synthetic

<400> SEQUENCE: 79

Arg Val Lys Phe Ser Arg Ser Ala Asp Ala Pro Ala Tyr Gln Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Pro Glu Met Gly Gly Lys
35 40 45

Pro Gln Arg Arg Lys Asn Pro Gln Glu Gly Leu Tyr Asn Glu Leu Gln
50 55 60

Lys Asp Lys Met Ala Glu Ala Tyr Ser Glu Ile Gly Met Lys Gly Glu
65 70 75 80

Arg Arg Arg Gly Lys Gly His Asp Gly Leu Tyr Gln Gly Leu Ser Thr
85 90 95

Ala Thr Lys Asp Thr Tyr Asp Ala Leu His Met Gln Ala Leu Pro Pro
100 105 110

Arg

<210> SEQ ID NO 80
<211> LENGTH: 112
<212> TYPE: PRT
<213> ORGANISM: Artificial Sequence
<220> FEATURE:
<223> OTHER INFORMATION: Synthetic

<400> SEQUENCE: 80

Arg Val Lys Phe Ser Arg Ser Ala Asp Ala Pro Ala Tyr Gln Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Pro Glu Met Gly Gly Lys
35 40 45

Pro Arg Arg Lys Asn Pro Gln Glu Gly Leu Tyr Asn Glu Leu Gln Lys

```
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 81
<211> LENGTH: 339
<212> TYPE: DNA
<213> ORGANISM: Artificial Sequence
<220> FEATURE:
<223> OTHER INFORMATION: Synthetic

<400> SEQUENCE: 81

```
agagtgaagt tcagcaggag cgcagacgcc cccgcgtacc agcagggcca gaaccagctc     60

tataacgagc tcaatctagg acgaagagag gagtacgatg ttttggacaa gagacgtggc    120

cgggaccctg agatgggggg aaagccgaga aggaagaacc ctcaggaagg cctgtacaat    180

gaactgcaga aagataagat ggcggaggcc tacagtgaga ttgggatgaa aggcgagcgc    240

cggaggggca aggggcacga tggcctttac cagggtctca gtacagccac caaggacacc    300

tacgacgccc ttcacatgca ggccctgccc cctcgctaa                           339
```

<210> SEQ ID NO 82
<211> LENGTH: 40
<212> TYPE: RNA
<213> ORGANISM: Artificial Sequence
<220> FEATURE:
<223> OTHER INFORMATION: Synthetic

<400> SEQUENCE: 82

```
rurcrargrg rgrururcru rgrgrarura rurcrurgru                           40
```

<210> SEQ ID NO 83
<211> LENGTH: 20
<212> TYPE: DNA
<213> ORGANISM: Artificial Sequence
<220> FEATURE:
<223> OTHER INFORMATION: Synthetic

<400> SEQUENCE: 83

```
agatgctatt tcccgtataa                                                 20
```

<210> SEQ ID NO 84
<211> LENGTH: 24
<212> TYPE: DNA
<213> ORGANISM: Artificial Sequence
<220> FEATURE:
<223> OTHER INFORMATION: Synthetic

<400> SEQUENCE: 84

```
ccatagacct catgtctagc acag                                            24
```

<210> SEQ ID NO 85
<211> LENGTH: 3261
<212> TYPE: DNA
<213> ORGANISM: Artificial Sequence
<220> FEATURE:
<223> OTHER INFORMATION: Synthetic

<400> SEQUENCE: 85

-continued

```
ggcaccatat tcattttgca ggtgaaattc ctgagatgta aggagctgct gtgacttgct     60
caaggcctta tatcgagtaa acggtagtgc tggggcttag acgcaggtgt tctgatttat    120
agttcaaaac ctctatcaat gagagagcaa tctcctggta atgtgataga tttcccaact    180
taatgccaac ataccataaa cctcccattc tgctaatgcc cagcctaagt tggggagacc    240
actccagatt ccaagatgta cagtttgctt tgctgggcct ttttcccatg cctgccttta    300
ctctgccaga gttatattgc tggggttttg aagaagatcc tattaaataa aagaataagc    360
agtattatta agtagccctg catttcaggt ttccttgagt ggcaggccag gcctggccgt    420
gaacgttcac tgaaatcatg gcctcttggc caagattgat agcttgtgcc tgtccctgag    480
tcccagtcca tcacgagcag ctggtttcta agatgctatt tcccgtataa agcatgagac    540
cgtgacttgc cagccccaca gagccccgcc cttgtccatc actggcatct ggactccagc    600
ctgggttggg gcaaagaggg aaatgagatc atgtcctaac cctgatcctc ttgtcccaca    660
gaattcgggc ggagttaggg cggagccaat cagcgtgcgc cgttccgaaa gttgcctttt    720
atggctgggc ggagaatggg cggtgaacgc cgatgattat ataaggacgc gccgggtgtg    780
gcacagctag ttccgtcgca gccgggattt gggtcgcggt tcttgtttgt ggatccctgt    840
gatcgtcact tgacagtaag tcactgactg tctatgcctg ggaaagggtg ggcaggagat    900
ggggcagtgc aggaaaagtg gcactatgaa ccctgcagcc ctaggaatgc atctagacaa    960
ttgtactaac cttcttctct ttcctctcct gacaggcctc gaggccgcca ccatggccct   1020
gcctgtgaca gccctgctgc tgcctctggc tctgctgctg catgccgcta gacccgatat   1080
ccagatgaca cagaccacca gcagcctgag cgccagcctg ggcgaccgag tgactatcag   1140
ctgccgggca tcccaggata tttctaagta tctgaactgg taccagcaga agcccgacgg   1200
cactgtcaaa ctgctgatct accacaccag tagactgcat tcaggggtgc ctagcaggtt   1260
ctccggatct ggcagtggga ctgactactc cctgaccatc tctaacctgg agcaggaaga   1320
tattgccacc tatttctgcc agcagggcaa tacactgcct tacacttttg gcgggggaac   1380
aaagctggag atcactggcg gaggaggatc tggaggagga ggaagtggag gaggaggatc   1440
agaggtgaaa ctgcaggaaa gcggaccagg actggtcgca ccttcacaga gcctgtccgt   1500
gacatgtact gtctccggag tgtctctgcc cgattacggc gtctcttgga tccggcagcc   1560
ccctagaaag ggactggagt ggctgggcgt gatctgggga agtgaaacta cctactataa   1620
tagtgctctg aaatcaagac tgaccatcat taaggacaac tctaaaagtc aggtgtttct   1680
gaagatgaat tccctgcaga ccgacgatac agcaatctac tattgcgcca aacactacta   1740
ttacggcggg agctatgcca tggattactg gggcagggga acttccgtca ccgtgagcag   1800
caccactact cccgctccaa ggccacccac ccctgccccg accatcgcct ctcagccgct   1860
ttccctgcgt ccggaggcat gtagacccgc agctggtggg gccgtgcata cccggggtct   1920
tgacttcgcc tgcgatatct acatttgggc ccctctggct ggtacttgcg ggtcctgct    1980
gctttcactc gtgatcactc tttactgtaa acggggcaga aagaaactcc tgtatatatt   2040
caaacaacca tttatgagac cagtacaaac tactcaagag gaagatggct gtagctgccg   2100
atttccagaa gaagaagaag gaggatgtga actgagagtg aagttcagca ggagcgcaga   2160
cgcccccgcg tacaagcagg gccagaacca gctctataac gagctcaatc taggacgaag   2220
agaggagtac gatgttttgg acaagagacg tggccgggac cctgagatgg ggggaaagcc   2280
gagaaggaag aaccctcagg aaggcctgta caatgaactg cagaaagata agatggcgga   2340
ggcctacagt gagattggga tgaaaggcga gcgccggagg ggcaaggggc acgatggcct   2400
```

ttaccagggt ctcagtacag ccaccaagga cacctacgac gcccttcaca tgcaggccct 2460
gccccctcgc tgataaaatt gttgttgtta acttgtttat tgcagcttat aatggttaca 2520
aataaagcaa tagcatcaca aatttcacaa ataaagcatt tttttcactg cattctagtt 2580
gtggtttgtc caaactcatc aatgtatctt agatatccag aaccctgacc ctgccgtgta 2640
ccagctgaga gactctaaat ccagtgacaa gtctgtctgc ctattcaccg attttgattc 2700
tcaaacaaat gtgtcacaaa gtaaggattc tgatgtgtat atcacagaca aaactgtgct 2760
agacatgagg tctatggact tcaagagcaa cagtgctgtg gcctggagca acaaatctga 2820
ctttgcatgt gcaaacgcct tcaacaacag cattattcca gaggacacct tcttccccag 2880
cccaggtaag ggcagctttg gtgccttcgc aggctgtttc cttgcttcag gaatggccag 2940
gttctgccca gagctctggt caatgatgtc taaaactcct ctgattggtg gtctcggcct 3000
tatccattgc caccaaaacc ctctttttac taagaaacag tgagccttgt tctggcagtc 3060
cagagaatga cacgggaaaa aagcagatga agagaaggtg gcaggagagg gcacgtggcc 3120
cagcctcagt ctctccaact gagttcctgc ctgcctgcct ttgctcagac tgtttgcccc 3180
ttactgctct tctaggcctc attctaagcc ccttctccaa gttgcctctc cttatttctc 3240
cctgtctgcc aaaaaatctt t 3261

<210> SEQ ID NO 86
<211> LENGTH: 3261
<212> TYPE: DNA
<213> ORGANISM: Artificial Sequence
<220> FEATURE:
<223> OTHER INFORMATION: Synthetic

<400> SEQUENCE: 86
ggcaccatat tcattttgca ggtgaaattc ctgagatgta aggagctgct gtgacttgct 60
caaggcctta tatcgagtaa acggtagtgc tggggcttag acgcaggtgt tctgatttat 120
agttcaaaac ctctatcaat gagagagcaa tctcctggta atgtgataga tttcccaact 180
taatgccaac ataccataaa cctcccattc tgctaatgcc cagcctaagt tggggagacc 240
actccagatt ccaagatgta cagtttgctt tgctgggcct ttttcccatg cctgccttta 300
ctctgccaga gttatattgc tggggttttg aagaagatcc tattaaataa aagaataagc 360
agtattatta agtagccctg catttcaggt ttccttgagt ggcaggccag gcctggccgt 420
gaacgttcac tgaaatcatg gcctcttggc caagattgat agcttgtgcc tgtccctgag 480
tcccagtcca tcacgagcag ctggtttcta agatgctatt tcccgtataa agcatgagac 540
cgtgacttgc cagccccaca gagccccgcc cttgtccatc actggcatct ggactccagc 600
ctgggttggg gcaaagaggg aaatgagatc atgtcctaac cctgatcctc ttgtcccaca 660
gaattcgggc ggagttaggg cggagccaat cagcgtgcgc cgttccgaaa gttgcctttt 720
atggctgggc ggagaatggg cggtgaacgc cgatgattat ataaggacgc gccgggtgtg 780
gcacagctag ttccgtcgca gccgggattt gggtcgcggt tcttgtttgt ggatccctgt 840
gatcgtcact tgacagtaag tcactgactg tctatgcctg ggaaagggtg ggcaggagat 900
ggggcagtgc aggaaaagtg gcactatgaa ccctgcagcc ctaggaatgc atctagacaa 960
ttgtactaac cttcttctct ttcctctcct gacaggcctc gaggccgcca ccatggccct 1020
gcctgtgaca gccctgctgc tgcctctggc tctgctgctg catgccgcta gacccgatat 1080
ccagatgaca cagaccacca gcagcctgag cgccagcctg ggcgaccgag tgactatcag 1140

-continued ctgccgggca tcccaggata tttctaagta tctgaactgg taccagcaga agcccgacgg 1200
cactgtcaaa ctgctgatct accacaccag tagactgcat tcaggggtgc ctagcaggtt 1260
ctccggatct ggcagtggga ctgactactc cctgaccatc tctaacctgg agcaggaaga 1320
tattgccacc tatttctgcc agcagggcaa tacactgcct tacacttttg gcgggggaac 1380
aaagctggag atcactggcg gaggaggatc tggaggagga ggaagtggag gaggaggatc 1440
agaggtgaaa ctgcaggaaa gcggaccagg actggtcgca ccttcacaga gcctgtccgt 1500
gacatgtact gtctccggag tgtctctgcc cgattacggc gtctcttgga tccggcagcc 1560
ccctagaaag ggactggagt ggctgggcgt gatctgggga agtgaaacta cctactataa 1620
tagtgctctg aaatcaagac tgaccatcat taaggacaac tctaaaagtc aggtgtttct 1680
gaagatgaat tccctgcaga ccgacgatac agcaatctac tattgcgcca aacactacta 1740
ttacggcggg agctatgcca tggattactg gggcaggga acttccgtca ccgtgagcag 1800
caccactact cccgctccaa ggccacccac ccctgccccg accatcgcct ctcagccgct 1860
ttccctgcgt ccggaggcat gtagacccgc agctggtggg gccgtgcata cccggggtct 1920
tgacttcgcc tgcgatatct acatttgggc ccctctggct ggtacttgcg gggtcctgct 1980
gctttcactc gtgatcactc tttactgtaa acggggcaga aagaaactcc tgtatatatt 2040
caaacaacca tttatgagac cagtacaaac tactcaagag gaagatggct gtagctgccg 2100
atttccagaa gaagaagaag gaggatgtga actgagagtg aagttcagca ggagcgcaga 2160
cgcccccgcg tacaagcagg gccagaacca gctctataac gagctcaatc taggacgaag 2220
agaggagtac gatgttttgg acaagagacg tggccgggac cctgagatgg ggggaaagcc 2280
gagaaggaag aaccctcagg aaggcctgta caatgaactg cagaaagata agatggcgga 2340
ggcctacagt gagattggga tgaaaggcga gcgccggagg ggcaaggggc acgatggcct 2400
ttaccagggt ctcagtacag ccaccaagga cacctacgac gcccttcaca tgcaggccct 2460
gccccctcgc tgataaaatt gttgttgtta acttgtttat tgcagcttat aatggttaca 2520
aataaagcaa tagcatcaca aatttcacaa ataaagcatt tttttcactg cattctagtt 2580
gtggtttgtc caaactcatc aatgtatctt agatatccag aaccctgacc ctgccgtgta 2640
ccagctgaga gactctaaat ccagtgacaa gtctgtctgc ctattcaccg attttgattc 2700
tcaaacaaat gtgtcacaaa gtaaggattc tgatgtgtat atcacagaca aaactgtgct 2760
agacatgagg tctatggact tcaagagcaa cagtgctgtg gcctggagca acaaatctga 2820
ctttgcatgt gcaaacgcct tcaacaacag cattattcca gaggacacct tcttccccag 2880
cccaggtaag ggcagctttg gtgccttcgc aggctgtttc cttgcttcag gaatggccag 2940
gttctgccca gagctctggt caatgatgtc taaaactcct ctgattggtg gtctcggcct 3000
tatccattgc caccaaaacc ctctttttac taagaaacag tgagccttgt tctggcagtc 3060
cagagaatga cacgggaaaa aagcagatga agagaaggtg gcaggagagg gcacgtggcc 3120
cagcctcagt ctctccaact gagttcctgc ctgcctgcct ttgctcagac tgtttgcccc 3180
ttactgctct tctaggcctc attctaagcc ccttctccaa gttgcctctc cttatttctc 3240
cctgtctgcc aaaaaatctt t 3261

<210> SEQ ID NO 87
<211> LENGTH: 3267
<212> TYPE: DNA
<213> ORGANISM: Artificial Sequence
<220> FEATURE:
<223> OTHER INFORMATION: Synthetic

<400> SEQUENCE: 87
ggcaccatat tcattttgca ggtgaaattc ctgagatgta aggagctgct gtgacttgct 60
caaggcctta tatcgagtaa acggtagtgc tggggcttag acgcaggtgt tctgatttat 120
agttcaaaac ctctatcaat gagagagcaa tctcctggta atgtgataga tttcccaact 180
taatgccaac ataccataaa cctcccattc tgctaatgcc cagcctaagt tggggagacc 240
actccagatt ccaagatgta cagtttgctt tgctgggcct ttttcccatg cctgccttta 300
ctctgccaga gttatattgc tggggttttg aagaagatcc tattaaataa aagaataagc 360
agtattatta agtagccctg catttcaggt ttccttgagt ggcaggccag gcctggccgt 420
gaacgttcac tgaaatcatg gcctcttggc caagattgat agcttgtgcc tgtccctgag 480
tcccagtcca tcacgagcag ctggtttcta agatgctatt tcccgtataa agcatgagac 540
cgtgacttgc cagccccaca gagccccgcc cttgtccatc actggcatct ggactccagc 600
ctgggttggg gcaaagaggg aaatgagatc atgtcctaac cctgatcctc ttgtcccaca 660
gaattcgggc ggagttaggg cggagccaat cagcgtgcgc cgttccgaaa gttgcctttt 720
atggctgggc ggagaatggg cggtgaacgc cgatgattat ataaggacgc gccgggtgtg 780
gcacagctag ttccgtcgca gccgggattt gggtcgcggt tcttgtttgt ggatccctgt 840
gatcgtcact tgacagtaag tcactgactg tctatgcctg ggaaagggtg ggcaggagat 900
ggggcagtgc aggaaaagtg gcactatgaa ccctgcagcc ctaggaatgc atctagacaa 960
ttgtactaac cttcttctct ttcctctcct gacaggcctc gaggccgcca ccatggccct 1020
gcctgtgaca gccctgctgc tgcctctggc tctgctgctg catgccgcta gacccgacat 1080
ccagatgacc cagtccccct ctacactgag cgcctccgtg ggcgatagag tgaccatcac 1140
atgtcgcgcc tctcagagca tcaacagctg gctggcttgg taccagcaga agcccggcaa 1200
ggcccctaag ctgctgatct ataaggcctc taccctggct agcggagtgc catcccggtt 1260
ctccggctct ggcagcggaa cagagtttac cctgacaatc agctccctgc agcccgacga 1320
tttcgccacc tactattgcc agcacggata catcaggggc gacctggata acgtgttcgg 1380
cggcggcaca aaggtggaga tcaagggagg aggaggcagc ggcggaggag gctccggcgg 1440
cggcggctct gaggtgcagc tggtggagtc cggaggagga ctggtgcagc ctggaggctc 1500
tctgagactg agctgtgccg ctagcggctt ctccctgtct agctcctact ggatctcttg 1560
ggtgcgccag gctccaggca agggactgga gtggatcggc agcatcgact ccggctctgt 1620
gggcatcacc tactatgcca catgggtgaa gggccggttt accatctcca gggacaactc 1680
taagaataca ctgtatctgc agatgaactc tctgcgggcc gaggataccg ccgtgtacta 1740
ttgcgccagg cacggcgaca attgggctct ggatctgtgg ggacagggca ccctggtgac 1800
agtgtctagc accactactc ccgctccaag gccacccacc cctgccccga ccatcgcctc 1860
tcagccgctt tccctgcgtc cggaggcatg tagacccgca gctggtgggg ccgtgcatac 1920
ccggggtctt gacttcgcct gcgatatcta catttgggcc cctctggctg gtacttgcgg 1980
ggtcctgctg ctttcactcg tgatcactct ttactgtagg agtaagagga gcaggctcct 2040
gcacagtgac tacatgaaca tgactccccg ccgccccggg cccacccgca agcattacca 2100
gccctatgcc ccaccacgcg acttcgcagc ctatcgctcc agagtgaagt tcagcaggag 2160
cgcagacgcc cccgcgtaca agcagggcca gaaccagctc tataacgagc tcaatctagg 2220
acgaagagag gagtacgatg ttttggacaa gagacgtggc cgggaccctg agatgggggg 2280

-continued

```
aaagccgaga aggaagaacc ctcaggaagg cctgtacaat gaactgcaga aagataagat    2340

ggcggaggcc tacagtgaga ttgggatgaa aggcgagcgc cggaggggca aggggcacga    2400

tggcctttac cagggtctca gtacagccac caaggacacc tacgacgccc ttcacatgca    2460

ggccctgccc cctcgctgat aaaattgttg ttgttaactt gtttattgca gcttataatg    2520

gttacaaata aagcaatagc atcacaaatt tcacaaataa agcatttttt tcactgcatt    2580

ctagttgtgg tttgtccaaa ctcatcaatg tatcttagat atccagaacc ctgaccctgc    2640

cgtgtaccag ctgagagact ctaaatccag tgacaagtct gtctgcctat tcaccgattt    2700

tgattctcaa acaaatgtgt cacaaagtaa ggattctgat gtgtatatca cagacaaaac    2760

tgtgctagac atgaggtcta tggacttcaa gagcaacagt gctgtggcct ggagcaacaa    2820

atctgacttt gcatgtgcaa acgccttcaa caacagcatt attccagagg acaccttctt    2880

ccccagccca ggtaagggca gctttggtgc cttcgcaggc tgtttccttg cttcaggaat    2940

ggccaggttc tgcccagagc tctggtcaat gatgtctaaa actcctctga ttggtggtct    3000

cggccttatc cattgccacc aaaaccctct ttttactaag aaacagtgag ccttgttctg    3060

gcagtccaga gaatgacacg ggaaaaaagc agatgaagag aaggtggcag gagagggcac    3120

gtggcccagc ctcagtctct ccaactgagt tcctgcctgc ctgcctttgc tcagactgtt    3180

tgccccttac tgctcttcta ggcctcattc taagcccctt ctccaagttg cctctcctta    3240

tttctccctg tctgccaaaa aatcttt                                        3267
```

<210> SEQ ID NO 88
<211> LENGTH: 3270
<212> TYPE: DNA
<213> ORGANISM: Artificial Sequence
<220> FEATURE:
<223> OTHER INFORMATION: Synthetic

<400> SEQUENCE: 88

```
ggcaccatat tcattttgca ggtgaaattc ctgagatgta aggagctgct gtgacttgct      60

caaggcctta tatcgagtaa acggtagtgc tggggcttag acgcaggtgt tctgatttat     120

agttcaaaac ctctatcaat gagagagcaa tctcctggta atgtgataga tttcccaact     180

taatgccaac ataccataaa cctcccattc tgctaatgcc cagcctaagt tggggagacc     240

actccagatt ccaagatgta cagtttgctt tgctgggcct ttttcccatg cctgccttta     300

ctctgccaga gttatattgc tggggttttg aagaagatcc tattaaataa aagaataagc     360

agtattatta agtagccctg catttcaggt ttccttgagt ggcaggccag gcctggccgt     420

gaacgttcac tgaaatcatg gcctcttggc caagattgat agcttgtgcc tgtccctgag     480

tcccagtcca tcacgagcag ctggtttcta agatgctatt tcccgtataa agcatgagac     540

cgtgacttgc cagccccaca gagccccgcc cttgtccatc actggcatct ggactccagc     600

ctgggttggg gcaaagaggg aaatgagatc atgtcctaac cctgatcctc ttgtcccaca     660

gaattcgggc ggagttaggg cggagccaat cagcgtgcgc cgttccgaaa gttgcctttt     720

atggctgggc ggagaatggg cggtgaacgc cgatgattat ataaggacgc gccgggtgtg     780

gcacagctag ttccgtcgca gccgggattt gggtcgcggt tcttgtttgt ggatccctgt     840

gatcgtcact tgacagtaag tcactgactg tctatgcctg ggaaagggtg ggcaggagat     900

ggggcagtgc aggaaaagtg gcactatgaa ccctgcagcc ctaggaatgc atctagacaa     960

ttgtactaac cttcttctct ttcctctcct gacaggcctc gaggccgcca ccatggccct    1020

gcctgtgaca gccctgctgc tgcctctggc tctgctgctg catgccgcta gacccgacat    1080
```

```
ccagatgacc cagtcccccct ctacactgag cgcctccgtg ggcgatagag tgaccatcac   1140

atgtcgcgcc tctcagagca tcaacagctg gctggcttgg taccagcaga agcccggcaa   1200

ggcccctaag ctgctgatct ataaggcctc taccctggct agcggagtgc catcccggtt   1260

ctccggctct ggcagcggaa cagagtttac cctgacaatc agctccctgc agcccgacga   1320

tttcgccacc tactattgcc agcacggata catcaggggc gacctggata acgtgttcgg   1380

cggcggcaca aaggtggaga tcaagggagg aggaggcagc ggcggaggag gctccggcgg   1440

cggcggctct gaggtgcagc tggtggagtc cggaggagga ctggtgcagc ctggaggctc   1500

tctgagactg agctgtgccg ctagcggctt ctccctgtct agctcctact ggatctcttg   1560

ggtgcgccag gctccaggca agggactgga gtggatcggc agcatcgact ccggctctgt   1620

gggcatcacc tactatgcca catgggtgaa gggccggttt accatctcca gggacaactc   1680

taagaataca ctgtatctgc agatgaactc tctgcgggcc gaggataccg ccgtgtacta   1740

ttgcgccagg cacggcgaca attgggctct ggatctgtgg ggacagggca ccctggtgac   1800

agtgtctagc accactactc ccgctccaag gccacccacc cctgccccga ccatcgcctc   1860

tcagccgctt tccctgcgtc cggaggcatg tagacccgca gctggtgggg ccgtgcatac   1920

ccggggtctt gacttcgcct gcgatatcta catttgggcc cctctggctg gtacttgcgg   1980

ggtcctgctg ctttcactcg tgatcactct ttactgtaaa cggggcagaa agaaactcct   2040

gtatatattc aaacaaccat ttatgagacc agtacaaact actcaagagg aagatggctg   2100

tagctgccga tttccagaag aagaagaagg aggatgtgaa ctgagagtga agttcagcag   2160

gagcgcagac gcccccgcgt acaagcaggg ccagaaccag ctctataacg agctcaatct   2220

aggacgaaga gaggagtacg atgttttgga caagagacgt ggccgggacc ctgagatggg   2280

gggaaagccg agaaggaaga accctcagga aggcctgtac aatgaactgc agaaagataa   2340

gatggcggag gcctacagtg agattgggat gaaaggcgag cgccggaggg gcaaggggca   2400

cgatggcctt taccagggtc tcagtacagc caccaaggac acctacgacg cccttcacat   2460

gcaggccctg ccccctcgct gataaaattg ttgttgttaa cttgtttatt gcagcttata   2520

atggttacaa ataaagcaat agcatcacaa atttcacaaa taaagcattt ttttcactgc   2580

attctagttg tggtttgtcc aaactcatca atgtatctta gatatccaga accctgaccc   2640

tgccgtgtac cagctgagag actctaaatc cagtgacaag tctgtctgcc tattcaccga   2700

ttttgattct caaacaaatg tgtcacaaag taaggattct gatgtgtata tcacagacaa   2760

aactgtgcta gacatgaggt ctatggactt caagagcaac agtgctgtgg cctggagcaa   2820

caaatctgac tttgcatgtg caaacgcctt caacaacagc attattccag aggacacctt   2880

cttccccagc ccaggtaagg gcagctttgg tgccttcgca ggctgtttcc ttgcttcagg   2940

aatggccagg ttctgcccag agctctggtc aatgatgtct aaaactcctc tgattggtgg   3000

tctcggcctt atccattgcc accaaaaccc tctttttact aagaaacagt gagccttgtt   3060

ctggcagtcc agagaatgac acgggaaaaa agcagatgaa gagaaggtgg caggagaggg   3120

cacgtggccc agcctcagtc tctccaactg agttcctgcc tgcctgcctt tgctcagact   3180

gtttgcccct tactgctctt ctaggcctca ttctaagccc cttctccaag ttgcctctcc   3240

ttatttctcc ctgtctgcca aaaaatcttt                                    3270
```

<210> SEQ ID NO 89
<211> LENGTH: 130
<212> TYPE: PRT

<213> ORGANISM: Artificial Sequence
<220> FEATURE:
<223> OTHER INFORMATION: Synthetic

<400> SEQUENCE: 89

```
Leu Glu Asp Leu Lys Asn Val Phe Pro Pro Glu Val Ala Val Phe Glu
1               5                   10                  15

Pro Ser Glu Ala Glu Ile Ser His Thr Gln Lys Ala Thr Leu Val Cys
            20                  25                  30

Leu Ala Thr Gly Phe Tyr Pro Asp His Val Glu Leu Ser Trp Trp Val
        35                  40                  45

Asn Gly Lys Glu Val His Ser Gly Val Cys Thr Asp Pro Gln Pro Leu
    50                  55                  60

Lys Glu Gln Pro Ala Leu Gln Asp Ser Arg Tyr Ala Leu Ser Ser Arg
65                  70                  75                  80

Leu Arg Val Ser Ala Thr Phe Trp Gln Asn Pro Arg Asn His Phe Arg
                85                  90                  95

Cys Gln Val Gln Phe Tyr Gly Leu Ser Glu Asn Asp Glu Trp Thr Gln
            100                 105                 110

Asp Arg Ala Lys Pro Val Thr Gln Ile Val Ser Ala Glu Ala Trp Gly
        115                 120                 125

Arg Ala
    130
```

<210> SEQ ID NO 90
<211> LENGTH: 95
<212> TYPE: PRT
<213> ORGANISM: Artificial Sequence
<220> FEATURE:
<223> OTHER INFORMATION: Synthetic

<400> SEQUENCE: 90

```
Pro Asp Ile Gln Asn Pro Asp Pro Ala Val Tyr Gln Leu Arg Asp Ser
1               5                   10                  15

Lys Ser Ser Asp Lys Ser Val Cys Leu Phe Thr Asp Phe Asp Ser Gln
            20                  25                  30

Thr Gln Val Ser Gln Ser Lys Asp Ser Asp Val Tyr Ile Thr Asp Lys
        35                  40                  45

Cys Val Leu Asp Met Arg Ser Met Asp Phe Lys Ser Asn Ser Ala Val
    50                  55                  60

Ala Trp Ser Gln Lys Ser Asp Phe Ala Cys Ala Asn Ala Phe Gln Asn
65                  70                  75                  80

Ser Ile Ile Pro Glu Asp Thr Phe Phe Pro Ser Pro Glu Ser Ser
                85                  90                  95
```

<210> SEQ ID NO 91
<211> LENGTH: 448
<212> TYPE: PRT
<213> ORGANISM: Artificial Sequence
<220> FEATURE:
<223> OTHER INFORMATION: Synthetic

<400> SEQUENCE: 91

```
Gln Val Gln Leu Val Gln Ser Gly Ala Glu Val Lys Lys Pro Gly Ser
1               5                   10                  15

Ser Val Lys Val Ser Cys Lys Ala Ser Gly Phe Ala Phe Thr Asp Tyr
            20                  25                  30

Tyr Ile His Trp Val Arg Gln Ala Pro Gly Gln Gly Leu Glu Trp Met
        35                  40                  45
```

```
Gly Trp Ile Ser Pro Gly Asn Val Asn Thr Lys Tyr Asn Glu Asn Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Ser Leu Tyr Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Cys Arg Glu Glu Met Thr Lys Asn Gln Val Ser Leu Trp
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

<210> SEQ ID NO 92
<211> LENGTH: 474

<212> TYPE: PRT
<213> ORGANISM: Artificial Sequence
<220> FEATURE:
<223> OTHER INFORMATION: Synthetic

<400> SEQUENCE: 92

```
Gln Val Gln Leu Val Gln Ser Gly Ala Glu Val Lys Lys Pro Gly Ser
1               5                   10                  15

Ser Val Lys Val Ser Cys Lys Ala Ser Gly Phe Ala Phe Thr Asp Tyr
            20                  25                  30

Tyr Ile His Trp Val Arg Gln Ala Pro Gly Gln Gly Leu Glu Trp Met
        35                  40                  45

Gly Trp Ile Ser Pro Gly Asn Val Asn Thr Lys Tyr Asn Glu Asn Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Ser Leu Tyr Tyr Phe Asp Tyr Trp Gly Gln Gly
            100                 105                 110

Thr Leu Val Thr Val Leu Glu Asp Leu Lys Asn Val Phe Pro Pro Glu
        115                 120                 125

Val Ala Val Phe Glu Pro Ser Glu Ala Glu Ile Ser His Thr Gln Lys
    130                 135                 140

Ala Thr Leu Val Cys Leu Ala Thr Gly Phe Tyr Pro Asp His Val Glu
145                 150                 155                 160

Leu Ser Trp Trp Val Asn Gly Lys Glu Val His Ser Gly Val Cys Thr
                165                 170                 175

Asp Pro Gln Pro Leu Lys Glu Gln Pro Ala Leu Gln Asp Ser Arg Tyr
            180                 185                 190

Ala Leu Ser Ser Arg Leu Arg Val Ser Ala Thr Phe Trp Gln Asn Pro
        195                 200                 205

Arg Asn His Phe Arg Cys Gln Val Gln Phe Tyr Gly Leu Ser Glu Asn
    210                 215                 220

Asp Glu Trp Thr Gln Asp Arg Ala Lys Pro Val Thr Gln Ile Val Ser
225                 230                 235                 240

Ala Glu Ala Trp Gly Arg Ala Ser Asp Lys Thr His Thr Cys Pro Pro
                245                 250                 255

Cys Pro Ala Pro Glu Ala Ala Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Cys Arg Glu
    370                 375                 380
```

```
Glu Met Thr Lys Asn Gln Val Ser Leu Trp Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly
465                 470


<210> SEQ ID NO 93
<211> LENGTH: 474
<212> TYPE: PRT
<213> ORGANISM: Artificial Sequence
<220> FEATURE:
<223> OTHER INFORMATION: Synthetic

<400> SEQUENCE: 93

Glu Val Gln Leu Val Gln Ser Gly Ala Glu Val Lys Lys Pro Gly Ser
1               5                   10                  15

Ser Val Lys Val Ser Cys Lys Ala Ser Gly Phe Ala Phe Thr Asp Tyr
            20                  25                  30

Tyr Ile His Trp Val Arg Gln Ala Pro Gly Gln Gly Leu Glu Trp Met
        35                  40                  45

Gly Trp Ile Ser Pro Gly Asn Val Asn Thr Lys Tyr Asn Glu Asn Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Ser Leu Tyr Tyr Phe Asp Tyr Trp Gly Gln Gly
            100                 105                 110

Thr Leu Val Thr Val Leu Glu Asp Leu Lys Asn Val Phe Pro Pro Glu
        115                 120                 125

Val Ala Val Phe Glu Pro Ser Glu Ala Glu Ile Ser His Thr Gln Lys
    130                 135                 140

Ala Thr Leu Val Cys Leu Ala Thr Gly Phe Tyr Pro Asp His Val Glu
145                 150                 155                 160

Leu Ser Trp Trp Val Asn Gly Lys Glu Val His Ser Gly Val Cys Thr
                165                 170                 175

Asp Pro Gln Pro Leu Lys Glu Gln Pro Ala Leu Gln Asp Ser Arg Tyr
            180                 185                 190

Ala Leu Ser Ser Arg Leu Arg Val Ser Ala Thr Phe Trp Gln Asn Pro
        195                 200                 205

Arg Asn His Phe Arg Cys Gln Val Gln Phe Tyr Gly Leu Ser Glu Asn
    210                 215                 220

Asp Glu Trp Thr Gln Asp Arg Ala Lys Pro Val Thr Gln Ile Val Ser
225                 230                 235                 240

Ala Glu Ala Trp Gly Arg Ala Ser Asp Lys Thr His Thr Cys Pro Pro
                245                 250                 255

Cys Pro Ala Pro Glu Ala Ala Gly Gly Pro Ser Val Phe Leu Phe Pro
            260                 265                 270
```

```
Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Cys Arg Glu
    370                 375                 380

Glu Met Thr Lys Asn Gln Val Ser Leu Trp Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly
465                 470


<210> SEQ ID NO 94
<211> LENGTH: 449
<212> TYPE: PRT
<213> ORGANISM: Artificial Sequence
<220> FEATURE:
<223> OTHER INFORMATION: Synthetic

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Ser
            20                  25                  30

Tyr Trp Ile Ser Trp Val Arg Gln Ala Pro Gly Lys Gly Leu Glu Trp
        35                  40                  45

Ile Gly Ser Ile Asp Ser Gly Ser Val Gly Ile Thr Tyr Tyr Ala Thr
    50                  55                  60

Trp Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asp Asn Trp Ala Leu Asp Leu Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
    195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Cys
        340                 345                 350

Thr Leu Pro Pro Ser Arg Glu Glu Met Thr Lys Asn Gln Val Ser Leu
    355                 360                 365

Ser Cys Ala Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly
```

<210> SEQ ID NO 95
<211> LENGTH: 682
<212> TYPE: PRT
<213> ORGANISM: Artificial Sequence
<220> FEATURE:
<223> OTHER INFORMATION: Synthetic

<400> SEQUENCE: 95

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Ser
            20                  25                  30

Tyr Trp Ile Ser Trp Val Arg Gln Ala Pro Gly Lys Gly Leu Glu Trp
        35                  40                  45

Ile Gly Ser Ile Asp Ser Gly Ser Val Gly Ile Thr Tyr Tyr Ala Thr
    50                  55                  60

Trp Val Lys Gly Arg Phe Thr Ile Ser Arg Asp Asn Ser Lys Asn Thr
```

-continued

```
65                  70                  75                  80

Leu Tyr Leu Gln Met Asn Ser Leu Arg Ala Glu Asp Thr Ala Val Tyr
                85                  90                  95

Tyr Cys Ala Arg His Gly Asp Asn Trp Ala Leu Asp Leu Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Gly
    210                 215                 220

Gly Gly Gly Ser Gly Gly Gly Gly Ser Glu Val Gln Leu Val Glu Ser
225                 230                 235                 240

Gly Gly Gly Leu Val Gln Pro Gly Gly Ser Leu Arg Leu Ser Cys Ala
                245                 250                 255

Ala Ser Gly Phe Ser Leu Ser Ser Ser Tyr Trp Ile Ser Trp Val Arg
            260                 265                 270

Gln Ala Pro Gly Lys Gly Leu Glu Trp Ile Gly Ser Ile Asp Ser Gly
        275                 280                 285

Ser Val Gly Ile Thr Tyr Tyr Ala Thr Trp Val Lys Gly Arg Phe Thr
    290                 295                 300

Ile Ser Arg Asp Asn Ser Lys Asn Thr Leu Tyr Leu Gln Met Asn Ser
305                 310                 315                 320

Leu Arg Ala Glu Asp Thr Ala Val Tyr Tyr Cys Ala Arg His Gly Asp
                325                 330                 335

Asn Trp Ala Leu Asp Leu Trp Gly Gln Gly Thr Leu Val Thr Val Ser
            340                 345                 350

Ser Ala Ser Thr Lys Gly Pro Ser Val Phe Pro Leu Ala Pro Ser Ser
        355                 360                 365

Lys Ser Thr Ser Gly Gly Thr Ala Ala Leu Gly Cys Leu Val Lys Asp
    370                 375                 380

Tyr Phe Pro Glu Pro Val Thr Val Ser Trp Asn Ser Gly Ala Leu Thr
385                 390                 395                 400

Ser Gly Val His Thr Phe Pro Ala Val Leu Gln Ser Ser Gly Leu Tyr
                405                 410                 415

Ser Leu Ser Ser Val Val Thr Val Pro Ser Ser Ser Leu Gly Thr Gln
            420                 425                 430

Thr Tyr Ile Cys Asn Val Asn His Lys Pro Ser Asn Thr Lys Val Asp
        435                 440                 445

Lys Arg Val Glu Pro Lys Ser Cys Asp Lys Thr His Thr Cys Pro Pro
    450                 455                 460

Cys Pro Ala Pro Glu Ala Ala Gly Gly Pro Ser Val Phe Leu Phe Pro
465                 470                 475                 480

Pro Lys Pro Lys Asp Thr Leu Met Ile Ser Arg Thr Pro Glu Val Thr
                485                 490                 495
```

```
Cys Val Val Val Asp Val Ser His Glu Asp Pro Glu Val Lys Phe Asn
            500                 505                 510

Trp Tyr Val Asp Gly Val Glu Val His Asn Ala Lys Thr Lys Pro Arg
        515                 520                 525

Glu Glu Gln Tyr Asn Ser Thr Tyr Arg Val Val Ser Val Leu Thr Val
    530                 535                 540

Leu His Gln Asp Trp Leu Asn Gly Lys Glu Tyr Lys Cys Lys Val Ser
545                 550                 555                 560

Asn Lys Ala Leu Pro Ala Pro Ile Glu Lys Thr Ile Ser Lys Ala Lys
                565                 570                 575

Gly Gln Pro Arg Glu Pro Gln Val Cys Thr Leu Pro Pro Ser Arg Glu
            580                 585                 590

Glu Met Thr Lys Asn Gln Val Ser Leu Ser Cys Ala Val Lys Gly Phe
        595                 600                 605

Tyr Pro Ser Asp Ile Ala Val Glu Trp Glu Ser Asn Gly Gln Pro Glu
    610                 615                 620

Asn Asn Tyr Lys Thr Thr Pro Pro Val Leu Asp Ser Asp Gly Ser Phe
625                 630                 635                 640

Phe Leu Val Ser Lys Leu Thr Val Asp Lys Ser Arg Trp Gln Gln Gly
                645                 650                 655

Asn Val Phe Ser Cys Ser Val Met His Glu Ala Leu His Asn His Tyr
            660                 665                 670

Thr Gln Lys Ser Leu Ser Leu Ser Pro Gly
        675                 680
```

<210> SEQ ID NO 96
<211> LENGTH: 475
<212> TYPE: PRT
<213> ORGANISM: Artificial Sequence
<220> FEATURE:
<223> OTHER INFORMATION: Synthetic

<400> SEQUENCE: 96

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Ser
            20                  25                  30

Tyr Trp Ile Ser Trp Val Arg Gln Ala Pro Gly Lys Gly Leu Glu Trp
        35                  40                  45

Ile Gly Ser Ile Asp Ser Gly Ser Val Gly Ile Thr Tyr Tyr Ala Thr
    50                  55                  60

Trp Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asp Asn Trp Ala Leu Asp Leu Trp Gly Gln
            100                 105                 110

Gly Thr Leu Val Thr Val Leu Glu Asp Leu Lys Asn Val Phe Pro Pro
        115                 120                 125

Glu Val Ala Val Phe Glu Pro Ser Glu Ala Glu Ile Ser His Thr Gln
    130                 135                 140

Lys Ala Thr Leu Val Cys Leu Ala Thr Gly Phe Tyr Pro Asp His Val
145                 150                 155                 160

Glu Leu Ser Trp Trp Val Asn Gly Lys Glu Val His Ser Gly Val Cys
                165                 170                 175
```

```
Thr Asp Pro Gln Pro Leu Lys Glu Gln Pro Ala Leu Gln Asp Ser Arg
            180                 185                 190

Tyr Ala Leu Ser Ser Arg Leu Arg Val Ser Ala Thr Phe Trp Gln Asn
        195                 200                 205

Pro Arg Asn His Phe Arg Cys Gln Val Gln Phe Tyr Gly Leu Ser Glu
    210                 215                 220

Asn Asp Glu Trp Thr Gln Asp Arg Ala Lys Pro Val Thr Gln Ile Val
225                 230                 235                 240

Ser Ala Glu Ala Trp Gly Arg Ala Ser Asp Lys Thr His Thr Cys Pro
                245                 250                 255

Pro Cys Pro Ala Pro Glu Ala Ala Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Cys Thr Leu Pro Pro Ser Arg
    370                 375                 380

Glu Glu Met Thr Lys Asn Gln Val Ser Leu Ser Cys Ala Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Val Ser Lys Leu Thr Val Asp Lys Ser Arg Trp Gln Gln
        435                 440                 445

Gly Asn Val Phe Ser Cys Ser Val Met His Glu Ala Leu His Asn His
    450                 455                 460

Tyr Thr Gln Lys Ser Leu Ser Leu Ser Pro Gly
465                 470                 475


<210> SEQ ID NO 97
<211> LENGTH: 732
<212> TYPE: PRT
<213> ORGANISM: Artificial Sequence
<220> FEATURE:
<223> OTHER INFORMATION: Synthetic

<400> SEQUENCE: 97

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Ser
            20                  25                  30

Tyr Trp Ile Ser Trp Val Arg Gln Ala Pro Gly Lys Gly Leu Glu Trp
        35                  40                  45

Ile Gly Ser Ile Asp Ser Gly Ser Val Gly Ile Thr Tyr Tyr Ala Thr
    50                  55                  60
```

```
Trp Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asp Asn Trp Ala Leu Asp Leu Trp Gly Gln
            100                 105                 110

Gly Thr Leu Val Thr Val Leu Glu Asp Leu Lys Asn Val Phe Pro Pro
        115                 120                 125

Glu Val Ala Val Phe Glu Pro Ser Glu Ala Glu Ile Ser His Thr Gln
    130                 135                 140

Lys Ala Thr Leu Val Cys Leu Ala Thr Gly Phe Tyr Pro Asp His Val
145                 150                 155                 160

Glu Leu Ser Trp Trp Val Asn Gly Lys Glu Val His Ser Gly Val Cys
                165                 170                 175

Thr Asp Pro Gln Pro Leu Lys Glu Gln Pro Ala Leu Gln Asp Ser Arg
            180                 185                 190

Tyr Ala Leu Ser Ser Arg Leu Arg Val Ser Ala Thr Phe Trp Gln Asn
        195                 200                 205

Pro Arg Asn His Phe Arg Cys Gln Val Gln Phe Tyr Gly Leu Ser Glu
    210                 215                 220

Asn Asp Glu Trp Thr Gln Asp Arg Ala Lys Pro Val Thr Gln Ile Val
225                 230                 235                 240

Ser Ala Glu Ala Trp Gly Arg Gly Gly Gly Gly Ser Gly Gly Gly Gly
                245                 250                 255

Ser Glu Val Gln Leu Val Glu Ser Gly Gly Gly Leu Val Gln Pro Gly
            260                 265                 270

Gly Ser Leu Arg Leu Ser Cys Ala Ala Ser Gly Phe Ser Leu Ser Ser
        275                 280                 285

Ser Tyr Trp Ile Ser Trp Val Arg Gln Ala Pro Gly Lys Gly Leu Glu
    290                 295                 300

Trp Ile Gly Ser Ile Asp Ser Gly Ser Val Gly Ile Thr Tyr Tyr Ala
305                 310                 315                 320

Thr Trp Val Lys Gly Arg Phe Thr Ile Ser Arg Asp Asn Ser Lys Asn
                325                 330                 335

Thr Leu Tyr Leu Gln Met Asn Ser Leu Arg Ala Glu Asp Thr Ala Val
            340                 345                 350

Tyr Tyr Cys Ala Arg His Gly Asp Asn Trp Ala Leu Asp Leu Trp Gly
        355                 360                 365

Gln Gly Thr Leu Val Thr Val Leu Glu Asp Leu Lys Asn Val Phe Pro
    370                 375                 380

Pro Glu Val Ala Val Phe Glu Pro Ser Glu Ala Glu Ile Ser His Thr
385                 390                 395                 400

Gln Lys Ala Thr Leu Val Cys Leu Ala Thr Gly Phe Tyr Pro Asp His
                405                 410                 415

Val Glu Leu Ser Trp Trp Val Asn Gly Lys Glu Val His Ser Gly Val
            420                 425                 430

Cys Thr Asp Pro Gln Pro Leu Lys Glu Gln Pro Ala Leu Gln Asp Ser
        435                 440                 445

Arg Tyr Ala Leu Ser Ser Arg Leu Arg Val Ser Ala Thr Phe Trp Gln
    450                 455                 460

Asn Pro Arg Asn His Phe Arg Cys Gln Val Gln Phe Tyr Gly Leu Ser
465                 470                 475                 480
```

```
Glu Asn Asp Glu Trp Thr Gln Asp Arg Ala Lys Pro Val Thr Gln Ile
                485                 490                 495

Val Ser Ala Glu Ala Trp Gly Arg Ala Ser Asp Lys Thr His Thr Cys
            500                 505                 510

Pro Pro Cys Pro Ala Pro Glu Leu Leu Gly Gly Pro Ser Val Phe Leu
        515                 520                 525

Phe Pro Pro Lys Pro Lys Asp Thr Leu Met Ile Ser Arg Thr Pro Glu
    530                 535                 540

Val Thr Cys Val Val Val Asp Val Ser His Glu Asp Pro Glu Val Lys
545                 550                 555                 560

Phe Asn Trp Tyr Val Asp Gly Val Glu Val His Asn Ala Lys Thr Lys
                565                 570                 575

Pro Arg Glu Glu Gln Tyr Asn Ser Thr Tyr Arg Val Val Ser Val Leu
            580                 585                 590

Thr Val Leu His Gln Asp Trp Leu Asn Gly Lys Glu Tyr Lys Cys Lys
        595                 600                 605

Val Ser Asn Lys Ala Leu Pro Ala Pro Ile Glu Lys Thr Ile Ser Lys
    610                 615                 620

Ala Lys Gly Gln Pro Arg Glu Pro Gln Val Cys Thr Leu Pro Pro Ser
625                 630                 635                 640

Arg Glu Glu Met Thr Lys Asn Gln Val Ser Leu Ser Cys Ala Val Lys
                645                 650                 655

Gly Phe Tyr Pro Ser Asp Ile Ala Val Glu Trp Glu Ser Asn Gly Gln
            660                 665                 670

Pro Glu Asn Asn Tyr Lys Thr Thr Pro Pro Val Leu Asp Ser Asp Gly
        675                 680                 685

Ser Phe Phe Leu Val Ser Lys Leu Thr Val Asp Lys Ser Arg Trp Gln
    690                 695                 700

Gln Gly Asn Val Phe Ser Cys Ser Val Met His Glu Ala Leu His Asn
705                 710                 715                 720

His Tyr Thr Gln Lys Ser Leu Ser Leu Ser Pro Gly
                725                 730
```

<210> SEQ ID NO 98
<211> LENGTH: 705
<212> TYPE: PRT
<213> ORGANISM: Artificial Sequence
<220> FEATURE:
<223> OTHER INFORMATION: Synthetic

<400> SEQUENCE: 98

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Ser
            20                  25                  30

Tyr Trp Ile Ser Trp Val Arg Gln Ala Pro Gly Lys Gly Leu Glu Trp
        35                  40                  45

Ile Gly Ser Ile Asp Ser Gly Ser Val Gly Ile Thr Tyr Tyr Ala Thr
    50                  55                  60

Trp Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asp Asn Trp Ala Leu Asp Leu Trp Gly Gln
            100                 105                 110
```

```
Gly Thr Leu Val Thr Val Leu Glu Asp Leu Lys Asn Val Phe Pro Pro
        115                 120                 125

Glu Val Ala Val Phe Glu Pro Ser Glu Ala Glu Ile Ser His Thr Gln
    130                 135                 140

Lys Ala Thr Leu Val Cys Leu Ala Thr Gly Phe Tyr Pro Asp His Val
145                 150                 155                 160

Glu Leu Ser Trp Trp Val Asn Gly Lys Glu Val His Ser Gly Val Cys
                165                 170                 175

Thr Asp Pro Gln Pro Leu Lys Glu Gln Pro Ala Leu Gln Asp Ser Arg
            180                 185                 190

Tyr Ala Leu Ser Ser Arg Leu Arg Val Ser Ala Thr Phe Trp Gln Asn
        195                 200                 205

Pro Arg Asn His Phe Arg Cys Gln Val Gln Phe Tyr Gly Leu Ser Glu
    210                 215                 220

Asn Asp Glu Trp Thr Gln Asp Arg Ala Lys Pro Val Thr Gln Ile Val
225                 230                 235                 240

Ser Ala Glu Ala Trp Gly Arg Gly Gly Gly Gly Ser Gly Gly Gly Gly
                245                 250                 255

Ser Gln Val Gln Leu Val Gln Ser Gly Ala Glu Val Lys Lys Pro Gly
            260                 265                 270

Ser Ser Val Lys Val Ser Cys Lys Ala Ser Gly Phe Ala Phe Thr Asp
        275                 280                 285

Tyr Tyr Ile His Trp Val Arg Gln Ala Pro Gly Gln Gly Leu Glu Trp
    290                 295                 300

Met Gly Trp Ile Ser Pro Gly Asn Val Asn Thr Lys Tyr Asn Glu Asn
305                 310                 315                 320

Phe Lys Gly Arg Val Thr Ile Thr Ala Asp Lys Ser Thr Ser Thr Ala
                325                 330                 335

Tyr Met Glu Leu Ser Ser Leu Arg Ser Glu Asp Thr Ala Val Tyr Tyr
            340                 345                 350

Cys Ala Arg Asp Gly Tyr Ser Leu Tyr Tyr Phe Asp Tyr Trp Gly Gln
        355                 360                 365

Gly Thr Leu Val Thr Val Ser Ser Ala Ser Thr Lys Gly Pro Ser Val
    370                 375                 380

Phe Pro Leu Ala Pro Ser Ser Lys Ser Thr Ser Gly Gly Thr Ala Ala
385                 390                 395                 400

Leu Gly Cys Leu Val Lys Asp Tyr Phe Pro Glu Pro Val Thr Val Ser
                405                 410                 415

Trp Asn Ser Gly Ala Leu Thr Ser Gly Val His Thr Phe Pro Ala Val
            420                 425                 430

Leu Gln Ser Ser Gly Leu Tyr Ser Leu Ser Ser Val Val Thr Val Pro
        435                 440                 445

Ser Ser Ser Leu Gly Thr Gln Thr Tyr Ile Cys Asn Val Asn His Lys
    450                 455                 460

Pro Ser Asn Thr Lys Val Asp Lys Arg Val Glu Pro Lys Ser Cys Asp
465                 470                 475                 480

Lys Thr His Thr Cys Pro Pro Cys Pro Ala Pro Glu Ala Ala Gly Gly
                485                 490                 495

Pro Ser Val Phe Leu Phe Pro Pro Lys Pro Lys Asp Thr Leu Met Ile
            500                 505                 510

Ser Arg Thr Pro Glu Val Thr Cys Val Val Val Asp Val Ser His Glu
        515                 520                 525

Asp Pro Glu Val Lys Phe Asn Trp Tyr Val Asp Gly Val Glu Val His
```

-continued

```
    530                 535                 540

Asn Ala Lys Thr Lys Pro Arg Glu Glu Gln Tyr Asn Ser Thr Tyr Arg
545                 550                 555                 560

Val Val Ser Val Leu Thr Val Leu His Gln Asp Trp Leu Asn Gly Lys
                565                 570                 575

Glu Tyr Lys Cys Lys Val Ser Asn Lys Ala Leu Pro Ala Pro Ile Glu
            580                 585                 590

Lys Thr Ile Ser Lys Ala Lys Gly Gln Pro Arg Glu Pro Gln Val Tyr
        595                 600                 605

Thr Leu Pro Pro Cys Arg Glu Glu Met Thr Lys Asn Gln Val Ser Leu
    610                 615                 620

Trp Cys Leu Val Lys Gly Phe Tyr Pro Ser Asp Ile Ala Val Glu Trp
625                 630                 635                 640

Glu Ser Asn Gly Gln Pro Glu Asn Asn Tyr Lys Thr Thr Pro Pro Val
                645                 650                 655

Leu Asp Ser Asp Gly Ser Phe Phe Leu Tyr Ser Lys Leu Thr Val Asp
            660                 665                 670

Lys Ser Arg Trp Gln Gln Gly Asn Val Phe Ser Cys Ser Val Met His
        675                 680                 685

Glu Ala Leu His Asn His Tyr Thr Gln Lys Ser Leu Ser Leu Ser Pro
    690                 695                 700

Gly
705


<210> SEQ ID NO 99
<211> LENGTH: 707
<212> TYPE: PRT
<213> ORGANISM: Artificial Sequence
<220> FEATURE:
<223> OTHER INFORMATION: Synthetic

<400> SEQUENCE: 99

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Ser
            20                  25                  30

Tyr Trp Ile Ser Trp Val Arg Gln Ala Pro Gly Lys Gly Leu Glu Trp
        35                  40                  45

Ile Gly Ser Ile Asp Ser Gly Ser Val Gly Ile Thr Tyr Tyr Ala Thr
    50                  55                  60

Trp Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asp Asn Trp Ala Leu Asp Leu Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
```

-continued

```
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Gly
    210                 215                 220

Gly Gly Gly Ser Gly Gly Gly Gly Ser Gln Val Gln Leu Val Gln Ser
225                 230                 235                 240

Gly Ala Glu Val Lys Lys Pro Gly Ser Ser Val Lys Val Ser Cys Lys
                245                 250                 255

Ala Ser Gly Phe Ala Phe Thr Asp Tyr Tyr Ile His Trp Val Arg Gln
            260                 265                 270

Ala Pro Gly Gln Gly Leu Glu Trp Met Gly Trp Ile Ser Pro Gly Asn
        275                 280                 285

Val Asn Thr Lys Tyr Asn Glu Asn Phe Lys Gly Arg Val Thr Ile Thr
    290                 295                 300

Ala Asp Lys Ser Thr Ser Thr Ala Tyr Met Glu Leu Ser Ser Leu Arg
305                 310                 315                 320

Ser Glu Asp Thr Ala Val Tyr Tyr Cys Ala Arg Asp Gly Tyr Ser Leu
                325                 330                 335

Tyr Tyr Phe Asp Tyr Trp Gly Gln Gly Thr Leu Val Thr Val Leu Glu
            340                 345                 350

Asp Leu Lys Asn Val Phe Pro Pro Glu Val Ala Val Phe Glu Pro Ser
        355                 360                 365

Glu Ala Glu Ile Ser His Thr Gln Lys Ala Thr Leu Val Cys Leu Ala
    370                 375                 380

Thr Gly Phe Tyr Pro Asp His Val Glu Leu Ser Trp Trp Val Asn Gly
385                 390                 395                 400

Lys Glu Val His Ser Gly Val Cys Thr Asp Pro Gln Pro Leu Lys Glu
                405                 410                 415

Gln Pro Ala Leu Gln Asp Ser Arg Tyr Ala Leu Ser Ser Arg Leu Arg
            420                 425                 430

Val Ser Ala Thr Phe Trp Gln Asn Pro Arg Asn His Phe Arg Cys Gln
        435                 440                 445

Val Gln Phe Tyr Gly Leu Ser Glu Asn Asp Glu Trp Thr Gln Asp Arg
    450                 455                 460

Ala Lys Pro Val Thr Gln Ile Val Ser Ala Glu Ala Trp Gly Arg Ala
465                 470                 475                 480

Ser Asp Lys Thr His Thr Cys Pro Pro Cys Pro Ala Pro Glu Ala Ala
                485                 490                 495

Gly Gly Pro Ser Val Phe Leu Phe Pro Pro Lys Pro Lys Asp Thr Leu
            500                 505                 510

Met Ile Ser Arg Thr Pro Glu Val Thr Cys Val Val Val Asp Val Ser
        515                 520                 525

His Glu Asp Pro Glu Val Lys Phe Asn Trp Tyr Val Asp Gly Val Glu
    530                 535                 540

Val His Asn Ala Lys Thr Lys Pro Arg Glu Glu Gln Tyr Asn Ser Thr
545                 550                 555                 560

Tyr Arg Val Val Ser Val Leu Thr Val Leu His Gln Asp Trp Leu Asn
                565                 570                 575

Gly Lys Glu Tyr Lys Cys Lys Val Ser Asn Lys Ala Leu Pro Ala Pro
            580                 585                 590

Ile Glu Lys Thr Ile Ser Lys Ala Lys Gly Gln Pro Arg Glu Pro Gln
        595                 600                 605
```

-continued

```
Val Tyr Thr Leu Pro Pro Cys Arg Glu Glu Met Thr Lys Asn Gln Val
    610                 615                 620

Ser Leu Trp Cys Leu Val Lys Gly Phe Tyr Pro Ser Asp Ile Ala Val
625                 630                 635                 640

Glu Trp Glu Ser Asn Gly Gln Pro Glu Asn Asn Tyr Lys Thr Thr Pro
                645                 650                 655

Pro Val Leu Asp Ser Asp Gly Ser Phe Phe Leu Tyr Ser Lys Leu Thr
            660                 665                 670

Val Asp Lys Ser Arg Trp Gln Gln Gly Asn Val Phe Ser Cys Ser Val
        675                 680                 685

Met His Glu Ala Leu His Asn His Tyr Thr Gln Lys Ser Leu Ser Leu
    690                 695                 700

Ser Pro Gly
705


<210> SEQ ID NO 100
<211> LENGTH: 219
<212> TYPE: PRT
<213> ORGANISM: Artificial Sequence
<220> FEATURE:
<223> OTHER INFORMATION: Synthetic

<400> SEQUENCE: 100

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Gln Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser His Thr Leu Arg Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 101
<211> LENGTH: 207
<212> TYPE: PRT
<213> ORGANISM: Artificial Sequence
```

<220> FEATURE:
<223> OTHER INFORMATION: Synthetic

<400> SEQUENCE: 101

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Leu Leu Asn Ser
20 25 30

Arg Thr Arg Lys Asn Tyr Leu Ala Trp Tyr Gln Gln Lys Pro Gly Gln
35 40 45

Pro Pro Lys Leu Leu Ile Tyr Trp Ala Ser Thr Arg Gln Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Thr Gln
85 90 95

Ser His Thr Leu Arg Thr Phe Gly Gly Gly Thr Lys Val Glu Ile Lys
100 105 110

Pro Asp Ile Gln Asn Pro Asp Pro Ala Val Tyr Gln Leu Arg Asp Ser
115 120 125

Lys Ser Ser Asp Lys Ser Val Cys Leu Phe Thr Asp Phe Asp Ser Gln
130 135 140

Thr Gln Val Ser Gln Ser Lys Asp Ser Asp Val Tyr Ile Thr Asp Lys
145 150 155 160

Cys Val Leu Asp Met Arg Ser Met Asp Phe Lys Ser Asn Ser Ala Val
165 170 175

Ala Trp Ser Gln Lys Ser Asp Phe Ala Cys Ala Asn Ala Phe Gln Asn
180 185 190

Ser Ile Ile Pro Glu Asp Thr Phe Phe Pro Ser Pro Glu Ser Ser
195 200 205

<210> SEQ ID NO 102
<211> LENGTH: 207
<212> TYPE: PRT
<213> ORGANISM: Artificial Sequence
<220> FEATURE:
<223> OTHER INFORMATION: Synthetic

<400> SEQUENCE: 102

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Leu Leu Asn Ser
20 25 30

Arg Thr Arg Lys Asn Tyr Leu Ala Trp Tyr Gln Gln Lys Pro Gly Gln
35 40 45

Pro Pro Lys Leu Leu Ile Tyr Trp Ala Ser Thr Arg Gln Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Thr Gln
85 90 95

Ser His Thr Leu Arg Thr Phe Gly Gly Gly Thr Lys Val Glu Ile Lys
100 105 110

Pro Asp Ile Gln Asn Pro Asp Pro Ala Val Tyr Gln Leu Arg Asp Ser
115 120 125

Lys Ser Ser Asp Lys Ser Val Cys Leu Phe Thr Asp Phe Asp Ser Gln

-continued

```
    130                 135                 140

Thr Gln Val Ser Gln Ser Lys Asp Ser Asp Val Tyr Ile Thr Asp Lys
145                 150                 155                 160

Cys Val Leu Asp Met Arg Ser Met Asp Phe Lys Ser Asn Ser Ala Val
                165                 170                 175

Ala Trp Ser Gln Lys Ser Asp Phe Ala Cys Ala Asn Ala Phe Gln Asn
            180                 185                 190

Ser Ile Ile Pro Glu Asp Thr Phe Phe Pro Ala Pro Glu Ser Ser
        195                 200                 205


<210> SEQ ID NO 103
<211> LENGTH: 217
<212> TYPE: PRT
<213> ORGANISM: Artificial Sequence
<220> FEATURE:
<223> OTHER INFORMATION: Synthetic

<400> SEQUENCE: 103

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Gly Tyr Ile Arg Gly Asp
                85                  90                  95

Leu Asp Asn Val Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215


<210> SEQ ID NO 104
<211> LENGTH: 205
<212> TYPE: PRT
<213> ORGANISM: Artificial Sequence
<220> FEATURE:
<223> OTHER INFORMATION: Synthetic

<400> SEQUENCE: 104

Asp Ile Gln Met Thr Gln Ser Pro Ser Thr Leu Ser Ala Ser Val Gly
1               5                   10                  15
```

-continued

```
Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Gly Tyr Ile Arg Gly Asp
                85                  90                  95

Leu Asp Asn Val Phe Gly Gly Gly Thr Lys Val Glu Ile Lys Pro Asp
            100                 105                 110

Ile Gln Asn Pro Asp Pro Ala Val Tyr Gln Leu Arg Asp Ser Lys Ser
        115                 120                 125

Ser Asp Lys Ser Val Cys Leu Phe Thr Asp Phe Asp Ser Gln Thr Gln
    130                 135                 140

Val Ser Gln Ser Lys Asp Ser Asp Val Tyr Ile Thr Asp Lys Cys Val
145                 150                 155                 160

Leu Asp Met Arg Ser Met Asp Phe Lys Ser Asn Ser Ala Val Ala Trp
                165                 170                 175

Ser Gln Lys Ser Asp Phe Ala Cys Ala Asn Ala Phe Gln Asn Ser Ile
            180                 185                 190

Ile Pro Glu Asp Thr Phe Phe Pro Ser Pro Glu Ser Ser
        195                 200                 205


<210> SEQ ID NO 105
<211> LENGTH: 205
<212> TYPE: PRT
<213> ORGANISM: Artificial Sequence
<220> FEATURE:
<223> OTHER INFORMATION: Synthetic

<400> SEQUENCE: 105

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Gly Tyr Ile Arg Gly Asp
                85                  90                  95

Leu Asp Asn Val Phe Gly Gly Gly Thr Lys Val Glu Ile Lys Pro Asp
            100                 105                 110

Ile Gln Asn Pro Asp Pro Ala Val Tyr Gln Leu Arg Asp Ser Lys Ser
        115                 120                 125

Ser Asp Lys Ser Val Cys Leu Phe Thr Asp Phe Asp Ser Gln Thr Gln
    130                 135                 140

Val Ser Gln Ser Lys Asp Ser Asp Val Tyr Ile Thr Asp Lys Cys Val
145                 150                 155                 160

Leu Asp Met Arg Ser Met Asp Phe Lys Ser Asn Ser Ala Val Ala Trp
                165                 170                 175
```

```
Ser Gln Lys Ser Asp Phe Ala Cys Ala Asn Ala Phe Gln Asn Ser Ile
            180                 185                 190

Ile Pro Glu Asp Thr Phe Phe Pro Ala Pro Glu Ser Ser
        195                 200                 205


<210> SEQ ID NO 106
<211> LENGTH: 449
<212> TYPE: PRT
<213> ORGANISM: Artificial Sequence
<220> FEATURE:
<223> OTHER INFORMATION: Synthetic

<400> SEQUENCE: 106

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Ser
            20                  25                  30

Tyr Trp Ile Ser Trp Val Arg Gln Ala Pro Gly Lys Gly Leu Glu Trp
        35                  40                  45

Ile Gly Ser Ile Asp Ser Gly Ser Val Gly Ile Thr Tyr Tyr Ala Thr
    50                  55                  60

Trp Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asp Asn Trp Ala Leu Asp Leu Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335
```

Lys Thr Ile Ser Lys Ala Lys Gly Gln Pro Arg Glu Pro Gln Val Tyr
340 345 350

Thr Leu Pro Pro Ser Arg Glu Glu Met Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly

<210> SEQ ID NO 107
<211> LENGTH: 226
<212> TYPE: PRT
<213> ORGANISM: Artificial Sequence
<220> FEATURE:
<223> OTHER INFORMATION: Synthetic

<400> SEQUENCE: 107

Asp Lys Thr His Thr Cys Pro Pro Cys Pro Ala Pro Glu Ala Ala Gly
1 5 10 15

Gly Pro Ser Val Phe Leu Phe Pro Pro Lys Pro Lys Asp Thr Leu Met
20 25 30

Ile Ser Arg Thr Pro Glu Val Thr Cys Val Val Val Asp Val Ser His
35 40 45

Glu Asp Pro Glu Val Lys Phe Asn Trp Tyr Val Asp Gly Val Glu Val
50 55 60

His Asn Ala Lys Thr Lys Pro Arg Glu Glu Gln Tyr Asn Ser Thr Tyr
65 70 75 80

Arg Val Val Ser Val Leu Thr Val Leu His Gln Asp Trp Leu Asn Gly
85 90 95

Lys Glu Tyr Lys Cys Lys Val Ser Asn Lys Ala Leu Pro Ala Pro Ile
100 105 110

Glu Lys Thr Ile Ser Lys Ala Lys Gly Gln Pro Arg Glu Pro Gln Val
115 120 125

Cys Thr Leu Pro Pro Ser Arg Glu Glu Met Thr Lys Asn Gln Val Ser
130 135 140

Leu Ser Cys Ala Val Lys Gly Phe Tyr Pro Ser Asp Ile Ala Val Glu
145 150 155 160

Trp Glu Ser Asn Gly Gln Pro Glu Asn Asn Tyr Lys Thr Thr Pro Pro
165 170 175

Val Leu Asp Ser Asp Gly Ser Phe Phe Leu Val Ser Lys Leu Thr Val
180 185 190

Asp Lys Ser Arg Trp Gln Gln Gly Asn Val Phe Ser Cys Ser Val Met
195 200 205

His Glu Ala Leu His Asn His Tyr Thr Gln Lys Ser Leu Ser Leu Ser
210 215 220

Pro Gly
225

<210> SEQ ID NO 108
<211> LENGTH: 1407
<212> TYPE: DNA
<213> ORGANISM: Artificial Sequence
<220> FEATURE:
<223> OTHER INFORMATION: Synthetic

<400> SEQUENCE: 108
atggagtttg ggctgagctg gctttttctt gtcgcgattc ttaagggtgt acagtgtcag 60
gtgcagcttg tgcagtctgg ggcagaagtg aagaagcctg ggtctagtgt caaggtgtca 120
tgcaaggcta gcgggttcgc ctttactgac tactacatcc actgggtgcg gcaggctccc 180
ggacaagggt tggagtggat gggatggatc tccccaggca atgtcaacac aaagtacaac 240
gagaacttca aaggccgcgt caccattacc gccgacaaga gcacctccac agcctacatg 300
gagctgtcca gcctcagaag cgaggacact gccgtctact actgtgccag ggatgggtac 360
tccctgtatt actttgatta ctggggccag ggcacactgg tgacagtgag ctccgcgtcg 420
accaagggcc catccgtctt cccccctggca ccctcctcca agagcacctc tgggggcaca 480
gcggccctgg gctgcctggt caaggactac ttccccgaac cggtgacggt gtcctggaac 540
tcaggcgctc tgaccagcgg cgtgcacacc ttcccggctg tcctacagtc ctcaggactc 600
tactccctca gcagcgtggt gaccgtgccc tccagcagct tgggcaccca gacctacatc 660
tgcaacgtga atcacaagcc cagcaacacc aaggtggaca agagagttga gcccaaatct 720
tgtgacaaaa ctcacacatg cccaccgtgc ccagcacctg aagccgccgg gggaccgtca 780
gtcttcctct tcccccccaaa acccaaggac accctcatga tctcccggac ccctgaggtc 840
acatgcgtgg tggtggacgt gagccacgaa gaccctgagg tcaagttcaa ctggtacgtg 900
gacggcgtgg aggtgcataa tgccaagaca aagccgcggg aggagcagta caacagcacg 960
taccgtgtgg tcagcgtcct caccgtcctg caccaggact ggctgaatgg caaggagtac 1020
aagtgcaagg tctccaacaa agccctccca gcccccatcg agaaaaccat ctccaaagcc 1080
aaagggcagc cccgagaacc acaggtctac accctgcccc catgccggga ggagatgacc 1140
aagaaccagg tcagcctgtg gtgcctggtc aaaggcttct atcccagcga catcgccgtg 1200
gagtgggaga gcaatgggca gccggagaac aactacaaga ccacgcctcc cgtgctggac 1260
tccgacggct ccttcttcct ctatagcaag ctcaccgtgg acaagagcag gtggcagcag 1320
gggaacgtct tctcatgctc cgtgatgcat gaggctctgc acaaccacta cacgcagaag 1380
agcttaagcc tgtctccggg ttaatag 1407

<210> SEQ ID NO 109
<211> LENGTH: 1422
<212> TYPE: DNA
<213> ORGANISM: Artificial Sequence
<220> FEATURE:
<223> OTHER INFORMATION: Synthetic

<400> SEQUENCE: 109
caggtgcagc ttgtgcagtc tggggcagaa gtgaagaagc ctgggtctag tgtcaaggtg 60
tcatgcaagg ctagcgggtt cgcctttact gactactaca tccactgggt gcggcaggct 120
cccggacaag ggttggagtg gatgggatgg atctccccag gcaatgtcaa cacaaagtac 180
aacgagaact tcaaaggccg cgtcaccatt accgccgaca agagcacctc cacagcctac 240
atggagctgt ccagcctcag aagcgaggac actgccgtct actactgtgc cagggatggg 300
tactccctgt attactttga ttactggggc cagggcacac tggtgacagt gctggaggac 360

```
ctgaagaacg tgttccctcc cgaggtggcc gtgttcgaac ccagcgaggc cgagatcagc    420
cacacccaga aggccaccct ggtgtgtctg gccaccggct tctaccccga ccacgtggag    480
ctgagctggt gggtgaacgg caaggaggtg cacagcggcg tgtgtaccga ccctcagccc    540
ctgaaggagc agcccgccct gcaggacagc aggtacgccc tgagcagcag gctgagagtg    600
agcgccacct tctggcagaa ccccaggaac cacttcaggt gccaggtgca gttctacggc    660
ctgagcgaga acgacgagtg gacccaggac agggccaagc ccgtgaccca gatcgtgagc    720
gctgaggcct ggggcagagc ctctgacaaa actcacacat gcccaccgtg tccagcacct    780
gaagccgccg gggggaccgtc agtcttcctc ttccccccaa aacccaagga caccctcatg    840
atctcccgga cccctgaggt cacatgcgtg gtggtggacg tgagccacga agaccctgag    900
gtcaagttca actggtacgt ggacggcgtg gaggtgcata atgccaagac aaagccgcgg    960
gaggagcagt acaacagcac gtaccgtgtg gtcagcgtcc tcaccgtcct gcaccaggac   1020
tggctgaatg gcaaggagta caagtgcaag gtctccaaca aagccctccc agcccccatc   1080
gagaaaacca tctccaaagc caaagggcag ccccgagaac cacaggtcta caccctgccc   1140
ccatgccggg aggagatgac caagaaccag gtcagcctgt ggtgcctggt caaaggcttc   1200
tatcccagcg acatcgccgt ggagtgggag agcaatgggc agccggagaa caactacaag   1260
accacgcctc ccgtgctgga ctccgacggc tccttcttcc tctatagcaa gctcaccgtg   1320
gacaagagca ggtggcagca ggggaacgtc ttctcatgct ccgtgatgca tgaggctctg   1380
cacaaccact acacgcagaa gagcttaagc ctgtctccgg gt                      1422
```

<210> SEQ ID NO 110
<211> LENGTH: 1485
<212> TYPE: DNA
<213> ORGANISM: Artificial Sequence
<220> FEATURE:
<223> OTHER INFORMATION: Synthetic

<400> SEQUENCE: 110

```
atggagtttg ggctgagctg gctttttctt gtcgcgattc ttaagggtgt acagtgtgag     60
gtgcagcttg tgcagtctgg ggcagaagtg aagaagcctg ggtctagtgt caaggtgtca    120
tgcaaggcta gcgggttcgc ctttactgac tactacatcc actgggtgcg gcaggctccc    180
ggacaagggt tggagtggat gggatggatc tccccaggca atgtcaacac aaagtacaac    240
gagaacttca aaggccgcgt caccattacc gccgacaaga gcacctccac agcctacatg    300
gagctgtcca gcctcagaag cgaggacact gccgtctact actgtgccag ggatgggtac    360
tccctgtatt actttgatta ctggggccag ggcacactgg tgacagtgct ggaggacctg    420
aagaacgtgt tccctcccga ggtggccgtg ttcgaaccca gcgaggccga gatcagccac    480
acccagaagg ccaccctggt gtgtctggcc accggcttct accccgacca cgtggagctg    540
agctggtggg tgaacggcaa ggaggtgcac agcggcgtgt gtaccgaccc tcagcccctg    600
aaggagcagc ccgccctgca ggacagcagg tacgccctga gcagcaggct gagagtgagc    660
gccaccttct ggcagaaccc caggaaccac ttcaggtgcc aggtgcagtt ctacggcctg    720
agcgagaacg acgagtggac ccaggacagg gccaagcccg tgacccagat cgtgagcgct    780
gaggcctggg gcagagcctc tgacaaaact cacacatgcc caccgtgtcc agcacctgaa    840
gccgccgggg gaccgtcagt cttcctcttc cccccaaaac ccaaggacac cctcatgatc    900
tcccggaccc ctgaggtcac atgcgtggtg gtggacgtga gccacgaaga ccctgaggtc    960
aagttcaact ggtacgtgga cggcgtggag gtgcataatg ccaagacaaa gccgcgggag   1020
```

gagcagtaca acagcacgta ccgtgtggtc agcgtcctca ccgtcctgca ccaggactgg 1080
ctgaatggca aggagtacaa gtgcaaggtc tccaacaaag ccctcccagc ccccatcgag 1140
aaaaccatct ccaaagccaa agggcagccc cgagaaccac aggtctacac cctgccccca 1200
tgccgggagg agatgaccaa gaaccaggtc agcctgtggt gcctggtcaa aggcttctat 1260
cccagcgaca tcgccgtgga gtgggagagc aatgggcagc cggagaacaa ctacaagacc 1320
acgcctcccg tgctggactc cgacggctcc ttcttcctct atagcaagct caccgtggac 1380
aagagcaggt ggcagcaggg gaacgtcttc tcatgctccg tgatgcatga ggctctgcac 1440
aaccactaca cgcagaagag cttaagcctg tctccgggtt aatag 1485

<210> SEQ ID NO 111
<211> LENGTH: 1410
<212> TYPE: DNA
<213> ORGANISM: Artificial Sequence
<220> FEATURE:
<223> OTHER INFORMATION: Synthetic

<400> SEQUENCE: 111
atggagtttg ggctgagctg gctttttctt gtcgcgattc ttaagggtgt acagtgtgag 60
gtgcagctcg tcgagtccgg aggaggttta gtccaacccg gtggatcttt aaggctgtct 120
tgtgctgctt ccggcttttc tttatcctcc agctactgga tctcttgggt gcggcaagct 180
cccggaaagg gactcgagtg gatcggctcc atcgattccg gatccgtggg cattacctac 240
tacgccacat gggtgaaagg tcgtttcaca atctcccggg acaactccaa gaacaccctc 300
tatttacaga tgaactcttt aagggccgag gataccgctg tgtactactg tgcccggcac 360
ggcgacaatt gggctttaga tctgtggggc caaggtacac tggtgacagt gagcagcgcg 420
tcgaccaagg gcccatccgt cttccccctg gcaccctcct ccaagagcac ctctgggggc 480
acagcggccc tgggctgcct ggtcaaggac tacttccccg aaccggtgac ggtgtcctgg 540
aactcaggcg ctctgaccag cggcgtgcac accttcccgg ctgtcctaca gtcctcagga 600
ctctactccc tcagcagcgt ggtgaccgtg ccctccagca gcttgggcac ccagacctac 660
atctgcaacg tgaatcacaa gcccagcaac accaaggtgg acaagagagt tgagcccaaa 720
tcttgtgaca aaactcacac atgcccaccg tgcccagcac ctgaagccgc cgggggaccg 780
tcagtcttcc tcttcccccc aaaacccaag gacaccctca tgatctcccg gacccctgag 840
gtcacatgcg tggtggtgga cgtgagccac gaagaccctg aggtcaagtt caactggtac 900
gtggacggcg tggaggtgca taatgccaag acaaagccgc gggaggagca gtacaacagc 960
acgtaccgtg tggtcagcgt cctcaccgtc ctgcaccagg actggctgaa tggcaaggag 1020
tacaagtgca aggtctccaa caaagccctc ccagccccca tcgagaaaac catctccaaa 1080
gccaaagggc agccccgaga accacaggtc tgcaccctgc ccccatcccg ggaggagatg 1140
accaagaacc aggtcagcct gagctgcgcg gtcaaaggct tctatcccag cgacatcgcc 1200
gtggagtggg agagcaatgg gcagccggag aacaactaca agaccacgcc tcccgtgctg 1260
gactccgacg gctccttctt cctcgttagc aagctcaccg tggacaagag caggtggcag 1320
caggggaacg tcttctcatg ctccgtgatg catgaggctc tgcacaacca ctacacgcag 1380
aagagcttaa gcctgtctcc gggttaatag 1410

<210> SEQ ID NO 112
<211> LENGTH: 2046
<212> TYPE: DNA

<213> ORGANISM: Artificial Sequence
<220> FEATURE:
<223> OTHER INFORMATION: Synthetic

<400> SEQUENCE: 112
gaggtgcagc tcgtcgagtc cggaggaggt ttagtccaac ccggtggatc tttaaggctg 60
tcttgtgctg cttccggctt ttctttatcc tccagctact ggatctcttg ggtgcggcaa 120
gctcccggaa agggactcga gtggatcggc tccatcgatt ccggatccgt gggcattacc 180
tactacgcca catgggtgaa aggtcgtttc acaatctccc gggacaactc caagaacacc 240
ctctatttac agatgaactc tttaagggcc gaggataccg ctgtgtacta ctgtgcccgg 300
cacggcgaca attgggcttt agatctgtgg ggccaaggta cactggtgac agtgagcagc 360
gcgtcgacca agggcccatc cgtcttcccc ctggcaccct cctccaagag cacctctggg 420
ggcacagcgg ccctgggctg cctggtcaag gactacttcc ccgaaccggt gacggtgtcc 480
tggaactcag gcgctctgac cagcggcgtg cacaccttcc cggctgtcct acagtcctca 540
ggactctact ccctcagcag cgtggtgacc gtgccctcca gcagcttggg cacccagacc 600
tacatctgca acgtgaatca caagcccagc aacaccaagg tggacaagag agttgagccc 660
aaatcttgtg gtggaggtgg cagtggaggc ggaggatctg aggtgcagct cgtcgagtcc 720
ggaggaggtt tagtccaacc cggtggatct ttaaggctgt cttgtgctgc ttccggcttt 780
tctttatcct ccagctactg gatctcttgg gtgcggcaag ctcccggaaa gggactcgag 840
tggatcggct ccatcgattc cggatccgtg ggcattacct actacgccac atgggtgaaa 900
ggtcgtttca caatctcccg ggacaactcc aagaacaccc tctatttaca gatgaactct 960
ttaagggccg aggataccgc tgtgtactac tgtgcccggc acggcgacaa ttgggcttta 1020
gatctgtggg gccaaggtac actggtgaca gtgagcagcg cgtcgaccaa gggcccatcc 1080
gtcttccccc tggcaccctc ctccaagagc acctctgggg gcacagcggc cctgggctgc 1140
ctggtcaagg actacttccc cgaaccggtg acggtgtcct ggaactcagg cgctctgacc 1200
agcggcgtgc acaccttccc ggctgtccta cagtcctcag gactctactc cctcagcagc 1260
gtggtgaccg tgccctccag cagcttgggc acccagacct acatctgcaa cgtgaatcac 1320
aagcccagca acaccaaggt ggacaagaga gttgagccca aatcttgtga caaaactcac 1380
acatgcccac cgtgcccagc acctgaagcc gccgggggac cgtcagtctt cctcttcccc 1440
ccaaaaccca aggacaccct catgatctcc cggacccctg aggtcacatg cgtggtggtg 1500
gacgtgagcc acgaagaccc tgaggtcaag ttcaactggt acgtggacgg cgtggaggtg 1560
cataatgcca agacaaagcc gcgggaggag cagtacaaca gcacgtaccg tgtggtcagc 1620
gtcctcaccg tcctgcacca ggactggctg aatggcaagg agtacaagtg caaggtctcc 1680
aacaaagccc tcccagcccc catcgagaaa accatctcca aagccaaagg gcagccccga 1740
gaaccacagg tctgcaccct gcccccatcc cgggaggaga tgaccaagaa ccaggtcagc 1800
ctgagctgcg cggtcaaagg cttctatccc agcgacatcg ccgtggagtg ggagagcaat 1860
gggcagccgg agaacaacta caagaccacg cctcccgtgc tggactccga cggctccttc 1920
ttcctcgtta gcaagctcac cgtggacaag agcaggtggc agcaggggaa cgtcttctca 1980
tgctccgtga tgcatgaggc tctgcacaac cactacacgc agaagagctt aagcctgtct 2040
ccgggt 2046

<210> SEQ ID NO 113
<211> LENGTH: 1488

<212> TYPE: DNA
<213> ORGANISM: Artificial Sequence
<220> FEATURE:
<223> OTHER INFORMATION: Synthetic

<400> SEQUENCE: 113
atggagtttg ggctgagctg gctttttctt gtcgcgattc ttaagggtgt acagtgtgag 60
gtgcagctcg tcgagtccgg aggaggttta gtccaacccg gtggatcttt aaggctgtct 120
tgtgctgctt ccggcttttc tttatcctcc agctactgga tctcttgggt gcggcaagct 180
cccggaaagg gactcgagtg gatcggctcc atcgattccg gatccgtggg cattacctac 240
tacgccacat gggtgaaagg tcgtttcaca atctcccggg acaactccaa gaacaccctc 300
tatttacaga tgaactcttt aagggccgag gataccgctg tgtactactg tgcccggcac 360
ggcgacaatt gggctttaga tctgtggggc caaggtacac tggtgacagt gctggaggac 420
ctgaagaacg tgttccctcc cgaggtggcc gtgttcgaac ccagcgaggc cgagatcagc 480
cacacccaga aggccaccct ggtgtgtctg gccaccggct tctaccccga ccacgtggag 540
ctgagctggt gggtgaacgg caaggaggtg cacagcggcg tgtgtaccga ccctcagccc 600
ctgaaggagc agcccgccct gcaggacagc aggtacgccc tgagcagcag gctgagagtg 660
agcgccacct tctggcagaa ccccaggaac cacttcaggt gccaggtgca gttctacggc 720
ctgagcgaga acgacgagtg gacccaggac agggccaagc ccgtgaccca gatcgtgagc 780
gctgaggcct ggggcagagc ctctgacaaa actcacacat gcccaccgtg cccagcacct 840
gaagccgccg gggggaccgtc agtcttcctc ttccccccaa aacccaagga caccctcatg 900
atctcccgga cccctgaggt cacatgcgtg gtggtggacg tgagccacga agaccctgag 960
gtcaagttca actggtacgt ggacggcgtg gaggtgcata atgccaagac aaagccgcgg 1020
gaggagcagt acaacagcac gtaccgtgtg gtcagcgtcc tcaccgtcct gcaccaggac 1080
tggctgaatg gcaaggagta caagtgcaag gtctccaaca aagccctccc agcccccatc 1140
gagaaaacca tctccaaagc caaagggcag ccccgagaac cacaggtctg caccctgccc 1200
ccatcccggg aggagatgac caagaaccag gtcagcctga gctgcgcggt caaaggcttc 1260
tatcccagcg acatcgccgt ggagtgggag agcaatgggc agccggagaa caactacaag 1320
accacgcctc ccgtgctgga ctccgacggc tccttcttcc tcgttagcaa gctcaccgtg 1380
gacaagagca ggtggcagca ggggaacgtc ttctcatgct ccgtgatgca tgaggctctg 1440
cacaaccact acacgcagaa gagcttaagc ctgtctccgg gttaatag 1488

<210> SEQ ID NO 114
<211> LENGTH: 2196
<212> TYPE: DNA
<213> ORGANISM: Artificial Sequence
<220> FEATURE:
<223> OTHER INFORMATION: Synthetic

<400> SEQUENCE: 114
gaggtgcagc tcgtcgagtc cggaggaggt ttagtccaac ccggtggatc tttaaggctg 60
tcttgtgctg cttccggctt ttctttatcc tccagctact ggatctcttg ggtgcggcaa 120
gctcccggaa agggactcga gtggatcggc tccatcgatt ccggatccgt gggcattacc 180
tactacgcca catgggtgaa aggtcgtttc acaatctccc gggacaactc caagaacacc 240
ctctatttac agatgaactc tttaagggcc gaggataccg ctgtgtacta ctgtgcccgg 300
cacggcgaca attgggcttt agatctgtgg ggccaaggta cactggtgac agtgctggag 360
gacctgaaga acgtgttccc tcccgaggtg gccgtgttcg aacccagcga ggccgagatc 420
agccacaccc agaaggccac cctggtgtgt ctggccaccg gcttctaccc cgaccacgtg 480
gagctgagct ggtgggtgaa cggcaaggag gtgcacagcg gcgtgtgtac cgaccctcag 540
cccctgaagg agcagcccgc cctgcaggac agcaggtacg ccctgagcag caggctgaga 600
gtgagcgcca ccttctggca gaaccccagg aaccacttca ggtgccaggt gcagttctac 660
ggcctgagcg agaacgacga gtggacccag gacagggcca agcccgtgac ccagatcgtg 720
agcgctgagg cctggggcag aggtggaggt ggcagtggag gcggaggatc tgaggtgcag 780
ctcgtcgagt ccggaggagg tttagtccaa cccggtggat ctttaaggct gtcttgtgct 840
gcttccggct tttctttatc ctccagctac tggatctctt gggtgcggca agctcccgga 900
aagggactcg agtggatcgg ctccatcgat tccggatccg tgggcattac ctactacgcc 960
acatgggtga aaggtcgttt cacaatctcc cgggacaact ccaagaacac cctctattta 1020
cagatgaact ctttaagggc cgaggatacc gctgtgtact actgtgcccg gcacggcgac 1080
aattgggctt tagatctgtg gggccaaggt acactggtga cagtgctgga ggacctgaag 1140
aacgtgttcc ctcccgaggt ggccgtgttc gaacccagcg aggccgagat cagccacacc 1200
cagaaggcca ccctggtgtg tctggccacc ggcttctacc ccgaccacgt ggagctgagc 1260
tggtgggtga acggcaagga ggtgcacagc ggcgtgtgta ccgaccctca gcccctgaag 1320
gagcagcccg ccctgcagga cagcaggtac gccctgagca gcaggctgag agtgagcgcc 1380
accttctggc agaaccccag gaaccacttc aggtgccagg tgcagttcta cggcctgagc 1440
gagaacgacg agtggaccca ggacagggcc aagcccgtga cccagatcgt gagcgctgag 1500
gcctggggca gagcctctga caaaactcac acatgcccac cgtgcccagc acctgaactc 1560
ctggggggac cgtcagtctt cctcttcccc ccaaaaccca aggacaccct catgatctcc 1620
cggacccctg aggtcacatg cgtggtggtg gacgtgagcc acgaagaccc tgaggtcaag 1680
ttcaactggt acgtggacgg cgtggaggtg cataatgcca agacaaagcc gcgggaggag 1740
cagtacaaca gcacgtaccg tgtggtcagc gtcctcaccg tcctgcacca ggactggctg 1800
aatggcaagg agtacaagtg caaggtctcc aacaaagccc tcccagcccc catcgagaaa 1860
accatctcca aagccaaagg gcagccccga gaaccacagg tctgcaccct gcccccatcc 1920
cgggaggaga tgaccaagaa ccaggtcagc ctgagctgcg cggtcaaagg cttctatccc 1980
agcgacatcg ccgtggagtg ggagagcaat gggcagccgg agaacaacta caagaccacg 2040
cctcccgtgc tggactccga cggctccttc ttcctcgtta gcaagctcac cgtggacaag 2100
agcaggtggc agcaggggaa cgtcttctca tgctccgtga tgcatgaggc tctgcacaac 2160
cactacacgc agaagagctt aagcctgtct ccgggt 2196

<210> SEQ ID NO 115
<211> LENGTH: 2178
<212> TYPE: DNA
<213> ORGANISM: Artificial Sequence
<220> FEATURE:
<223> OTHER INFORMATION: Synthetic

<400> SEQUENCE: 115
atggagtttg ggctgagctg gctttttctt gtcgcgattc ttaagggtgt acagtgtgag 60
gtgcagctcg tcgagtccgg aggaggttta gtccaacccg gtggatcttt aaggctgtct 120
tgtgctgctt ccggcttttc tttatcctcc agctactgga tctcttgggt gcggcaagct 180
cccggaaagg gactcgagtg gatcggctcc atcgattccg gatccgtggg cattacctac 240

```
tacgccacat gggtgaaagg tcgtttcaca atctcccggg acaactccaa gaacaccctc    300
tatttacaga tgaactcttt aagggccgag gataccgctg tgtactactg tgcccggcac    360
ggcgacaatt gggctttaga tctgtggggc caaggtacac tggtgacagt gctggaggac    420
ctgaagaacg tgttccctcc cgaggtggcc gtgttcgaac ccagcgaggc cgagatcagc    480
cacacccaga aggccaccct ggtgtgtctg gccaccggct tctaccccga ccacgtggag    540
ctgagctggt gggtgaacgg caaggaggtg cacagcggcg tgtgtaccga ccctcagccc    600
ctgaaggagc agcccgccct gcaggacagc aggtacgccc tgagcagcag gctgagagtg    660
agcgccacct tctggcagaa ccccaggaac cacttcaggt gccaggtgca gttctacggc    720
ctgagcgaga acgacgagtg gacccaggac agggccaagc ccgtgaccca gatcgtgagc    780
gcggaggcct ggggcagagg tggaggtggc agtggaggcg gaggatctca ggtgcagctt    840
gtgcagtctg gggcagaagt gaagaagcct gggtctagtg tcaaggtgtc atgcaaggct    900
agcgggttcg cctttactga ctactacatc cactgggtgc ggcaggctcc cggacaaggg    960
ttggagtgga tgggatggat ctccccaggc aatgtcaaca caaagtacaa cgagaacttc   1020
aaaggccgcg tcaccattac cgccgacaag agcacctcca cagcctacat ggagctgtcc   1080
agcctcagaa gcgaggacac tgccgtctac tactgtgcca gggatgggta ctccctgtat   1140
tactttgatt actggggcca gggcacactg gtgacagtga gctccgcgtc gaccaagggc   1200
ccatccgtct tcccccctggc accctcctcc aagagcacct ctgggggcac agcggccctg   1260
ggctgcctgg tcaaggacta cttccccgaa ccggtgacgg tgtcctggaa ctcaggcgct   1320
ctgaccagcg gcgtgcacac cttcccggct gtcctacagt cctcaggact ctactccctc   1380
agcagcgtgg tgaccgtgcc ctccagcagc ttgggcaccc agacctacat ctgcaacgtg   1440
aatcacaagc ccagcaacac caaggtggac aagagagttg agcccaaatc ttgtgacaaa   1500
actcacacat gcccaccgtg cccagcacct gaagccgccg gggggaccgtc agtcttcctc   1560
ttccccccaa aacccaagga caccctcatg atctcccgga cccctgaggt cacatgcgtg   1620
gtggtggacg tgagccacga agaccctgag gtcaagttca actggtacgt ggacggcgtg   1680
gaggtgcata atgccaagac aaagccgcgg gaggagcagt acaacagcac gtaccgtgtg   1740
gtcagcgtcc tcaccgtcct gcaccaggac tggctgaatg gcaaggagta caagtgcaag   1800
gtctccaaca aagccctccc agcccccatc gagaaaacca tctccaaagc caaagggcag   1860
ccccgagaac cacaggtcta caccctgccc ccatgccggg aggagatgac caagaaccag   1920
gtcagcctgt ggtgcctggt caaaggcttc tatcccagcg acatcgccgt ggagtgggag   1980
agcaatgggc agccggagaa caactacaag accacgcctc ccgtgctgga ctccgacggc   2040
tccttcttcc tctatagcaa gctcaccgtg gacaagagca ggtggcagca ggggaacgtc   2100
ttctcatgct ccgtgatgca tgaggctctg cacaaccact acacgcagaa gagcttaagc   2160
ctgtctccgg gttaatag                                                 2178
```

<210> SEQ ID NO 116
<211> LENGTH: 2121
<212> TYPE: DNA
<213> ORGANISM: Artificial Sequence
<220> FEATURE:
<223> OTHER INFORMATION: Synthetic

<400> SEQUENCE: 116

```
gaggtgcagc tcgtcgagtc cggaggaggt ttagtccaac ccggtggatc tttaaggctg     60
```

-continued

```
tcttgtgctg cttccggctt ttctttatcc tccagctact ggatctcttg ggtgcggcaa    120

gctcccggaa agggactcga gtggatcggc tccatcgatt ccggatccgt gggcattacc    180

tactacgcca catgggtgaa aggtcgtttc acaatctccc gggacaactc caagaacacc    240

ctctatttac agatgaactc tttaagggcc gaggataccg ctgtgtacta ctgtgcccgg    300

cacggcgaca attgggcttt agatctgtgg ggccaaggta cactggtgac agtgagcagc    360

gcgtcgacca agggcccatc cgtcttcccc ctggcaccct cctccaagag cacctctggg    420

ggcacagcgg ccctgggctg cctggtcaag gactacttcc ccgaaccggt gacggtgtcc    480

tggaactcag gcgctctgac cagcggcgtg cacaccttcc cggctgtcct acagtcctca    540

ggactctact ccctcagcag cgtggtgacc gtgccctcca gcagcttggg cacccagacc    600

tacatctgca acgtgaatca caagcccagc aacaccaagg tggacaagag agttgagccc    660

aaatcttgtg gtggaggtgg cagtggaggc ggaggatctc aggtgcagct tgtgcagtct    720

ggggcagaag tgaagaagcc tgggtctagt gtcaaggtgt catgcaaggc tagcgggttc    780

gcctttactg actactacat ccactgggtg cggcaggctc ccggacaagg gttggagtgg    840

atgggatgga tctccccagg caatgtcaac acaaagtaca acgagaactt caaaggccgc    900

gtcaccatta ccgccgacaa gagcacctcc acagcctaca tggagctgtc cagcctcaga    960

agcgaggaca ctgccgtcta ctactgtgcc agggatgggt actccctgta ttactttgat   1020

tactggggcc agggcacact ggtgacagtg ctggaggacc tgaagaacgt gttccctccc   1080

gaggtggccg tgttcgaacc cagcgaggcc gagatcagcc acacccagaa ggccaccctg   1140

gtgtgtctgg ccaccggctt ctaccccgac cacgtggagc tgagctggtg ggtgaacggc   1200

aaggaggtgc acagcggcgt gtgtaccgac cctcagcccc tgaaggagca gcccgccctg   1260

caggacagca ggtacgccct gagcagcagg ctgagagtga gcgccacctt ctggcagaac   1320

cccaggaacc acttcaggtg ccaggtgcag ttctacggcc tgagcgagaa cgacgagtgg   1380

acccaggaca gggccaagcc cgtgacccag atcgtgagcg ctgaggcctg gggcagagcc   1440

tctgacaaaa ctcacacatg cccaccgtgt ccagcacctg aagccgccgg gggaccgtca   1500

gtcttcctct tccccccaaa acccaaggac accctcatga tctcccggac ccctgaggtc   1560

acatgcgtgg tggtggacgt gagccacgaa gaccctgagg tcaagttcaa ctggtacgtg   1620

gacggcgtgg aggtgcataa tgccaagaca aagccgcggg aggagcagta caacagcacg   1680

taccgtgtgg tcagcgtcct caccgtcctg caccaggact ggctgaatgg caaggagtac   1740

aagtgcaagg tctccaacaa agccctccca gcccccatcg agaaaaccat ctccaaagcc   1800

aaagggcagc cccgagaacc acaggtctac accctgcccc catgccggga ggagatgacc   1860

aagaaccagg tcagcctgtg gtgcctggtc aaaggcttct atcccagcga catcgccgtg   1920

gagtgggaga gcaatgggca gccggagaac aactacaaga ccacgcctcc cgtgctggac   1980

tccgacggct ccttcttcct ctatagcaag ctcaccgtgg acaagagcag gtggcagcag   2040

gggaacgtct tctcatgctc cgtgatgcat gaggctctgc acaaccacta cacgcagaag   2100

agcttaagcc tgtctccggg t                                             2121
```

<210> SEQ ID NO 117
<211> LENGTH: 729
<212> TYPE: DNA
<213> ORGANISM: Artificial Sequence
<220> FEATURE:
<223> OTHER INFORMATION: Synthetic

<400> SEQUENCE: 117
atggacatgc gcgtgcccgc ccagctgctg ggcctgctgc tgctgtggtt ccccggatcc 60
cgatgcgata tcgtgatgac ccagagccca gactcccttg ctgtctccct cggcgaaaga 120
gcaaccatca actgcaagag ctcccaaagc ctgctgaact ccaggaccag gaagaattac 180
ctggcctggt atcagcagaa gcccggccag cctcctaagc tgctcatcta ctgggcctcc 240
acccggcagt ctggggtgcc cgatcggttt agtggatctg ggagcgggac agacttcaca 300
ttgacaatta gctcactgca ggccgaggac gtggccgtct actactgtac tcagagccac 360
actctccgca cattcggcgg agggactaaa gtggagatta agcgtacggt ggctgcacca 420
tctgtcttca tcttcccgcc atctgatgag cagttgaaat ctggaactgc ctctgttgtg 480
tgcctgctga ataacttcta tcccagagag gccaaagtac agtggaaggt ggataacgcc 540
ctccaatcgg gtaactccca ggagagtgtc acagagcagg acagcaagga cagcacctac 600
agcctcagca gcaccctgac gctgagcaaa gcagactacg agaaacacaa agtctacgcc 660
tgcgaagtca cccatcaggg cctgagctcg cccgtcacaa agagcttcaa caggggagag 720
tgttaatag 729

<210> SEQ ID NO 118
<211> LENGTH: 621
<212> TYPE: DNA
<213> ORGANISM: Artificial Sequence
<220> FEATURE:
<223> OTHER INFORMATION: Synthetic

<400> SEQUENCE: 118
gatatcgtga tgacccagag cccagactcc cttgctgtct ccctcggcga aagagcaacc 60
atcaactgca agagctccca aagcctgctg aactccagga ccaggaagaa ttacctggcc 120
tggtatcagc agaagcccgg ccagcctcct aagctgctca tctactgggc ctccacccgg 180
cagtctgggg tgcccgatcg gtttagtgga tctgggagcg ggacagactt cacattgaca 240
attagctcac tgcaggccga ggacgtggcc gtctactact gtactcagag ccacactctc 300
cgcacattcg gcggagggac taaagtggag attaagcccg acatccagaa ccccgacccc 360
gccgtgtacc agctgagaga cagcaagagc agcgacaaga gcgtgtgcct gttcaccgac 420
ttcgacagcc agacccaggt gagccagagc aaggactccg acgtgtatat caccgacaag 480
tgcgtgctgg acatgaggag catggacttc aagagcaaca gcgccgtggc ctggagccag 540
aagagcgact tcgcctgcgc caacgccttc cagaacagca tcatccccga ggacaccttc 600
ttccccagcc ccgagagcag c 621

<210> SEQ ID NO 119
<211> LENGTH: 693
<212> TYPE: DNA
<213> ORGANISM: Artificial Sequence
<220> FEATURE:
<223> OTHER INFORMATION: Synthetic

<400> SEQUENCE: 119
atggacatgc gcgtgcccgc ccagctgctg ggcctgctgc tgctgtggtt ccccggatcc 60
cgatgcgata tcgtgatgac ccagagccca gactcccttg ctgtctccct cggcgaaaga 120
gcaaccatca actgcaagag ctcccaaagc ctgctgaact ccaggaccag gaagaattac 180
ctggcctggt atcagcagaa gcccggccag cctcctaagc tgctcatcta ctgggcctcc 240
acccggcagt ctggggtgcc cgatcggttt agtggatctg ggagcgggac agacttcaca 300

-continued ttgacaatta gctcactgca ggccgaggac gtggccgtct actactgtac tcagagccac 360
actctccgca cattcggcgg agggactaaa gtggagatta agcccgacat ccagaacccc 420
gaccccgccg tgtaccagct gagagacagc aagagcagcg acaagagcgt gtgcctgttc 480
accgacttcg acagccagac ccaggtgagc cagagcaagg actccgacgt gtatatcacc 540
gacaagtgcg tgctggacat gaggagcatg gacttcaaga gcaacagcgc cgtggcctgg 600
agccagaaga gcgacttcgc ctgcgccaac gccttccaga acagcatcat ccccgaggac 660
accttcttcc ccgcccccga gagcagctaa tag 693

<210> SEQ ID NO 120
<211> LENGTH: 723
<212> TYPE: DNA
<213> ORGANISM: Artificial Sequence
<220> FEATURE:
<223> OTHER INFORMATION: Synthetic

<400> SEQUENCE: 120
atggacatgc gcgtgcccgc ccagctgctg ggcctgctgc tgctgtggtt ccccggatcc 60
cgatgcgaca tccagatgac ccagtcccct agcacactgt ccgccagcgt gggcgatcgt 120
gtgaccatca cttgtcgggc ttcccagagc atcagcagct ggctggcttg gtatcagcag 180
aagcccggca aggcccccaa gctgctgatc tacaaggctt ccactttagc tagcggcgtg 240
ccttctcgtt tctccggatc cggatccggc accgagttca ctttaaccat cagctcttta 300
cagcccgacg acttcgccac atactactgc cagcacggct acatccgggg cgatttagac 360
aatgtgttcg gcggcggcac caaggtcgag atcaagcgta cggtggctgc accatctgtc 420
ttcatcttcc cgccatctga tgagcagttg aaatctggaa ctgcctctgt tgtgtgcctg 480
ctgaataact tctatcccag agaggccaaa gtacagtgga aggtggataa cgccctccaa 540
tcgggtaact cccaggagag tgtcacagag caggacagca aggacagcac ctacagcctc 600
agcagcaccc tgacgctgag caaagcagac tacgagaaac acaaagtcta cgcctgcgaa 660
gtcacccatc agggcctgag ctcgcccgtc acaaagagct tcaacagggg agagtgttaa 720
tag 723

<210> SEQ ID NO 121
<211> LENGTH: 615
<212> TYPE: DNA
<213> ORGANISM: Artificial Sequence
<220> FEATURE:
<223> OTHER INFORMATION: Synthetic

<400> SEQUENCE: 121
gacatccaga tgacccagtc ccctagcaca ctgtccgcca gcgtgggcga tcgtgtgacc 60
atcacttgtc gggcttccca gagcatcagc agctggctgg cttggtatca gcagaagccc 120
ggcaaggccc ccaagctgct gatctacaag gcttccactt tagctagcgg cgtgccttct 180
cgtttctccg gatccggatc cggcaccgag ttcactttaa ccatcagctc tttacagccc 240
gacgacttcg ccacatacta ctgccagcac ggctacatcc ggggcgattt agacaatgtg 300
ttcggcggcg gcaccaaggt cgagatcaag cccgacatcc agaaccccga ccccgccgtg 360
taccagctga gagacagcaa gagcagcgac aagagcgtgt gcctgttcac cgacttcgac 420
agccagaccc aggtgagcca gagcaaggac tccgacgtgt atatcaccga caagtgcgtg 480
ctggacatga ggagcatgga cttcaagagc aacagcgccg tggcctggag ccagaagagc 540
gacttcgcct gcgccaacgc cttccagaac agcatcatcc ccgaggacac cttcttcccc 600
agccccgaga gcagc 615

<210> SEQ ID NO 122
<211> LENGTH: 687
<212> TYPE: DNA
<213> ORGANISM: Artificial Sequence
<220> FEATURE:
<223> OTHER INFORMATION: Synthetic

<400> SEQUENCE: 122
atggacatgc gcgtgcccgc ccagctgctg ggcctgctgc tgctgtggtt ccccggatcc 60
cgatgcgaca tccagatgac ccagtcccct agcacactgt ccgccagcgt gggcgatcgt 120
gtgaccatca cttgtcgggc ttcccagagc atcagcagct ggctggcttg gtatcagcag 180
aagcccggca aggcccccaa gctgctgatc tacaaggctt ccactttagc tagcggcgtg 240
ccttctcgtt tctccggatc cggatccggc accgagttca ctttaaccat cagctcttta 300
cagcccgacg acttcgccac atactactgc cagcacggct acatccgggg cgatttagac 360
aatgtgttcg gcggcggcac caaggtcgag atcaagcccg acatccagaa ccccgacccc 420
gccgtgtacc agctgagaga cagcaagagc agcgacaaga gcgtgtgcct gttcaccgac 480
ttcgacagcc agacccaggt gagccagagc aaggactccg acgtgtatat caccgacaag 540
tgcgtgctgg acatgaggag catggacttc aagagcaaca gcgccgtggc ctggagccag 600
aagagcgact tcgcctgcgc caacgccttc cagaacagca tcatccccga ggacaccttc 660
ttccccgccc ccgagagcag ctaatag 687

<210> SEQ ID NO 123
<211> LENGTH: 1410
<212> TYPE: DNA
<213> ORGANISM: Artificial Sequence
<220> FEATURE:
<223> OTHER INFORMATION: Synthetic

<400> SEQUENCE: 123
atggagtttg ggctgagctg gctttttctt gtcgcgattc ttaagggtgt acagtgtgag 60
gtgcagctcg tcgagtccgg aggaggttta gtccaacccg gtggatcttt aaggctgtct 120
tgtgctgctt ccggcttttc tttatcctcc agctactgga tctcttgggt gcggcaagct 180
cccggaaagg gactcgagtg gatcggctcc atcgattccg gatccgtggg cattacctac 240
tacgccacat gggtgaaagg tcgtttcaca atctcccggg acaactccaa gaacaccctc 300
tatttacaga tgaactcttt aagggccgag gataccgctg tgtactactg tgcccggcac 360
ggcgacaatt gggctttaga tctgtggggc caaggtacac tggtgacagt gagcagcgct 420
agcaccaagg gcccatcggt cttcccccctg gcaccctcct ccaagagcac ctctgggggc 480
acagcggccc tgggctgcct ggtcaaggac tacttccccg aaccggtgac ggtgtcgtgg 540
aactcaggcg ccctgaccag cggcgtgcac accttcccgg ccgtcctaca gtcctcagga 600
ctctactccc tcagcagcgt ggtgaccgtg ccctccagca gcttgggcac ccagacctac 660
atctgcaacg tgaatcacaa gcccagcaac accaaggtgg acaagcgggt tgagcccaaa 720
tcttgtgaca aaactcacac atgcccaccg tgcccagcac ctgaagccgc agggggaccg 780
tcagtcttcc tcttcccccc aaaacccaag gacaccctca tgatctcccg gacccctgag 840
gtcacatgcg tggtggtgga cgtgagccac gaagaccctg aggtcaagtt caactggtac 900
gtggacggcg tggaggtgca taatgccaag acaaagccgc gggaggagca gtacaacagc 960

-continued

```
acgtaccgtg tggtcagcgt cctcaccgtc ctgcaccagg actggctgaa tggcaaggag   1020

tacaagtgca aggtctccaa caaagccctc ccagccccca tcgagaaaac catctccaaa   1080

gccaaagggc agccccgaga accacaggtg tacaccctgc ccccatcccg ggaggagatg   1140

accaagaacc aggtcagcct gacctgcctg gtcaaaggct tctatcccag cgacatcgcc   1200

gtggagtggg agagcaatgg gcagccggag aacaactaca agaccacgcc tcccgtgctg   1260

gactccgacg gctccttctt cctctacagc aagctcaccg tggacaagag caggtggcag   1320

caggggaacg tcttctcatg ctccgtgatg catgaggctc tgcacaacca ctacacgcag   1380

aagagcctct ccctgtctcc gggttgatga                                    1410


<210> SEQ ID NO 124
<211> LENGTH: 756
<212> TYPE: DNA
<213> ORGANISM: Artificial Sequence
<220> FEATURE:
<223> OTHER INFORMATION: Synthetic

<400> SEQUENCE: 124

atggtgctcg ccgcccctct cctgctcgga tttctcctgc tggctctcga actgagaccc     60

aggggagagg ccgacaaaac tcacacatgc ccaccgtgcc cagcacctga agccgccggg    120

ggaccgtcag tcttcctctt ccccccaaaa cccaaggaca ccctcatgat ctcccggacc    180

cctgaggtca catgcgtggt ggtggacgtg agccacgaag accctgaggt caagttcaac    240

tggtacgtgg acggcgtgga ggtgcataat gccaagacaa agccgcggga ggagcagtac    300

aacagcacgt accgtgtggt cagcgtcctc accgtcctgc accaggactg gctgaatggc    360

aaggagtaca agtgcaaggt ctccaacaaa gccctcccag cccccatcga gaaaaccatc    420

tccaaagcca aagggcagcc ccgagaacca caggtctgca ccctgccccc atcccgggag    480

gagatgacca agaaccaggt cagcctgagc tgcgcggtca aaggcttcta tcccagcgac    540

atcgccgtgg agtgggagag caatgggcag ccggagaaca actacaagac cacgcctccc    600

gtgctggact ccgacggctc cttcttcctc gttagcaagc tcaccgtgga caagagcagg    660

tggcagcagg ggaacgtctt ctcatgctcc gtgatgcatg aggctctgca caaccactac    720

acgcagaaga gcttaagcct gtctccgggt taatag                              756
```

ANTI-LILRB4 ANTIBODIES AND DERIVATIVE PRODUCTS

CROSS-REFERENCE TO RELATED APPLICATIONS

This application claims priority to U.S. provisional patent application No. 62/988,892, filed Mar. 12, 2020, the disclosure of which is incorporated herein by reference.

SEQUENCE LISTING

The sequence listing that is contained in the file named "066564-8013W001_ST25", which is 150,794 bytes (as measured in Microsoft Windows) and was created on Mar. 12, 2021, is filed herewith by electronic submission and is incorporated by reference herein.

FIELD OF THE INVENTION

The present disclosure relates generally to the fields of medicine, oncology, and immunology. More particular, the disclosure relates to antibodies that bind to LILRB4.

BACKGROUND

Human Leukocyte Immunoglobulin-Like Receptor subfamily B member 4 (LILRB4), also known as Immunoglobulin-like transcript 3 (ILT3 or ILT-3), Leukocyte Immunoglobulin-like Receptor 5 (LIR5 or LIR-5), and CD85k or CD85K, is a type I membrane protein that contains cytoplasmic immunoreceptor tyrosine-based inhibition motif (ITIM) and involves in negative regulation of immune cell activation. LILRB4 is expressed on monocytes, macrophages and dendritic cells and can inhibit innate immunity in a cell-autonomous manner as well as suppress T cell activation through an indirect mechanism. LILRB4 is a specific marker for monocytic acute myeloid leukemia (AML) including refractory and relapsed disease. It has been shown that LILRB4 supports tumor cell infiltration into tissues and suppresses T cell activity via a signaling pathway that involves APOE, LILRB4, SHP-2, uPAR and ARG1 in AML cells (Deng M. et al., Nature (2018) 562:605-09). There is a significant need for novel anti-LILRB4 antibodies.

BRIEF SUMMARY OF THE INVENTION

The present disclosure provides anti-LILRB4 antibodies and antigen-binding fragment thereof, amino acid and nucleotide sequences thereof, anti-LILRB4 chimeric antigen receptors, and uses thereof.

In one aspect, the present disclosure provides an isolated anti-LILRB4 antibody or an antigen-binding fragment thereof. In some embodiments, the anti-LILRB4 antibody or an antigen-binding fragment comprises: (a) a heavy chain variable region comprising a heavy chain complementarity determining region (HC-CDR) 1 having an amino acid sequence of SEQ ID NO: 5, an HC-CDR2 having an amino acid sequence of SEQ ID NO: 6 and an HC-CDR3 having an amino acid sequence of SEQ ID NO: 7; and (b) a light chain variable region comprising a light chain complementarity determining region (LC-CDR) 1 having an amino acid sequence of SEQ ID NO: 8 with a mutation at amino acid residues NS, an LC-CDR2 having an amino acid sequence of SEQ ID NO: 9 and an LC-CDR3 having an amino acid sequence of SEQ ID NO: 10.

In certain embodiments, the LC-CDR1 has an amino acid sequence of SEQ ID NO: 28.

In certain embodiments, the heavy chain variable region has an amino acid sequence at least about 90% identical to SEQ ID NO: 1; and wherein the light chain variable region has an amino acid sequence at least about 90% identical to SEQ ID NO: 27.

In certain embodiments, the heavy chain variable region has an amino acid sequence of SEQ ID NO: 1; and wherein the light chain variable region has an amino acid sequence of SEQ ID NO: 27.

In certain embodiments, the antibody or the antigen-binding fragment further comprises an immunoglobulin constant region, optionally a constant region of Ig, or optionally a constant region of human IgG.

In certain embodiments, the antibody described herein is of the IgG1, IgG2, IgG3 or IgG4 isotype.

In certain embodiments, the antibody or the antigen-binding fragment is humanized.

In certain embodiments, the antigen-binding fragment is a camelized single domain antibody, a diabody, a ds (disulfide-stabilized) diabody or ds diabody, a scFv, a scFv dimer, a BsFv, a dsFv, a $(dsFv)_2$, a dsFv-dsFv', an Fv fragment, a Fab, a Fab', a $F(ab')_2$, a bispecific antibody, a nanobody, a domain antibody, or a bivalent antibody.

In certain embodiments, the anti-LILRB4 antibody described herein is a bispecific antibody. In some embodiments, the anti-LILRB4 bispecific antibody is against a T-cell receptor such as CD3. In some embodiments, the anti-LILRB4 bispecific antibody is against an NK-cell receptor such as CD16A.

Therefore, the present disclosure in another aspect provides a bispecific antibody or antigen-binding fragment capable of binding to LILRB4 and CD3.

In certain embodiments, the bispecific antibody or antigen-binding fragment provided herein comprises: (a) a first antigen-binding region comprising a first light chain variable ($V_L$) domain and a first heavy chain variable ($V_H$) domain; and (b) a second antigen-binding region comprising a second $V_L$ domain and a second $V_H$ domain, wherein the first antigen-binding region is capable of binding to LILRB4 and the second antigen-binding region is capable of binding to CD3, or vice versa.

In certain embodiments, the first $V_L$ domain and the first heavy chain variable domain link to a first pair of constant domains, respectively, and wherein the second $V_L$ domain and the second $V_H$ domain link to a second pair of constant domains, respectively.

In certain embodiments, the first $V_L$ domain links to a first light chain constant ($C_L$) domain, and the first $V_H$ domain links to a first heavy chain constant domain 1 ($C_H1$). In certain embodiments, the first $V_L$ domain links to a first $C_H1$ domain, and the $V_H$ domain links to a second $C_L$ domain.

In certain embodiments, the second $V_L$ domain links to a second $C_L$ domain, and the second $V_H$ domain links to a second $C_H1$ domain. In certain embodiments, the second $V_L$ domain links to a second $C_H1$ domain, and the second $V_H$ domain links to a second $C_L$ domain. In certain embodiments, the second $V_L$ domain links to a T cell receptor (TCR) $\alpha$ chain constant domain, and the second $V_H$ domain links to a TCR $\beta$ chain constant domain. In certain embodiments, the second $V_L$ domain links to a TCR $\beta$ chain constant domain, and the second $V_H$ domain links to a TCR $\alpha$ chain constant domain.

In certain embodiments, the first antigen-binding region and/or the second antigen-binding region is a single chain variable fragment (scFv).

In certain embodiments, the antibody or antigen-binding fragment provided herein further comprises a third antigen-binding region comprising a third $V_L$ domain and a third $V_H$ domain, wherein the third antigen-binding region is capable of binding to LILRB4 or CD3.

In certain embodiments, the third $V_L$ domain and the third heavy chain variable domain link to a first pair of constant domains, respectively. In certain embodiments, the third $V_L$ domain links to a third $C_L$ domain, and the third $V_H$ domain links to a third $C_H1$ domain. In certain embodiments, the third $V_L$ domain links to a third $C_H1$ domain, and the third $V_H$ domain links to a third $C_L$ domain. In certain embodiments, the third $V_L$ domain links to a second TCR α chain constant domain, and the third $V_H$ domain links to a second TCR β chain constant domain. In certain embodiments, the third $V_L$ domain links to a second TCR β chain constant domain, and the third $V_H$ domain links to a second TCR α chain constant domain.

In certain embodiments, the TCR α chain constant domain has an amino acid sequence of SEQ ID NO: 89. In certain embodiments, the TCR α chain constant domain has a S91A mutation of SEQ ID NO: 89.

In certain embodiments, the antibody or the antigen-binding fragment is linked to one or more conjugate moieties. In certain embodiments, the conjugate moiety comprises a clearance-modifying agent, a toxin, a detectable label, a chemotherapeutic agent, or purification moiety.

In another aspect, the present disclosure provides a pharmaceutical composition comprising the antibody or antigen-binding fragment thereof described herein, and a pharmaceutically acceptable carrier.

In another aspect, the present disclosure provides an isolated polynucleotide encoding the antibody or antigen-binding fragment thereof described herein.

In another aspect, the present disclosure provides a vector comprising the isolated polynucleotide described herein.

In another aspect, the present disclosure provides a host cell comprising the vector described herein. In certain embodiments, the host cell is a mammalian cell, e.g., a CHO cell.

In another aspect, the present disclosure provides a hybridoma encoding or producing the anti-LILRB4 antibody as provided herein.

In another aspect, the present disclosure provides a method of expressing the antibody or antigen-binding fragment thereof described herein. In some embodiments, the method comprises culturing the host cell described herein under the condition at which the vector described herein is expressed.

In another aspect, the present disclosure provides a method of treating or ameliorating the effect of a cancer in a subject. In some embodiments, the method comprises administering to the subject a therapeutically effective amount of the antibody or antigen-binding fragment thereof described herein or the pharmaceutical composition described herein.

The method may reduce or eradicate the tumor burden in the subject, may reduce the number of tumor cells, may reduce tumor size, may reduce tumor infiltration, may reduce tumor metastasis, may eradicate the tumor in the subject. The cancer may be a solid tumor or hematologic malignancy.

In certain embodiments, the cancer is adrenal cancer, bile duct carcinoma, bone cancer, brain cancer, breast cancer, cervical cancer, choriocarcinoma, colon cancer, colorectal cancer, esophageal cancer, eye cancer, gastric cancer, gastroesophageal cancer, glioblastoma, head and neck cancer, kidney cancer, liver cancer, lung cancer, non-small cell lung cancer, bronchioloalveolar cell lung cancer, mesothelioma, squamous cell carcinoma, melanoma, merkel cell cancer, nasopharyngeal carcinoma, neuroblastoma, oral cancer, ovarian cancer, pancreatic cancer, penile cancer, prostate cancer, renal cell cancer, retinoblastoma, sarcoma, skin cancer, testicular cancer, thymic carcinoma, thyroid cancer, uterine cancer, and vaginal cancer.

In some embodiments, the cancer is a metastatic, recurrent or drug-resistant cancer.

In some embodiments, said cancers are hematologic malignancies including acute lymphocytic/lymphoblastic leukemia (ALL), acute myeloid leukemia (AML), B-cell leukemia, blastic plasmacytoid dendritic cell neoplasm (BPDCN), chronic lymphoblastic leukemia (CLL), chronic myelomonocytic leukemia (CMML), chronic myelocytic leukemia (CMIL), diffuse large B-cell lymphoma (DLBCL), extranodal NK/T-cell lymphoma, hairy cell leukemia, HHV8-associated primary effusion lymphoma, plasmablastic lymphoma, pre-B acute lymphocytic leukemia (Pre-B ALL), primary CNS lymphoma, primary mediastinal large B-cell lymphoma, T-cell/histiocyte-rich B-cell lymphoma, heavy chain disease, Hodgkin's lymphoma, non-Hodgkin's lymphoma, Waldenstrom's macroglobulinemia, multiple myeloma (MM), myelodysplastic syndromes (MDS), myeloproliferative neoplasms, and polycythemia vera.

In certain embodiments, said hematologic malignancies include subsets or subtypes of acute myeloid leukemia (AML), acute promyelocytic leukemia (APL) or M3 AML, acute myelomonocytic leukemia or M4 AML, acute monocytic/monoblastic leukemia or M5 AML, and acute myeloblastic leukemia.

In certain embodiments, said hematologic malignancies include acute myeloid leukemia (AML) that is resistant to venetoclax, or venetoclax in combination with azacytidine/azacitidine, that is relapsed after treatment with azacytidine/azacitidine and/or venetoclax, that is resistant to venetoclax in combination with decitabine or is relapsed after treatment with azacytidine/azacitidine and decitabine.

In certain embodiments, the antibody or an antigen-binding fragment thereof is administered intravenously, intra-arterially, intra-tumorally, or subcutaneously.

In certain embodiments, the method further comprises administering to the subject one or more drugs selected from the group consisting of a topoisomerase inhibitor, an anthracycline topoisomerase inhibitor, an anthracycline, a daunorubicin, a nucleoside metabolic inhibitor, a cytarabine, a hypomethylating agent, a low dose cytarabine (LDAC), a combination of daunorubicin and cytarabine, a daunorubicin and cytarabine liposome for injection, Vyxeos®, an azacytidine, Vidaza®, a decitabine, an all-trans-retinoic acid (ATRA), an arsenic, an arsenic trioxide, a histamine dihydrochloride, Ceplene®, an interleukin-2, an aldesleukin, Proleukin®, a gemtuzumab ozogamicin, Mylotarg®, an FLT-3 inhibitor, a midostaurin, Rydapt®, a clofarabine, a farnesyl transferase inhibitor, a decitabine, an IDH1 inhibitor, an ivosidenib, Tibsovo®, an IDH2 inhibitor, an enasidenib, Idhifa®, a smoothened (SMO) inhibitor, a glasdegib, an arginase inhibitor, an IDO inhibitor, an epacadostat, a BCL-2 inhibitor, a venetoclax, Venclexta®, a platinum complex derivative, oxaliplatin, a kinase inhibitor, a tyrosine kinase inhibitor, a PI3 kinase inhibitor, a BTK inhibitor, an ibrutinib, IMBRUVICA®, an acalabrutinib, CALQUENCE®, a zanubrutinib, a PD-1 antibody, a PD-L1 antibody, a CTLA-4 antibody, a LAG3 antibody, an ICOS antibody, a TIGIT antibody, a TIM3 antibody, a CD40 antibody, a 4-1BB antibody, a CD47 antibody, a SIRP1α antibody or fusions protein, a CD70 antibody, and CLL1 antibody, a CD123 antibody, an antagonist of E-selectin, an antibody binding to a tumor antigen, an antibody binding to a T-cell surface marker, an antibody binding to a myeloid cell or NK cell surface marker, an alkylating agent, a nitrosourea agent, an antimetabolite, an antitumor antibiotic, an alkaloid derived from a plant, a hormone therapy medicine, a hormone antagonist, an aromatase inhibitor, and a P-glycoprotein inhibitor.

In certain embodiments, the method further comprises administering to the subject initially a monotherapy of anti-LILRB4 antibodies for a period of time followed by addition of one or more drugs selected from the group consisting of an azacytidine, Vidaza®, a BCL-2 inhibitor, a venetoclax, and Venclexta®.

In yet another aspect, the present disclosure provides a method for detecting a cancer cell or cancer stem cell in a sample or subject. In certain embodiments, the method comprises: (a) contacting a subject or a sample from the subject with the antibody or an antigen-binding fragment thereof described herein; and (b) detecting binding of said antibody to a cancer cell or cancer stem cell in said subject or sample.

In some embodiments, the sample is a body fluid or biopsy. In some embodiments, the sample is blood, sputum, tears, saliva, mucous, serum, urine or feces.

In some embodiments, the detection comprises immunohistochemistry, flow cytometry, immunoassays (including ELISA, RIA etc.) or Western blot.

In some embodiments, the method further comprises performing steps (a) and (b) a second time or additional times and determining a change in detection levels as compared to the first time.

The anti-LILRB4 antibody or an antigen binding fragment thereof may further comprise a label, such as a peptide tag, an enzyme, a magnetic particle, a chromophore, a fluorescent molecule, a chemo-luminescent molecule, or a dye. The isolated monoclonal antibody or an antigen binding fragment thereof may be conjugated to a liposome or nanoparticle.

In another aspect, the present disclosure provides use of the antibody or antigen-binding fragment thereof described herein in the manufacture of a medicament for treating cancer in a subject.

In another aspect, the present disclosure provides a kit comprising the antibody or antigen-binding fragment thereof described herein, useful in detecting LILRB4.

In another aspect, the present disclosure provides an anti-LILRB4 chimeric antigen receptor (CAR) protein. In some embodiments, the CAR protein comprises: (a) a heavy chain variable region comprising an HC-CDR1 having an amino acid sequence of SEQ ID NO: 5, an HC-CDR2 having an amino acid sequence of SEQ ID NO: 6 and an HC-CDR3 having an amino acid sequence of SEQ ID NO: 7; and (b) a light chain variable region comprising an LC-CDR1 having an amino acid sequence of SEQ ID NO: 8 with a mutation at amino acid residues NS, an LC-CDR2 having an amino acid sequence of SEQ ID NO: 9 and an LC-CDR3 having an amino acid sequence of SEQ ID NO: 10. In some embodiments, the LC-CDR1 has an amino acid sequence of SEQ ID NO: 28.

In some embodiments, the heavy chain variable region of the LILRB4 CAR protein has an amino acid sequence at least about 90% identical to SEQ ID NO: 1; and the light chain variable region of the CAR protein has an amino acid sequence at least about 90% identical to SEQ ID NO: 27. In some embodiments, the heavy chain variable region has an amino acid sequence of SEQ ID NO: 1; and wherein the light chain variable region has an amino acid sequence of SEQ ID NO: 27. In some embodiments, the CAR protein comprises a single-chain variable fragment (scFv) having an amino acid sequence at least 85%, 90%, 95% or 99% identical to SEQ ID NO: 66 or SEQ ID NO: 68. In some embodiments, the CAR protein has a scFv having an amino acid sequence identical to SEQ ID NO: 66 or SEQ ID NO: 68.

In another aspect, the present disclosure provides a polynucleotide molecule encoding a CAR protein described herein. In some embodiments, the polynucleotide molecule further comprises a promoter active in eukaryotic cells. In some embodiments, the polynucleotide molecule is an expression vector.

In another aspect, the present disclosure provides an engineered cell comprising the polynucleotide molecule encoding a CAR protein described herein. In some embodiments, the cell is a T cell, an NK cell or a macrophage.

In another aspect, the present disclosure provides a method of treating or ameliorating cancer in a subject in need thereof comprising administering to the subject an effective amount of a cell therapy comprising one or more cells comprising the polynucleotide molecule encoding a CAR protein described herein. In some embodiments, the method further comprises administering to said human subject a second cancer therapy. In some embodiments, the second cancer therapy is chemotherapy, immunotherapy, radiotherapy, hormone therapy or surgery. In some embodiments, the second cancer therapy is administered at the same time as the cell therapy. In some embodiments, said second cancer therapy is administered before or after the cell therapy. In some embodiments, the method further comprises administering to said human subject a second administration of an effective amount of one or more cells comprising the polynucleotide molecule encoding a CAR protein described herein.

In some embodiments, said cell therapy is administered local to cancer site, regional to a cancer site, or systemically.

In some embodiments, said cancer is hematologic malignancies including acute lymphocytic/lymphoblastic leukemia (ALL), acute myeloid leukemia (AML), B-cell leukemia, blastic plasmacytoid dendritic cell neoplasm (BPDCN), chronic lymphoblastic leukemia (CLL), chronic myelomonocytic leukemia (CMML), chronic myelocytic leukemia (CML), diffuse large B-cell lymphoma (DLBCL), extranodal NK/T-cell lymphoma, follicular lymphoma, hairy cell leukemia, HHV8-associated primary effusion lymphoma, plasmablastic lymphoma, pre-B acute lymphocytic leukemia (Pre-B ALL), primary CNS lymphoma, primary mediastinal large B-cell lymphoma, T-cell/histiocyte-rich B-cell lymphoma, heavy chain disease, Hodgkin's lymphoma, non-Hodgkin's lymphoma, Waldenstrom's macroglobulinemia, multiple myeloma (MM), myelodysplastic syndromes (MDS), myeloproliferative neoplasms, and polycythemia vera.

In certain embodiments, said hematologic malignancies include subsets or subtypes of acute myeloid leukemia (AML), acute promyelocytic leukemia (APL) or M3 AML, acute myelomonocytic leukemia or M4 AML, acute monocytic/monoblastic leukemia or M5 AML, and acute myeloblastic leukemia.

In still an additional aspect, there is provided a method of treating or ameliorating the effect of an autoimmune disease in a subject, the method comprising administering to the subject a therapeutically effective amount of the antibody or an antigen-binding fragment thereof as defined herein. The antibody or an antigen-binding fragment thereof may be administered intravenously, intra-arterially, intraperitoneally, or subcutaneously. The method may further comprise administering to the subject one or more drugs selected from the group consisting of a steroid or an NSAID. The autoimmune disease may be Guillain-Barre syndrome, Chronic inflammatory demyelinating polyneuropathy, ankylosing spondylitis, psoriatic arthritis, enteropathic arthritis, reactive arthritis, undifferentiated spondyloarthropathy, juvenile spondyloarthropathy, Behcet's disease, enthesitis, ulcerative colitis, Crohn's disease, irritable bowel syndrome, inflammatory bowel disease, fibromyalgia, chronic fatigue syndrome, pain conditions associated with systemic inflammatory disease, systemic lupus erythematosus, Sjogren's syndrome, rheumatoid arthritis, juvenile rheumatoid arthritis, juvenile onset diabetes mellitus (also known as Type I diabetes mellitus), Wegener's granulomatosis, polymyositis, dermatomyositis, inclusion body myositis, multiple endocrine failure, Schmidt's syndrome, autoimmune uveitis, Addison's disease, Grave's Disease, Hashimoto's thyroiditis, autoimmune thyroid disease, pernicious anemia, gastric atrophy, chronic hepatitis, lupoid hepatitis, atherosclerosis, multiple sclerosis, amyotrophic lateral sclerosis, hypoparathyroidism, Dressler's syndrome, myasthenia gravis, Eaton-Lambert syndrome, autoimmune thrombocytopenia, idiopathic thrombocytopenic purpura, hemolytic anemia, pemphigus vulgaris, pemphigus, dermatitis herpetiformis, alopecia, scleroderma, progressive systemic sclerosis, CREST syndrome (calcinosis, Raynaud's phenomenon, esophageal dysmotility, sclerodactyly, and telangtasia), adult onset diabetes mellitus (also known as Type II diabetes mellitus), mixed connective tissue disease, polyarteritis nodosa, systemic necrotizing vasculitis, glomerulonephritis, atopic dermatitis, atopic rhinitis, Goodpasture's syndrome, Chagas' disease, sarcoidosis, rheumatic fever, asthma, antiphospholipidsyndrome, erythema multiforme, Cushing's syndrome, autoimmune chronic active hepatitis, allergic disease, allergic encephalomyelitis, transfusion reaction, leprosy, malaria, leshmaniasis, trypanosomiasis, Takayasu's arteritis, polymyalgia rheumatica, temporal arteritis, shistosomiasis, giant cell arteritis, eczema, lymphomatoid granulomatosis, Kawasaki's disease, endophthalmitis, psoriasis, erythroblastosis fetalis, eosinophilic faciitis, Shulman's syndrome, Felty's syndrome, Fuch's cyclitis, IgA nephropathy, Henoch-Schonlein purpura, graft versus host disease, transplantation rejection, tularemia, periodic fever syndromes, pyogenic arthritis, Familial Mediterranean Fever, TNF-receptor associated periodic syndrome (TRAPS), Muckle-Wells syndrome, or hyper-IgD syndrome.

BRIEF DESCRIPTION OF FIGURES

FIG. 12A. Binding signal of H7K3m5 or its isotype control on various myeloid cell subsets infiltrating the TME. FIG. 12B. Binding signal of H7K3m5 or its isotype control on various myeloid cell subsets from peripheral blood.

FIGS. 13A and 13C show lack of monocyte killing by PBMCs from two different donors and FIGS. 13B and 13D show corresponding B cell killing as positive control.

FIGS. 14A and 14C show representative monocyte killing through ADCC by PBMCs from two different donors. ADCC on monocyte by afucosylated H7K3m5 was observed in donor 024 but activity was minimal in donor 13. No ADCC was observed by wild type H7K3m5. FIGS. 14B and 14D show corresponding B cell killing as positive control.

FIGS. 17A and 17B show ADCP of THP-1-GFP cells by wild type H7K3m5 from macrophages differentiated from two separate heathy donors.

FIG. 39A is a schematic of the "window" design for dose escalation. FIG. 39B is a schematic of anti-LILRB4 monotherapy.

DETAILED DESCRIPTION OF THE INVENTION

Figure 1:
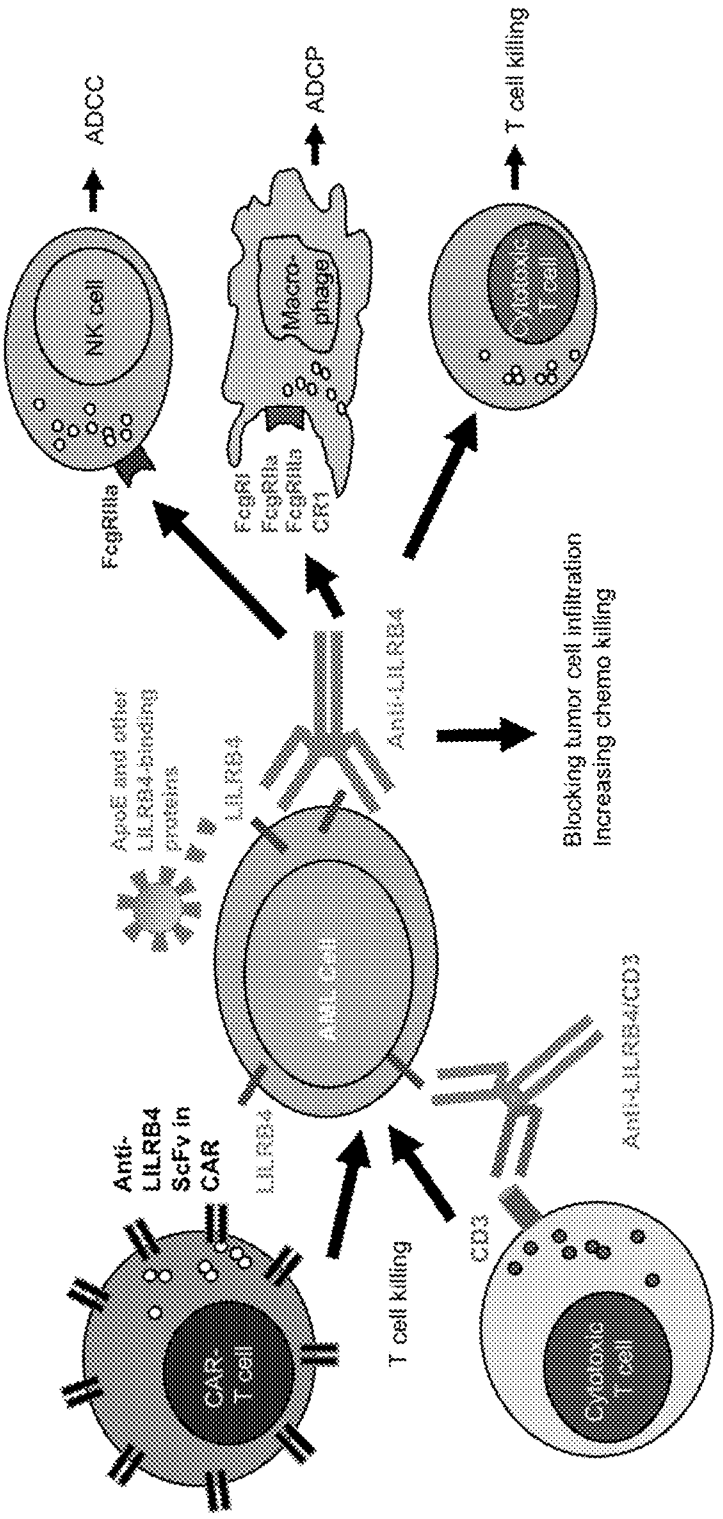
FIG. 1 shows the schematics of the mechanisms of action of anti-LILRB4 antibodies and derivative products.
Figure 2:
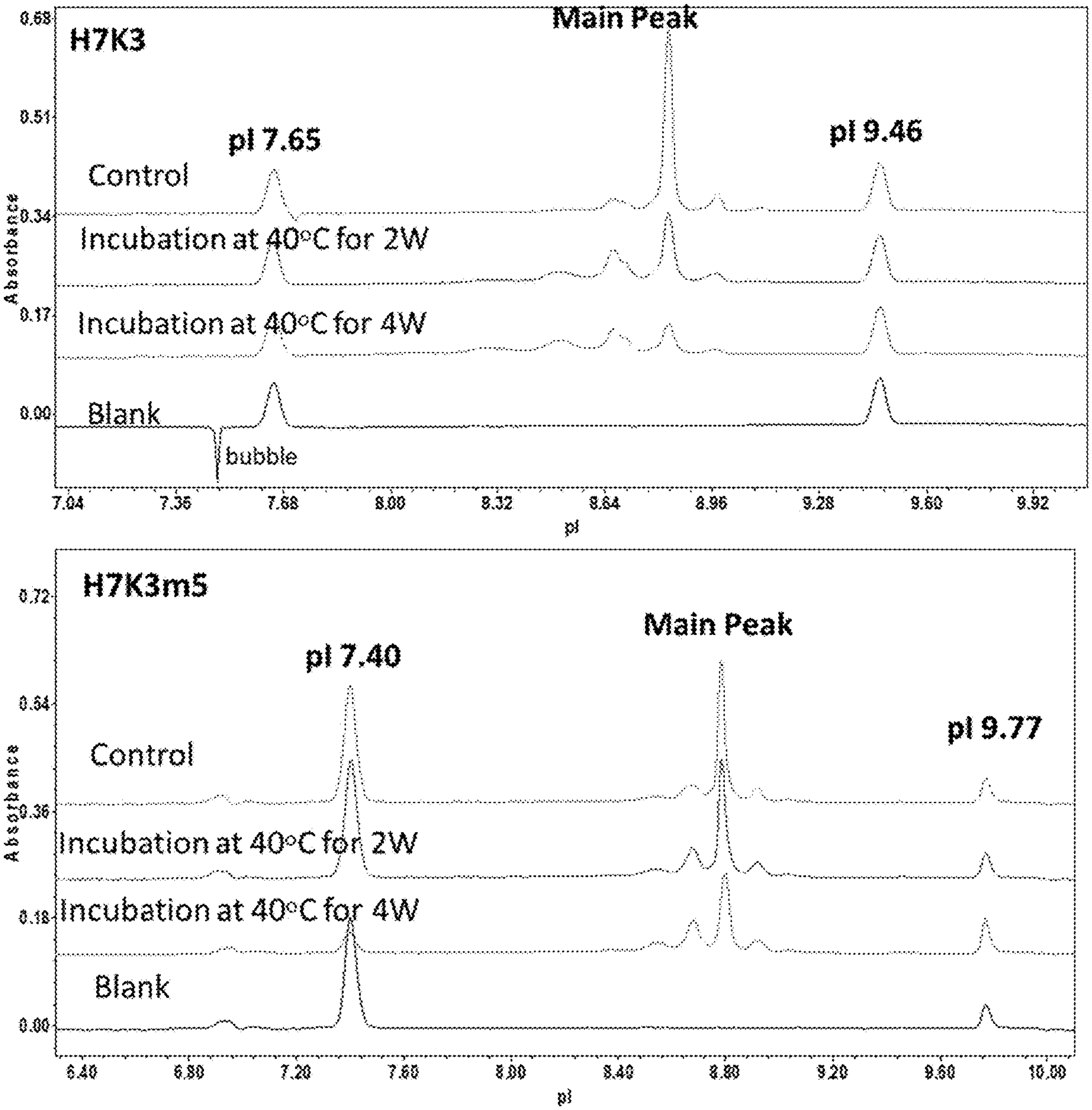
FIG. 2 shows the comparison of icIEF results of H7K3 (Molecule A) and H7K3m5 (Molecule B) at 40° C. for 2W or 4W.

The following description of the disclosure is merely intended to illustrate various embodiments of the disclosure. As such, the specific modifications discussed are not to be construed as limitations on the scope of the disclosure. It will be apparent to one skilled in the art that various equivalents, changes, and modifications may be made without departing from the scope of the disclosure, and it is understood that such equivalent embodiments are to be included herein. All references cited herein, including publications, patents and patent applications are incorporated herein by reference in their entirety.

I. Definitions

It is to be understood that both the foregoing general description and the following detailed description are exemplary and explanatory only and are not restrictive of the invention as claimed. In this application, the use of the singular includes the plural unless specifically stated otherwise. In this disclosure, the term "or" is used to mean "and/or" unless explicitly indicated to refer to alternatives only or the alternatives are mutually exclusive. As used herein "another" may mean at least a second or more. Furthermore, the use of the term "including", as well as other forms, such as "includes" and "included", is not limiting. Also, terms such as "element" or "component" encompass both element or component comprising one unit and elements or components that comprise more than one subunit unless specifically stated otherwise. Also, the use of the term "portion" can include part of a moiety or the entire moiety.

As used herein, the singular forms "a", "an" and "the" include plural references unless the context clearly dictates otherwise.

The term "antibody" as used herein includes any immunoglobulin, monoclonal antibody, polyclonal antibody, multivalent antibody, bivalent antibody, monovalent antibody, multi-specific antibody, or bispecific antibody that binds to a specific antigen. A native intact antibody comprises two heavy (H) chains and two light (L) chains. Mammalian heavy chains are classified as alpha, delta, epsilon, gamma, and mu, each heavy chain consists of a variable domain ($V_H$) and a constant region including a first, second, and third constant domain ($C_{H1}$, $C_{H2}$, $C_{H3}$, respectively); mammalian light chains are classified as λ or κ, while each light chain consists of a variable domain ($V_L$) and a constant domain ($C_L$). A typical IgG antibody has a "Y" shape, with the stem of the Y typically consisting of the second and third constant domains of two heavy chains bound together via disulfide bonding. Each arm of the Y includes the variable domain and first constant domain of a single heavy chain bound to the variable and constant domains of a single light chain. The variable domains of the light and heavy chains are responsible for antigen binding. The variable domains in both chains generally contain three highly variable loops called the complementarity determining regions (CDRs) (light chain CDRs including LCDR1, LCDR2, and LCDR3, heavy chain CDRs including HCDR1, HCDR2, HCDR3). CDR boundaries for the antibodies and antigen-binding fragments disclosed herein may be defined or identified by the conventions of Kabat, IMGT, Chothia, or Al-Lazikani (Al-Lazikani, B., Chothia, C., Lesk, A. M., J. Mol. Biol., 273(4), 927 (1997); Chothia, C. et al., J Mol Biol. (1985) 186(3): 651-63; Chothia, C. and Lesk, A. M., J. Mol. Biol. (1987) 196:901; Chothia, C. et al., Nature (1989) 342(6252):877-83; Marie-Paule Lefranc et al., Developmental and Comparative Immunology (2003) 27: 55-77; Marie-Paule Lefranc et al., Immunome Research (2005) 1(3); Marie-Paule Lefranc, Molecular Biology of B cells (second edition), chapter 26, 481-514, (2015)). The three CDRs are interposed between flanking stretches known as framework regions (FRs), which are more highly conserved than the CDRs and form a scaffold to support the hypervariable loops. The constant domains of the heavy and light chains are not involved in antigen-binding but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of alpha, delta, epsilon, gamma, and mu heavy chains, respectively. Several of the major antibody classes are divided into subclasses such as IgG1 (gamma1 heavy chain), IgG2 (gamma2 heavy chain), IgG3 (gamma3 heavy chain), IgG4 (gamma4 heavy chain), IgA1 (alpha1 heavy chain), or IgA2 (alpha2 heavy chain).

The term “antigen” refers to a substance capable of inducing adaptive immune responses. Specifically, an antigen is a substance specifically bound by antibodies or T lymphocyte antigen receptors. Antigens are usually proteins and polysaccharides, less frequently also lipids. Suitable antigens include without limitation parts of bacteria (coats, capsules, cell walls, flagella, fimbrai, and toxins), viruses, and other microorganisms. Antigens also include tumor antigens, e.g., antigens generated by mutations in tumors. As used herein, antigens also include immunogens and haptens.

The term “antigen-binding fragment” as used herein refers to an antibody fragment formed from a portion of an antibody comprising one or more CDRs, or any other antibody fragment that binds to an antigen but does not comprise an intact native antibody structure. Examples of antigen-binding fragment include, without limitation, a diabody, a Fab, a Fab', a $F(ab')_2$, an Fv fragment, a disulfide stabilized Fv fragment (dsFv), a $(dsFv)_2$, a bispecific dsFv (dsFv-dsFv'), a disulfide stabilized diabody (ds diabody), a single-chain antibody molecule (scFv), an scFv dimer (bivalent diabody), a bispecific antibody, a multispecific antibody, a camelized single domain antibody, a nanobody, a domain antibody, and a bivalent domain antibody. An antigen-binding fragment is capable of binding to the same antigen to which the parent antibody binds.

A “Fab fragment” comprises one light chain and the $C_H1$ and variable domains of one heavy chain. The heavy chain of a Fab molecule cannot form a disulfide bond with another heavy chain molecule.

A “Fab' fragment” comprises one light chain and a portion of one heavy chain that contains the $V_H$ domain and the $C_H1$ domain and also the region between the $C_H1$ and $C_H2$ domains, such that an interchain disulfide bond can be formed between the two heavy chains of two Fab' fragments to form an $F(ab')_2$ molecule.

A “$F(ab')_2$ fragment” contains two light chains and two heavy chains containing a portion of the constant region between the $C_H1$ and $C_H2$ domains, such that an interchain disulfide bond is formed between the two heavy chains. A $F(ab')_2$ fragment thus is composed of two Fab' fragments that are held together by a disulfide bond between the two heavy chains.

“Fv” with regard to an antibody refers to the smallest fragment of the antibody to bear the complete antigen-binding site. An Fv fragment consists of the variable domain of a single light chain bound to the variable domain of a single heavy chain.

“Single-chain Fv antibody” or “scFv” refers to an engineered antibody consisting of a light chain variable domain and a heavy chain variable domain connected to one another directly or via a peptide linker sequence (Huston J S et al., Proc Natl Acad Sci USA (1988) 85:5879).

An “Fc” region comprises two heavy chain fragments comprising the $C_H2$ and $C_H3$ domains of an antibody. The two heavy chain fragments are held together by two or more disulfide bonds and by hydrophobic interactions of the $C_H3$ domains. The Fc region of the antibody is responsible for various effector functions such as antibody-dependent cell-mediated cytotoxicity (ADCC), and complement dependent cytotoxicity (CDC), but does not function in antigen binding.

“Single-chain Fv-Fc antibody” or “scFv-Fc” refers to an engineered antibody consisting of a scFv connected to the Fc region of an antibody.

A “dsFv” refers to a disulfide-stabilized Fv fragment that the linkage between the variable domain of a single light chain and the variable domain of a single heavy chain is a disulfide bond. In some embodiments, a “$(dsFv)_2$” or “(dsFv-dsFv')” comprises three peptide chains: two $V_H$ domains linked by a peptide linker (e.g., a long flexible linker) and bound to two $V_L$ domains, respectively, via disulfide bridges. In some embodiments, dsFv-dsFv' is bispecific in which each disulfide paired heavy and light chain has a different antigen specificity.

“Camelized single domain antibody,” “heavy chain antibody,” or “HCAb” refers to an antibody that contains two $V_H$ domains and no light chains (Riechmann L. and Muyldermans S., J Immunol Methods. December 10; 231(1-2): 25-38 (1999); Muyldermans S., J Biotechnol. June; 74(4): 277-302 (2001); WO94/04678; WO94/25591; U.S. Pat. No. 6,005,079). Heavy chain antibodies were originally derived from Camelidae (camels, dromedaries, and llamas). Although devoid of light chains, camelized antibodies have an authentic antigen-binding repertoire (Hamers-Casterman C. et al., Nature (1993) 363:446-8; Nguyen V K. et al., Immunogenetics (2002) 54:39-47; Nguyen V K. et al., Immunology (2003) 109:93-101). The variable domain of a heavy chain antibody (VHH domain) represents the smallest known antigen-binding unit generated by adaptive immune responses (Koch-Nolte F. et al., FASEB J. (2007) 21:3490-8).

A “nanobody” refers to an antibody fragment that consists of a VHH domain from a heavy chain antibody and two constant domains, CH2 and CH3.

“Diabodies” or “dAbs” include small antibody fragments with two antigen-binding sites, wherein the fragments comprise a $V_H$ domain connected to a $V_L$ domain in the same polypeptide chain ($V_H$-$V_L$ or $V_L$-$V_H$) (see, e.g., Holliger P. et al., Proc Natl Acad Sci USA. July 15; 90(14):6444-8 (1993); EP404097; WO93/11161). By using a linker that is too short to allow pairing between the two domains on the same chain, the domains are forced to pair with the complementary domains of another chain, thereby creating two antigen-binding sites. The antigen-binding sites may target the same or different antigens (or epitopes). In certain embodiments, a “bispecific ds diabody” is a diabody target two different antigens (or epitopes).

In certain embodiments, an “scFv dimer” is divalent (or bivalent) single-chain variable fragments (di-scFvs, bi-scFvs) that can be engineered by linking two scFvs. A bivalent diabody or bivalent scFv (BsFv, di-scFvs, bi-scFvs) comprising $V_H$—$V_L$ (linked by a peptide linker) dimerized with another $V_H$-$V_L$ moiety such that $V_H$'s of one moiety coordinate with the $V_L$'s of the other moiety and form two binding sites which can target the same antigens (or epitopes) or different antigens (or epitopes). In other embodiments, an “scFv dimer” is a bispecific diabody comprising $V_{H1}$-$V_{L2}$ (linked by a peptide linker) associated with $V_{L1}$-$V_{H2}$ (also linked by a peptide linker) such that $V_{H1}$ and $V_{L1}$ coordinate and $V_{H2}$ and $V_{L2}$ coordinate and each coordinated pair has a different antigen specificity.

A "domain antibody" refers to an antibody fragment containing only the variable domain of a heavy chain or the variable domain of a light chain. In certain instances, two or more $V_H$ domains are covalently joined with a peptide linker to create a bivalent or multivalent domain antibody. The two $V_H$ domains of a bivalent domain antibody may target the same or different antigens.

A "bispecific" antibody refers to an artificial antibody which has fragments derived from two different monoclonal antibodies and is capable of binding to two different epitopes. The two epitopes may present on the same antigen, or they may present on two different antigens.

"Cancer" as used herein refers to any medical condition characterized by malignant cell growth or neoplasm, abnormal proliferation, infiltration or metastasis, and includes both solid tumors and non-solid cancers (hematologic malignancies) such as leukemia. As used herein "solid tumor" refers to a solid mass of neoplastic and/or malignant cells. Examples of cancer or tumors include hematological malignancies, oral carcinomas (for example of the lip, tongue or pharynx), digestive organs (for example esophagus, stomach, small intestine, colon, large intestine, or rectum), peritoneum, liver and biliary passages, pancreas, respiratory system such as larynx or lung (small cell and non-small cell), bone, connective tissue, skin (e.g., melanoma), breast, reproductive organs (fallopian tube, uterus, cervix, testicles, ovary, or prostate), urinary tract (e.g., bladder or kidney), brain and endocrine glands such as the thyroid. In certain embodiments, the cancer is selected from ovarian cancer, breast cancer, head and neck cancer, renal cancer, bladder cancer, hepatocellular cancer, and colorectal cancer. In certain embodiments, the cancer is selected from a lymphoma, Hodgkin's lymphoma, non-Hodgkin's lymphoma and B-cell lymphoma.

The term "chimeric" as used herein, means an antibody or antigen-binding fragment, having a portion of heavy and/or light chain derived from one species, and the rest of the heavy and/or light chain derived from a different species. In an illustrative example, a chimeric antibody may comprise a constant region derived from human and a variable region from a non-human animal, such as from mouse or rabbit. In some embodiments, the non-human animal is a mammal, for example, a mouse, a rat, a rabbit, a goat, a sheep, a guinea pig, or a hamster.

The term "specific binding" or "specifically binds" as used herein refers to a non-random binding reaction between two molecules, such as for example between an antibody and an antigen. In certain embodiments, the antibodies or antigen-binding fragments provided herein specifically bind to human LILRB4 with a binding affinity ($K_D$) of $\leq 10^{-6}$ M (e.g., $\leq 5\times10^{-7}$ M, $\leq 2\times10^{-7}$ M, $\leq 10^{-7}$ M, $\leq 5\times10^{-8}$ M, $\leq 2\times10^{-8}$ M, $\leq 10^{-8}$ M, $\leq 5\times10^{-9}$ M, $\leq 4\times10^{-9}$M, $\leq 3\times10^{-9}$M, $\leq 2\times10^{-9}$ M, or $\leq 10^{-9}$ M). $K_D$ used herein refers to the ratio of the dissociation rate to the association rate ($k_{off}/k_{on}$), which may be determined by using any conventional method known in the art, including but are not limited to surface plasmon resonance method, microscale thermophoresis method, HPLC-MS method and flow cytometry (such as FACS) method. In certain embodiments, the $K_D$ value can be appropriately determined by using flow cytometry.

The ability to "block binding" or to "compete for the same epitope" as used herein refers to the ability of an antibody or antigen-binding fragment to inhibit the binding interaction between two molecules (e.g. human LILRB4 and an anti-LILRB4 antibody) to any detectable degree. In certain embodiments, an antibody or antigen-binding fragment that blocks binding between two molecules inhibits the binding interaction between the two molecules by at least 85%, or at least 90%. In certain embodiments, this inhibition may be greater than 85%, or greater than 90%.

Those skilled in the art will recognize that it is possible to determine, without undue experimentation, if a given antibody binds to the same epitope as the antibody of present disclosure by ascertaining whether the former prevents the latter from binding to a LILRB4 antigen polypeptide. If the given antibody competes with the antibody of present disclosure, as shown by a decrease in binding by the antibody of present disclosure to the LILRB4 antigen polypeptide, then the two antibodies bind to the same, or a closely related, epitope. Or if the binding of a given antibody to the LILRB4 antigen polypeptide was inhibited by the antibody of present disclosure, then the two antibodies bind to the same, or a closely related, epitope.

The term "chimeric antigen receptor" or "CAR", as used herein, refer to engineered receptors that are capable of grafting a desired specificity to an antigen into immune effector cells, such as T cells, NK cells and macrophages. Typically, a CAR protein comprises an extracellular domain that introduces the desired specificity, a transmembrane domain and an intracellular domain that transmits a signal to the immune effector cells when the immune effector cells bind to the antigen. In certain embodiments, the extracellular domain comprises a leader peptide, an antigen recognition region and a spacer region. In certain embodiments, the antigen recognition region is derived from an antibody that specifically binds to the antigen. In certain embodiments, the antigen recognition region is a single-chain variable fragment (scFv) derived from the antibody. In certain embodiments, the single-chain variable fragment (scFv) is derived from a humanized antibody. In certain embodiment, the single-chain variable fragment comprises a heavy chain variable region fused to a light chain variable region through a flexible linker.

A "conservative substitution" with reference to amino acid sequence refers to replacing an amino acid residue with a different amino acid residue having a side chain with similar physiochemical properties. For example, conservative substitutions can be made among amino acid residues with hydrophobic side chains (e.g. Met, Ala, Val, Leu, and Ile), among residues with neutral hydrophilic side chains (e.g. Cys, Ser, Thr, Asn and Gln), among residues with acidic side chains (e.g. Asp, Glu), among amino acids with basic side chains (e.g. His, Lys, and Arg), or among residues with aromatic side chains (e.g. Trp, Tyr, and Phe). As known in the art, conservative substitution usually does not cause significant change in the protein conformational structure, and therefore could retain the biological activity of a protein.

"Effector functions" as used herein refer to biological activities attributable to the binding of Fc region of an antibody to its effectors such as C1 complex and Fc receptor. Exemplary effector functions include: complement dependent cytotoxicity (CDC) induced by interaction of antibodies and C1q on the C1 complex; antibody-dependent cell-mediated cytotoxicity (ADCC) induced by binding of Fc region of an antibody to Fc receptor on an effector cell; and phagocytosis.

The term "epitope" as used herein refers to the specific group of atoms or amino acids on an antigen to which an antibody binds. Two antibodies may bind the same or a closely related epitope within an antigen if they exhibit competitive binding for the antigen. For example, if an antibody or antigen-binding fragment blocks binding of a reference antibody to the antigen by at least 85%, or at least 90%, or at least 95%, then the antibody or antigen-binding fragment may be considered to bind the same/closely related epitope as the reference antibody.

The term "homologue" and "homologous" as used herein are interchangeable and refer to nucleic acid sequences (or its complementary strand) or amino acid sequences that have sequence identity of at least 80% (e.g., at least 85%, 88%, 90%, 91%, 92%, 93%, 94%, 95%, 96%, 97%, 98%, 99%) to another sequences when optimally aligned.

The phrase "host cell" as used herein refers to a cell into which an exogenous polynucleotide and/or a vector has been introduced.

The term "humanized" as used herein means that the antibody or antigen-binding fragment comprises CDRs derived from non-human animals, FR regions derived from human, and when applicable, the constant regions derived from human.

An "isolated" substance has been altered by the hand of man from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide is "isolated" if it has been sufficiently separated from the coexisting materials of its natural state so as to exist in a substantially pure state. An "isolated nucleic acid sequence" refers to the sequence of an isolated nucleic acid molecule. In certain embodiments, an "isolated antibody or antigen-binding fragment thereof" refers to the antibody or antigen-binding fragments having a purity of at least 60%, 70%, 75%, 80%, 81%, 82%, 83%, 84%, 85%, 86%, 87%, 88%, 89%, 90%, 91%, 92%, 93%, 94%, 95%, 96%, 97%, 98%, 99% as determined by electrophoretic methods (such as SDS-PAGE, isoelectric focusing, capillary electrophoresis), or chromatographic methods (such as ion exchange chromatography or reverse phase HPLC).

A "leader peptide" refers to a peptide having a length of about 5-30 amino acids that is present at the N-terminus of newly synthesized proteins that form part of the secretory pathway. Proteins of the secretory pathway include, but are not limited to proteins that reside either inside certain organelles (the endoplasmic reticulum, Golgi or endosomes), are secreted from the cell, or are inserted into a cellular membrane. In some embodiments, the leader peptide forms part of the transmembrane domain of a protein.

"LILRB4" as used herein, refers to LILRB4 derived from any vertebrate source, including mammals such as primates (e.g., humans, monkeys) and rodents (e.g., mice and rats). Exemplary sequence of human LILRB4 includes GenBank SEQ Reference No. NP_001265355, AAH26309, ABM83015, ABM86208, AIC55892. The term "LILRB4" as used herein is intended to encompass any form of human LILRB4, for example, 1) native unprocessed LILRB4 molecule, "full-length" LILRB4 chain or naturally occurring variants of LTLRB4, including, for example, splice variants or allelic variants; 2) any form of LILRB4 that results from processing in the cell; or 3) full length, a fragment (e.g., a truncated form, an extracellular/transmembrane domain) or a modified form (e.g. a mutated form, a glycosylated/PEGylated, a His-tag/immunofluorescence fused form) of LILRB4 subunit generated through recombinant method.

The term "anti-LILRB4 antibody" refers to an antibody that is capable of specifically binding to LILRB4 (e.g. human or monkey LILRB4).

A "LILRB4-related" disease or condition as used herein refers to any disease or condition caused by, exacerbated by, or otherwise linked to increased or decreased expression or activities of LILRB4. In some embodiments, the LILRB4 related condition is immune-related disorder, such as, for example, cancer, autoimmune disease, inflammatory disease or infectious disease.

The term "link" as used herein refers to the association via intramolecular interaction, e.g., covalent bonds, metallic bonds, and/or ionic bonding, or inter-molecular interaction, e.g., hydrogen bond or noncovalent bonds.

The term "operably linked" refers to an arrangement of elements wherein the components so described are configured so as to perform their usual function. Thus, a given signal peptide that is operably linked to a polypeptide directs the secretion of the polypeptide from a cell. In the case of a promoter, a promoter that is operably linked to a coding sequence will direct the expression of the coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

"Percent (%) sequence identity" with respect to amino acid sequence (or nucleic acid sequence) is defined as the percentage of amino acid (or nucleic acid) residues in a candidate sequence that are identical to the amino acid (or nucleic acid) residues in a reference sequence, after aligning the sequences and, if necessary, introducing gaps, to achieve the maximum number of identical amino acids (or nucleic acids). Conservative substitution of the amino acid residues may or may not be considered as identical residues. Alignment for purposes of determining percent amino acid (or nucleic acid) sequence identity can be achieved, for example, using publicly available tools such as BLASTN, BLASTp (available on the website of U.S. National Center for Biotechnology Information (NCBI), see also, Altschul S. F. et al., J. Mol. Biol. (1990) 215:403-410; Stephen F. et al., Nucleic Acids Res. (1997) 25:3389-3402), ClustalW2 (available on the website of European Bioinformatics Institute, see also, Higgins D. G. et al., Methods in Enzymology (1996) 266:383-402; Larkin M. A. et al., Bioinformatics (2007) 23:2947-8), and ALIGN or Megalign (DNASTAR) software. Those skilled in the art may use the default parameters provided by the tool, or may customize the parameters as appropriate for the alignment, such as for example, by selecting a suitable algorithm.

The term "polynucleotide" or "nucleic acid" includes both single-stranded and double-stranded nucleotide polymers. The nucleotides comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate.

The term "polypeptide" or "protein" means a string of at least two amino acids linked to one another by peptide bonds. Polypeptides and proteins may include moieties in addition to amino acids (e.g., may be glycosylated) and/or may be otherwise processed or modified. Those of ordinary skill in the art will appreciate that a "polypeptide" or "protein" can be a complete polypeptide chain as produced by a cell (with or without a signal sequence), or can be a functional portion thereof. Those of ordinary skill will further appreciate that a polypeptide or protein can sometimes include more than one polypeptide chain, for example linked by one or more disulfide bonds or associated by other means. The term also includes amino acid polymers in which one or more amino acids are chemical analogs of a corresponding naturally-occurring amino acid and polymers.

The term "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

The term "therapeutically effective amount" or "effective dosage" as used herein refers to the dosage or concentration of a drug effective to treat a disease or condition. For example, with regard to the use of the monoclonal antibodies or antigen-binding fragments thereof disclosed herein to treat cancer, a therapeutically effective amount is the dosage or concentration of the monoclonal antibody or antigen-binding fragment thereof capable of reducing the tumor volume, eradicating all or part of a tumor, inhibiting or slowing tumor growth or cancer cell infiltration into other organs, inhibiting growth or proliferation of cells mediating a cancerous condition, inhibiting or slowing tumor cell metastasis, ameliorating any symptom or marker associated with a tumor or cancerous condition, preventing or delaying the development of a tumor or cancerous condition, or some combination thereof.

"Treating" or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof.

The term "vector" as used herein refers to a vehicle into which a polynucleotide encoding a protein may be operably inserted so as to bring about the expression of that protein. A vector may be used to transform, transduce, or transfect a host cell so as to bring about expression of the genetic element it carries within the host cell. Examples of vectors include plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Categories of animal viruses used as vectors include retrovirus (including lentivirus), adenovirus, adeno-associated virus, herpesvirus (e.g., herpes simplex virus), poxvirus, baculovirus, papillomavirus, and papovavirus (e.g., SV40). A vector may contain a variety of elements for controlling expression, including promoter sequences, transcription initiation sequences, enhancer sequences, selectable elements, and reporter genes. In addition, the vector may contain an origin of replication. A vector may also include materials to aid in its entry into the cell, including but not limited to a viral particle, a liposome, or a protein coating. A vector can be an expression vector or a cloning vector. The present disclosure provides vectors (e.g., expression vectors) containing the nucleic acid sequence provided herein encoding the antibody or antigen-binding fragment thereof, at least one promoter (e.g., SV40, CMV, EF-1α) operably linked to the nucleic acid sequence, and at least one selection marker. Examples of vectors include, but are not limited to, retrovirus (including lentivirus), adenovirus, adeno-associated virus, herpesvirus (e.g., herpes simplex virus), poxvirus, baculovirus, papillomavirus, papovavirus (e.g., SV40), lambda phage, and M13 phage, plasmid pcDNA3.3, pMD18-T, pOptivec, pCMV, pEGFP, pIRES, pQD-Hyg-GSeu, pALTER, pBAD, pcDNA, pCal, pL, pET, pGEMEX, pGEX, pCI, pEGFT, pSV2, pFUSE, pVITRO, pVIVO, pMAL, pMONO, pSELECT, pUNO, pDUO, Psg5L, pBABE, pWPXL, pBI, p15TV-L, pPro18, pTD, pRS10, pLexA, pACT2.2, pCMV-SCRIPT®, pCDM8, pCDNA1.1/amp, pcDNA3.1, pRc/RSV, PCR 2.1, pEF-1, pFB, pSG5, pXT1, pCDEF3, pSVSPORT, pEF-Bos etc.

II. Anti-LILRB4 Antibody and Antigen-Binding Fragment

The present disclosure in one aspect provides an anti-LILRB4 antibody and antigen-binding fragment thereof that has a high binding affinity to LTLRB4. In some embodiments, when bound to LTLRB4, such antibodies modulate the activation of LILRB4. In certain embodiments, the antibody or antigen-binding fragment, when bound to LTLRB4, suppresses activation of LILRB4. In certain embodiments, the antibody or antigen-binding fragment, when bound to LILRB4, can specifically interfere with, block or reduce the interaction between ApoE and LILRB4. In certain embodiments, the antibody or antigen-binding fragment provided herein is capable of inhibiting ApoE-mediated activity of LILRB4. In certain embodiments, the antibodies or antigen-binding fragments provided herein specifically or selectively bind to human LILRB4.

Binding affinity of the antibody and antigen-binding fragment provided herein can be represented by $K_D$ value, which represents the ratio of dissociation rate to association rate ($k_{off}/k_{on}$) when the binding between the antigen and antigen-binding molecule reaches equilibrium. The antigen-binding affinity (e.g., $K_D$) can be appropriately determined using suitable methods known in the art, including, for example, bio-layer interferometry.

Binding of the antibodies to human LILRB4 can also be represented by "half maximal effective concentration" ($EC_{50}$) value, which refers to the concentration of an antibody where 50% of its maximal effect (e.g., binding or inhibition etc.) is observed. The $EC_{50}$ value can be measured by methods known in the art, for example, sandwich assay such as ELISA, Western Blot, flow cytometry assay, and other binding assays.

Specific Anti-LILRB4 Antibodies

The present disclosure in one aspect provides an anti-LILRB4 antibody and antigen-binding fragment thereof comprising one or more (e.g. 1, 2, 3, 4, 5, or 6) CDR sequences of an anti-LILRB4 antibody disclosed herein. CDRs are known to be responsible for antigen binding, however, it has been found that not all of the 6 CDRs are indispensable or unchangeable. In other words, it is possible to replace or change or modify one or more CDRs in anti-LILRB4 antibody disclosed herein, yet substantially retain the specific binding affinity to LILRB4.

In certain embodiments, the LILRB4 antibody is derived from the antibody H7K3 having heavy chain variable region sequence of SEQ ID NO: 1 and light chain variable region sequence of SEQ ID NO: 3. In particular embodiments, the anti-LILRB4 antibody has enhanced stability compared to H7K3, yet substantially retain the specific binding affinity to LILRB4.

In certain embodiments, the LILRB4 antibody has a heavy chain variable region comprising a heavy chain complementarity determining region (HC-CDR) 1 having an amino acid sequence of SEQ ID NO: 5, an HC CDR2 having an amino acid sequence of SEQ ID NO: 6 and an HC CDR3 having an amino acid sequence of SEQ ID NO: 7. In certain embodiments, the HC-CDR3 has an amino acid sequence of SEQ ID NO: 7 with a mutation at amino acid residue W.

In certain embodiments, the LILRB4 antibody has a light chain variable region comprising a light chain complementarity determining region (LC-CDR) 1 having an amino acid sequence of SEQ ID NO: 8, an LC-CDR2 having an amino acid sequence of SEQ ID NO: 9 and an LC-CDR3 having an amino acid sequence of SEQ ID NO: 10. In certain embodiments, the light chain variable region comprises an LC-CDR1 has an amino acid sequence of SEQ ID NO: 8 with a mutation at amino acid residues NS, an LC-CDR2 having an amino acid sequence of SEQ ID NO: 9 and an LC-CDR3 having an amino acid sequence of SEQ ID NO: 10. In certain embodiments, the LC-CDR1 has an amino acid sequence selected from SEQ ID NOs: 20, 22, 24, 26, 28, 30, 32, 34, In certain embodiments, the LILRB4 antibody has a CDR sequence as listed in Table 1 below.

TABLE 1

CDR sequences of the anti-LILRB4 antibodies

| Antibody VH/VL # | CDR1 | CDR2 | CDR3 |
|---|---|---|---|
| H7 | SEQ ID NO: 5<br>GFSLSSSYW | SEQ ID NO: 6<br>IDSGSVGIT | SEQ ID NO: 7<br>ARHGDNWALDL |
| K3 | SEQ ID NO: 8<br>QSI**NS**W | SEQ ID NO: 9<br>KASTLAS | SEQ ID NO: 10<br>HGYIRGDLDNV |
| H7m1 | SEQ ID NO: 5<br>GFSLSSSYW | SEQ ID NO: 6<br>IDSGSVGIT | SEQ ID NO: 12<br>ARHGDN**V**ALDL |
| H7m2 | SEQ ID NO: 5<br>GFSLSSSYW | SEQ ID NO: 6<br>IDSGSVGIT | SEQ ID NO: 14<br>ARHGDN**Y**ALDL |
| H7m3 | SEQ ID NO: 5<br>GFSLSSSYW | SEQ ID NO: 6<br>IDSGSVGIT | SEQ ID NO: 16<br>ARHGDN**F**ALDL |
| H7m4 | SEQ ID NO: 5<br>GFSLSSSYW | SEQ ID NO: 6<br>IDSGSVGIT | SEQ ID NO: 18<br>ARHGDN**Q**ALDL |
| K3m1 | SEQ ID NO: 20<br>QSI**VS**W | SEQ ID NO: 9<br>KASTLAS | SEQ ID NO: 10<br>HGYIRGDLDNV |
| K3m2 | SEQ ID NO: 22<br>QSI**DS**W | SEQ ID NO: 9<br>KASTLAS | SEQ ID NO: 10<br>HGYIRGDLDNV |
| K3m3 | SEQ ID NO: 24<br>QSI**ES**W | SEQ ID NO: 9<br>KASTLAS | SEQ ID NO: 10<br>HGYIRGDLDNV |
| K3m4 | SEQ ID NO: 26<br>QSI**QS**W | SEQ ID NO: 9<br>LLIYKASTLAS | SEQ ID NO: 10<br>HGYIRGDLDNV |
| K3m5 | SEQ ID NO: 28<br>QSI**SS**W | SEQ ID NO: 9<br>KASTLAS | SEQ ID NO: 10<br>HGYIRGDLDNV |

TABLE 1-continued

CDR sequences of the anti-LILRB4 antibodies

| Antibody VH/VL # | CDR1 | CDR2 | CDR3 |
|---|---|---|---|
| K3m6 | SEQ ID NO: 30<br>QSI**TS**W | SEQ ID NO: 9<br>KASTLAS | SEQ ID NO: 10<br>HGYIRGDLDNV |
| K3m7 | SEQ ID NO: 32<br>QSI**NQ**W | SEQ ID NO: 9<br>KASTLAS | SEQ ID NO: 10<br>HGYIRGDLDNV |
| K3m8 | SEQ ID NO: 34<br>QSI**NV**W | SEQ ID NO: 9<br>KASTLAS | SEQ ID NO: 10<br>HGYIRGDLDNV |

The heavy chain and light chain variable region amino acid sequences of the anti-LILRB4 antibodies above are provided below.

H7

(SEQ ID NO: 1)

EVQLVESGGGLVQPGGSLRLSCAASGFSLSSSYWISWVRQAPGKGLE
WIGSIDSGSVGITYYATWVKGRFTISRDNSKNTLYLQMNSLRAEDTAVYY
CARHGDNWALDLWGQGTLVTVSS

K3

(SEQ ID NO: 3)

DIQMTQSPSTLSASVGDRVTITCRASQSINSWLAWYQQKPGKAPKLLIYK
ASTLASGVPSRFSGSGSGTEFTLTISSLQPDDFATYYCQHGYIRGDLDNV
FGGGTKVEIK

H7m1

(SEQ ID NO: 11)

EVQLVESGGGLVQPGGSLRLSCAASGFSLSSSYWISWVRQAPGKGLE
WIGSIDSGSVGITYYATWVKGRFTISRDNSKNTLYLQMNSLRAEDTAVYY
CARHGDNVALDLWGQGTLVTVSS

H7m2

(SEQ ID NO: 13)

EVQLVESGGGLVQPGGSLRLSCAASGFSLSSSYWISWVRQAPGKGLEWIG
SIDSGSVGITYYATWVKGRFTISRDNSKNTLYLQMNSLRAEDTAVYYC
ARHGDNYALDLWGQGTLVTVSS

H7m3

(SEQ ID NO: 15)

EVQLVESGGGLVQPGGSLRLSCAASGFSLSSSYWISWVRQAPGKGLE
WIGSIDSGSVGITYYATWVKGRFTISRDNSKNTLYLQMNSLRAEDTAVYY
CARHGDNFALDLWGQGTLVTVSS

H7m4

(SEQ ID NO: 17)

EVQLVESGGGLVQPGGSLRLSCAASGFSLSSSYWISWVRQAPGKGLE
WIGSIDSGSVGITYYATWVKGRFTISRDNSKNTLYLQMNSLRAEDTAVYY
CARHGDNQALDLWGQGTLVTVSS

K3m1

(SEQ ID NO: 19)

DIQMTQSPSTLSASVGDRVTITCRASQSIVSWLAWYQQKPGKAPKLLIYK
ASTLASGVPSRFSGSGSGTEFTLTISSLQPDDFATYYCQHGYIRGDLDNV
FGGGTKVEIK

-continued

K3m2

(SEQ ID NO: 21)
DIQMTQSPSTLSASVGDRVTITCRASQSIDSWLAWYQQKPGKAPKLLIYK
ASTLASGVPSRFSGSGSGTEFTLTISSLQPDDFATYYCQHGYIRGDLDNV
FGGGTKVEIK

K3m3

(SEQ ID NO: 23)
DIQMTQSPSTLSASVGDRVTITCRASQSIESWLAWYQQKPGKAPKLLIYK
ASTLASGVPSRFSGSGSGTEFTLTISSLQPDDFATYYCQHGYIRGDLDNV
FGGGTKVEIK

K3m4

(SEQ ID NO: 25)
DIQMTQSPSTLSASVGDRVTITCRASQSIQSWLAWYQQKPGKAPKLLIYK
ASTLASGVPSRFSGSGSGTEFTLTISSLQPDDFATYYCQHGYIRGDLDNV
FGGGTKVEIK

K3m5

(SEQ ID NO: 27)
DIQMTQSPSTLSASVGDRVTITCRASQSISSWLAWYQQKPGKAPKLLIYK
ASTLASGVPSRFSGSGSGTEFTLTISSLQPDDFATYYCQHGYIRGDLDNV
FGGGTKVEIK

K3m6

(SEQ ID NO: 29)
DIQMTQSPSTLSASVGDRVTITCRASQSITSWLAWYQQKPGKAPKLLIYK
ASTLASGVPSRFSGSGSGTEFTLTISSLQPDDFATYYCQHGYIRGDLDNV
FGGGTKVEIK

K4m7

(SEQ ID NO: 31)
DIQMTQSPSTLSASVGDRVTITCRASQSINQWLAWYQQKPGKAPKLLIYK
ASTLASGVPSRFSGSGSGTEFTLTISSLQPDDFATYYCQHGYIRGDLDNV
FGGGTKVEIK

K4m8

(SEQ ID NO: 33)
DIQMTQSPSTLSASVGDRVTITCRASQSINVWLAWYQQKPGKAPKLLIYK
ASTLASGVPSRFSGSGSGTEFTLTISSLQPDDFATYYCQHGYIRGDLDNV
FGGGTKVEIK

In certain embodiments, the antibodies and antigen-binding fragments thereof provided herein comprise suitable framework region (FR) sequences, as long as the antibodies and antigen-binding fragments thereof can specifically bind to LILRB4. The CDR sequences provided in Table 1 can be grafted to any suitable FR sequences of any suitable species such as mouse, human, rat, rabbit, among others, using suitable methods known in the art such as recombinant techniques.

In certain embodiments, the antibodies and antigen-binding fragments thereof provided herein are humanized. A humanized antibody or antigen-binding fragment is desirable in its reduced immunogenicity in human. A humanized antibody is chimeric in its variable regions, as non-human CDR sequences are grafted to human or substantially human FR sequences. Humanization of an antibody or antigen-binding fragment can be essentially performed by substituting the non-human (such as murine) CDR genes for the corresponding human CDR genes in a human immunoglobulin gene (see, for example, Jones et al., Nature (1986) 321:522-525; Riechmann et al., Nature (1988) 332:323-327; Verhoeyen et al., Science (1988) 239:1534-1536).

Suitable human heavy chain and light chain variable domains can be selected to achieve this purpose using methods known in the art. In an illustrative example, "best-fit" approach can be used, where a non-human (e.g. rodent) antibody variable domain sequence is screened or BLASTed against a database of known human variable domain sequences, and the human sequence closest to the non-human query sequence is identified and used as the human scaffold for grafting the non-human CDR sequences (see, for example, Sims et al., J. Immunol. (1993) 151:2296; Chothia et al., J. Mot. Biol. (1987) 196:901). Alternatively, a framework derived from the consensus sequence of all human antibodies may be used for the grafting of the non-human CDRs (see, for example, Carter et at. Proc. Natl. Acad. Sci. USA (1992) 89:4285; Presta et al., J. Immunol. (1993) 151:2623).

In certain embodiments, the humanized antibodies or antigen-binding fragments provided herein are composed of substantially all human sequences except for the CDR sequences which are non-human. In some embodiments, the variable region FRs, and constant regions if present, are entirely or substantially from human immunoglobulin sequences. The human FR sequences and human constant region sequences may be derived different human immunoglobulin genes, for example, FR sequences derived from one human antibody and constant region from another human antibody.

In certain embodiments, the humanized antibodies and antigen-binding fragment thereof provided herein comprise a heavy chain FR sequence of H7 and/or a light chain FR sequence of K3. In some embodiments, the FR regions derived from human may comprise the same amino acid sequence as the human immunoglobulin from which it is derived. In some embodiments, one or more amino acid residues of the human FR are substituted with the corresponding residues from the parent non-human antibody. This may be desirable in certain embodiments to make the humanized antibody or its fragment closely approximate the non-human parent antibody structure. In certain embodiments, the humanized antibody or antigen-binding fragment provided herein comprises no more than 10, 9, 8, 7, 6, 5, 4, 3, 2, or 1 amino acid residue substitutions in each of the human FR sequences, or no more than 10, 9, 8, 7, 6, 5, 4, 3, 2, or 1 amino acid residue substitutions in all the FRs of a heavy or a light chain variable domain. In some embodiments, such change in amino acid residue could be present in heavy chain FR regions only, in light chain FR regions only, or in both chains.

In certain embodiments, the antibodies and antigen-binding fragments thereof provided herein comprise a heavy chain variable domain sequence selected from the group consisting of SEQ ID NOs: 1, 11, 13, 15, and 17. In certain embodiments, the antibodies and antigen-binding fragments thereof provided herein comprise a light chain variable domain sequence selected from the group consisting of SEQ ID NOs: 3, 19, 21, 23, 25, 27, 29, 31, and 33.

In some embodiments, the anti-LTLRB4 antibodies and the antigen-binding fragments provided herein comprise all or a portion of the heavy chain variable domain and/or all or a portion of the light chain variable domain. In one embodiment, the anti-LILRB4 antibodies and the antigen-binding fragments provided herein is a single domain antibody which consists of all or a portion of the heavy chain variable domain provided herein. More information of such a single domain antibody is available in the art (see, e.g., U.S. Pat. No. 6,248,516).

In certain embodiments, the anti-LTLRB4 antibodies and the fragments thereof provided herein further comprise an immunoglobulin constant region. In some embodiments, an immunoglobulin constant region comprises a heavy chain and/or a light chain constant region. The heavy chain constant region comprises CH1, hinge, and/or CH2-CH3 regions. In certain embodiments, the heavy chain constant region comprises an Fc region. In certain embodiments, the light chain constant region comprises Cκ or Cλ.

The antibodies or antigen-binding fragments thereof provided herein can be a monoclonal antibody, polyclonal antibody, humanized antibody, chimeric antibody, recombinant antibody, bispecific antibody, labeled antibody, bivalent antibody, or anti-idiotypic antibody. A recombinant antibody is an antibody prepared in vitro using recombinant methods rather than in animals.

Antibody Variants

The antibodies and antigen-binding fragments thereof provided herein also encompass various variants thereof. In certain embodiments, the antibodies and antigen-binding fragments thereof encompasses various types of variants of an exemplary antibody provided herein.

In certain embodiments, the antibody variants comprise one or more modifications or substitutions in one or more CDR sequences as provided in Table 1, one or more variable region sequences (but not in any of the CDR sequences) provided herein, and/or the constant region (e.g., Fc region). Such variants retain specific binding affinity to LILRB4 of their parent antibodies, but have one or more desirable properties conferred by the modification(s) or substitution(s). For example, the antibody variants may have improved antigen-binding affinity, improved glycosylation pattern, reduced risk of glycosylation, reduced deamidation or deamination, improved or increased effector function(s), reduced or depleted effector function(s), improved FcRn receptor binding, increased pharmacokinetic half-life, pH sensitivity, and/or compatibility to conjugation (e.g., one or more introduced cysteine residues).

The parent antibody sequence may be screened to identify suitable or preferred residues to be modified or substituted, using methods known in the art, for example "alanine scanning mutagenesis" (see, for example, Cunningham and Wells (1989) Science, 244:1081-1085). Briefly, target residues (e.g., charged residues such as Arg, Asp, His, Lys, and Glu) can be identified and replaced by a neutral or negatively charged amino acid (e.g., alanine or polyalanine), and the modified antibodies are produced and screened for the interested property. If substitution at a particular amino acid location demonstrates an interested functional change, then the position can be identified as a potential residue for modification or substitution. The potential residues may be further assessed by substituting with a different type of residue (e.g. cysteine residue, positively charged residue, etc.).

Affinity Variant

Affinity variant may contain modifications or substitutions in one or more CDR sequences, one or more FR sequences, or the heavy or light chain variable region sequences provided herein. The affinity variants retain specific binding affinity to LILRB4 of the parent antibody, or even have improved LILRB4 specific binding affinity over the parent antibody.

Various methods known in the art can be used to achieve this purpose. For example, a library of antibody variants (such as Fab or scFv variants) can be generated and expressed with phage display technology, and then screened for the binding affinity to human LILRB4. For another example, computer software can be used to virtually simulate the binding of the antibodies to human LILRB4, and identify the amino acid residues on the antibodies which form the binding interface. Such residues may be either avoided in the substitution so as to prevent reduction in binding affinity or targeted for substitution to provide for a stronger binding.

In certain embodiments, the humanized antibody or antigen-binding fragment provided herein comprises one or more amino acid residue substitutions in one or more CDR sequences, and/or one or more FR sequences. In certain embodiments, an affinity variant comprises no more than 10, 9, 8, 7, 6, 5, 4, 3, 2, or 1 substitution in the CDR sequences and/or FR sequences in total.

In certain embodiments, the anti-LILRB4 antibodies and antigen-binding fragments thereof comprise 1, 2, or 3 CDR sequences having at least 80% (e.g. at least 85%, 88%, 90%, 91%, 92%, 93%, 94%, 95%, 96%, 97%, 98%, 99%) sequence identity to that (or those) listed in Table 1, and in the meantime retain the binding affinity to LILRB4 at a level similar to or even higher than its parent antibody.

In certain embodiments, the anti-LILRB4 antibodies and antigen-binding fragments thereof comprise one or more variable region sequences having at least 80% (e.g. at least 85%, 88%, 90%, 91%, 92%, 93%, 94%, 95%, 96%, 97%, 98%, 99%) sequence identity to that (or those) provided herein, and in the meantime retain the binding affinity to LILRB4 at a level similar to or even higher than its parent antibody. In some embodiments, the substitutions, insertions, or deletions occur in regions outside the CDRs (e.g., in the FRs).

Glycosylation Variant

In still another embodiment, the antibody comprises a particular glycosylation pattern. For example, an aglycosylated antibody can be made (i.e., the antibody lacks glycosylation). The glycosylation pattern of an antibody may be altered to, for example, increase the affinity or avidity of the antibody for an antigen. Such modifications can be accomplished by, for example, altering one or more of the glycosylation sites within the antibody sequence. For example, one or more amino acid substitutions can be made that result removal of one or more of the variable region framework glycosylation sites to thereby eliminate glycosylation at that site. Such aglycosylation may increase the affinity or avidity of the antibody for antigen. See, e.g., U.S. Pat. Nos. 5,714,350 and 6,350,861.

An antibody may also be made in which the glycosylation pattern includes hypofucosylated or afucosylated glycans, such as a hypofucosylated antibodies or afucosylated antibodies have reduced amounts of fucosyl residues on the glycan. The antibodies may also include glycans having an increased amount of bisecting GlcNac structures. Such altered glycosylation patterns have been demonstrated to increase the ADCC ability of antibodies. Such modifications can be accomplished by, for example, expressing the antibodies in a host cell in which the glycosylation pathway was been genetically engineered to produce glycoproteins with particular glycosylation patterns. These cells have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 (α (1,6)-fucosyltransferase), such that antibodies expressed in the Ms704, Ms705, and Ms709 cell lines lack fucose on their carbohydrates. The Ms704, Ms705, and Ms709 FUT8−/− cell lines were created by the targeted disruption of the FUT8 gene in CHO/DG44 cells using two replacement vectors (see U.S. Patent Publication No. 20040110704. As another example, EP 1 176 195 describes a cell line with a functionally disrupted FUT8 gene, which encodes a fucosyl transferase, such that antibodies expressed in such a cell line exhibit hypofucosylation by reducing or eliminating the α-1,6 bond-related enzyme. EP 1 176 195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 2003/035835 describes a variant CHO cell line, Lec13 cells, with reduced ability to attach fucose to Asn(297)-linked carbohydrates, also resulting in hypofucosylation of antibodies expressed in that host cell. Antibodies with a modified glycosylation profile can also be produced in chicken eggs, as described in PCT Publication WO 06/089231. Alternatively, antibodies with a modified glycosylation profile can be produced in plant cells, such as Lemna (U.S. Pat. No. 7,632,983). Methods for production of antibodies in a plant system are disclosed in the U.S. Pat. Nos. 6,998,267 and 7,388,081. PCT Publication WO1999/054342 describes cell lines engineered to express glycoprotein-modifying glycosyl transferases (e.g., β(1,4)-N-acetylglucosaminyltransferase III (GnTIII)) such that antibodies expressed in the engineered cell lines exhibit increased bisecting GlcNac structures which results in increased ADCC activity of the antibodies. Hypofucosylation is also called afucosylation when fucosylation is minimal on antibodies.

Alternatively, the fucose residues of the antibodies can be cleaved off using a fucosidase enzyme; e.g., the fucosidase α-L-fucosidase removes fucosyl residues from antibodies. Antibodies disclosed herein further include those produced in lower eukaryote host cells, in particular fungal host cells such as yeast and filamentous fungi have been genetically engineered to produce glycoproteins that have mammalian- or human-like glycosylation patterns. A particular advantage of these genetically modified host cells over currently used mammalian cell lines is the ability to control the glycosylation profile of glycoproteins that are produced in the cells such that compositions of glycoproteins can be produced wherein a particular N-glycan structure predominates (see, e.g., U.S. Pat. Nos. 7,029,872 and 7,449,308). These genetically modified host cells have been used to produce antibodies that have predominantly particular N-glycan structures.

In addition, since fungi such as yeast or filamentous fungi lack the ability to produce fucosylated glycoproteins, antibodies produced in such cells will lack fucose unless the cells are further modified to include the enzymatic pathway for producing fucosylated glycoproteins (See for example, PCT Publication WO2008112092). In particular embodiments, the antibodies disclosed herein further include those produced in lower eukaryotic host cells and which comprise fucosylated and nonfucosylated hybrid and complex N-glycans, including bisected and multiantennary species, including but not limited to N-glycans such as GlcNAc(1-4)Man3GlcNAc2; Gal(1-4)GlcNAc(1-4)Man3GlcNAc2; NANA(1-4)Gal(1-4)GlcNAc(1-4)Man3GlcNAc2. In particular embodiments, the antibody compositions provided herein may comprise antibodies having at least one hybrid N-glycan selected from the group consisting of GlcNAcMan5GlcNAc2; GalGlcNAcMan5GlcNAc2; and NANAGalGlcNAcMan5GlcNAc2. In particular aspects, the hybrid N-glycan is the predominant N-glycan species in the composition. In further aspects, the hybrid N-glycan is a particular N-glycan species that comprises about 30%, 40%, 50%, 60%, 70%, 80%, 90%, 95%, 97%, 98%, 99%, or 100% of the hybrid N-glycans in the composition.

In particular embodiments, the antibody compositions provided herein comprise antibodies having at least one complex N-glycan selected from the group consisting of GlcNAcMan3GlcNAc2; GalGlcNAcMan3GlcNAc2; NANAGalGlcNAcMan3GlcNAc2; GlcNAc2Man3GlcNAc2; GalGlcNAc2Man3GlcNAc2; Gal2GlcNAc2Man3GlcNAc2; NANAGal2GlcNAc2Man3GlcNAc2; and NANA2Gal2GlcNAc2Man3GlcNAc2. In particular aspects, the complex N-glycan is the predominant N-glycan species in the composition. In further aspects, the complex N-glycan is a particular N-glycan species that comprises about 30%, 40%, 50%, 60%, 70%, 80%, 90%, 95%, 97%, 98%, 99%, or 100% of the complex N-glycans in the composition. In particular embodiments, the N-glycan is fusosylated. In general, the fucose is in an α1,3-linkage with the GlcNAc at the reducing end of the N-glycan, an α1,6-linkage with the GlcNAc at the reducing end of the N-glycan, an α1,2-linkage with the Gal at the non-reducing end of the N-glycan, an α1,3-linkage with the GlcNac at the non-reducing end of the N-glycan, or an α1,4-linkage with a GlcNAc at the non-reducing end of the N-glycan.

Therefore, in particular aspects of the above the glycoprotein compositions, the glycoform is in an α1,3-linkage or α1,6-linkage fucose to produce a glycoform selected from the group consisting of Man5GlcNAc2(Fuc), GlcNAcMan5GlcNAc2(Fuc), Man3GlcNAc2(Fuc), GlcNAcMan3GlcNAc2(Fuc), GlcNAc2Man3GlcNAc2(Fuc), GalGlcNAc2Man3GlcNAc2(Fuc), Gal2GlcNAc2Man3GlcNAc2(Fuc), NANAGal2GlcNAc2Man3GlcNAc2(Fuc), and NANA2Gal2GlcNAc2Man3GlcNAc2(Fuc); in an α1,3-linkage or α1,4-linkage fucose to produce a glycoform selected from the group consisting of GlcNAc(Fuc)Man5GlcNAc2, GlcNAc(Fuc)Man3GlcNAc2, GlcNAc2(Fuc1-2)Man3GlcNAc2, GalGlcNAc2(Fuc1-2)Man3GlcNAc2, Gal2GlcNAc2(Fuc1-2)Man3GlcNAc2, NANAGal2GlcNAc2(Fuc1-2)Man3GlcNAc2, and NANA2Gal2GlcNAc2(Fuc1-2)Man3GlcNAc2; or in an α1,2-linkage fucose to produce a glycoform selected from the group consisting of Gal(Fuc)GlcNAc2Man3GlcNAc2, Gal2(Fuc1-2)GlcNAc2Man3GlcNAc2, NANAGal2(Fuc1-2)GlcNAc2Man3GlcNAc2, and NANA2Gal2(Fuc1-2)GlcNAc2Man3GlcNAc2.

In further aspects, the antibodies comprise high mannose N-glycans, including but not limited to, Man8GlcNAc2, Man7GlcNAc2, Man6GlcNAc2, Man5GlcNAc2, Man4GlcNAc2, or N-glycans that consist of the Man3GlcNAc2 N-glycan structure. In further aspects of the above, the complex N-glycans further include fucosylated and non-fucosylated (or afucosylated) bisected and multiantennary species. As used herein, the terms "N-glycan" and "glycoform" are used interchangeably and refer to an N-linked oligosaccharide, for example, one that is attached by an asparagine-N-acetylglucosamine linkage to an asparagine residue of a polypeptide. N-linked glycoproteins contain an N-acetylglucosamine residue linked to the amide nitrogen of an asparagine residue in the protein.

The anti-LILRB4 antibodies and antigen-binding fragments provided herein also encompass a glycosylation variant, which can be obtained to either increase or decrease the extent of glycosylation of the antibody or antigen binding fragment.

The antibody or antigen binding fragment thereof may comprise one or more amino acid residues with a side chain to which a carbohydrate moiety (e.g. an oligosaccharide structure) can be attached. Glycosylation of antibodies is typically either N-linked or O-linked. N-linked refers to the attachment of the carbohydrate moiety to the side chain of an asparagine residue, for example, an asparagine residue in a tripeptide sequence such as asparagine-X-serine and asparagine-X-threonine, where X is any amino acid except proline. O-linked glycosylation refers to the attachment of one of the sugars N-aceylgalactosamine, galactose, or xylose to a hydroxyamino acid, most commonly to serine or threonine. Removal of a native glycosylation site can be conveniently accomplished, for example, by altering the amino acid sequence such that one of the above-described tripeptide sequences (for N-linked glycosylation sites) or serine or threonine residues (for O-linked glycosylation sites) present in the sequence in the is substituted. A new glycosylation site can be created in a similar way by introducing such a tripeptide sequence or serine or threonine residue.

Figure 15A:
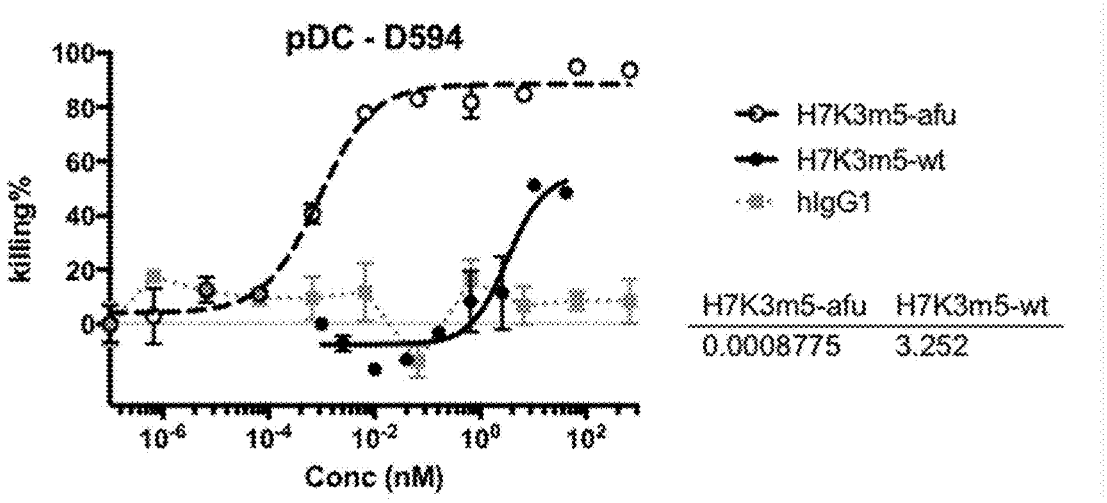
FIGS. 15A-15D show autologous ADCC of pDC or monocytes by wild type (WT) or afucosylated (afu) H7K3m5-mediated autologous ADCC. ADCC against pDCs was observed by both wild type and afucosylated H7K3m5 in two donors. In the meantime, monocytes may be killed only with afucosylated H7K3m5, depending on donors. Moreover, the afucosylated H7K3m5 showed much stronger ADCC activity than the wild-type towards pDC or monocytes (FIGS. 15A-15B).
Figure 15B:
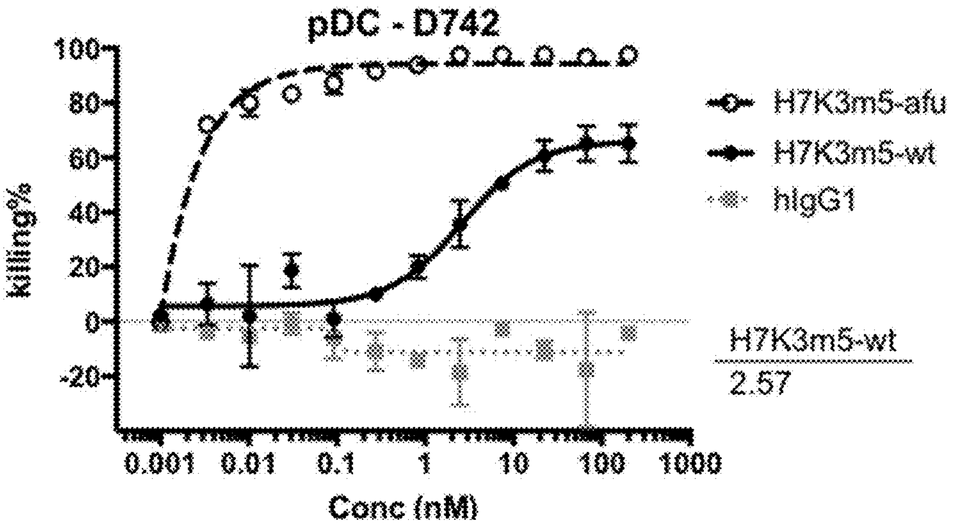
Figure 15C:
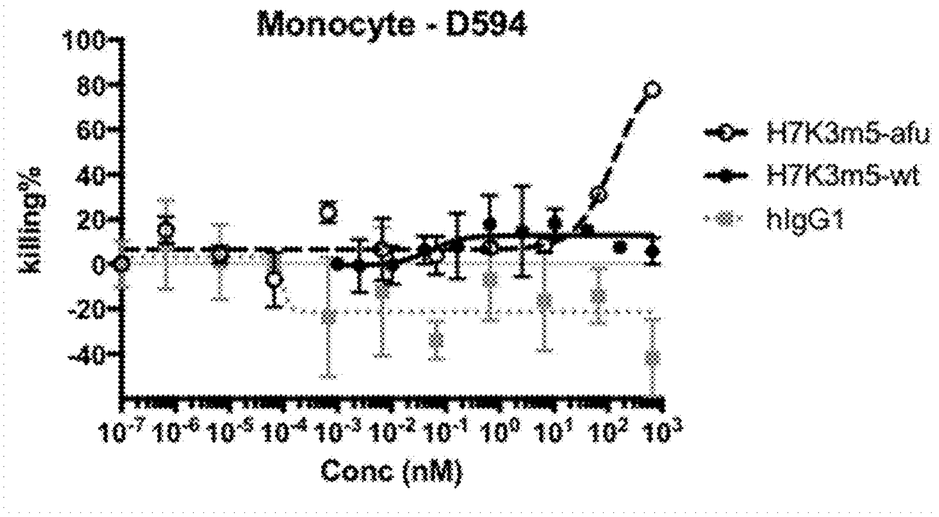
Figure 15D:
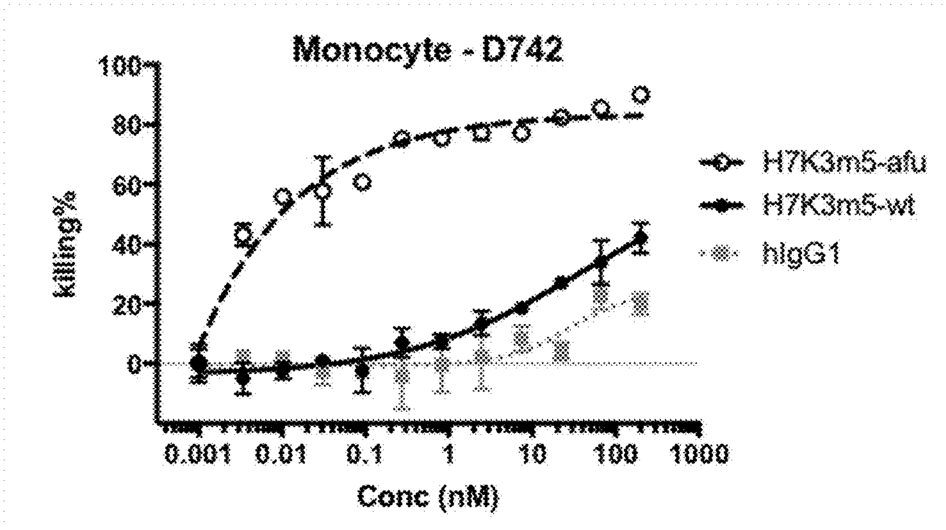

One type of glycosylation modification is made with antibody-producing cells deficient for certain enzymatic pathways that are responsible for site-specific glycosylation, including fucosylation. For example, an antibody lacking fucosylation (referred to as afucosylated antibody) generally has enhanced ADCC activity. With afucosylated H7K3m5, killing of normal monocytes via ADCC was observed in 25-50% of tested PBMC donors (FIGS. 14A-14D, and FIGS. 15C-15D). In addition, as shown in FIGS. 15A-15B, both afucosylated and wild type H7K3m5 resulted in killing of pDCs via autologous ADCC. In the meantime, monocytes may be killed only with afucosylated H7K3m5, depending on donors, and not with wild-type H7K3m5 (FIGS. 15C-15D).

Cysteine-Engineered Variant

The anti-LILRB4 antibodies and antigen-binding fragments provided herein also encompass a cysteine-engineered variant, which comprises one or more introduced free cysteine amino acid residues.

A free cysteine residue is one which is not part of a disulfide bridge. A cysteine-engineered variant is useful for conjugation with for example, a cytotoxic and/or imaging compound, a label, or a radioisoptype among others, at the site of the engineered cysteine, through for example a maleimide or haloacetyl. Methods for engineering antibodies or antigen-binding fragments to introduce free cysteine residues are known in the art, see, for example, WO2006/034488.

Fc Variant

The antibodies disclosed herein can also be engineered to include modifications within the Fc region, typically to alter one or more functional properties of the antibody, such as serum half-life, complement fixation, Fc receptor binding, and/or effector function (e.g., antigen-dependent cellular cytotoxicity). Furthermore, the antibodies disclosed herein can be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat. The antibodies disclosed herein also include antibodies with modified (or blocked) Fc regions to provide altered effector functions. See, e.g., U.S. Pat. No. 5,624,821; WO2003/086310; US2004/0002587; US2005/0152894; US2005/0249723; WO2006/019447. Such modification can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc. Changes to the Fc can also alter the half-life of antibodies in therapeutic antibodies, enabling less frequent dosing and thus increased convenience and decreased use of material. This mutation has been reported to abolish the heterogeneity of inter-heavy chain disulfide bridges in the hinge region.

In one embodiment, the hinge region of CH1 is modified such that the number of cysteine residues in the hinge region is increased or decreased. This approach is described further in U.S. Pat. No. 5,677,425. The number of cysteine residues in the hinge region of CH1 is altered, for example, to facilitate assembly of the light and heavy chains or to increase or decrease the stability of the antibody. In another embodiment, the antibody is modified to increase its biological half-life. Various approaches are possible. For example, one or more of the following mutations can be introduced: T252L, T254S, T256F, as described in U.S. Pat. No. 6,277,375. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022. In yet other embodiments, the Fc region is altered by replacing at least one amino acid residue with a different amino acid residue to alter the effector function(s) of the antibodies. For example, one or more amino acids selected from amino acid residues 234, 235, 236, 237, 297, 318, 320 and 322 can be replaced with a different amino acid residue such that the antibody has an altered affinity for an effector ligand but retains the antigen binding ability of the parent antibody. The effector ligand to which affinity is altered can be, for example, an Fc receptor or the C1 component of complement. This approach is described in further detail in U.S. Pat. Nos. 5,624,821 and 5,648,260.

In another example, one or more amino acid residues within amino acid positions 231 and 239 are altered to thereby alter the ability of the antibody to fix complement. This approach is described further in PCT Publication WO1994/029351. In yet another example, the Fc region is modified to increase or decrease the ability of the antibodies to mediate antibody dependent cellular cytotoxicity (ADCC) and/or to increase or decrease the affinity of the antibodies for an Fcγ receptor by modifying one or more amino acids at the following positions: 238, 239, 243, 248, 249, 252, 254, 255, 256, 258, 264, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 2000/042072. Moreover, the binding sites on human IgG1 for FcγR1, FcγRII, FcγRIII and FcRn have been mapped and variants with improved binding have been described. Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

In one embodiment, the Fc region is modified to decrease the ability of the antibodies to mediate effector function and/or to increase anti-inflammatory properties by modifying residues 243 and 264. In one embodiment, the Fc region of the antibody is modified by changing the residues at positions 243 and 264 to alanine. In one embodiment, the Fc region is modified to decrease the ability of the antibody to mediate effector function and/or to increase anti-inflammatory properties by modifying residues 243, 264, 267 and 328.

In one embodiment, the Fc region is modified to abolish the ability of the antibodies to mediate effector function by modifying residues 234, 235 and 329 to alanine or glycine (L234A-L235A-P329G).

The anti-LILRB4 antibodies and antigen-binding fragments provided herein also encompass an Fc variant, which comprises one or more amino acid residue modifications or substitutions at its Fc region and/or hinge region.

In certain embodiments, the anti-LILRB4 antibodies or antigen-binding fragments comprise one or more amino acid substitution(s) that improves pH-dependent binding to neonatal Fc receptor (FcRn). Such a variant can have an extended pharmacokinetic half-life, as it binds to FcRn at acidic pH which allows it to escape from degradation in the lysosome and then be translocated and released out of the cell. Methods of engineering an antibody and antigen-binding fragment thereof to improve binding affinity with FcRn are well-known in the art, see, for example, Vaughn, D. et al., Structure, 6(1): 63-73, 1998; Kontermann, R. et al., Antibody Engineering, Volume 1, Chapter 27: Engineering of the Fc region for improved PK, published by Springer, 2010; Yeung, Y. et al., Cancer Research (2010) 70: 3269-3277; and Hinton, P. et al., J. Immunology (2006) 176:346-356.

In certain embodiments, the anti-LILRB4 antibodies or antigen-binding fragments comprise one or more amino acid substitution(s) that alters the antibody-dependent cellular cytotoxicity (ADCC). Certain amino acid residues at CH2 domain of the Fc region can be substituted to provide for enhanced ADCC activity. Alternatively, or additionally, carbohydrate structures on the antibody can be changed to enhance ADCC activity. Methods of altering ADCC activity by antibody engineering have been described in the art, see for example, Shields R L. et al., J Biol Chem. (2001) 276(9): 6591-604; Idusogie E E. et al., J Immunol. (2000) 164(8): 4178-84; Steurer W. et al., J Immunol. (1995) 155(3): 1165-74; Idusogie E E. et al., J Immunol. (2001) 166(4): 2571-5; Lazar G A. et al., PNAS (2006) 103(11): 4005-4010; Ryan M C. et al., Mol. Cancer Ther. (2007) 6: 3009-3018; Richards J O. et al., Mol Cancer Ther. (2008) 7(8): 2517-27; Shields R. L. et al., J. Biol. Chem, 2002, 277: 26733-26740; Shinkawa T. et al., J. Biol. Chem (2003) 278: 3466-3473.

In certain embodiments, the anti-LILRB4 antibodies or antigen-binding fragments comprise one or more amino acid substitution(s) that alters Complement Dependent Cytotoxicity (CDC), for example, by improving or diminishing C1q binding and/or CDC (see, for example, WO99/51642; Duncan & Winter Nature 322:738-40 (1988); U.S. Pat. Nos. 5,648,260; 5,624,821); and WO1994/029351 concerning other examples of Fe region variants.

In certain embodiments, the anti-LILRB4 antibodies or antigen-binding fragments comprise one or more amino acid substitution(s) in the interface of the Fc region to facilitate and/or promote heterodimerization. These modifications comprise introduction of a protuberance into a first Fc polypeptide and a cavity into a second Fc polypeptide, wherein the protuberance can be positioned in the cavity so as to promote interaction of the first and second Fc polypeptides to form a heterodimer or a complex. Methods of generating antibodies with these modifications are known in the art, e.g., as described in U.S. Pat. No. 5,731,168.

Antigen-Binding Fragments

Provided herein are also anti-LILRB4 antigen-binding fragments. Various types of antigen-binding fragments are known in the art and can be developed based on the anti-LILRB4 antibodies provided herein, including for example, the exemplary antibodies whose CDR and variable sequences are provided herein, and their different variants (such as affinity variants, glycosylation variants, Fc variants, cysteine-engineered variants and so on).

In certain embodiments, an anti-LILRB4 antigen-binding fragment provided herein is a camelized single domain antibody, a diabody, a single chain Fv fragment (scFv), an scFv dimer, a BsFv, a dsFv, a $(dsFv)_2$, a dsFv-dsFv', an Fv fragment, a Fab, a Fab', a $F(ab')_2$, a bispecific antibody, a ds diabody, a nanobody, a domain antibody, a single domain antibody, or a bivalent domain antibody.

A Single Chain Variable Fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alaine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5\times10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stabilizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., Nhydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338 describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

Various techniques can be used for the production of such antigen-binding fragments. Illustrative methods include, enzymatic digestion of intact antibodies (see, e.g., Morimoto et al., Journal of Biochemical and Biophysical Methods (1992) 24:107-117; and Brennan et al., Science (1985) 229:81), recombinant expression by host cells such as *E. coli* (e.g. for Fab, Fv and ScFv antibody fragments), screening from a phase display library as discussed above (e.g. for ScFv), and chemical coupling of two Fab'-SH fragments to form $F(ab')_2$ fragments (Carter et al., Bio/Technology (1992) 10:163-167). Other techniques for the production of antibody fragments will be apparent to a skilled practitioner.

In certain embodiments, the antigen-binding fragment is a scFv. Generation of scFv is described in, for example, WO 93/16185; U.S. Pat. Nos. 5,571,894; and 5,587,458. scFv may be fused to an effector protein at either the amino or the carboxyl terminus to provide for a fusion protein (see, for example, Antibody Engineering, ed. Borrebaeck).

Bispecific Antibodies

In certain embodiments, the LILRB4 antibody disclosed herein is a bispecific antibody. In certain embodiments, the LTLRB4 bispecific antibody can be used to treat hematologic and solid malignancies via redirecting the cytotoxic T-cells or NK-cells toward cancer cells by engaging both antigens on the T-cells or NK-cells and LTLRB4 on the cancer cells. In some embodiments, the anti-LTLRB4 bispecific antibody is against a T-cell receptor such as CD3. In some embodiments, the anti-LILRB4 bispecific antibody is against an NK-cell receptor such as CD16A.

Figure 28A:
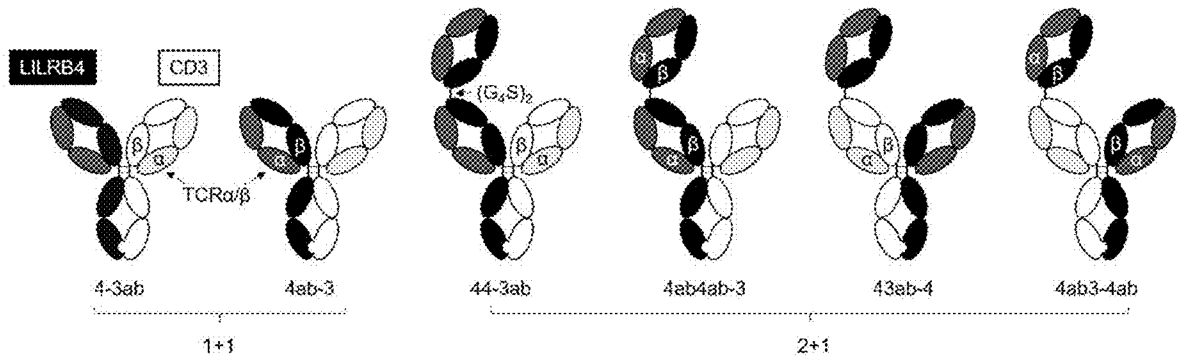
FIGS. 28A and 28B show the schematic representation of configurations of LILRB4/CD3 bispecific antibodies.
Figure 28B:
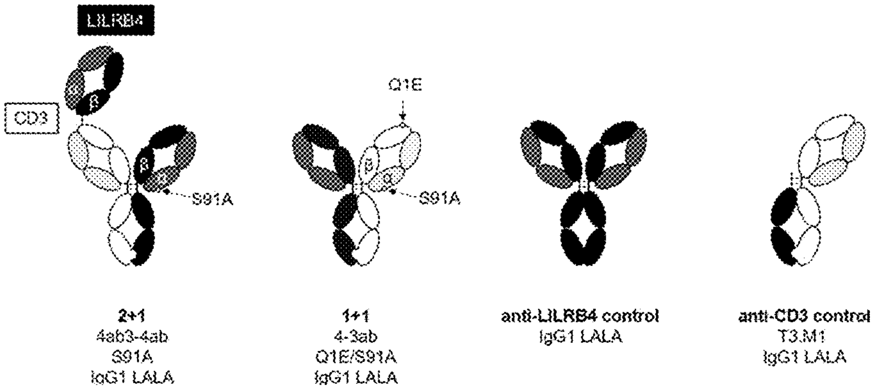

It is appreciated that the anti-LILRB4 bispecific antibodies of the present disclosure can have various forms and structures, which can be understood by the exemplary embodiments of the bispecific antibody specifically binds to LILRB4 and CD3 (LILRB4/CD3 bispecific) as illustrated in FIGS. 28A and 28B.

As illustrated in FIG. 28A, in an exemplary embodiment of the invention, the LILRB4/CD3 bispecific antibody is Y shaped and comprises two arms. One arm of the antibody, formed by a portion of a first heavy chain polypeptide and a first light chain polypeptide, comprises a pair of heavy chain variable domain ($V_H1$) and light chain variable domain ($V_L1$), which form an antigen-binding site capable of specifically binding to LILRB4. The other arm of the antibody, formed by a portion of a second heavy chain polypeptide and a second light chain polypeptide, comprises a second pair of heavy chain variable domains ($V_H2$) and light chain variable domain ($V_L2$). The $V_H2$ and $V_L2$ form a second antigen-binding site capable of specifically binding to CD3. In this configuration, each bispecific antibody comprises a single copy of the antigen binding site against LILRB4 and a single copy of the antigen binding site against CD3, which is referred to as 1+1

Referring to the embodiment 4-3ab in FIG. 28A, the first heavy chain polypeptide comprises from N to C terminus $V_H1$-$C_H1$-$C_H2$-$C_H3$, wherein $C_H1$, $C_H2$, and $C_H3$ refers to heavy chain constant domain 1, 2 and 3; the first light chain polypeptide comprises from N to C terminus $V_L1$-$C_L$, wherein $C_L$ refers to a light chain constant domain; the second heavy chain polypeptide comprises from N to C terminus $V_H2$-TCRβ-$C_H2$-$C_H3$; and the second light chain polypeptide comprises from N to C terminus $V_L2$-TCRα. The use of TCRα and TCRβ constant domain in the bispecific antibody enables correct association of the light chains and their cognate heavy chain, leading to higher yield of desired bispecific antibody against LILRB4 and CD3 (see, e.g., WO2019057122A1). In certain embodiments, the TCRα domain has an amino acid sequence of SEQ ID NO: 89, the TCRβ domain has an amino acid sequence of SEQ ID NO: 90.

Alternatively, as illustrated in the 4ab-3 embodiment in FIG. 28A, the first heavy chain polypeptide comprises from N to C terminus $V_H1$-TCRβ-$C_H2$-$C_H3$; the first light chain polypeptide comprises from N to C terminus $V_L1$-TCRα; the second heavy chain polypeptide comprises from N to C terminus $V_H2$-$C_H1$-$C_H2$-$C_H3$; and the second light chain polypeptide comprises from N to C terminus $V_L2$-$C_L$.

As illustrated in FIG. 28A, the stem of the Y shaped antibody comprises a Fc region consisting of the second and the third constant domains ($C_H2$ and $C_H3$) of the first and second heavy chain polypeptides bound together via disulfide bonding. In certain embodiments, the Fc region is engineered with knobs in holes (KiH) technology (Ridgway J B et al, *Protein Eng* (1996) 9:617-21; Atwell S et al, *J Mol Biol* (1997) 270:26-35; Merchant et al, *Nature Biotech* (1998) 16, 677-681), which prevents homodimerization of the heavy chain polypeptides. In short, each of the constant region of the two heavy chain polypeptides is mutated to create either a knob or a hole, which pairs to promote heterodimerization. The design of the LILRB4/CD3 bispecific antibody using KiH technology enable heterodimerization of the heavy chains and correct association of the light chains and their cognate heavy chain, leading to higher yield of desired bispecific antibody against LILRB4 and CD3.

In certain embodiments, the configuration of the bispecific antibody comprises two copies of the antigen binding sites against LILRB4 and a single copy of the antigen binding site against CD3. This configuration is referred to as 2+1 and illustrated in FIG. 28A. In such configuration, the LILRB4/CD3 bispecific antibody comprises two pairs of heavy chain/light chain polypeptides, which forms a first antigen-binding region and a second antigen-binding region that bind to LILRB4 and CD3, respectively. Distinctive from the 1+1 configuration, in the 2+1 configuration, one heavy chain polypeptide comprises a third heavy chain variable domain ($V_H3$) cognate to a third light variable domain in a third light chain polypeptide, forming a third antigen-binding region binding to LILRB4.

Referring to the embodiment 44-3ab in FIG. 28A, in an exemplary embodiment of the invention, the LILRB4/CD3 bispecific antibody, which is Y shaped and comprises two arms, comprises a first heavy chain polypeptide, a first light chain polypeptide, a second heavy chain polypeptide, a second light chain polypeptide and a third light chain polypeptide. The first heavy chain polypeptide comprises from N to C terminus $V_H3$-$C_H1$-L-$V_H1$-$C_H1$-$C_H2$-$C_H3$, wherein L is a linker (e.g., $(G_4S)_2$); the first light chain polypeptide comprises from N to C terminus $V_L1$-$C_L$; the second heavy chain polypeptide comprises from N to C terminus $V_H2$-TCRβ-$C_H2$-$C_H3$; and the second light chain polypeptide comprises from N to C terminus $V_L2$-TCRα; the third light chain polypeptide comprises from N to C terminus $V_L3$-$C_L$. On one arm of the antibody, the $V_H1$ and $V_L1$ form a first antigen-binding site against LILRB4, while the $V_H3$ and $V_L3$ form a second antigen-binding site against LILRB4. On the other arm of the antibody, the $V_H2$ and $V_L2$ form an antigen-binding site capable of specifically binding to CD3. In certain embodiment, the third light chain polypeptide $V_L3$-$C_L$ may be identical to the first light chain polypeptide $V_L1$-$C_L$.

Referring to the embodiment 4ab4ab-3 in FIG. 28A, in an exemplary embodiment of the invention, the LILRB4/CD3 bispecific antibody comprises a first heavy chain polypeptide, a first light chain polypeptide, a second heavy chain polypeptide, a second light chain polypeptide and a third light chain polypeptide. The first heavy chain polypeptide comprises from N to C terminus $V_H3$-TCRβ-L-$V_H1$-TCRβ-$C_H2$-$C_H3$, wherein L is a linker (e.g., $(G_4S)_2$); the first light chain polypeptide comprises from N to C terminus $V_L1$-TCRα; the second heavy chain polypeptide comprises from N to C terminus $V_H2$-$C_H1$-$C_H2$-$C_H3$; and the second light chain polypeptide comprises from N to C terminus $V_L2$-$C_L$; the third light chain polypeptide comprises from N to C terminus $V_L3$-TCRα. On one arm of the antibody, the $V_H1$ and $V_L1$ form a first antigen-binding site against LILRB4, while the $V_H3$ and $V_L3$ form a second antigen-binding site against LILRB4. On the other arm of the antibody, the $V_H2$ and $V_L2$ form an antigen-binding site capable of specifically binding to CD3. In certain embodiment, the third light chain polypeptide $V_L3$-TCRα may be identical to the first light chain polypeptide $V_L1$-TCRα.

Referring to the embodiment 43ab-4 in FIG. 28A, in an exemplary embodiment of the invention, the LILRB4/CD3 bispecific antibody comprises a first heavy chain polypeptide, a first light chain polypeptide, a second heavy chain polypeptide, a second light chain polypeptide and a third light chain polypeptide. The first heavy chain polypeptide comprises from N to C terminus $V_H3$-$C_H1$-L-$V_H2$-TCRβ-$C_H2$-$C_H3$, wherein L is a linker (e.g., $(G_4S)_2$); the first light chain polypeptide comprises from N to C terminus $V_L2$-TCRα; the second heavy chain polypeptide comprises from N to C terminus $V_H1$-$C_H1$-$C_H2$-$C_H3$; and the second light chain polypeptide comprises from N to C terminus $V_L1$-$C_L$; the third light chain polypeptide comprises from N to C terminus $V_L3$-$C_L$. On one arm of the antibody, the $V_H1$ and $V_L1$ form a first antigen-binding site against LILRB4. On the other arm of the antibody, the $V_H3$ and $V_L3$ form a second antigen-binding site against LILRB4, while the $V_H2$ and $V_L2$ form an antigen-binding site capable of specifically binding to CD3. In certain embodiment, the third light chain polypeptide $V_L3$-$C_L$ may be identical to the first light chain polypeptide $V_L1$-$C_L$.

Referring to the embodiment 4ab3-4ab in FIG. 28A, in an exemplary embodiment of the invention, the LILRB4/CD3 bispecific antibody comprises a first heavy chain polypeptide, a first light chain polypeptide, a second heavy chain polypeptide, a second light chain polypeptide and a third light chain polypeptide. The first heavy chain polypeptide comprises from N to C terminus $V_H3$-TCRβ-L-$V_H2$-$C_H1$-$C_H2$-$C_H3$, wherein L is a linker (e.g., $(G_4S)_2$); the first light chain polypeptide comprises from N to C terminus $V_L2$-$C_L$; the second heavy chain polypeptide comprises from N to C terminus $V_H1$-TCRβ-$C_H2$-$C_H3$; and the second light chain polypeptide comprises from N to C terminus $V_L1$-TCRα; the third light chain polypeptide comprises from N to C terminus $V_L3$-TCRα. On one arm of the antibody, the $V_H1$ and $V_L1$ form a first antigen-binding site against LILRB4. On the other arm of the antibody, the $V_H3$ and $V_L3$ form a second antigen-binding site against LILRB4, while the $V_H2$ and $V_L2$ form an antigen-binding site against CD3. In certain embodiment, the third light chain polypeptide $V_L3$-TCRα may be identical to the first light chain polypeptide $V_L1$-TCRα.

In certain embodiments, the antigen-binding site directed to CD3 is generated based on the anti-CD3 antibodies known in the art, e.g., the anti-CD3 antibodies described in WO2019057099, SP34 (Pessano et al *EMBO J*(1985) 4, 337-334), OKT3 (Ortho, Raritan, NJ; Van Wauwe et al, *J Immunol* (1984) 133, 129-32), M291 (Protein Design Laboratories, Fremont, CA), BC3 (Fred Hutchinson Cancer Research Center, Seattle, WA), TR66 (Novus Biologicals, Centennial, CO) and BMA030 (Walker C et al., *Eur J Immunol*. (1907) 17:1611-8).

In certain embodiments, the LILRB4/CD3 bispecific antibody can be engineered to improve homogeneity and manufacturability. In some embodiments, as illustrated in FIG. 28B, the TCRα can be mutated at S91A of SEQ ID NO: 89 to remove 0-glycan modification site. In some embodiment, a Q1E mutation can be made at the N-terminal of the heavy chain or light polypeptide to prevent N-terminal pyro-Q formation.

In certain embodiments, anti-LILRB4 bispecific antibodies could be constructed in many other ways as reviewed by Konterman et al 2017, 9 182-212. In particular anti-LILRB4 bispecific antibodies could be constructed as covalent antibody conjugates, asymmetric F(ab')2, CovX-bodies, mouse/rat chimeric IgGs, κλ-bodies with common heavy chains, tandem single-chain variable domains (scFv), BiTEs, triplebodies, diabodies, tandem domain antibodies, scFv fusions with CH1/CL domains, Fab-scFv bibodies or tribodies, Fab-Fv fusion, Fab-single domain antibody (sdAb)/VHH fusions, orthogonal Fab-Fab, scFv2-albumin/toxin fusions, single-chain diabody-albumin/toxin fusion, tandem scFv albumin/toxin fusions, dock-and-lock (DNL) $Fab_3$, DNL-$Fab_2$-scFv, DNL-Fab-IgG fusions, ImmTAC TCR-scFv fusions, IgG with different heavy chains and different or common light chains, IgG-scFv fusions to the heavy or light chain N or C terminus, IgG single-chain Fab (scFab) fusions to the heavy or light chain N- or C-terminus, single-chain IgG (scIgG) with scFv fusions, dual-variable domain (DVD) bispecific antibodies, asymmetric scFv-Fc, tandem-scFv-Fc fusions, dual affinity re-tarting antibodies (DART) with or without Fc fusion, asymmetric Fab-scFv-Fc fusions, scFv-CH3 fusions, TriFabs, IgG tandem scFv fusions, IgG-crossFab fusions, tandem Fab-IgG fusions with orthogonal Fabs, didiabody-Fc fusion, single-chain diabody Fc-fusion, Fab-scFv-Fc fusions, $scFv_4$-Fc fusion, scFv2-Fcab, Di-diabody, single-chain diabody CH3 fusion, IgE/M CH2 fusions, $F(ab')_2$ fusions, CH1/CK fusions, two-in-one dual action Fabs (DAF), or DutaMab, DNL-$Fab_2$-IgG fusion.

Heterodimizeration of heavy chains for bispecific antibodies which contain Fc domains can be accomplished by a number of means including but not limited to knob-in-holes (Ridgway et al PEDS 1996; Atwell et al J Mol Biol 1997; Merchant et al Nat Biotechnol 1998), HA-TF mutations (Moore et al Mabs 2011), ZW1 (Von Kreudenstein et al MAbs 2013), CH3 charge pairs (Gunasekaran et al J Biol Chem 2010), IgG1 hinge/CH3 charge pairs (Strop et al J Mol Biol 2012), IgG2 hinge/CH3 charge pairs (Strop et al J Mol Biol 2012), EW-RVT mutations with or without an engineered disulfide (Choi et al Mol Cancer Ther 2013; Choi et al Mol Immunol 2015), biclonic (Geuijen et al J Clinical Onc 2014), DuoBody (Labrijn et al Proc Natl Acad Sci USA 2013), SEEDbody IgG/A chimera (David et al Protein Eng Des Sel 2010), BEAT (Moretti et al BMC Proceedings 2013), 7.8.60 or 29.8.34 (Leaver-Fey et al Structure 2016). Correct pairing of different light chains can be accomplished by a variety of methods including, but not limited to CrossMab (Schaefer et al Cancer Cell 2011), orthologonal Fab (Lewis et al Nat Biotechnol 2014), T-cell receptor fusions (Wu et al MAbs 2015), CR3 (Golay et al J Immunol 2016), MUT4 (Golay et al J Immunol 2016), DuetMab (Mazor et al MAbs 2015, 7, 377-89; Mazor et al MAbs 2015, 7, 461-669).

In certain embodiments, bispecific antibodies could be targeted to LILRB4 and another target including, but not limited to CD3, CD2, CD16a, NKp46, CD137, OX40, PD-1, PD-L1, CD40, CTLA4, LAG3, TIM3, CD47.

Conjugates

In some embodiments, the anti-LILRB4 antibodies and antigen-binding fragments thereof further comprise a conjugate moiety. The conjugate moiety can be linked to the antibodies and antigen-binding fragments thereof. A conjugate moiety is a proteinaceous or non-proteinaceous moiety that can be attached to the antibody or antigen-binding fragment thereof. It is contemplated that a variety of conjugate moieties may be linked to the antibodies or antigen-binding fragments provided herein (see, for example, "Conjugate Vaccines", Contributions to Microbiology and Immunology, J. M. Cruse and R. E. Lewis, Jr. (eds.), Carger Press, New York, (1989)). These conjugate moieties may be linked to the antibodies or antigen-binding fragments by covalent binding, affinity binding, intercalation, coordinate binding, complexation, association, blending, or addition, among other methods.

In certain embodiments, the antibodies and antigen-binding fragments disclosed herein may be engineered to contain specific sites outside the epitope binding portion that may be utilized for binding to one or more conjugate moieties. For example, such a site may include one or more reactive amino acid residues, such as for example cysteine or histidine residues, to facilitate covalent linkage to a conjugate moiety.

In certain embodiments, the antibodies may be linked to a conjugate moiety indirectly, or through another conjugate moiety. For example, the antibody or antigen-binding fragments may be conjugated to biotin, then indirectly conjugated to a second conjugate that is conjugated to avidin. The conjugate can be a clearance-modifying agent, a toxin (e.g., a chemotherapeutic agent), a detectable label (e.g., a radioactive isotope, a lanthanide, a luminescent label, a fluorescent label, or an enzyme-substrate label), or purification moiety.

A "toxin" can be any agent that is detrimental to cells or that can damage or kill cells. Examples of toxin include, without limitation, taxol, cytochalasin B, gramicidin D, ethidium bromide, emetine, mitomycin, etoposide, tenoposide, vincristine, monomethyl auristatin E (MMAE), monomethyl auristatin F (MMAF), mertansine, emtansine, DM1, maytansinoid DM1, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin and analogs thereof, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), anti-mitotic agents (e.g., vincristine and vinblastine), a topoisomerase inhibitor, and a tubulin-binders.

Examples of detectable label may include a fluorescent labels (e.g. fluorescein, rhodamine, dansyl, phycoerythrin, or Texas Red), enzyme-substrate labels (e.g. horseradish peroxidase, alkaline phosphatase, luceriferases, glucoamylase, lysozyme, saccharide oxidases or β-D-galactosidase), radioisotopes (e.g. $^{123}I$, $^{124}I$, $^{125}I$, $^{131}I$, $^{35}S$, $^{3}H$, $^{111}In$, $^{112}In$, $^{14}C$, $^{64}Cu$, $^{67}Cu$, $^{86}Y$, $^{88}Y$, $^{90}Y$, $^{177}Lu$, $^{211}At$, $^{186}Re$, $^{188}Re$, $^{153}Sm$, $^{212}Bi$, and $^{32}P$, other lanthanides), luminescent labels, chromophoric moiety, digoxigenin, biotin/avidin, a DNA molecule or gold for detection.

In certain embodiments, the conjugate moiety can be a clearance-modifying agent which helps increase half-life of the antibody. Illustrative examples include water-soluble polymers, such as PEG, carboxymethylcellulose, dextran, polyvinyl alcohol, polyvinyl pyrrolidone, copolymers of ethylene glycol/propylene glycol, and the like. The polymer may be of any molecular weight, and may be branched or unbranched. The number of polymers attached to the antibody may vary, and if more than one polymers are attached, they can be the same or different molecules.

In certain embodiments, the conjugate moiety can be a purification moiety such as a magnetic bead.

In certain embodiments, the antibodies and antigen-binding fragments thereof provided herein is used for a base for a conjugate.

Polynucleotides and Recombinant Methods

The present disclosure provides isolated polynucleotides that encode the anti-LTLRB4 antibodies and antigen-binding fragments thereof. In certain embodiments, the isolated polynucleotides comprise one or more nucleotide sequences as shown in SEQ ID NOs: 2, 4, and 35, which encodes the variable region of the exemplary antibodies provided herein. DNA encoding the monoclonal antibody is readily isolated and sequenced using conventional procedures (e.g., by using oligonucleotide probes that are capable of binding specifically to genes encoding the heavy and light chains of the antibody). The encoding DNA may also be obtained by synthetic methods.

The isolated polynucleotide that encodes the anti-LTLRB4 antibodies and antigen-binding fragments can be inserted into a vector for further cloning (amplification of the DNA) or for expression, using recombinant techniques known in the art. Many vectors are available. The vector components generally include, but are not limited to, one or more of the following: a signal sequence, an origin of replication, one or more marker genes, an enhancer element, a promoter (e.g. SV40, CMV, EF-1α), and a transcription termination sequence.

The present disclosure provides vectors (e.g., expression vectors) containing the nucleic acid sequence provided herein encoding the antibodies or antigen-binding fragments, at least one promoter (e.g., SV40, CMV, EF-1α) operably linked to the nucleic acid sequence, and at least one selection marker. Examples of vectors include, but are not limited to, retrovirus (including lentivirus), adenovirus, adeno-associated virus, herpesvirus (e.g., herpes simplex virus), poxvirus, baculovirus, papillomavirus, papovavirus (e.g., SV40), lambda phage, and M13 phage, plasmid pcDNA3.3, pMD18-T, pOptivec, pCMV, pEGFP, pIRES, pQD-Hyg-GSeu, pALTER, pBAD, pcDNA, pCal, pL, pET, pGEMEX, pGEX, pCI, pEGFT, pSV2, pFUSE, pVITRO, pVIVO, pMAL, pMONO, pSELECT, pUNO, pDUO, Psg5L, pBABE, pWPXL, pBI, p15TV-L, pPro18, pTD, pRS10, pLexA, pACT2.2, pCMV-SCRIPT®, pCDM8, pCDNA1.1/amp, pcDNA3.1, pRc/RSV, PCR 2.1, pEF-1, pFB, pSG5, pXT1, pCDEF3, pSVSPORT, pEF-Bos etc.

Vectors comprising the polynucleotide sequence encoding the antibody or antigen-binding fragment can be introduced to a host cell for cloning or gene expression. Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., 8 i E. coli, Enterobacter, Erwinia, Klebsiella, Proteus, Salmonella, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*.

In addition to prokaryotes, eukaryotic microbes such as filamentous fungi or yeast are suitable cloning or expression hosts for anti-LILRB4 antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; Yarrowia* (EP 402,226); *Pichia pastoris* (EP 183,070); *Candida; Trichoderma* reesia (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated antibodies or antigen-fragment provided here are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruiffly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, *petunia*, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. (1977) 36:59); baby hamster kidney cells (BHK, ATCC CCL 10); Chinese Hamster Ovary cells (CHO), CHO cells deficient in dihydrofolate reductase (DHFR) activity, CHO-DHFR (Urlaub et al., Proc. Natl. Acad. Sci. USA (1980) 77:4216); mouse sertoli cells (TM4, Mather, Biol. Reprod. (1980) 23:243-251); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. (1982) 383:44-68); MRC 5 cells; FS4 cells; and a human hepatoma line (Hep G2). In some preferable embodiments, the host cell is 293F cell.

Host cells are transformed with the above-described expression or cloning vectors for anti-LILRB4 antibody production and cultured in conventional nutrient media modified as appropriate for inducing promoters, selecting transformants, or amplifying the genes encoding the desired sequences. In another embodiment, the antibody may be produced by homologous recombination known in the art.

The host cells used to produce the antibodies or antigen-binding fragments provided herein may be cultured in a variety of media. Commercially available media such as Ham's F10 (Sigma), Minimal Essential Medium (MEM) (Sigma), RPMI-1640 (Sigma), and Dulbecco's Modified Eagle's Medium (DMEM), Sigma) are suitable for culturing the host cells. In addition, any of the media described in Ham et al., Meth. Enz. 58:44 (1979), Barnes et al., Anal. Biochem. (1980) 102:255, U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., Bio/Technology (1992) 10:163-167 describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The anti-LILRB4 antibodies and antigen-binding fragments thereof prepared from the cells can be purified using, for example, hydroxylapatite chromatography, gel electrophoresis, dialysis, DEAE-cellulose ion exchange chromatography, ammonium sulfate precipitation, salting out, and affinity chromatography, with affinity chromatography being the preferred purification technique.

In certain embodiments, Protein A immobilized on a solid phase is used for immunoaffinity purification of the antibody and antigen-binding fragment thereof. The suitability of protein A as an affinity ligand depends on the species and isotype of any immunoglobulin Fc domain that is present in the antibody. Protein A can be used to purify antibodies that are based on human gamma1, gamma2, or gamma4 heavy chains (Lindmark et al., J. Immunol. Meth. (1983) 62:1-13). Protein G is recommended for all mouse isotypes and for human gamma3 (Guss et al., EMBO J. (1986)5:1567-75). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies are bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the number of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

III. Pharmaceutical Composition

The present disclosure further provides pharmaceutical compositions comprising the anti-LTLRB4 antibodies or antigen-binding fragments thereof and one or more pharmaceutically acceptable carriers.

Pharmaceutical acceptable carriers for use in the pharmaceutical compositions disclosed herein may include, for example, pharmaceutically acceptable liquid, gel, or solid carriers, aqueous vehicles, nonaqueous vehicles, antimicrobial agents, isotonic agents, buffers, antioxidants, anesthetics, suspending/dispending agents, sequestering or chelating agents, diluents, adjuvants, excipients, or non-toxic auxiliary substances, other components known in the art, or various combinations thereof.

Suitable components may include, for example, antioxidants, fillers, binders, disintegrants, buffers, preservatives, lubricants, flavorings, thickeners, coloring agents, emulsifiers or stabilizers such as sugars and cyclodextrins. Suitable antioxidants may include, for example, methionine, ascorbic acid, EDTA, sodium thiosulfate, platinum, catalase, citric acid, cysteine, thioglycerol, thioglycolic acid, thiosorbitol, butylated hydroxanisol, butylated hydroxytoluene, and/or propyl gallate. As disclosed herein, inclusion of one or more antioxidants such as methionine in a composition comprising an antibody or antigen-binding fragment and conjugates as provided herein decreases oxidation of the antibody or antigen-binding fragment. This reduction in oxidation prevents or reduces loss of binding affinity, thereby improving antibody stability and maximizing shelf-life. Therefore, in certain embodiments compositions are provided that comprise one or more antibodies or antigen-binding fragments as disclosed herein and one or more antioxidants such as methionine. Further provided are methods for preventing oxidation of, extending the shelf-life of, and/or improving the efficacy of an antibody or antigen-binding fragment as provided herein by mixing the antibody or antigen-binding fragment with one or more antioxidants such as methionine.

To further illustrate, pharmaceutical acceptable carriers may include, for example, aqueous vehicles such as sodium chloride injection, Ringer's injection, isotonic dextrose injection, sterile water injection, or dextrose and lactated Ringer's injection, nonaqueous vehicles such as fixed oils of vegetable origin, cottonseed oil, corn oil, sesame oil, or peanut oil, antimicrobial agents at bacteriostatic or fungistatic concentrations, isotonic agents such as sodium chloride or dextrose, buffers such as phosphate or citrate buffers, antioxidants such as sodium bisulfate, local anesthetics such as procaine hydrochloride, suspending and dispersing agents such as sodium carboxymethylcelluose, hydroxypropyl methylcellulose, or polyvinylpyrrolidone, emulsifying agents such as Polysorbate 80 (TWEEN-80), sequestering or chelating agents such as EDTA (ethylenediaminetetraacetic acid) or EGTA (ethylene glycol tetraacetic acid), ethyl alcohol, polyethylene glycol, propylene glycol, sodium hydroxide, hydrochloric acid, citric acid, or lactic acid. Antimicrobial agents utilized as carriers may be added to pharmaceutical compositions in multiple-dose containers that include phenols or cresols, mercurials, benzyl alcohol, chlorobutanol, methyl and propyl p-hydroxybenzoic acid esters, thimerosal, benzalkonium chloride and benzethonium chloride. Suitable excipients may include, for example, water, saline, dextrose, glycerol, or ethanol. Suitable non-toxic auxiliary substances may include, for example, wetting or emulsifying agents, pH buffering agents, stabilizers, solubility enhancers, or agents such as sodium acetate, sorbitan monolaurate, triethanolamine oleate, or cyclodextrin.

The pharmaceutical compositions can be a liquid solution, suspension, emulsion, pill, capsule, tablet, sustained release formulation, or powder. Oral formulations can include standard carriers such as pharmaceutical grades of mannitol, lactose, starch, magnesium stearate, polyvinyl pyrollidone, sodium saccharine, cellulose, magnesium carbonate, etc.

In certain embodiments, the pharmaceutical compositions are formulated into an injectable composition. The injectable pharmaceutical compositions may be prepared in any conventional form, such as for example liquid solution, suspension, emulsion, or solid forms suitable for generating liquid solution, suspension, or emulsion. Preparations for injection may include sterile and/or non-pyretic solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use, and sterile and/or non-pyretic emulsions. The solutions may be either aqueous or nonaqueous.

In certain embodiments, unit-dose parenteral preparations are packaged in an ampoule, a vial or a syringe with a needle. All preparations for parenteral administration should be sterile and not pyretic, as is known and practiced in the art.

In certain embodiments, a sterile, lyophilized powder is prepared by dissolving an antibody or antigen-binding fragment as disclosed herein in a suitable solvent. The solvent may contain an excipient which improves the stability or other pharmacological components of the powder or reconstituted solution, prepared from the powder. Excipients that may be used include, but are not limited to, water, dextrose, sorbital, fructose, corn syrup, xylitol, glycerin, glucose, sucrose or other suitable agents. The solvent may contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides a desirable formulation. In one embodiment, the resulting solution will be apportioned into vials for lyophilization. Each vial can contain a single dosage or multiple dosages of the anti-LILRB4 antibody or antigen-binding fragment thereof or composition thereof. Overfilling vials with a small amount above that needed for a dose or set of doses (e.g., about 10%) is acceptable so as to facilitate accurate sample withdrawal and accurate dosing. The lyophilized powder can be stored under appropriate conditions, such as at about 4° C. to room temperature.

Reconstitution of a lyophilized powder with water for injection provides a formulation for use in parenteral administration. In one embodiment, for reconstitution the sterile and/or non-pyretic water or other liquid suitable carrier is added to lyophilized powder. The precise amount depends upon the selected therapy being given, and can be empirically determined.

IV. Methods of Use of Anti-LILRB4 Antibodies

The present disclosure also provides therapeutic methods comprising: administering a therapeutically effective amount of the antibody or antigen-binding fragment as provided herein to a subject in need thereof, thereby treating or preventing a LILRB4-related condition or a disorder. In some embodiment, the LILRB4-related condition or a disorder is cancer, autoimmune disease, inflammatory disease, or infectious disease.

Examples of cancer can be generally categorized into solid tumors and hematologic malignancies. Solid tumors include but are not limited to, non-small cell lung cancer (squamous/non-squamous), small cell lung cancer, renal cell cancer, colorectal cancer, colon cancer, ovarian cancer, breast cancer (including basal breast carcinoma, ductal carcinoma and lobular breast carcinoma), pancreatic cancer, gastric carcinoma, bladder cancer, esophageal cancer, mesothelioma, melanoma, head and neck cancer, thyroid cancer, sarcoma, prostate cancer, glioblastoma, cervical cancer, thymic carcinoma, melanoma, multiple myeloma, mycoses fungoides, Merkel cell cancer, hepatocellular carcinoma (HCC), fibrosarcoma, myxosarcoma, liposarcoma, chondrosarcoma, osteogenic sarcoma, and other sarcomas, synovioma/synovial sarcoma, mesothelioma, Ewing's sarcoma, leiomyosarcoma, rhabdomyosarcoma, basal cell carcinoma, adenocarcinoma, sweat gland carcinoma, medullary thyroid carcinoma, papillary thyroid carcinoma, pheochromocytoma, sebaceous gland carcinoma, papillary carcinoma, papillary adenocarcinomas, medullary carcinoma, bronchogenic carcinoma, hepatoma, bile duct carcinoma, choriocarcinoma, Wilms' tumor, cervical cancer, testicular tumor, seminoma, mast cell derived tumors, EBV-positive and -negative PTLD, nasopharyngeal carcinoma, spinal axis tumor, brain stem glioma, astrocytoma, medulloblastoma, craniopharyogioma, ependymoma, pinealoma, hemangioblastoma, acoustic neuroma, oligodendroglioma, meningioma, melanoma, neuroblastoma and retinoblastoma.

Solid tumors are characterized by multiple biologic hallmarks including sustaining proliferative signaling, evading growth suppressors, resisting cell death, enabling replicative immortality, inducing angiogenesis, activating invasion and metastasis, tumor promoting inflammation, avoiding immune destruction, genomic instability and mutation, and deregulating cellular energetics. Treatment efforts have evolved from cytotoxic chemotherapies targeting rapidly dividing cells to small molecules inhibiting select signaling pathways to monoclonal antibodies targeting surface proteins. More recently the concept of cancer immunotherapy to reinvigorate endogenous immunity or cellular therapies utilizing synthetic immunity have shown promise. Despite these advances, most patients with advanced solid tumors still do not survive long-term. The use of immune checkpoint inhibitors such as anti-CTLA-4 or anti-PD-1/PD-L1 have led to long-term progression-free and overall survival in a minority of patients.

Newer immunotherapy approaches targeting different aspects of immune biology and different tumor-infiltrating cells are needed to improve outcomes, such as those targeting LILRB4 as an inhibitory receptor expressed on subset of myeloid cells, including myeloid derived suppressor cells (MDSC). These myeloid cells are described functionally as myeloid derived suppressive cells because their immune suppressive/anti-inflammatory phenotype can inhibit the activation, proliferation and cytotoxic activity of tumor antigen-specific T cells.

In some embodiments, depleting MDSC may revert the suppressive effect on tumor antigen-specific T cells for solid tumor treatment.

In some embodiments, blocking LILRB4 on myeloid cells could also unlock its inhibitory effects on antigen presentation cells (APCs), including dendritic cells or myeloid leukemia cells which express LILRB4. Increased antigen presenting activity can be observed by certain cytokines produced APCs, and can leads to T cell activation, cytotoxicity and T cell cytokine production.

Hematologic malignancies include but are not limited to acute lymphocytic/lymphoblastic leukemia (ALL), acute myeloid leukemia (AML), B-cell leukemia, blastic plasmacytoid dendritic cell neoplasm (BPDCN), chronic lymphoblastic leukemia (CLL), chronic lymphocytic leukemia (CLL), chronic myeloid leukemia (CML), chronic myelomonocytic leukemia (CMML), classical Hodgkin lymphoma (CHL), diffuse large B-cell lymphoma (DLBCL), extranodal NK/T-cell lymphoma, hairy cell leukemia, heavy chain disease, HHV8-associated primary effusion lymphoma, lymphoid malignancy, multiple myeloma (MM), myelodysplasia, myelodysplastic syndrome (MDS), non-Hodgkin's lymphoma, plasmablastic lymphoma, pre-B acute lymphocytic leukemia (Pre-B ALL), primary CNS lymphoma, primary mediastinal large B-cell lymphoma, T-cell/histiocyte-rich B-cell lymphoma, myeloproliferative neoplasms, and Waldenstrom's macroglobulinemia.

Autoimmune or inflammatory diseases include, but are not limited to, Acquired Immunodeficiency Syndrome (AIDS, which is a viral disease with an autoimmune component), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, CREST syndrome, Crohn's disease, Degos' disease, dermatomyositis-juvenile, discoid lupus, essential mixed cryoglobulinemia, fibromyalgia-fibromyositis, Graves' disease, Guillain-Barre syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Meniere's disease, mixed connective tissue disease, multiple sclerosis, myasthenia gravis, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma, systemic scleroderma, progressive systemic sclerosis (PSS), systemic sclerosis (SS), Sjogren's syndrome, stiff-man syndrome, systemic lupus erythematosus (SLE), Takayasu arteritis, temporal arteritis/giant cell arteritis, inflammatory bowel disease (IBD), ulcerative colitis, Cohn's disease, intestinal mucosal inflammation, wasting disease associated with colitis, uveitis, vitiligo and Wegener's granulomatosis, Alzheimer's disease, asthma, atopic allergy, allergy, atherosclerosis, bronchial asthma, eczema, glomerulonephritis, graft vs. host disease, hemolytic anemias, osteoarthritis, sepsis, stroke, transplantation of tissue and organs, vasculitis, diabetic retinopathy, ventilator induced lung injury, viral infections, autoimmune diabetes and the like. Inflammatory disorders, include, for example, chronic and acute inflammatory disorders.

Infectious disease include, but are not limited to, fungus infection, parasite/protozoan infection or chronic viral infection, for example, malaria, coccidioiodmycosis immitis, histoplasmosis, onychomycosis, aspergillosis, blastomycosis, candidiasis albicans, paracoccidiodomycosis, microsporidiosis, *Acanthamoeba keratitis*, Amoebiasis, Ascariasis, Babesiosis, Balantidiasis, Baylisascariasis, Chagas disease, Clonorchiasis, *Cochliomyia*, Cryptosporidiosis, Diphyllobothriasis, Dracunculiasis, Echinococcosis, Elephantiasis, Enterobiasis, Fascioliasis, Fasciolopsiasis, Filariasis, Giardiasis, Gnathostomiasis, Hymenolepiasis, Isosporiasis, Katayama fever, Leishmaniasis, Lyme disease, Metagonimiasis, Myiasis, Onchocerciasis, Pediculosis, Scabies, Schistosomiasis, Sleeping sickness, Strongyloidiasis, Taeniasis, Toxocariasis, Toxoplasmosis, Trichinosis, Trichuriasis, Trypanosomiasis, helminth infection, infection of hepatitis B (HBV), hepatitis C (HCV), herpes virus, Epstein-Barr virus, HIV, cytomegalovirus, herpes simplex virus type I, herpes simplex virus type II, human papilloma virus, adenovirus, human immunodeficiency virus I, human immunodeficiency virus II, Kaposi West sarcoma associated herpes virus epidemics, thin ring virus (Torquetenovirus), human T lymphotrophic virus I, human T lymphotrophic virus II, varicella zoster, JC virus or BK virus.

The therapeutically effective amount of an antibody or antigen-binding fragment as provided herein will depend on various factors known in the art, such as for example body weight, age, past medical history, present medications, state of health of the subject and potential for cross-reaction, allergies, sensitivities and adverse side-effects, as well as the administration route and extent of disease development. Dosages may be proportionally reduced or increased by one of ordinary skill in the art (e.g., physician or veterinarian) as indicated by these and other circumstances or requirements.

In certain embodiments, the antibody or antigen-binding fragment as provided herein may be administered at a therapeutically effective dosage of about 0.0001 mg/kg to about 100 mg/kg. In certain of these embodiments, the antibody or antigen-binding fragment is administered at a dosage of about 50 mg/kg or less, and in certain of these embodiments the dosage is 10 mg/kg or less, 5 mg/kg or less, 3 mg/kg or less, 1 mg/kg or less, 0.5 mg/kg or less, or 0.1 mg/kg or less. In certain embodiments, the administration dosage may change over the course of treatment. For example, in certain embodiments the initial administration dosage may be higher than subsequent administration dosages. In certain embodiments, the administration dosage may vary over the course of treatment depending on the reaction of the subject.

Dosage regimens may be adjusted to provide the optimum desired response (e.g., a therapeutic response). For example, a single dose may be administered, or several divided doses may be administered over time.

The antibodies and antigen-binding fragments disclosed herein may be administered by any route known in the art, such as for example parenteral (e.g., subcutaneous, intraperitoneal, intravenous, including intravenous infusion, intramuscular, or intradermal injection) or non-parenteral (e.g., oral, intranasal, intraocular, sublingual, rectal, or topical) routes.

In some embodiments, the antibodies or antigen-binding fragments disclosed herein may be administered alone or in combination with one or more additional therapeutic means or agents. For example, the antibodies or antigen-binding fragments disclosed herein may be administered in combination with another therapeutic agent, for example, a chemotherapeutic agent or an anti-cancer drug.

In certain of these embodiments, an antibody or antigen-binding fragment as disclosed herein that is administered in combination with one or more additional therapeutic agents may be administered simultaneously with the one or more additional therapeutic agents, and in certain of these embodiments the antibody or antigen-binding fragment and the additional therapeutic agent(s) may be administered as part of the same pharmaceutical composition. However, an antibody or antigen-binding fragment administered "in combination" with another therapeutic agent does not have to be administered simultaneously with or in the same composition as the agent. An antibody or antigen-binding fragment administered prior to or after another agent is considered to be administered "in combination" with that agent as the phrase is used herein, even if the antibody or antigen-binding fragment and second agent are administered via different routes. Where possible, additional therapeutic agents administered in combination with the antibodies or antigen-binding fragments disclosed herein are administered according to the schedule listed in the product information sheet of the additional therapeutic agent, or according to the Prescriber's Digital Reference (available online only at pdr.net) or protocols well known in the art.

Particular agents contemplated for combination therapy with antibodies of the present disclosure include chemotherapy. Chemotherapy may include cytarabine (ara-C) and an anthracycline (most often daunorubicin), high-dose cytarabine alone, all-trans-retinoic acid (ATRA) in addition to induction chemotherapy, usually an anthracycline, histamine dihydrochloride (Ceplene) and interleukin 2 (Proleukin) after the completion of consolidation therapy, gemtuzumab ozogamicin (Mylotarg) for patients aged more than 60 years with relapsed AML who are not candidates for high-dose chemotherapy, clofarabine, as well as targeted therapies, such as kinase inhibitors, farnesyl transferase inhibitors, decitabine, and inhibitors of MDR1 (multidrug-resistance protein), or arsenic trioxide or relapsed acute promyelocytic leukemia (APL).

In certain embodiments, the agents for combination therapy are one or more drugs selected from the group consisting of a topoisomerase inhibitor, an anthracycline topoisomerase inhibitor, an anthracycline, a daunorubicin, a nucleoside metabolic inhibitor, a cytarabine, a hypomethylating agent, a low dose cytarabine (LDAC), a combination of daunorubicin and cytarabine, a daunorubicin and cytarabine liposome for injection, Vyxeos®, an azacytidine/azacitidine, Vidaza®, a decitabine, an all-trans-retinoic acid (ATRA), an arsenic, an arsenic trioxide, a histamine dihydrochloride, Ceplene®, an interleukin-2, an aldesleukin, Proleukin®, a gemtuzumab ozogamicin, Mylotarg®, an FLT-3 inhibitor, a midostaurin, Rydapt®, a clofarabine, a farnesyl transferase inhibitor, a decitabine, an IDH1 inhibitor, an ivosidenib, Tibsovo®, an IDH2 inhibitor, an enasidenib, Idhifa®, a smoothened (SMO) inhibitor, a glasdegib, an arginase inhibitor, an IDO inhibitor, an epacadostat, a BCL-2 inhibitor, a venetoclax, Venclexta®, a platinum complex derivative, oxaliplatin, a kinase inhibitor, a tyrosine kinase inhibitor, a PI3 kinase inhibitor, a BTK inhibitor, an ibrutinib, IMBRUVICA®, an acalabrutinib, CALQUENCE®, a zanubrutinib, a PD-1 antibody, a PD-L1 antibody, a CTLA-4 antibody, a LAG3 antibody, an ICOS antibody, a TIGIT antibody, a TIM3 antibody, a CD40 antibody, a 4-1BB antibody, a CD47 antibody, a SIRP1α antibody or fusions protein, an antagonist of E-selectin, an antibody binding to a tumor antigen, an antibody binding to a T-cell surface marker, an antibody binding to a myeloid cell or NK cell surface marker, an alkylating agent, a nitrosourea agent, an antimetabolite, an antitumor antibiotic, an alkaloid derived from a plant, a hormone therapy medicine, a hormone antagonist, an aromatase inhibitor, and a P-glycoprotein inhibitor.

In certain embodiments, the LILRB4-related condition or a disorder is acute myeloid leukemia (AML), Acute Myelomonocytic Leukemia (FAB M4) subtype and Acute Monoblastic/Monocytic Leukemia (FAB M5) subtype.

In certain embodiments, AML that is resistant or refractory to standard of care treatment such as venetoclax and azacytidine/azacitidine.

AML is an aggressive malignancy with poor prognosis. In the World Health Organization (WHO) classification, acute myelomonocytic leukemia (M4 in the French-American-British [FAB] classification) and acute monoblastic/monocytic leukemia (M5 in the FAB classification) are subtypes of AML, Not Otherwise Specified (AML, NOS).

Acute myelomonocytic leukemia in the WHO system (FAB M4) has blasts consisting of myeloblasts, monoblasts, and promonocytes (total of ≥20%), and ≥20% to 79% of monocytic lineage. Acute monoblastic/monocytic leukemia (FAB M5) has monoblasts/promonocytes ≥20%, and ≥280% of marrow cells with monocytic features. Acute myelomonocytic leukemia (M4) and acute monocytic leukemia (M5) account for approximately 20% and 10% of all cases of AML, respectively (Ganzel et al., 2016). AML patients with a significant monocytic component are more likely to have evidence of extramedullary disease (Ganzel et al., 2016) and hyperleukocytosis (defined as $\geq 100\times10^3/\mu L$ white blood cells in the peripheral blood) (Rollig and Ehninger, 2015).

LILRB4 is expressed on AML cells with monocytic differentiation (Deng et al., 2018; Dobrowolska et al., 2013) and CMML (Chien et al., 2019). The expression level of LILRB4 may be equivalent to normal monocytes or up to 10-fold higher on AML blasts with monocytic differentiation (Deng et al., 2018). Moreover, both functional and immunophenotypic studies suggest that LILRB4 is expressed by leukemic stem cells from monocytic AML (Deng et al., 2018).

In 2008, AZA was approved by the European Medicines Agency (EMA) for the treatment of AML patients with 20% to 30% bone marrow (BM) blasts, older than 64 years and who are ineligible for hematopoietic stem cell transplant (HSCT). Hematologists at specialized centers started treating AML patients with >30% BM blasts with AZA as early as 2007, indicating that the physicians were convinced they were doing the best for their patients. This assumption was based on the significant improvement of overall survival (OS) obtained in the AZA-MDS-001 trial and the Cancer and Leukemia Group B protocols, in which 32% and 38% of the trial population had AML with 20% to 30% BM blasts, respectively.

In 2010, the international phase 3 randomized AZA-AML-001 clinical trial testing AZA versus conventional care regimens (CCR) (intensive chemotherapy, low-dose cytarabine or best supportive care as preselected by the treating physician) in AML patients older than 65 years with newly-diagnosed AML, >30% BM blasts and $\leq 15\times10^9$/L white blood cell (WBC) count was initiated. In this trial, a clinically meaningful improvement in OS for AZA versus CCR (10.4 vs. 6.5 months; p=0.1009) was reported. Additionally, the overall response (complete remission [CR]+complete remission with incomplete blood count recovery [CRi]) rates were comparable in the AZA (27.8%) and CCR (25.1%) arms (P=0.5384) and the EMA approval of AZA was expanded on 30 Oct. 2015 to include AML patients with >30% BM blasts.

In certain embodiments, the LILRB4-related condition or a disorder is Chronic Myelomonocytic Leukemia (CMML).

CMML diagnostic classification is based on clinical examination, morphology, cytogenetics, and, whenever possible, flow cytometry and molecular biology should be integrated to classify patients according to WHO 2016 categories. WHO classification (Arber et al., 2016) includes CMML-0 for cases with <2% blasts in peripheral blood and <5% blasts in BM; CMML-1 for cases with 2% to 4% blasts in peripheral blood and/or 5% to 9% blasts in BM; and CMML-2 for cases with 5% to 19% blasts in peripheral blood, 10% to 19% in BM, and/or when Auer rods are present.

The distinction between "dysplastic" CMML and "proliferative" CMML initially proposed by the FAB classification based on a WBC cutoff of $13\times10^9$/L remains useful, as their clinical features differ (cytopenia vs. organomegaly, high WBC, and constitutional symptoms), and consequently, their clinical management.

Extramedullary leukemia, apart from splenomegaly and hepatomegaly, mainly includes specific serous effusions (pleural and less often pericardial or peritoneal) and specific cutaneous infiltration, all associated with worse prognosis.

VIDAZA® (azacitidine) is a nucleoside metabolic inhibitor indicated for the treatment of patients with the following FAB myelodysplastic syndrome (MDS) subtypes: Refractory anemia or refractory anemia with ringed sideroblasts (if accompanied by neutropenia or thrombocytopenia or requiring transfusions), refractory anemia with excess blasts, refractory anemia with excess blasts in transformation, and chronic myelomonocytic leukemia (CMML).

The present disclosure further provides methods of using the anti-LILRB4 antibodies or antigen-binding fragments thereof to detect presence or amount of LILRB4 in a sample, comprising contacting the sample with the antibody or antigen-binding fragment thereof, and determining the presence or the amount of LILRB4 in the sample. The method of detecting LILRB4 using an anti-LILRB4 antibody includes, without limitation, ELISA, Western-blot, flow cytometry and FACS.

In some embodiments, the present disclosure provides methods of diagnosing a LILRB4 related disease or condition in a subject, comprising: a) contacting a sample obtained from the subject with the antibody or antigen-binding fragment thereof provided herein; b) determining presence or amount of LILRB4 in the sample; and c) correlating the existence of the LILRB4 to the LILRB4 related disease or condition in the subject.

In some embodiments, the present disclosure provides kits comprising the antibody or antigen-binding fragment thereof provided herein, optionally conjugated with a detectable moiety. The kits may be useful in detection of LILRB4 or diagnosis of LILRB4 related disease.

In some embodiments, the present disclosure also provides use of the antibody or antigen-binding fragment thereof provided herein in the manufacture of a medicament for treating a LILRB4 related disease or condition in a subject, in the manufacture of a diagnostic reagent for diagnosing a LILRB4 related disease or condition.

V. Chimeric Antigen Receptors

The present disclosure in another aspect provides a chimeric antigen receptor (CAR) protein that binds LILRB4 (LILRB4 CAR protein). In certain embodiments, the CAR protein comprises an antigen recognition region, i.e., an antibody or antigen-binding fragment that recognizes LILRB4 as described herein, and other membrane and intracellular components. In some embodiments, the LILRB4 CAR protein comprises a LILRB4 antigen recognition region, a transmembrane domain and an intracellular co-stimulatory signal domain. In certain embodiments, the single chain LILRB4 CAR protein also comprises a leader peptide, a spacer region and an intracellular T cell signaling domain.

In certain embodiments, the antigen recognition region comprises multiple polypeptide chains.

In some embodiments, the CAR protein comprises a first polypeptide including an antibody heavy chain variable domain and a polypeptide including an antibody light chain variable domain, wherein the first or the second polypeptide further includes a transmembrane domain, and wherein the antibody heavy chain variable domain and the antibody light chain variable domain together form an antigen recognition region.

In some embodiments, the CAR protein comprises a first polypeptide including an antibody heavy chain variable domain and a second polypeptide including an antibody light chain variable domain and an antibody light chain constant domain, wherein the first polypeptide further includes a transmembrane domain, and wherein the antibody heavy chain variable domain, the antibody light chain variable domain and the antibody light chain constant domain together form an antigen recognition region. In some embodiments, the first portion further includes an intracellular co-stimulatory signaling domain and a CD3ζ intracellular T cell signaling domain.

In some embodiments, the CAR protein comprises a first polypeptide including an antibody heavy chain variable domain and an antibody heavy chain constant domain, and a second polypeptide including an antibody light chain variable domain, wherein the first polypeptide further includes a transmembrane domain, and wherein the antibody heavy chain variable domain, the antibody heavy chain constant domain, and the antibody light chain variable domain together form an antigen recognition region. In some embodiments, the first portion further includes an intracellular co-stimulatory signaling domain and a CD3ζ intracellular T cell signaling domain.

In some embodiments, the CAR protein comprises a first polypeptide including an antibody heavy chain variable domain and a second polypeptide including an antibody light chain variable domain, wherein the second polypeptide further includes a transmembrane domain, and wherein the antibody heavy chain variable domain, the antibody light chain variable domain and the antibody light chain constant domain together form an antigen recognition region. In some embodiments, the second portion further includes an intracellular co-stimulatory signaling domain and a CD3ζ intracellular T cell signaling domain.

In some embodiments, the CAR protein comprises a first polypeptide including an antibody heavy chain variable domain and an antibody heavy chain constant domain, and a second polypeptide including an antibody light chain variable domain, wherein the second polypeptide further includes a transmembrane domain, and wherein the antibody heavy chain variable domain, the antibody heavy chain constant domain, and the antibody light chain variable domain together form an antigen recognition region. In some embodiments, the second portion further includes an intracellular co-stimulatory signaling domain and a CD3ζ intracellular T cell signaling domain.

In certain embodiments, the CAR protein is a single chain polypeptide that comprises an anti-LILRB4 scFv as described herein, i.e., an anti-LILRB4 heavy chain variable domain and an anti-LILRB4 light chain variable domain, which are linked by a linker domain. In one embodiment, the CAR protein includes from the N-terminus to the C-terminus: a leader peptide, an anti-LILRB4 heavy chain variable domain, a linker domain, an anti-LILRB4 light chain variable domain, a hinge region, a transmembrane domain, an intracellular co-stimulatory signal domain. In one embodiment, the CAR protein includes from the N-terminus to the C-terminus: a leader peptide, an anti-LILRB4 light chain variable domain, a linker domain, an anti-LILRB4 heavy chain variable domain, a hinge region, a transmembrane domain, an intracellular co-stimulatory signal domain. In some embodiments, the CAR protein further includes a CD3ζ intracellular T cell signaling domain.

In certain embodiment, the linker domain generally is comprised of helix- and turn-promoting amino acid residues such as alanine, serine and glycine. However, other residues can function as well. In some embodiment, the linker domain is inserted between the VH and VL of the scFv. In some embodiments, the linker domain is between the transmembrane domain and the intracellular co-stimulatory signaling domain. In some embodiments, the linker domain is between the intracellular T cell signaling domain and the intracellular co-stimulatory signaling domain. In some embodiments, the linker domain comprises the sequence GGGGSGGGGSGGGGS (SEQ ID NO: 70).

In some embodiments, the transmembrane domain is a CD8a transmembrane domain which has at least 90%, 95%, 96%, 97%, 98%, 99% or 100% amino acid sequence identity compared to a naturally occurring CD8a transmembrane domain polypeptide (SEQ ID NO: 71). In some embodiments, the CD8a transmembrane domain is encoded by the nucleic acid sequence of SEQ ID NO: 72.

In some embodiments, the transmembrane domain is a CD28 transmembrane domain which has at least 90%, 95%, 96%, 97%, 98%, 99% or 100% amino acid sequence identity compared to a naturally occurring CD28 transmembrane domain polypeptide (SEQ ID NO: 73). In some embodiments, the CD28 transmembrane domain is encoded by the nucleic acid sequence of SEQ ID NO: 74.

The intracellular co-stimulatory signaling domain includes amino acid sequences capable of providing co-stimulatory signaling in response to binding of an antigen to the CAR. In some embodiments, the signaling of the costimulatory signaling domain results in the production of cytokines and proliferation of the T cell or NK cell expressing the same. In some embodiments, the intracellular co-stimulatory signaling domain is a CD28 intracellular co-stimulatory signaling domain, a 4-1BB intracellular co-stimulatory signaling domain, an ICOS intracellular co-stimulatory signaling domain, an OX-40 intracellular co-stimulatory signaling domain or any combination thereof. In some embodiments, the CD28 co-stimulating domain has the polypeptide sequence of SEQ ID NO: 75. In some embodiments, the CD28 intracellular co-stimulatory signaling domain is encoded by the nucleic acid sequence of SEQ ID NO: 76. In some embodiments, the 4-1BB intracellular co-stimulatory signaling domain has the polypeptide sequence of SEQ ID NO: 77. In some embodiments, the 4-1BB intracellular co-stimulatory signaling domain is encoded by the nucleic acid sequence of SEQ ID NO: 78.

A "hinge region" as provided herein is a polypeptide connecting the antigen-binding region with the transmembrane domain. In some embodiments, the hinge region connects a heavy chain variable region with the transmembrane domain. In some embodiments, the hinge region connects a heavy chain constant region with the transmembrane domain. In some embodiments, the hinge region connects a light chain variable region with the transmembrane domain. In some embodiments, the hinge region connects a light chain constant region with the transmembrane domain. In some embodiments, the binding affinity of the antigen-binding region to an antigen is increased compared to the absence of the hinge region. In some embodiments, the steric hindrance between an antigen-binding region and an antigen is decreased in the presence of the hinge region. In some embodiments, the hinge region is a CD8a hinge region. In some embodiments, the hinge region is a CD28 hinge region.

In some embodiments, the intracellular T cell signaling domain includes the signaling domain of the zeta (ζ) chain of the human CD3 complex, i.e., a CD3ζ intracellular T cell signaling domain. In some embodiments, the intracellular T cell signaling domain is the protein CD3zIso1 with the amino acid sequence of SEQ ID No: 79. In some embodiments, the intracellular T cell signaling domain is the protein CD3zIso3 with the amino acid sequence of SEQ ID No: 80, encoded by the nucleic acid sequence of SEQ ID NO: 81.

In one example, the CAR protein is a single chain polypeptide that includes from the N-terminus to the C-terminus: a CD8a leader peptide, an anti-LILRB4 scFv, a CD8a hinge region, a CD8a transmembrane domain (or a CD28 transmembrane domain), a 4-1BB intracellular co-stimulatory signaling domain (or a CD28 intracellular co-stimulatory signaling domain, or a CD28 intracellular co-stimulatory signaling domain followed by a 4-1BB intracellular co-stimulatory signaling domain) and a CD3ζ intracellular T cell signaling domain in one of two isoforms (CD3zIso1 or CD3zIso3).

In certain embodiments, the LILRB4 CAR protein provided herein demonstrates a high affinity to LTLRB4. In certain embodiments, the CAR protein provided herein has a binding affinity to LILRB4 ($EC_{50}$ as measured by ELISA) of less than 1 nM, 0.9 nM, 0.8 nM, 0.7 nM, 0.6 nM, 0.5 nM, 0.4 nM, 0.3 nM, 0.2 nM, 0.1 nM, 0.09 nM, 0.08 nM, 0.07 nM, 0.06 nM or 0.05 nM. For the purposes of this application, ELISA $EC_{50}$ values may be determined as follows. LILRB-4 extracellular domain protein (with 6 HIS tag at the C-terminus) was produced recombinantly in HEK293 cells and coated onto a high binding 96-well clear plate (Corning-Costar, Fisher Scientific) at 1 μg/ml concentration (100 μl/well) at 4° C. for 14 to 16 hours. The coated plates were washed with PBS, pH 7.4, briefly and blocked with 200 μl/well of 5% non-fat milk in PBS for 2 hours at 37° C. Serial dilutions of the testing monoclonal antibodies (IgGs or scFvs fragments), starting from 10 μg/ml and 3-fold titration down for 12 steps, were added to the 96-well plate for binding by incubating 45 minutes at 37° C. with a cover on the assay plate. Then the plates were washed with PBS containing Tween 20 (0.05% concentration) for 3 times and PBS one time. Secondary antibody of anti-human or anti-rabbit, or other species IgG specific antibodies with HRP conjugate (Jackson ImmunoResearch) was added for incubation at room temperature for 1 hour per manufacturer's suggested dilution. Detection was conducted by adding HRP substrate, TMB (ThermoFisher) for 10 minutes, and stopped by adding 50 μl/well of 2N $H_2SO_4$. The plates were read for absorbance at 450 nm using a plate reader (SpectraMax M4, Molecular Devices). Data were collected and graphed using a 4-parameter fitting curve with GrapPad Prism 7 software for $EC_{50}$ calculation.

In another aspect, the present disclosure provides a polynucleotide molecule encoding a CAR protein described herein. In some embodiments, the polynucleotide molecule further comprises a promoter active in eukaryotic cells. In some embodiments, the promoter is the JeT promoter. The JeT promoter is a recombinant promoter with transcriptional activity comparable to a number of strong mammalian promoters. The JeT promoter consists of five key elements: (1) a TATA box; (2) a transcription initiation site (Inr); (3) a CAT consensus sequence in conjunction with (4) a CArG element and finally, (5) four Spl transcription binding sites (GGGCGG) arranged in two tandems (US 2002/0098547 A1). In some embodiments, the polynucleotide molecule is an expression vector. In some embodiment, the vector is generated based on pLVX-EF1alpha-IRES-ZsGreen from Clontech, or pSIN-EF1alpha-IRES-Puromycin or pSIN-EF1alpha. In one example, the polynucleotide molecule of the present disclosure comprises the following elements sequentially: (1) JeT promoter; (2) sequence encoding a CD8-alpha leader; (3) sequence encoding a heavy chain variable region; (4) sequence encoding a linker; (5) sequence encoding a light chain variable region; (6) sequence encoding a CD8 hinge and TM domain; (7) sequence encoding a 4-1BB co-stimulatory domain; (8) sequence encoding a CD3-zeta activation domain. In one example, the elements described above are flanked by 5' and 3' homologous arms that facilitate the insertion of the polynucleotide molecule to a target locus, e.g., T cell receptor alpha constant (TRAC) locus.

VI. Engineered Cells Expressing Anti-LILRB4 CAR Protein

In another aspect, the present disclosure provides engineered immune cells which express a CAR protein described herein. The immune cells may be T cells (e.g., regulatory T cells, CD4+ T cells, CD8+ T cells, or gamma-delta T cells), Natural Killer (NK) cells, invariant NK cells, NKT cells, or macrophages. Also provided herein are methods of producing and engineering the immune cells as well as methods of using and administering the cells for adoptive cell therapy, in which case the cells may be autologous or allogeneic. Thus, the engineered immune cells may be used as immunotherapy, such as to target cancer cells.

Expressing the CAR protein allows the engineered immune cells to bind to a target cell, such as a cancer cell, by recognizing an antigen present on the target cell. Upon binding to the target cell, the engineered immune cell becomes activated, then proceed to proliferate and become cytotoxic, eventually destroys the target cell. CAR-T cell immunotherapy has demonstrated success in clinical trials and been approved by U.S. FDA to treat refractory B-cell acute lymphoblastic leukemia and B-cell non-Hodgkin lymphoma (Hartmann J et al., EMBO Mol Med (2017) 9:1183-97). CAR NK cells and CAR macrophages have been developed recently as immunotherapy options in addition to CAR-T cells (Kloess S et al., Transfusion Medicine and Hemotherapy (2019) 46:4-13; Klichinsky M et al., AACR Annual Meeting 2017, Abstract 4575). Therefore, in certain embodiments of the present disclosure, the immune cells that express the CAR protein described herein are T cells, NK cells or macrophages.

The immune cells may be isolated from subjects, particularly human subjects. The immune cells can be obtained from a subject of interest, such as a subject suspected of having a particular disease or condition, a subject suspected of having a predisposition to a particular disease or condition, a subject who is undergoing therapy for a particular disease or condition, a subject who is a healthy volunteer or healthy donor, or from blood bank. Immune cells can be collected from any location in which they reside in the subject including, but not limited to, blood, cord blood, spleen, thymus, lymph nodes, and bone marrow. The isolated immune cells may be used directly, or they can be stored for a period of time, such as by freezing.

The immune cells may be enriched/purified from any tissue where they reside including, but not limited to, blood (including blood collected by blood banks or cord blood banks), spleen, bone marrow, tissues removed and/or exposed during surgical procedures, and tissues obtained via biopsy procedures. Tissues/organs from which the immune cells are enriched, isolated, and/or purified may be isolated from both living and non-living subjects, wherein the non-living subjects are organ donors. In particular embodiments, the immune cells are isolated from blood, such as peripheral blood or cord blood. In some aspects, immune cells isolated from cord blood have enhanced immunomodulation capacity, such as measured by CD4- or CD8-positive T cell suppression. In specific aspects, the immune cells are isolated from pooled blood, particularly pooled cord blood, for enhanced immunomodulation capacity. The pooled blood may be from 2 or more sources, such as 3, 4, 5, 6, 7, 8, 9, 10 or more sources (e.g., donor subjects).

The population of immune cells can be obtained from a subject in need of therapy or suffering from a disease associated with reduced immune cell activity. Thus, the cells will be autologous to the subject in need of therapy. Alternatively, the population of immune cells can be obtained from a donor, preferably a histocompatibility matched donor. The immune cell population can be harvested from the peripheral blood, cord blood, bone marrow, spleen, or any other organ/tissue in which immune cells reside in said subject or donor. The immune cells can be isolated from a pool of subjects and/or donors, such as from pooled cord blood.

When the population of immune cells is obtained from a donor distinct from the subject, the donor is preferably allogeneic, provided the cells obtained are subject-compatible in that they can be introduced into the subject. Allogeneic donor cells may or may not be human-leukocyte-antigen (HLA)-compatible. To be rendered subject-compatible, allogeneic cells can be treated to reduce immunogenicity.

The immune cells can be genetically engineered to express the CARs using suitable methods of modification are known in the art. See, for instance, Sambrook and Ausubel, CURRENT PROTOCOLS IN MOLECULAR BIOLOGY, Greene Publishing Associates and John Wiley & Sons, N Y, 1994. In some embodiments, the immune cells comprise one or more nucleic acids introduced via genetic engineering that encode one or more CAR proteins. In certain embodiments, the nucleic acids encoding the CAR proteins are inserted in the genome of the immune cells using gene editing methods, e.g. CRISPR/Cas technology. In one example, the nucleic acids encoding the CAR proteins are inserted at the T-cell receptor alpha constant (TRAC) locus (see, e.g., Eyquem J et al., *Nature* (2017) 543:113-117).

Also provided are methods for immunotherapy comprising administering an effective amount of the immune cells of the present disclosure. In some embodiments, a medical disease or disorder is treated by transfer of a population of immune cells described herein that elicits an immune response. In certain embodiments, the medical disease or disorder is a cancer. In certain embodiments, the medical disease or disorder is an autoimmune or inflammatory disease.

The following examples are provided to better illustrate the claimed invention and are not to be interpreted as limiting the scope of the invention. All specific compositions, materials, and methods described below, in whole or in part, fall within the scope of the present invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the present invention. It is the intention of the inventors that such variations are included within the scope of the invention.

Example 1

Materials and Methods

SEC: The procedure of size exclusion chromatography (SEC) is as follows. Dilute sample to 10.0 mg/mL with mobile phase before SEC analysis if the sample concentration is above 10.0 mg/mL. 100 μg of sample was injected into column. The equipment used was the Agilent 1260 HPLC system with a TSKgel G3000SWXL column (7.8× 300 mm, 5 μm particle size) and a UV detector (detection wavelength: 280 nm). Mobile phase was 50 mM phosphate buffer with 300 mM Sodium Chloride (pH 6.8±0.1). An isocratic gradient was applied for 20 min at a flow rate of 1.0 mL/min.

Imaged Capillary Isoelectric Focusing (icIEF): 20 μL of the reference standard or sample (diluted to 1.0 mg/mL) was mixed individually with ~80 μL of a master mixture, which is composed of 0.5 μL of pI 7.40 marker, 0.5 μL of pI 9.77 marker, 1.0 μL of Pharmalyte 3-10, 3.0 μL of Pharmalyte 8-10.5, 35 μL of 1% methyl cellulose (MC), 37.5 μL of 8 M urea solution, 0.07 μL of acetic acid and 2.5 μL of ultrapure water. The loading mixture was then analyzed with iCE3 Capillary Isoelectric Focusing Analyzer equipped with a FC-COATED whole-column detection capillary. The focusing was carried out by two steps: (1) 1.5 kV for 1 minute; (2)

3 kV for 8 minutes, and the auto-sampler tray was maintained at 15° C. Absorbance detection took place at 280 nm. After the analysis, the raw data were processed with Empower 3.

EC50 FACS: Stable CHO-K1 cells expressing either human LILRB4 or flag-tagged cynomolgus monkey LILRB4 were used to determine binding capacity of stability samples of H7K3 antibody. CHO-K1 cells ($1\times10^5$) were stained with serially titrated stability samples followed by secondary staining with fluorescent-conjugated anti-human IgG (Biolegend). Geometric mean fluorescence (MFI) was measured and $EC_{50}$ were calculated by Prism.

EC50 ELISA: Human LILRB4 ECD-his recombinant protein (Sino Biological) or cynomolgus monkey LILRB4 ECD-his recombinant protein (ACRObiosystems) was coated onto EIA/RIA plates (Corning) overnight at 4° C. After blocking for 2 hours at 37° C. with 5% non-fat milk, 100 μL of serial diluted anti-LILRB4 antibodies were added into the well and incubated for 45 min at 37° C. Subsequently, the plates were washed with PBS-Tween 20 (0.05%) for three times, and PBS one time before incubated for 35 min with H1RP-conjugated anti-hFc antibody (Jackson ImmunoResearch Laboratories) at room temperature. Signals were developed with TMB substrates (Sigma), stopped by the addition of 2 M sulfuric acid before read at 450 nm with a plate reader (Molecular Devices). $EC_{50}$ was calculated based on $OD_{450}$ measurement using Prism (GraphPad).

ApoE inhibition (IC50): A mouse T hybridoma cell line expressing LILRB4 extracellularly linked with the nuclear factor of activated T cells (NFAT)-GFP reporter system was used to screen ligand blocking capacity of H7K3 variants. When LILRB4-reporter cells ($2\times10^4$ per well) were co-cultured with immobilized recombinant APOE3 protein (Novoprotein Cat #CI02) at 10 ug/mL, GFP expression was induced by binding of APOE to receptor LILRB4 and the GFP signal was quantified using flow cytometry. In the presence of serially titrated LILRB4 blocking antibody H7K3, the GFP expression was reduced in a dose-dependent manner and $IC_{50}$ was calculated by flow cytometry signals.

Autologous ADCC: PBMCs were freshly isolated from healthy donors and cultured overnight in the presence of rhIL-2 at 50 ng/mL and serially titrated antibodies. Cells were stained with fluorescent conjugated anti-CD14, anti-CD19, anti-CD303, and anti-CD123 antibodies, and acquired by FACS Celesta to count live monocytes, pDC and B cells. Dead cells were excluded by adding 7-AAD. Percent of killing was calculated as 100−[(# of cells with antibody treatment)/(# of cells without antibody treatment)].

ADCC of THP-1-GFP cells: THP-1-GFP cells and freshly isolated PBMCs were co-cultured (E:T ratio=50:1) overnight in the presence of rhIL-2 at 50 ng/mL and serially titrated antibodies. Live THP-1-GFP cell count was obtained by gating on $GFP^+$ and 7-AAD-cells. Percent of killing was calculated using the same formulation of autologous ADCC.

ADCC of MDSC: MDSC and NK cells from two different healthy donors were prepared. MDSC was generated by co-culturing PBMCs with SKMELS cells in the presence of GM-CSF at 40 ng/mL for 8 days and purified using CD33+ microbeads. IL-2 (100 ng/mL) was added for NK cell activation. MDSC:NK=1:2.5 (duplicates) with 50,000 of MDSC and 125,000 of NK cells were co-cultured for 21 hrs. After incubation of 21 hrs, cells were stained with CD14-FITC. THP-1-luc-GFP cells were used as positive control in the same setting. Percent of killing was calculated using the same formulation of autologous ADCC.

ADCP: Human monocytes were isolated from PBMCs from healthy donors using negative selection (Miltenyi Biotec) and cultured in X-vivo 10+10% FBS medium for 7 days in the presence of 50 ng/mL M-CSF (R&D system). In the last 24 hrs, 50 ng/mL of interferon gamma was added to prime macrophages. THP-1-GFP cells ($2.5\times10^4$) were co-cultured with macrophages (E:T=5:1) for 24 hrs in the presence of serially titrated anti-LILRB4 antibody, stained with RPE-conjugated anti-CD163 and anti-CD206. Live THP-1 cells were acquired by flow cytometry by gating on $GFP^+$ cells. Percent of killing was calculated based on both absolute count of THP-1 cells and GFP+%.

T-cell mediated cytotoxicity: A FACS based approach was used to determine the ability of anti-LILRB4 to mediate tumor cell killing by naïve T cells. Human buffy coats were obtained from heathy donors and peripheral blood mononuclear cells (PBMC) were isolated from buffy coats by Ficoll Paque Plus (GE Healthcare Catalog No. 17-1440-03) density gradient cell separation. Pan T cells were further isolated from PBMCs using a human Pan T cell isolation kit (Miltenyi Biotec Catalog No. 130-096-535). $4\times10^5$ freshly isolated human pan T cells were used as effector cells and $1\times10^5$ THP-1-GFP were used as target cells in a 4:1 ratio. Human pan T cells, THP-1-GFP cells, and increasing concentrations of anti-LILRB4 antibody or isotype control human IgG1 (BioXcell Catalog No. BE0297) were mixed in 200 μL total in RPMI 1640 (Gibco Catalog No. 61870-036)+10% heat-inactivated FBS (Gibco Catalog No. 10082-147) in U-shaped 96-well plate and incubated for 48 hrs at 37° C. At the end of incubation, 40 uL of supernatant was collected for cytokine Luminex assay. 7-AAD (BD Pharmingen Catalog No. 559925) was added to cells and 100 uL of cells was acquired by FACS Celesta and the percentage of GFP-positive cells were measured. Flow cytometry data were analyzed using Flowjo software (Flowjo LLC) and cell cytotoxicity was calculated as: percent of cytotoxicity=100−([TINT]×100), where T and NT are the percentages of GFP+ cells treated with or without test antibodies, respectively.

Cytokine assays by Luminex: Cell supernatants were tested using a custom 15 plex panel kit (R&D Systems). In order to perform the DA Bead assay using the wall less plate and the reagents of the 15 plex kit, the protocol of the R&D Systems kit was slightly modified. First, the DA Bead wall less plate was blocked for 30 minutes at room temperature with 10 μL 1% bovine serum albumin (BSA) in PBS. The DA Bead plate was subsequently washed once using the automatic washing station LT MX (Curiox Biosystems) with 0.1% BSA 0.05% Tween 20 in PBS (wash buffer). Each well received 7.5 μL of premixed magnetic beads. The appropriate wells then received 7.5 μL of diluted samples, standards or blank. The DA Bead plate was then vortexed for approximately 10 seconds on an analog microplate Genie Shaker (Scientific Industries Inc., Bohemia, NY) at an intensity scale of 4. DA Bead plate was placed on a 3 mm span orbital shaker (Orbit 300, Labnet, Edison, NJ) and shaken for 120 minutes at 350 revolutions per minute (rpm) (0.2×g) at room temperature. DA Bead plate was then washed 3 times with the LT MX washing station. Each used well received 10 μL of detection antibody diluent. The DA Bead was subsequently placed for approximately 10 seconds on an analog microplate genie shaker, as described above, and incubated on the orbital shaker for 60 minutes at 350 rpm at room temperature. The DA Bead plate was then washed 3 times using the LT MX station. Each well received 10 μL of streptavidin phycoerythrin diluent. The DA Bead plate was placed for approximately 10 seconds on the Genie Shaker, as described above, and incubated for 30 minutes on the orbital shaker at 350 rpm at room temperature. The DA Bead plate was washed 3 times in the LT MX station. The beads were resuspended with a total volume of 65 μL wash buffer and transferred to a skirted PCR plate and read in a Luminex reader for data acquisition (MAGPIX, a dual laser flow-based detection instrument, Luminex).

FACS analysis of co-cultured T-cells and THP-1 cells: Human buffy coats were obtained from heathy donors and peripheral blood mononuclear cells (PBMC) were isolated from buffy coats by Ficoll Paque Plus (GE Healthcare Catalog No. 17-1440-03) density gradient cell separation. Pan T cells were further isolated from frozen PBMCs by negative depletion using a human Pan T cell isolation kit (Miltenyi Biotec Catalog No. 130-096-535). $8\times10^5$ purified human pan T cells were used as effector cells and $1\times10^5$ THP-1-GFP were used as target cells in an 8:1 ratio. Human pan T cells, THP-1-GFP cells, and anti-LILRB4 antibody or isotype control human IgG1 (BioXcell Catalog No. BE0297) were mixed in 200 μL total in X-vivo 10 (Lonza Catalog No. 04-380Q)+10% heat-inactivated fetal bovine serum (FBS; Gibco Catalog No. 10082-147) in U-shaped 96-well plate and incubated for 48 hrs at 37° C. The final concentration of anti-LILRB4 antibody or human IgG1 was 3 μg/mL (20 nM). To measure intracellular TNFα and IFNγ production, protein transport inhibitor (BD Biosciences Catalog No. 555029) was added in the last 11 hrs of incubation. At the end of incubation, the cells were spun down out of the medium containing protein transport inhibitor and incubated with human IgG (Sigma Aldrich Catalog No. 14506) at room temperature for 10 minutes to block Fc receptors. The cells were then stained for surface antigens with directly conjugated anti-CD4 (Catalog No. 564975) and anti-CD8 (Catalog No. 563256), fixed and permeabilized using Fixation/Permeabilization kit (Catalog NO. 555028), and stained with anti-IFNγ (Catalog No. 554552) and anti-TNFα (Catalog No. 554514) or isotype control antibodies (Catalog NO. 554681, 555749). The antibodies against surface and intracellular antigens are from Becton, Dickinson and Company.

FACS analysis of T-cell and THP-1 cell activation: Surface expression of T-cell activation markers was evaluated with directly conjugated anti-CD4 (Catalog No. 564975), anti-CD8 (Catalog No. 563256), anti-CD69 (Catalog No. 555533), and anti-CD25 (Catalog No. 555432) antibodies from BD Biosciences. Surface expression of THP-1 cell markers was assessed with directly conjugated anti-HLA-DR (Catalog No. 559866), anti-CD80 (Catalog No. 563084), anti-CD83 (Catalog No. 565336), anti-CD86 (Catalog No. 562432), anti-CD205 (Catalog No. 558156), anti-CD87 (Catalog No. 743096) from BD Biosciences, and anti-CD40 (Catalog No. 334310), anti-HLA-A, B, C (Catalog No. 311406), anti-LTLRB4 (Catalog No. 333008) from Biolegend. Cells were acquired by FACS Celesta after 7-aminoactinomycin D (7AAD; BD Pharmingen Catalog No. 559925) was added to cells. Flow cytometry data were analyzed using Flowjo software (Flowjo LLC) and graphed by Prism GraphPad software.

PCR fragments for CAR-encoding fragments: PCR were performed with PRIMESTAR DNA Polymerase (Takara Bio R010B) using Venti thermocycler using the follow conditions: 98° C._30 s, (98° C._10 s, 64° C._5 s 72° C._30 s)×35 cycles, 72° C._7 min. The PCR products were further purified using PCR clean up kit (Macherey-Nagel 740609.250) and the eluted DNA were further washed/concentrated by ethanol precipitation.

Gene targeting: The inventors used TransAct to activate T cells first, then wash off TransAct before electroporation. 72 h after TransAct activation of PMBC, the CD3/CD28 beads were magnetically removed, and the T cells were transfected by 5 ug and 100 pmol/l RNA duplex using neon transfection system (thermo fisher, 10 ul tip). $4\times10^5$ cells were mixed with the RNP complex and 2.5 ug PCR fragment encoding CAR. Following electroporation cells were diluted into culture medium and incubated at 37° C., 7% CO2. Subsequently, edited cells were cultured using standard conditions (37° C. and expanded in T-cell growth medium, replenished as needed to maintain a density of $\sim1\times10^6$ cells per ml every 2 to 3 days).

TCRalpha KO T cells: Human primary T cells were transfected with CRISPR-Cas9 RNP complexes including a guide RNA targeting the 5' end of the first exon of TRAC and supplied with DNA template for homologous recombination-based knock in. After knocking out TCRalpha, the cells were grown in complete Optimizer medium with IL-2 300 IU/ml and without anti-CD3/28 added. Following transfection, cells were expanded in culture for 2 weeks.

Flow cytometry assays of CAR-T transduction: LILRB4 CAR-T were identified by binding to LILRB4-Fc fusion protein (ACRObiosystems CDK-H5259) and anti-Fc antibody (Biolegend B278652). Success in knock-out of the endogenous TCR alpha (TRAC) locus (KO) was measured by anti-CD3 staining (anti-CD3 PE, BD 555333).

Antigen stimulation assays: 1 ug/ml recombinant control antigen or LILRB4 antigen were coated on 96 well plate overnight in PBS buffer. Plate were washed twice with PBS buffer. $1\times10^5$ CAR-T cells in culture media (without any cytokine added) were added to each well and incubated for 72 hours. Cell culture supernatant were collected for cytokine release measurement by Luminex assay (R&D Systems FCS™-18).

CAR-T cell mediated cytotoxicity assays: CHO K1 RB4 cells were seeded at different density ($6\times10^4$, $2\times10^4$ or $7\times10^3$) for 12 hours. $1\times10^5$ CAR-T cells were added and cytotoxicity were measured by removing the supernatant CAR-T cells and washing the plate 2 times with PBS. Total viable adherent CHO K1 RB4 cells were measured by Promega CTG2.0 luminescence kit, and the % cytotoxicity was calculated by dividing the Luminescent signal of each condition with the same E:T ratio activated T cell control.

Phase 1 design: During the Part 1A monotherapy escalation phase (single dose on Day 1) patients will be enrolled into sequential cohorts of increasing doses of anti-LILRB4 monotherapy. The goal of Part 1A is to determine the maximum tolerated dose (MTD) of anti-LILRB4 monotherapy (MTD1). DLTs for MTD1 will be evaluated during the first 14 days of treatment (prior to the first dose of anti-LILRB4 in combination with azacytidine/azacitidine), i.e., the first dose-interval for anti-LILRB4. The initial dose-escalation begins with an accelerated titration design followed by a standard escalation phase that will use a 3+3 design. Part 1 will include both relapsed and/or refractory myelomonocytic (M4) and monocytic/monoblastic (M5) AML patients and chronic myelomonocytic leukemia (CMML) patients as described above. This 2-week monotherapy lead-in ("window") of anti-LILRB4 enables the studying of the effects of a monoclonal antibody that specifically targets LILRB4 as monotherapy. During Part 1B (starting on Day 15), patients without DLTs during Part 1A will receive the same dose of anti-LILRB4 that was administered in Part 1A in combination with a standard dose of azacytidine/azacitidine (75 mg/$m^2$ subcutaneously for 7 days every 28 days). The MTD of anti-LILRB4 in combination with azacytidine/azacitidine (MTD2) will be determined in the 28-day DLT window, consisting of the 14 days of monotherapy and 14 days of the combination treatment. The overall DLT period of Part 1 (Part 1A and Part 1B combined) is 28 days. Subsequent cycles will be anti-LILRB4 in combination with azacytidine/azacitidine.

Example 2

The inventors previously identified a rabbit anti-LILRB4 antibody named B4-193 that has a high binding affinity to human LTLRB4 and can inhibit cancer development in a xenograft AML mouse model. (see U.S. Provisional Application No. 62/730,715, the disclosure of which is incorporated herein in its entirety)

The inventors generated a humanized anti-LILRB4 antibody that contains the same CDRs as B4-193. The humanized anti-LILRB4 antibody, named H7K3, has a heavy chain variable region sequence of SEQ ID NO: 1 and a light chain variable region sequence of SEQ ID NO: 3.

The in silico analysis of the H7K3 indicated that it has a potential oxidation site at the amino acid residue W in the heavy chain CDR3 and a potential deamidation site at the amino acid residues NS in the light chain CDR1, which may potentially decrease the stability of the antibody.

The inventors then assessed the stability of the antibody H7K3 at 40° C. in PBS or a formulation buffer, the results of which are summarized in the Tables 2 and 3. The results indicate that the antibody H7K3 is unstable.

TABLE 2

Stability of H7K3 in PBS

| | SEC (HMW/MP/LMW) | icIEF (Acidic/MP/Basic) | FACS Human EC50 nM | FACS Cyno EC50 nM |
|---|---|---|---|---|
| H7K3 | | | 0.6501 | 1.185 |
| $T_0$ | 3.7/96.3/0 | 20.9/69.5/9.6 | 0.7337 | 1.205 |
| 2 w 40° C. | 4.3/93.8/1.9 | 88.8/9.4/1.8 | 0.8954 | 1.706 |
| 4 w 40° C. | 3.6/93.2/3.2 | 94.9/4.3/0.7 | 0.6956 | 1.72 |
| Changes at 40° C. | Very slight change | Dramatic increase in acidic species | No change in binding | Decrease in binding |

TABLE 3

Stability of H7K3 in Formulation buffer

| | SEC (HMW/MP/LMW) | icIEF (Acidic/MP/Basic) | FACS Human EC50 nM | FACS Cyno EC50 nM |
|---|---|---|---|---|
| H7K3 | | | 0.6501 | 1.185 |
| $T_0$ | 1.0/99.0/0 | 17.1/72.3/10.6 | 0.5574 | 0.8835 |
| 2 w 40° C. | 1.0/98.6/0.4 | 52.8/39.2/8.0 | 1.424 | 3.806 |
| 4 w 40° C. | 1.2/98.0/0.4 | 71.7/23.1/5.2 | 2.144 | 6.051 |
| Changes at 40° C. | Very slight change | Dramatic increase in acidic species | Decrease in binding | Log decrease in binding |

Example 3

To reengineer H7K3 to correct deamination and oxidation liabilities, the inventors generated a series of variants having mutations at the potential oxidation site and deamination site. The sequences of the H7K3 variants are summarized in the Table 4.

TABLE 4

H7K3 variants

| Variant | Mutation | Heavy Chain variable sequence | Light chain variable sequence |
|---|---|---|---|
| 1 | H7m1 (W/V) | SEQ ID NO: 11 | SEQ ID NO: 3 |
| 2 | H7m2 (W/Y) | SEQ ID NO: 13 | SEQ ID NO: 3 |
| 3 | H7m3 (W/F) | SEQ ID NO: 15 | SEQ ID NO: 3 |
| 4 | H7m4 (W/Q) | SEQ ID NO: 17 | SEQ ID NO: 3 |
| 5 | K3m1 (N/V) | SEQ ID NO: 1 | SEQ ID NO: 19 |
| 6 | K3m2 (N/D) | SEQ ID NO: 1 | SEQ ID NO: 21 |
| 7 | K3m3 (N/E) | SEQ ID NO: 1 | SEQ ID NO: 23 |
| 8 | K3m4 (N/Q) | SEQ ID NO: 1 | SEQ ID NO: 25 |
| 9 | K3m5 (N/S) | SEQ ID NO: 1 | SEQ ID NO: 27 |
| 10 | K3m6 (N/T) | SEQ ID NO: 1 | SEQ ID NO: 29 |
| 11 | K3m7 (S/Q) | SEQ ID NO: 1 | SEQ ID NO: 31 |
| 12 | K3m8 (S/V) | SEQ ID NO: 1 | SEQ ID NO: 33 |

The inventors tested the binding affinity of the H7K3 variants via FACS using CHO-stable cells expressing human and cyno LILRB4. The results are summarized in the Table 5 below.

TABLE 5

| | | EC50 (nM) | EC50 (nM) |
|---|---|---|---|
| Variant | Mutation | Human | Cyno |
| 5 | K3m1 (N/V) | 0.4626 | 1.233 |
| 8 | K3m4 (N/Q) | 0.4796 | 0.9889 |
| 9 | K3m5 (N/S) | 0.4152 | 1.125 |
| 11 | K3m7 (S/Q) | 0.4552 | 0.9741 |
| 12 | K3m8 (S/V) | 0.402 | 0.9331 |
| WT | K3 | 0.5431 | 1.333 |

Binding affinity of H7K3 variants

The inventors further tested the stability of the H7K3 variants. Oxidized species was observed (confirmed by mapping results) in H7K3 after incubation at 40° C. for 4W compared to the control sample without incubation at 40° C., as summarized in the Table 6 below. No obvious oxidation was observed in H7K3m5 after incubation at 40° C. for 4 weeks. It can be concluded that H7K3m5 is more stable than H7K3.

TABLE 6

Comparison in Deglycosylated Reduced Mass (DRM) results of H7K3 and H7K3m5

| Molecule | Buffer | Condition | Subunit Modification | Theoretical Mass (Da) | Measured Mass (Da) | Difference (ppm) |
|---|---|---|---|---|---|---|
| H7K3 | 20 mM Histidine-HCl, pH 6.0, 7.0% sucrose, 0.02% PS80 | Control | LC: partial reduced | 23601.3 | 23601.0 | −12.7 |
| | | | HC: partial reduced, deglycosylated, —K | 48969.3 | 48969.9 | 12.3 |
| | | Incubation at 40° C. for 4 W | LC: partial reduced | 23601.3 | 23601.7 | 16.9 |
| | | | LC: partial reduced, with modification | NA | 23583.9 | NA |
| | | | LC: partial reduced, Oxide | 23617.3 | 23617.7 | 16.9 |
| | | | LC: partial reduced, 2*Oxide | 23633.3 | 23633.8 | 21.2 |
| | | | HC: partial reduced, deglycosylated, —K, 2*Oxide, with unknown modification | NA | 48992.4 | NA |
| H7K3m5 | | Control | LC: partial reduced | 23574.3 | 23574.1 | −8.5 |
| | | | HC: partial reduced, deglycosylated, —K | 48969.3 | 48969.6 | 6.1 |
| | | Incubation at 40° C. for 4 W | LC: partial reduced | 23574.3 | 23574.0 | −12.7 |
| | | | HC: partial reduced, deglycosylated, —K | 48969.3 | 48969.6 | 6.1 |

The inventors further tested the stability of the H7K3 variants. About ~50% decrease in main peak were observed in H7K3 after incubation at 40° C. for 4 weeks compared to the control sample without incubation at 40° C. About 16% decrease in main peak % were observed in H7K3m5 after incubation at 40° C. for 4 weeks compared to the control. It can be concluded that H7K3m5 is more stable than H7K3.

TABLE 7

Comparison in icIEF results of H7K3 and H7K3m5

| | | | pI of | Area % | | |
|---|---|---|---|---|---|---|
| Molecule | Sample | Buffer Composition | main peak | Acidic peaks | Main peak | Basic peaks |
| H7K3 | Control | 20 mM Histidine-HCl, 7% sucrose, 0.02% PS80, pH 6.0 | 8.8 | 17.1 | 72.3 | 10.6 |
| | 40° C. for 2 W | | 8.8 | 52.8 | 39.2 | 8.0 |
| | 40° C. for 4 W | | 8.8 | 71.7 | 23.1 | 5.2 |
| H7K3m5 | Control | | 8.8 | 26.3 | 62.5 | 11.1 |
| | 40° C. for 2 W | | 8.8 | 34.3 | 52.4 | 13.3 |
| | 40° C. for 4 W | | 8.8 | 41.6 | 46.4 | 11.9 |

No significant oxidation was detected in H7K3m5 under the light exposure. Consistency between DRM and peptide mapping results was obtained for H7K3m5 with light exposure. The results indicated that H7K3m5 showed acceptable stability under oxidizing environment (light).

For H7K3m5 after incubation at 40° C. for 4 weeks, the DRM results indicated there is no significant oxidation. H7K3m5 appears more stable than H7K3 regarding DRM and icIEF results. icIEF is capable of monitoring the oxidation and deamidation even with low ratio.

Example 4

This example illustrates the biological function of H7K3m5.

Figure 3:
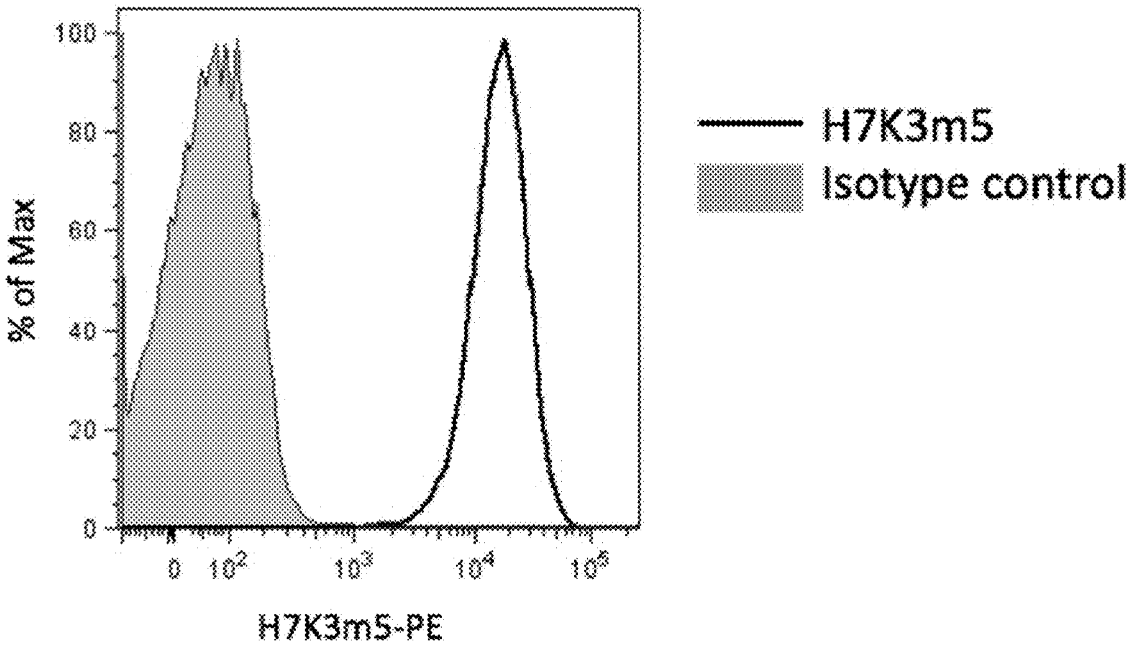
FIG. 3 shows recognition of human endogenous LILRB4 on THP-1 cells by the anti-LILRB4 antibody H7K3m5.
Figure 4:
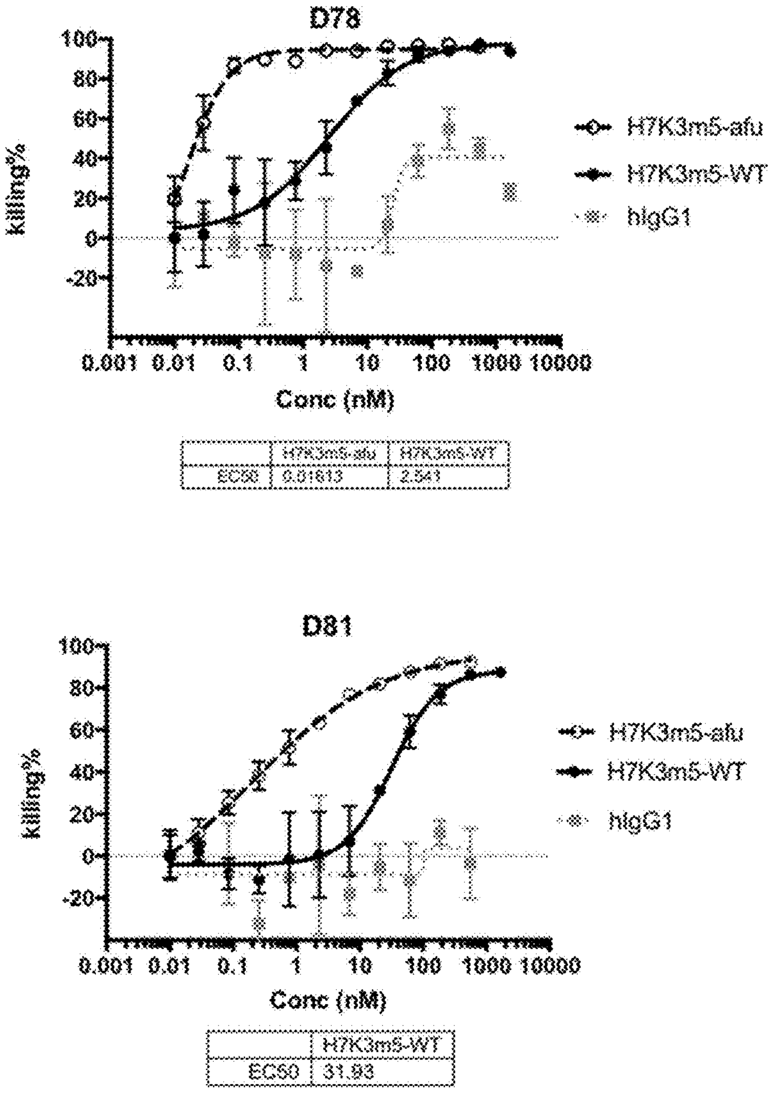
FIG. 4 shows ADCC of THP-1-GFP cells by wild type (WT) or afucosylated (afu) H7K3m5.
Figure 5:
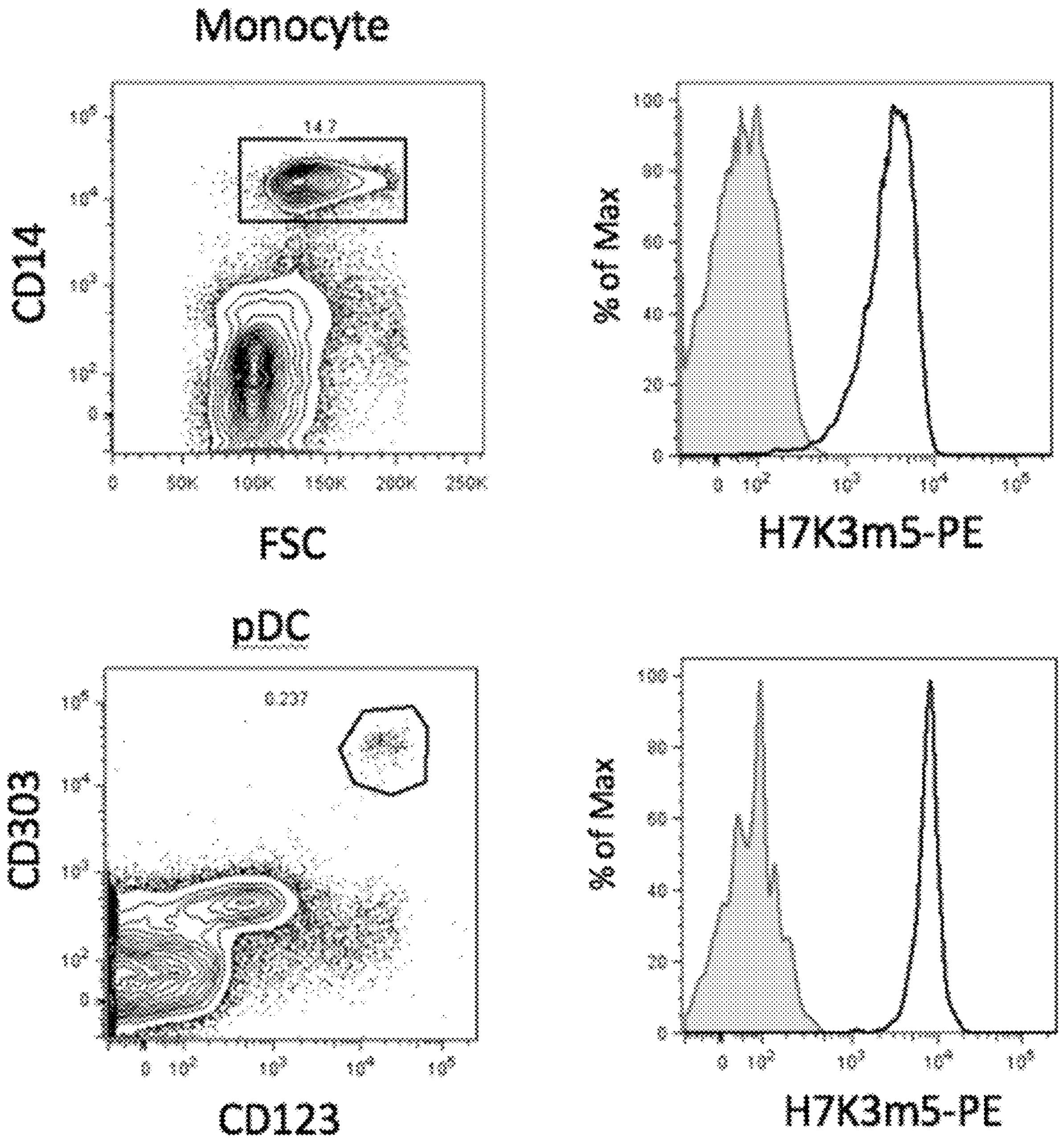
FIG. 5 shows LILRB4 expression on human monocytes and plasmacytoid dendritic cells (pDC).

The inventors first assessed whether H7K3m5 binds to the LILRB4 expressed on cell surface. As shown in FIG. 3, H7K3m5 recognized LILRB4 expressed on THP-1-GFP cells. H7K3m5 is capable of inducing ADCC activity against THP-1 cells in the presence of PBMC in vitro, as shown in FIG. 4. Notably, afucosylated H7K3m5 showed enhanced cell killing compared to wild-type H7K3m5, with EC50 enhanced by more than 100-fold. As shown in FIG. 5, H7K3m5 also binds to LILRB4 expressed on human monocytes and plasmacytoid dendritic cells (pDC).

Figure 6:
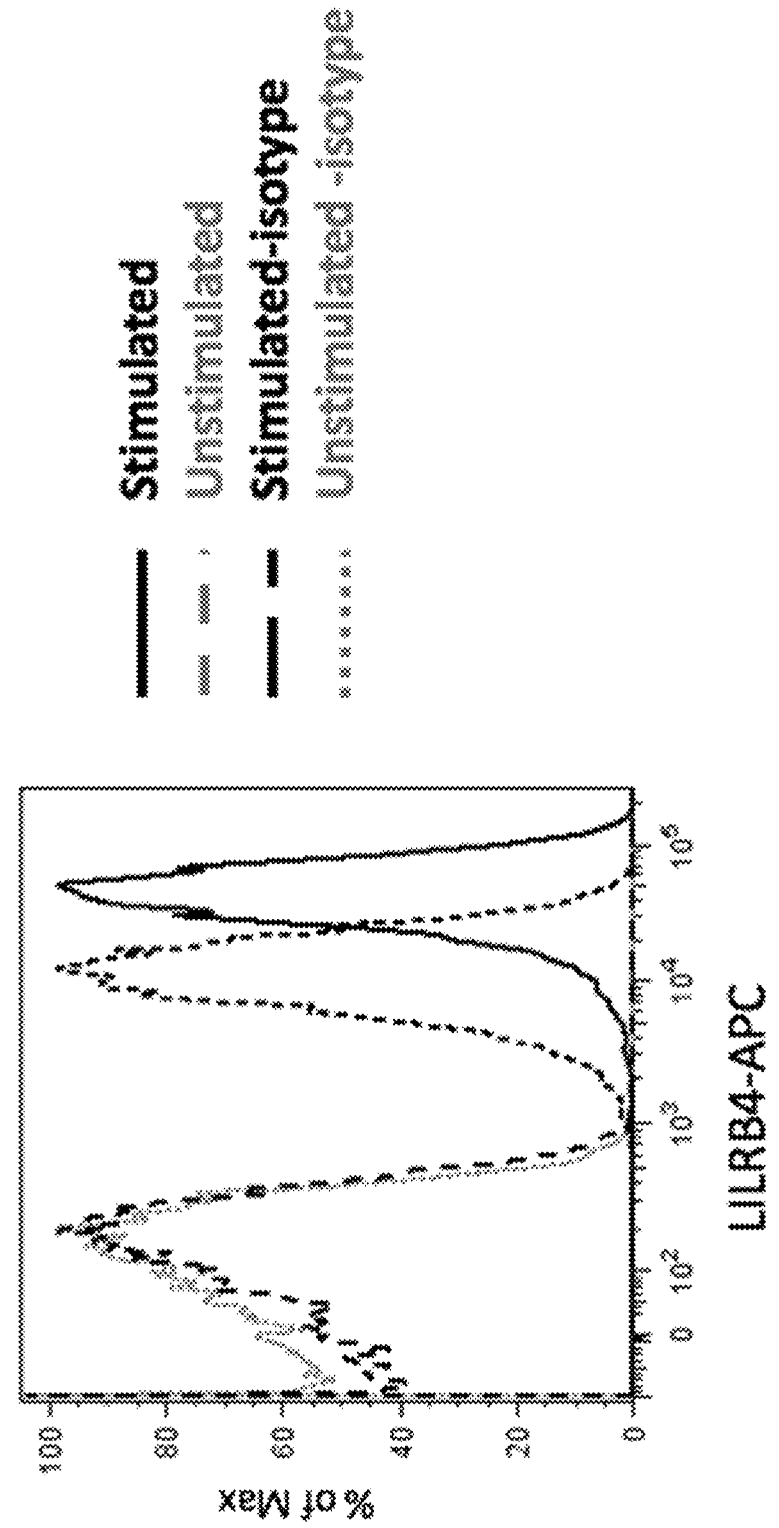
FIG. 6 shows up-regulation of LILRB4 expression by IL-10 and IFNα treatment in human monocytes.

As shown in FIG. 6, LILRB4 expression in human monocytes can be up-regulated by IL-10 and IFNα treatment. Human monocytes were isolated from human PBMC by negative selection, and stimulated by 50 ng/ml IL-10 plus 1500 U IFNα in RPMI medium with 10% FBS and 1×L-glutamin for 24 hours. Cells were stained by CD14-PE and anti-LILRB4-APC at 2 ug/ml.

Figure 7:
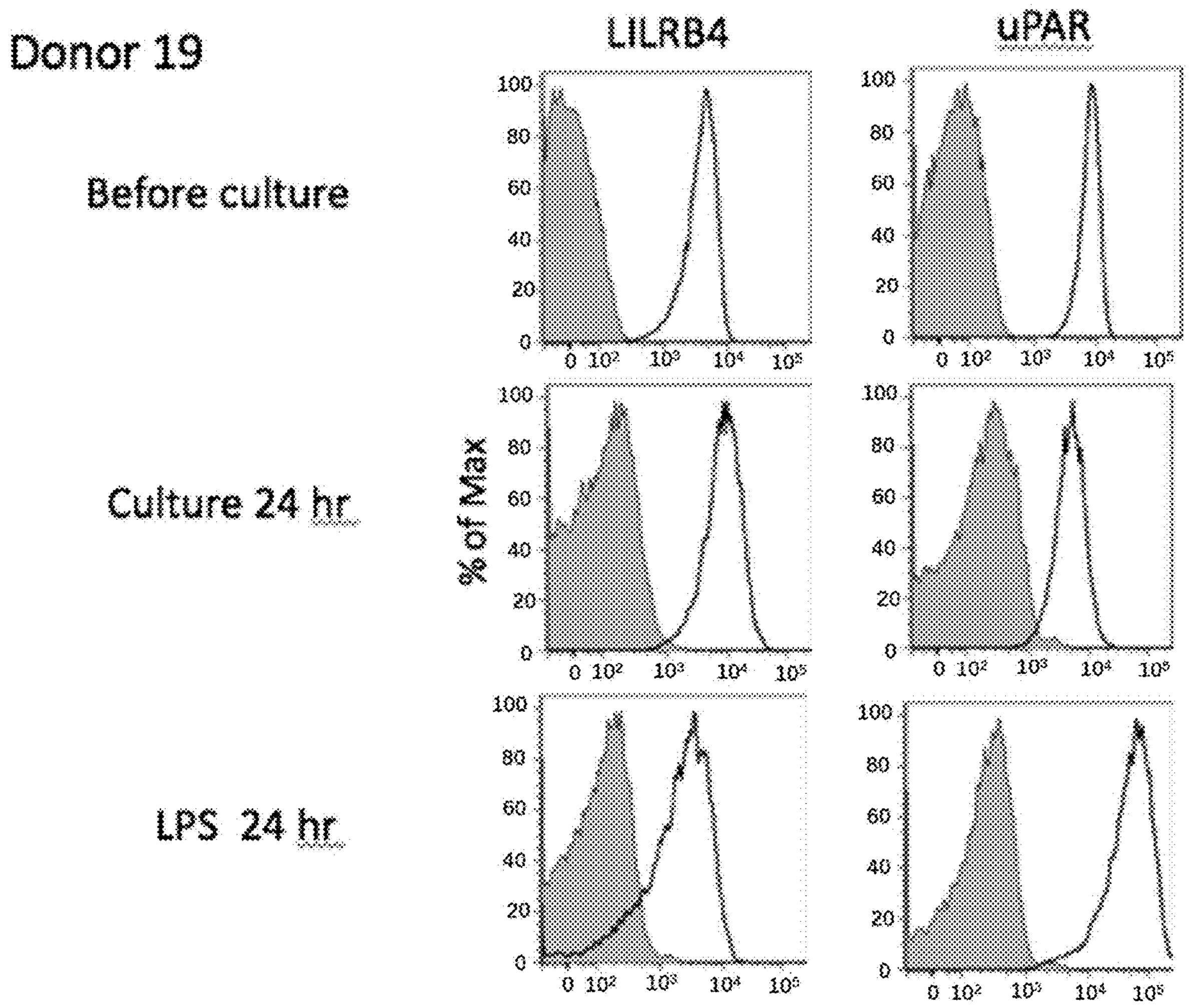
FIG. 7 shows LILRB4 level down-regulated and uPAR level up-regulated on human monocytes stimulated by LPS.

On the other hand, human monocytes treated by LPS down-regulated LILRB4 expression and increased uPAR expression level (FIG. 7).

Figure 8A:
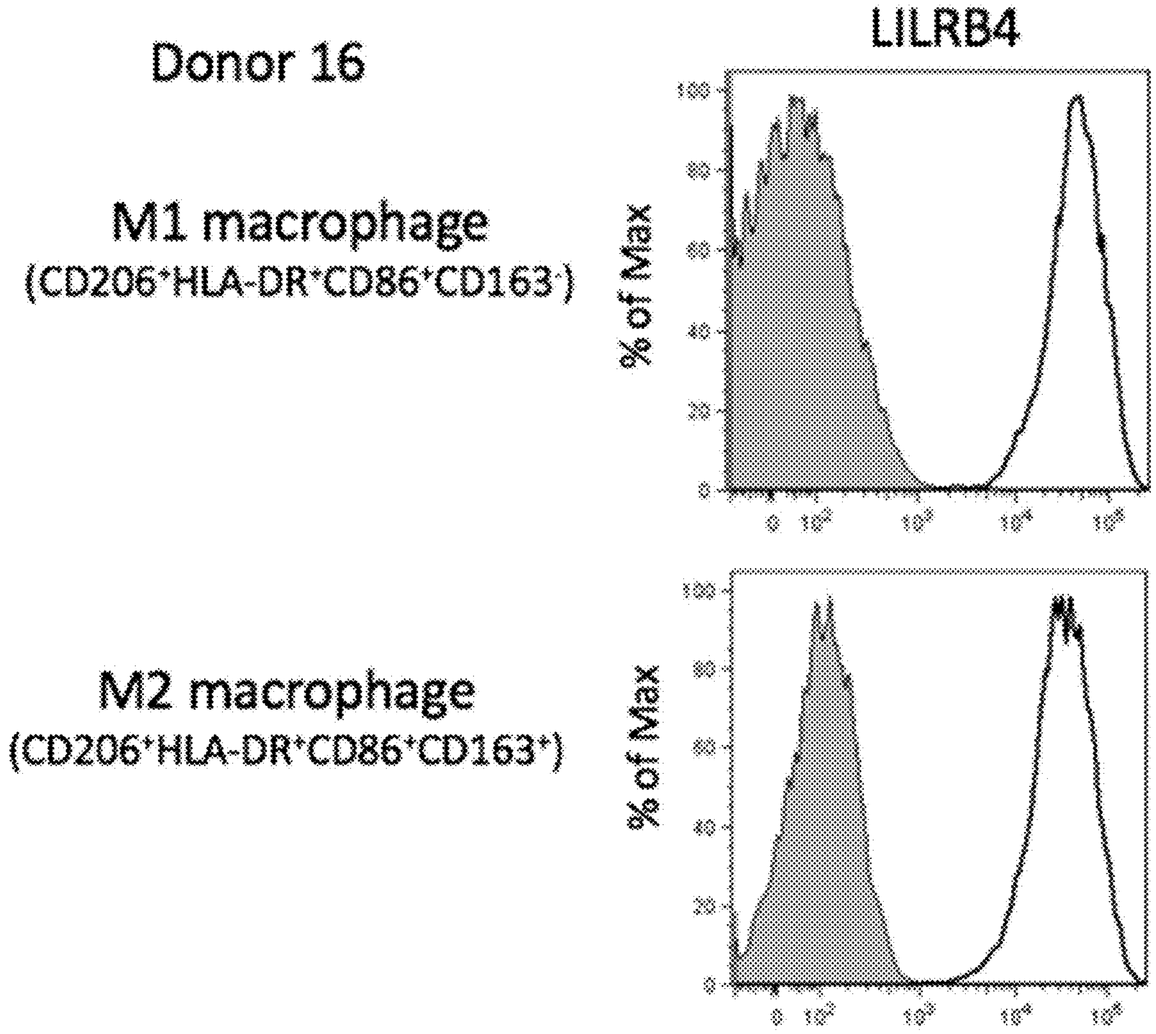
FIG. 8A shows LILRB4 expression on in vitro human monocytes differentiated macrophages.
Figure 8B:
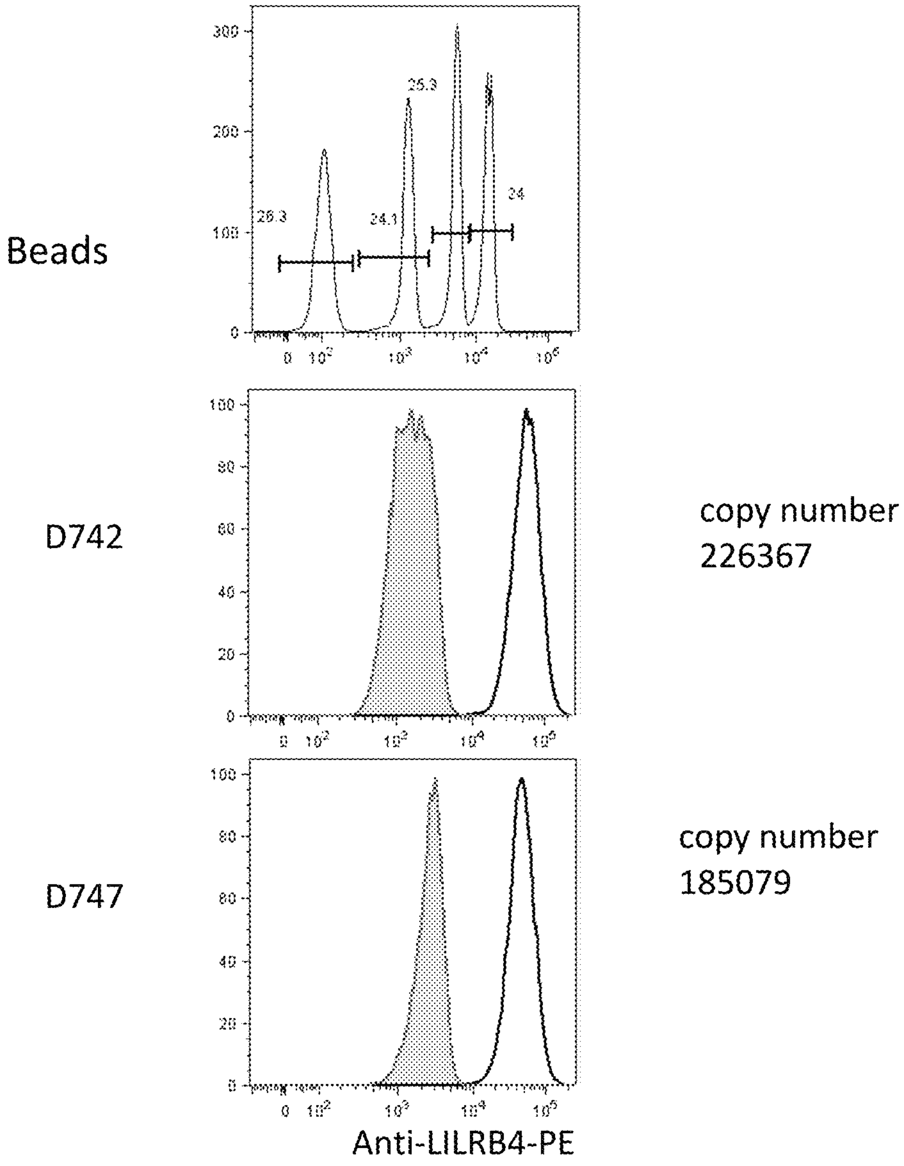
FIG. 8B shows copy number of LILRB4 on in vitro monocyte-derived human macrophages.

As shown in FIGS. 8A and 8B, LILRB4 is expressed on in vitro differentiated human macrophages. The copy number of LILRB4 on in vitro monocyte-derived human macrophages is very high, close to 150,000 copies/cell.

Figure 9:
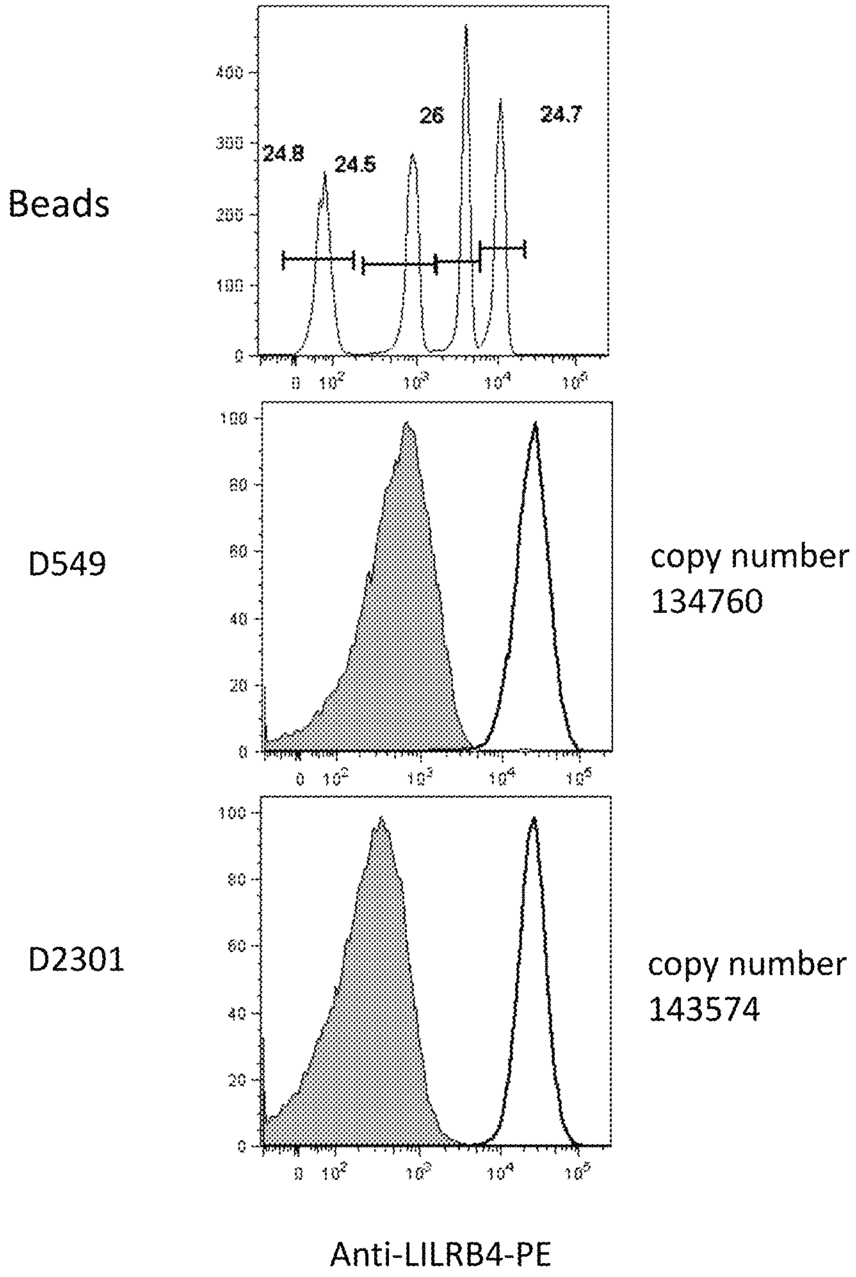
FIG. 9 shows copy number of LILRB4 on in vitro differentiated MDSCs.

As shown in FIG. 9, LILRB4 expression is greatly increased in myeloid-derived suppressor cells (MDSC). The copy number of LILRB4 on in vitro differentiated MDSCs can be as high as 200,000 copies/cell.

Figure 10A:
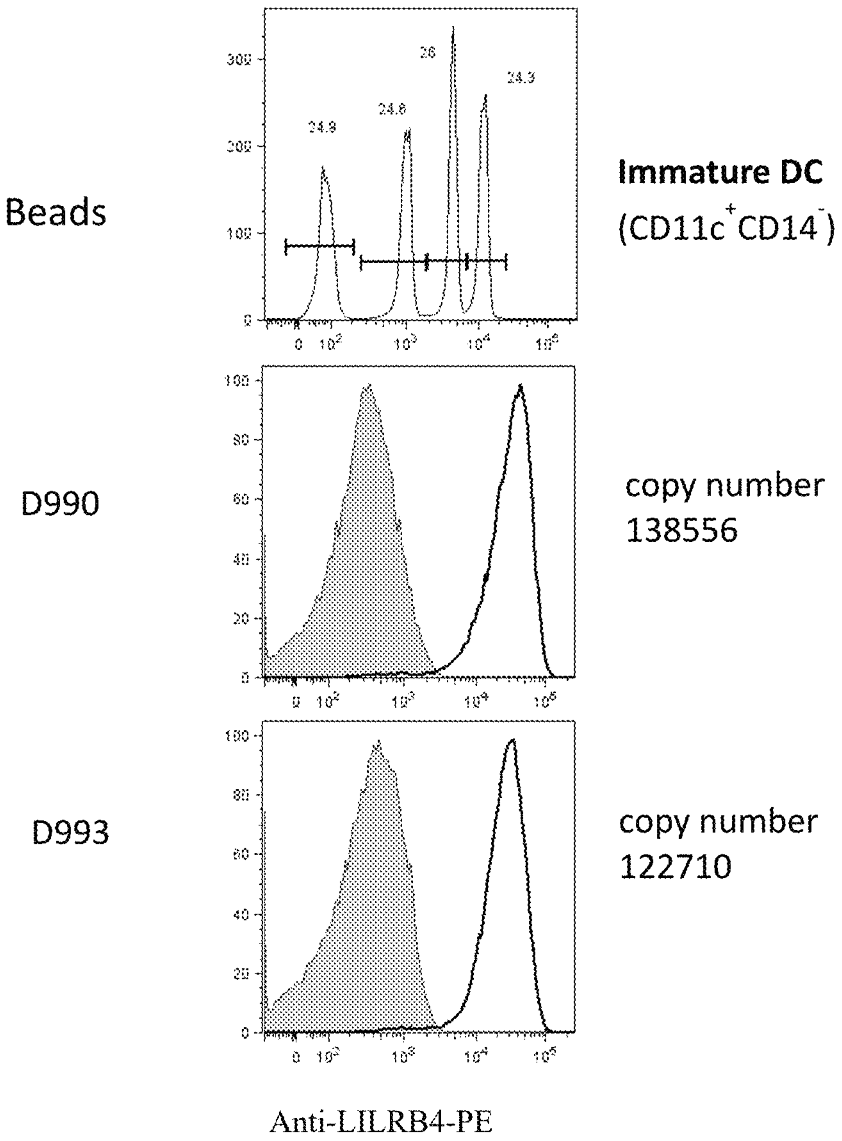
FIGS. 10A-10B show copy number of LILRB4 on human monocyte-derived dendritic cells (DCs). LILRB4 level is seen in the following order from high to low: Tolerogenic DC>Activated DC>Immature DC
Figure 10B:
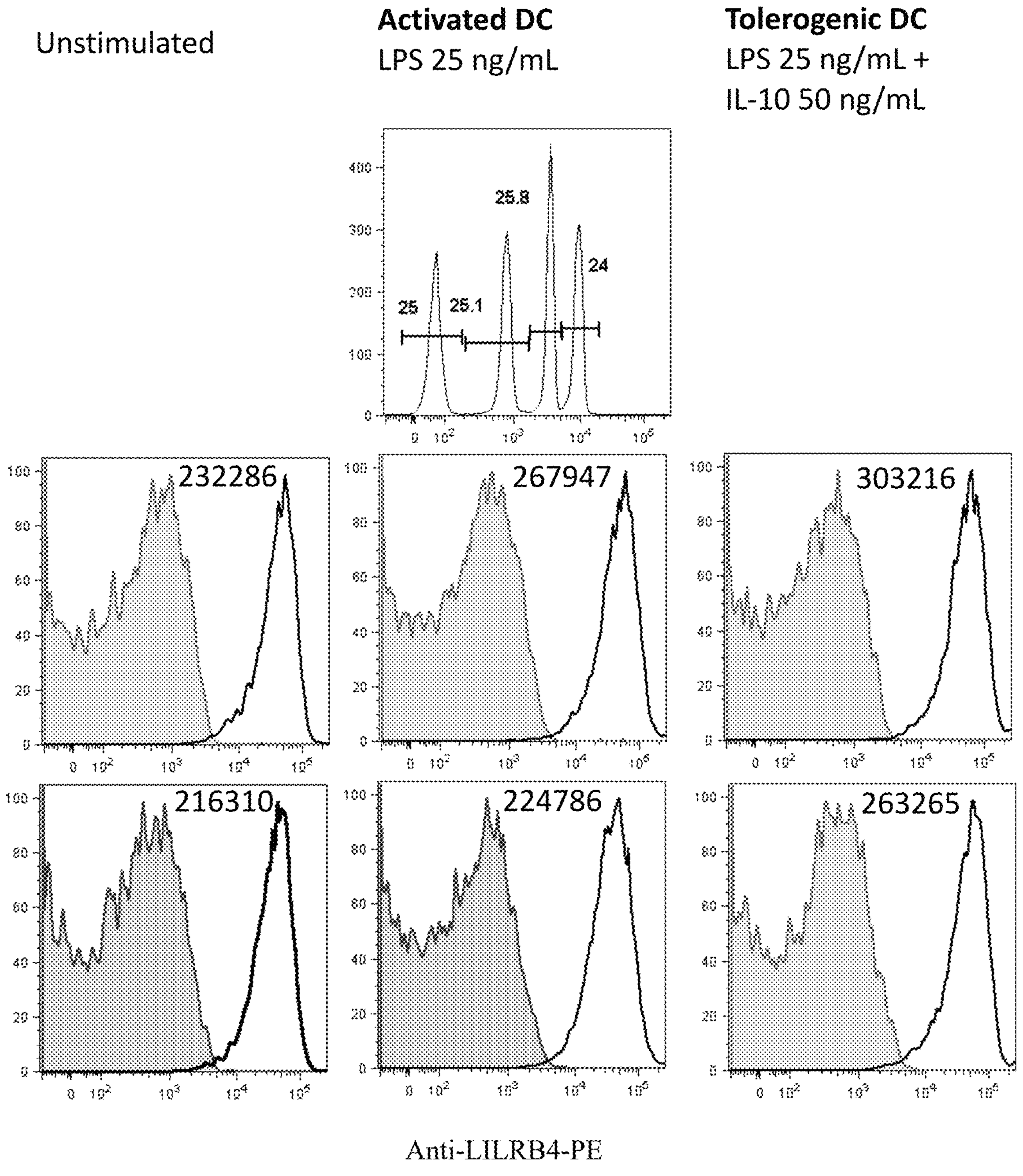

As shown in FIGS. 10A-10B, LILRB4 is also highly expressed on human monocyte-derived dendritic cells (DCs). LILRB4 level is seen in the following order from high to low: Tolerogenic DC>Activated DC>Immature DC.

TABLE 8

Comparison of copy numbers of LILRB4 on different types of human primary cells and AML cell line

| Cell type | Range of LILRB4 copy number/cell | Average of LILRB4 copy number/cell |
|---|---|---|
| Human monocyte from healthy donors (n = 12) | 2355-7886 | 5061 |
| In vitro differentiated MDSCs (n = 2) | 134,760; 143,574 | 139,167 |
| In vitro monocyte-derived macrophages (n = 2) | 226,367; 185,079 | 205,723 |
| AML cell line THP-1 (n = 1) | 57,211 | 57,211 |

Figure 11:
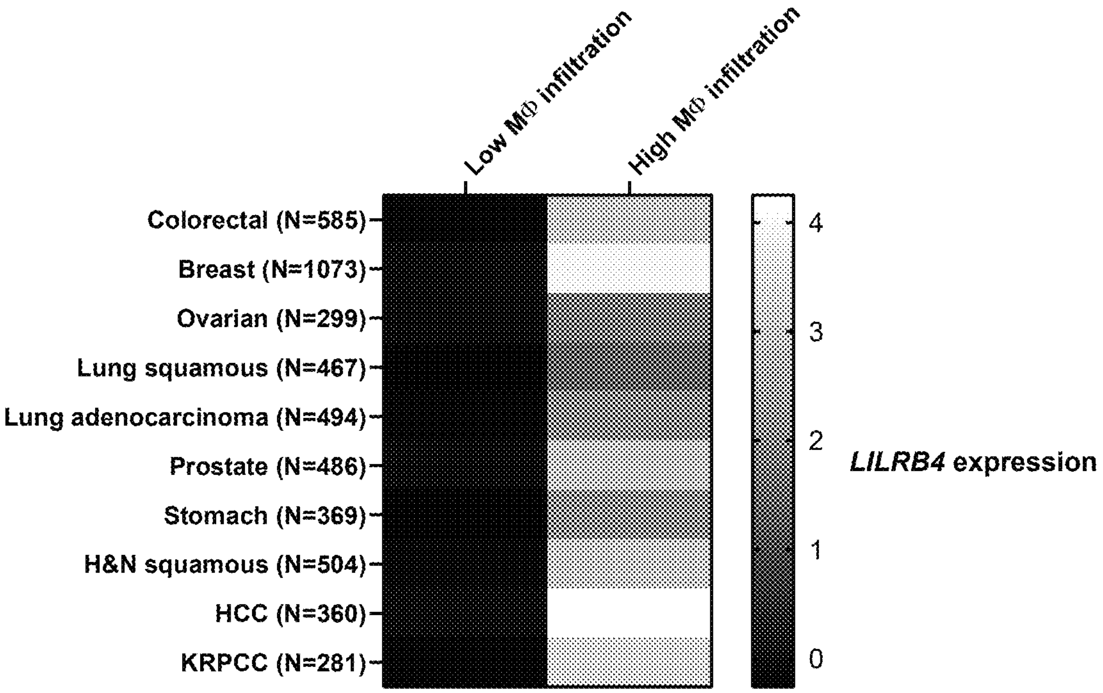
FIG. 11 shows the comparison of LILRB4 mRNA expression levels between solid tumor samples from the TCGA RNA sequencing database with high and low signals for macrophage infiltration, based on a macrophage gene expression "signature" genera rated through computational biology approaches. The total number of samples for each tumor type that was included in the analysis is indicated in parentheses. The results shown here are in part based upon RNA sequencing data generated by the TCGA Research Network.

The inventors then compared the LILRB4 mRNA expression levels between solid tumor samples with high and low signal for macrophage infiltration. RNA sequencing data from the TCGA database was analyzed using computational biology and statistical approaches to identify samples presenting coordinated up-regulated expression of multiple transcripts primarily expressed by tumor-associated macrophages (collectively defining a macrophage gene expression "signature") within each tumor type. Samples presenting high signal for the macrophage gene expression "signature" were classified as highly infiltrated by tumor-associated macrophages. The expression levels of LILRB4 transcript were then compared between those tumor samples and the remaining samples in which a macrophage gene expression "signature" was not apparent (grouped as low macrophage infiltrated samples). As shown in FIG. 11, higher LILRB4 mRNA expression levels are correlated to the macrophage infiltration.

Figure 12A:
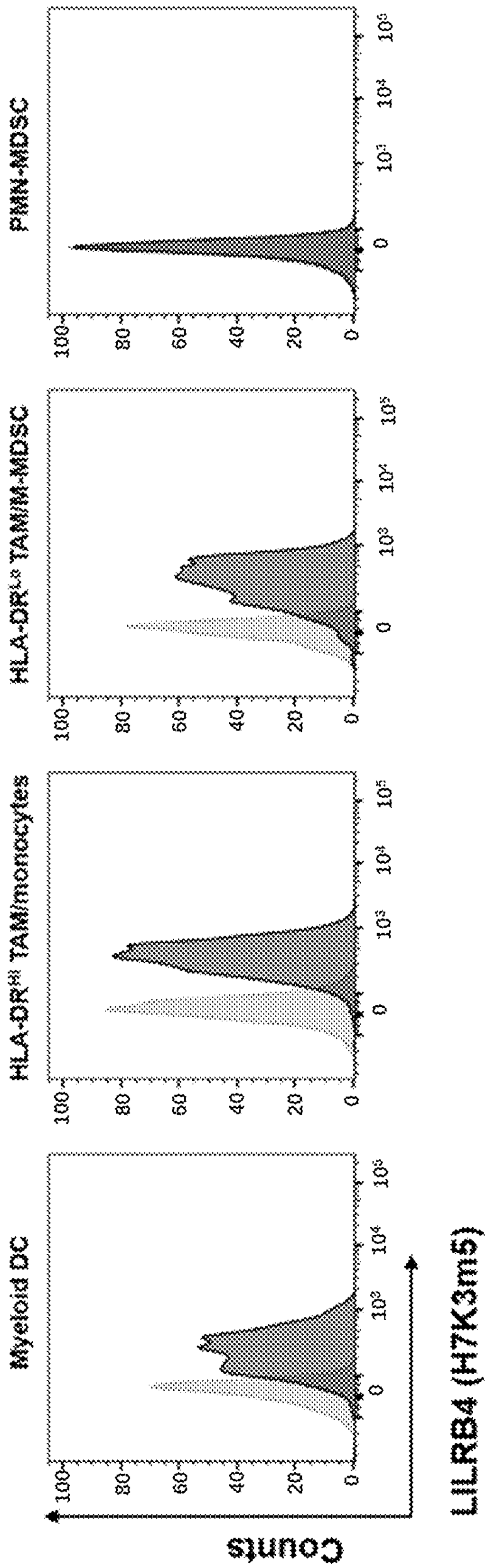
FIGS. 12A-12B illustrate the representative flow cytometry data showing that H7K3m5 specifically binds monocytic myeloid cells infiltrated into solid tumor microenvironment (TME), as well as peripheral blood monocytic myeloid cells from solid tumor patients. Dark grey-filled histogram: sample incubated with H7K3m5; light grey-filled histogram: sample incubated with human IgG1 isotype control.
Figure 12B:
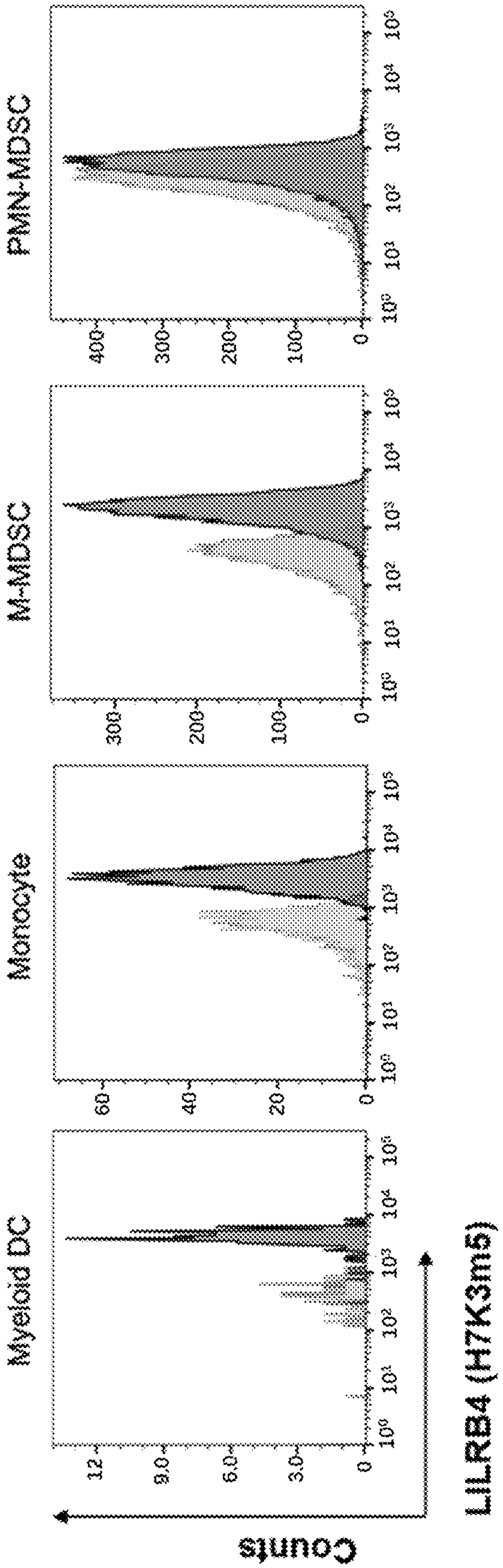
Figure 13A:
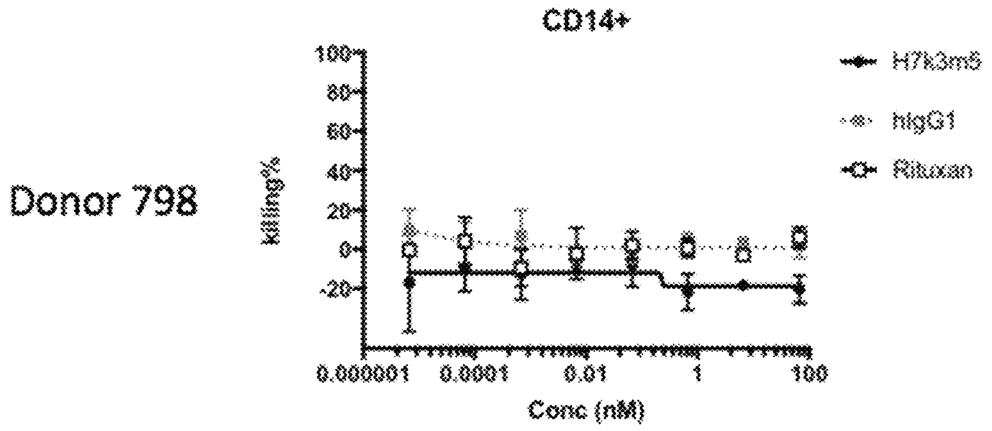
FIGS. 13A-13D show no H7K3m5 mediated monocyte killing in autologous ADCC using fresh PBMCs. Freshly isolated PBMCs from healthy donors were incubated overnight in the presence of serially titrated H7K3m5, isotype control human IgG1, or rituximab as positive control. Monocytes and B cells were identified and counted as $CD14^+CD19^-$ and $CD19^+CD14^-$ by flow cytometry.
Figure 13B:
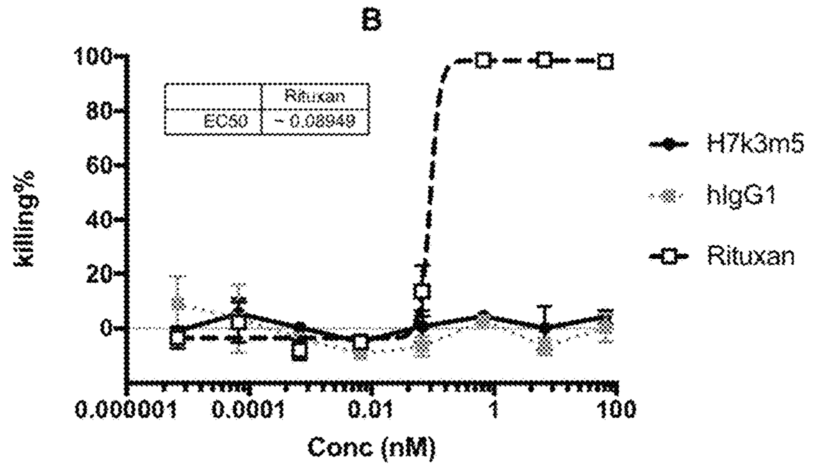
Figure 13C:
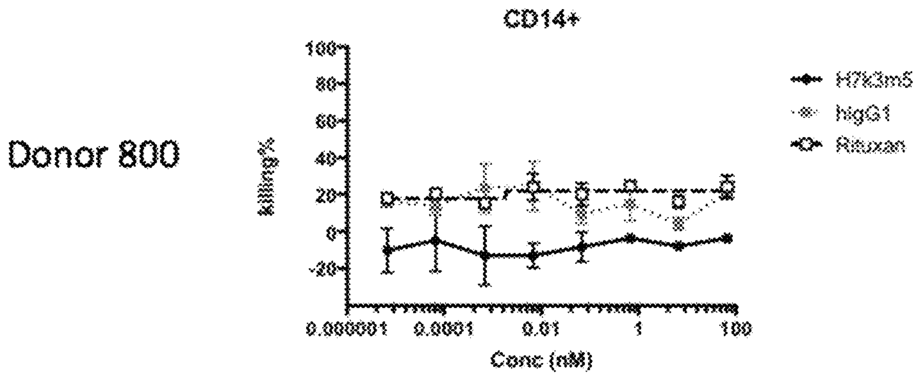
Figure 13D:
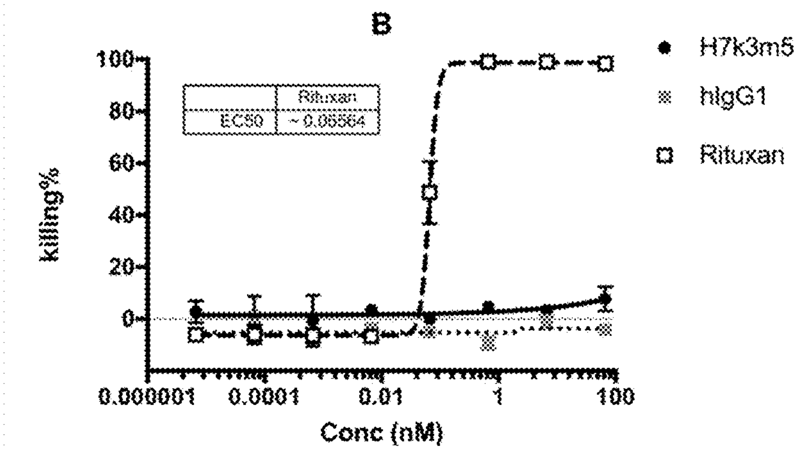
Figure 14A:
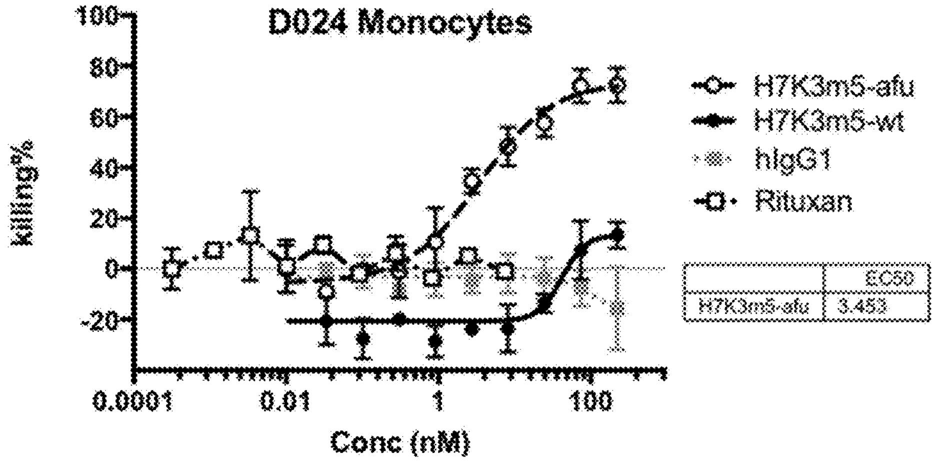
FIGS. 14A-14D show autologous ADCC of normal monocytes by wild type (WT) or afucosylated (afu) H7K3m5.
Figure 14B:
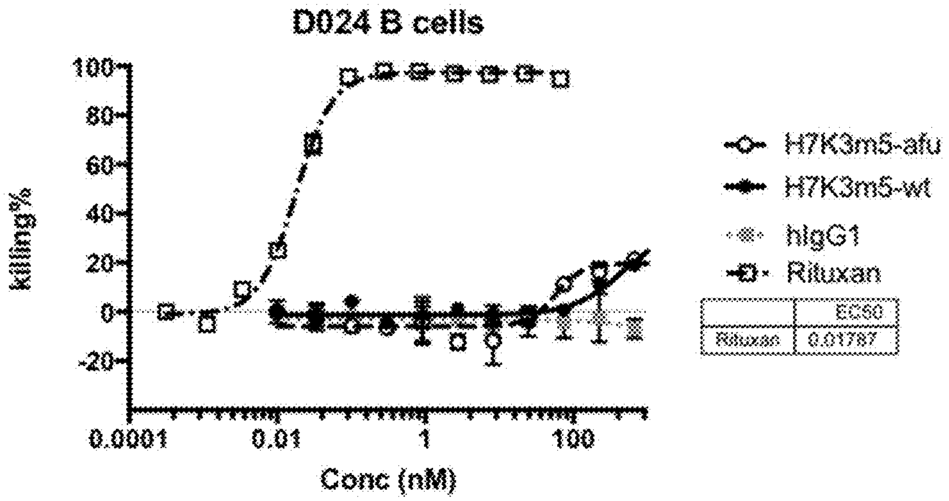
Figure 14C:
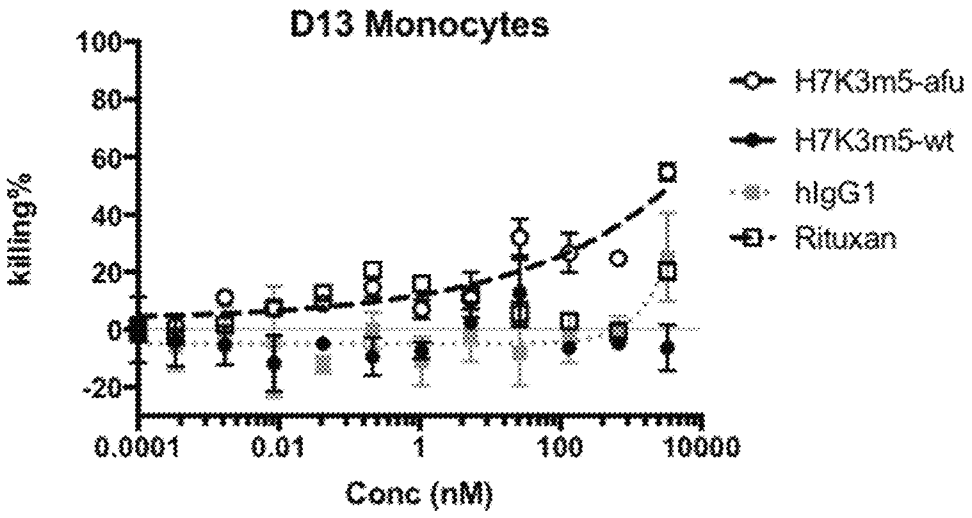
Figure 14D:
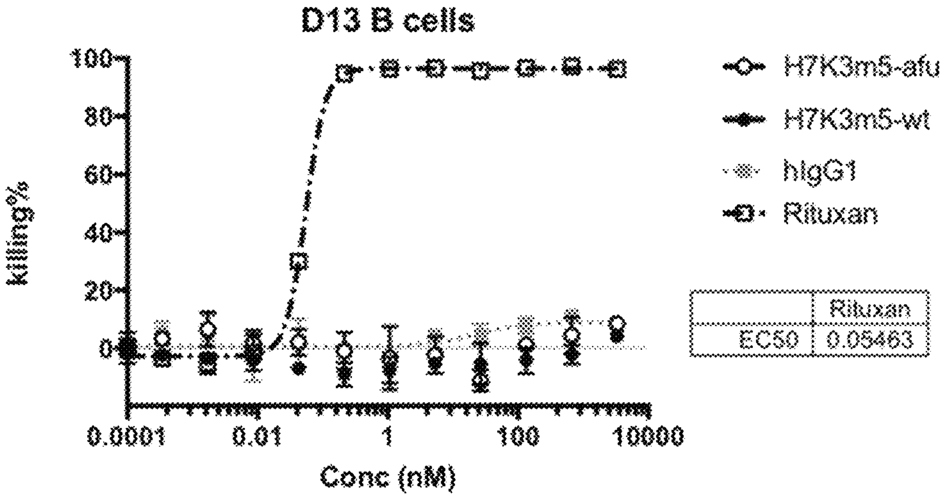

The inventors then determined the type of cells bound by LILRB4 antibody (H7K3m5) in solid tumors. Tissue samples from solid tumors were dissociated into single cells using mechanical methods and PBS-10 mM EDTA. In some cases, a peripheral blood sample was also obtained from same donor as tumor tissue sample and processed for flow cytometric analysis using standard methods. The resultant cells were incubated with H7K3m5 and an antibody cocktail for markers of myeloid cells at 4° C., using standard methods, and the stained samples were analyzed by flow cytometry. The gating in tumor samples were as follows. Myeloid dendritic cells (DC, $CD11b^+CD15^-CD14^-HLA\text{-}DR^+CD11c^+$), HLA-$DR^{Hi}$ tumor-associated macrophages (TAM)/monocytes ($CD11b^+CD15^-CD14^+HLA\text{-}DR^+$), HLA-$DR^{Lo}$ TAM/monocytic myeloid-derived suppressor cells (M-MDSC, $CD11b^+CD15^-CD14^+HLA\text{-}DR^-$), PMN-MDSC ($CD11b^+CD15^+CD14^-$). The gating in the peripheral blood were as follows: myeloid DC ($CD11b^+CD14^-CD11c^+$), monocytes ($CD111b^+CD14^+HLA\text{-}DR^{Hi}$), M-MDSC ($CD111b^+CD14^+HLA\text{-}DR^{Lo}$), PMN-MDSC ($CD11b^+CD15^+CD14^-HLA\text{-}DR^-Lox\text{-}1^+$). As shown in FIGS. 12A-12B, the results of these experiments demonstrate that H7K3m5 binds monocytic (but not granulocytic) myeloid cells in the tumor microenvironment and in the periphery. This finding is consistent with the expression pattern of LILRB4, which is restricted to myeloid cells of the monocytic lineage.

Although LILRB4 is expressed on primary normal monocytes, binding of H7K3m5 did not result in monocyte killing via ADCC (FIGS. 13A-13D). With afucosylated H7K3m5, killing of normal monocytes via ADCC was observed in 25-50% of tested PBMC donors (FIGS. 14A-14D, and FIGS. 15C-15D). In addition, as shown in FIGS. 15A-15B, both afucosylated and wild type H7K3m5 resulted in killing of pDCs via autologous ADCC. In the meantime, monocytes may be killed only with afucosylated H7K3m5, depending on donors (FIGS. 15C-15D).

Figure 16A:
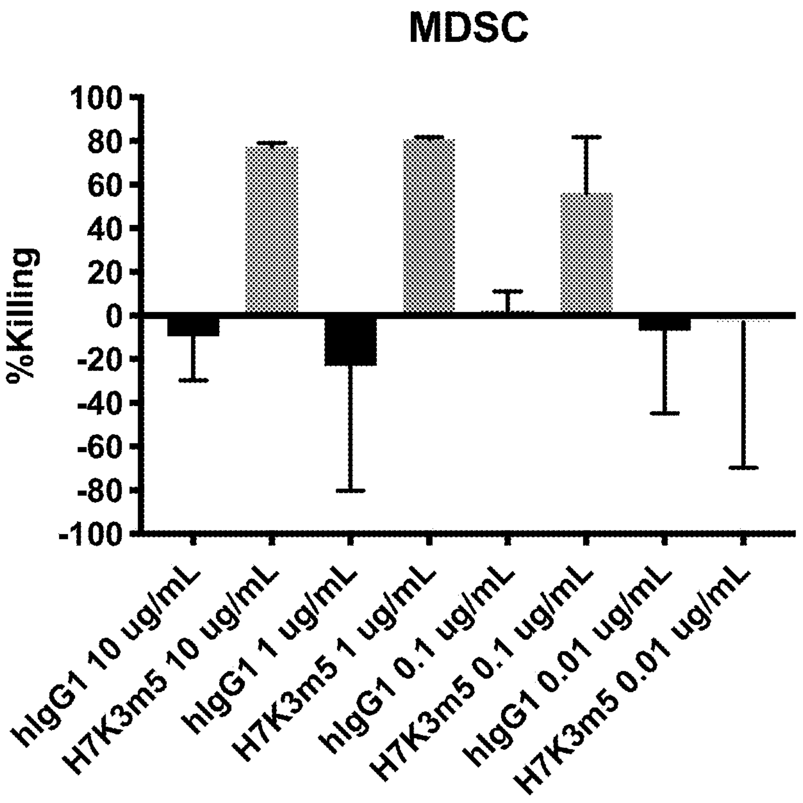
FIGS. 16A-16B show dose-dependent ADCC of CD33+ MDSC cells with purified NK cells in the presence of H7K3m5, which has no ADCC effect on monocytes at the same dose levels. H7K3m5 showed ADCC activity against the AML cell line THP-1 in the same experiment (FIG. 16B).
Figure 16B:
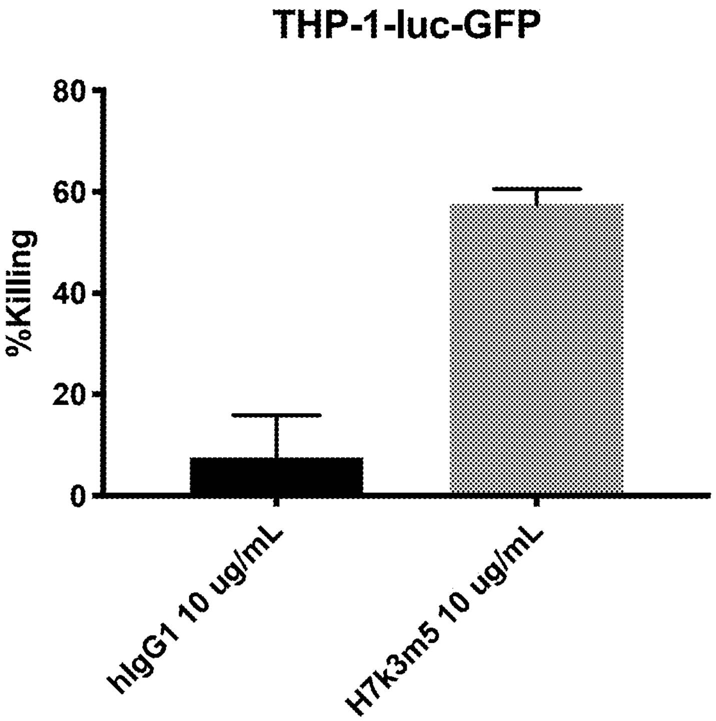

As shown in FIGS. 16A and 16B, anti-LILRB4 antibody such as H7K3m5 depleted in vitro-derived (tumor cell conditioned) myeloid-derived suppressor cells (MDSCs) via ADCC. This is a potential mechanism of action for anti-LILRB4 in the treatment of solid tumors.

Figure 17A:
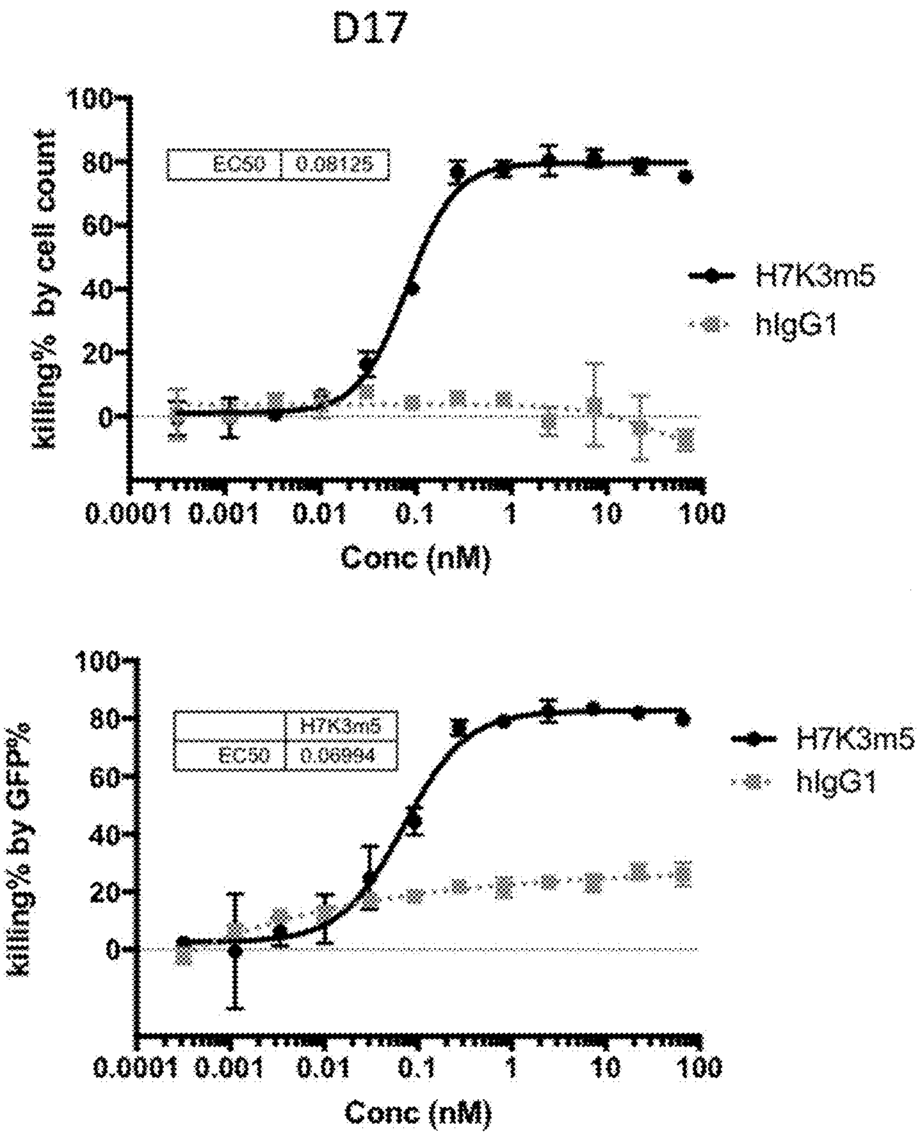
FIGS. 17A-17B show ADCP of THP-1-GFP cells by anti-LILRB4. THP-1-GFP cells were co-cultured with in-vitro differentiated macrophages for 24 hours in the presence of serially titrated wild type H7K3m5 or isotype control human IgG1. THP-1-GFP cells and macrophages were identified and quantified as $GFP^+$ and $CD163^+CD206^+$, respectively. Percent of THP-1 cell killing were calculated from absolute count of GFP+ cells or from GFP+% cells.
Figure 17B:
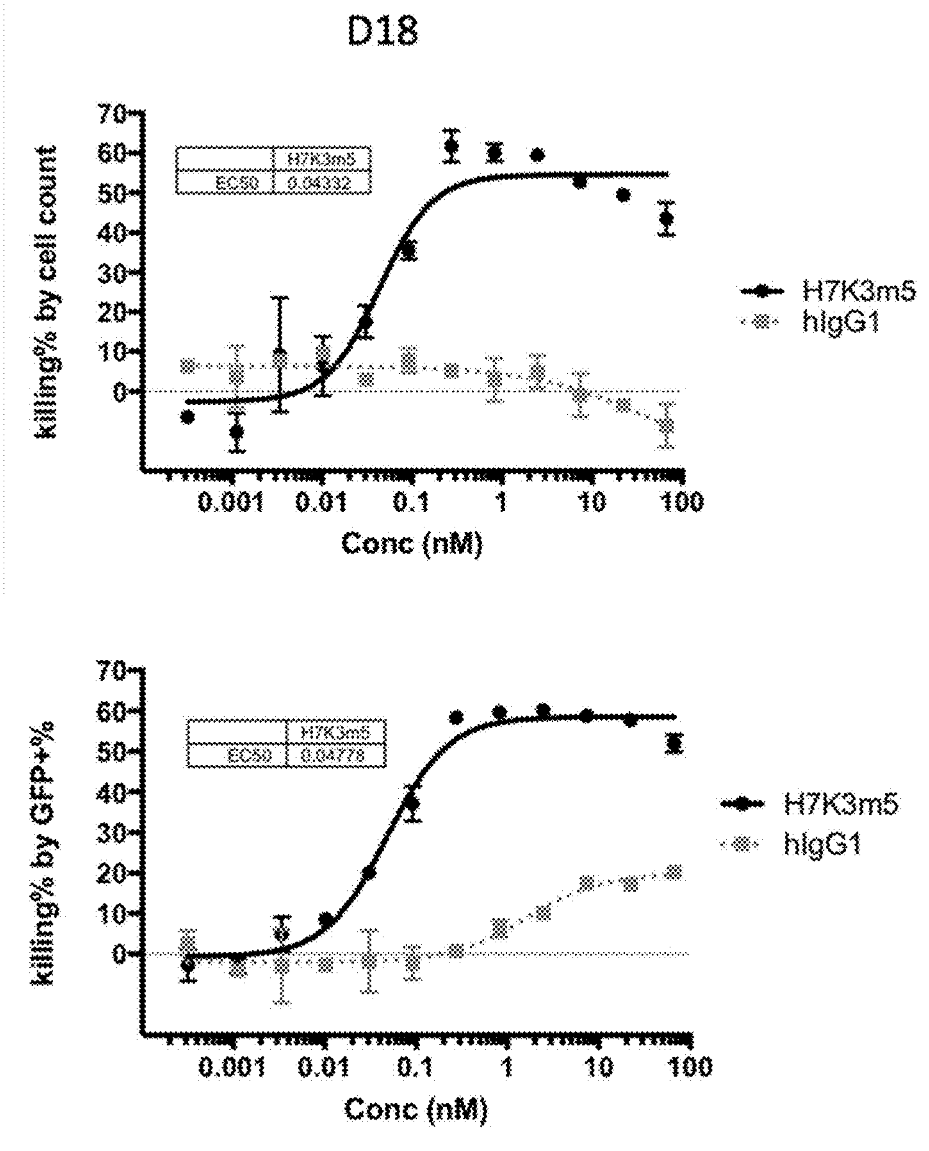

Besides ADCC, wild type H7K3m5 also demonstrated cell killing via ADCP towards THP-1 cells (FIGS. 17A-17B).

Figure 18:
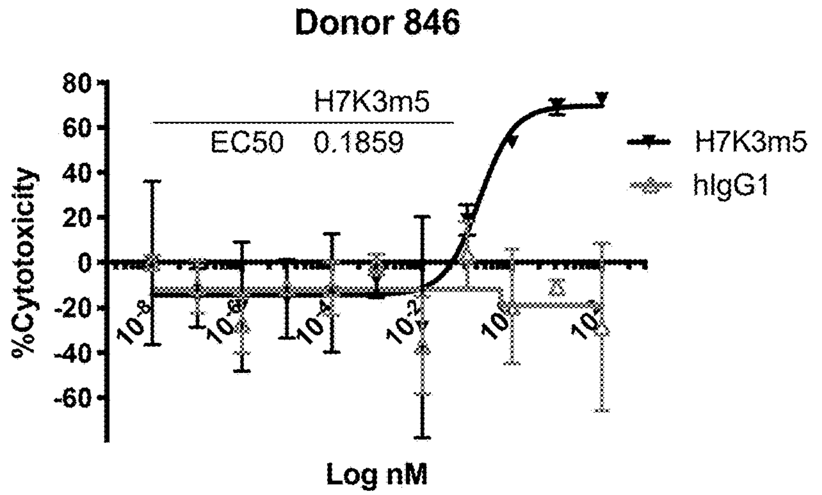
FIG. 18 shows in vitro T cell cytotoxicity against THP-1-GFP cells with anti-LILRB4. THP-1-GFP cells were co-cultured with purified naïve T cells. Anti-LILRB4 H7K3m5 can induce T-cell cytotoxicity against AML cells. Effector pan T cells were from 3 different healthy donors. The curves are plotted as mean±SD. The EC50 values are in nano molar units.
Figure 18:
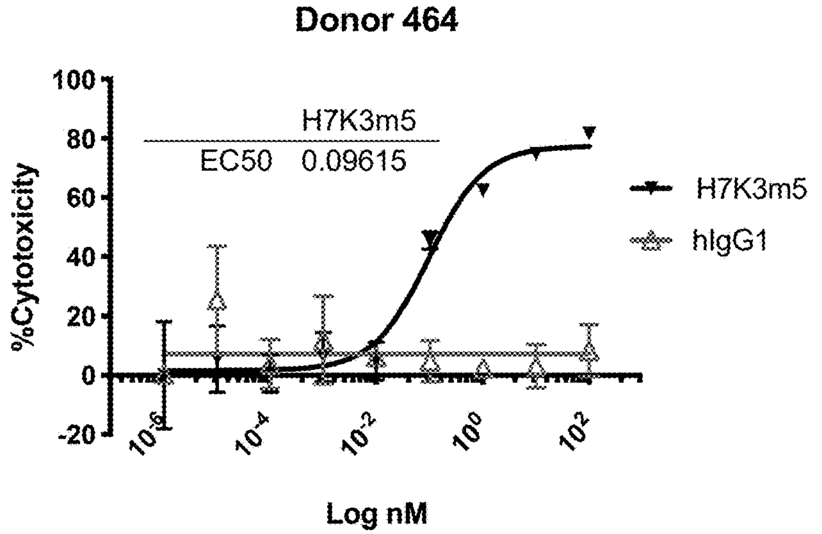
Figure 18:
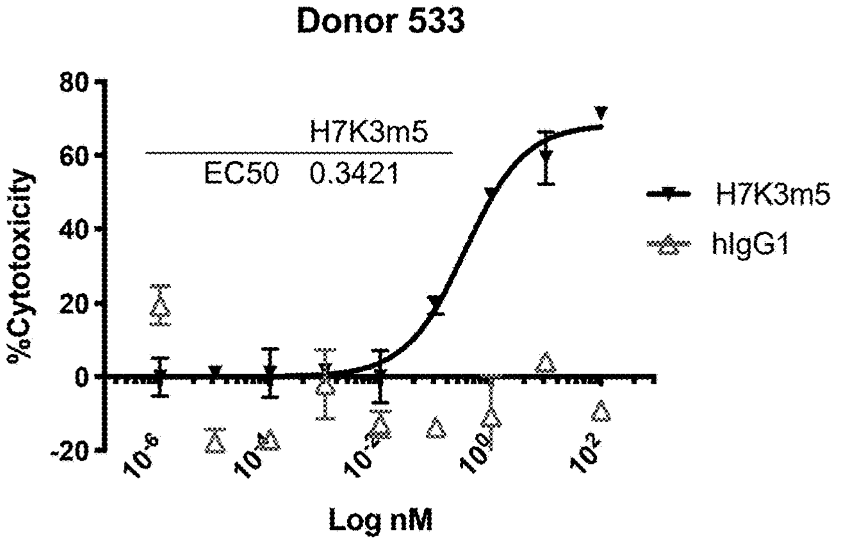

Anti-LILRB4 antibody also enhances T-cell mediated cytotoxicity against tumor cells. As shown in FIG. 18, anti-LILRB4 can induce T-cell cytotoxicity against AMIL cell line THP-1-GFP whereas no T cell cytotoxicity was observed with isotype control antibody. H7K3m5 treatment induced naïve T cells to kill THP-1 AML cells in a dose-dependent manner. The mean EC50 was 0.208±0.125 nM (31.2±18.8 ng/mL) (n=3).

Figure 19:
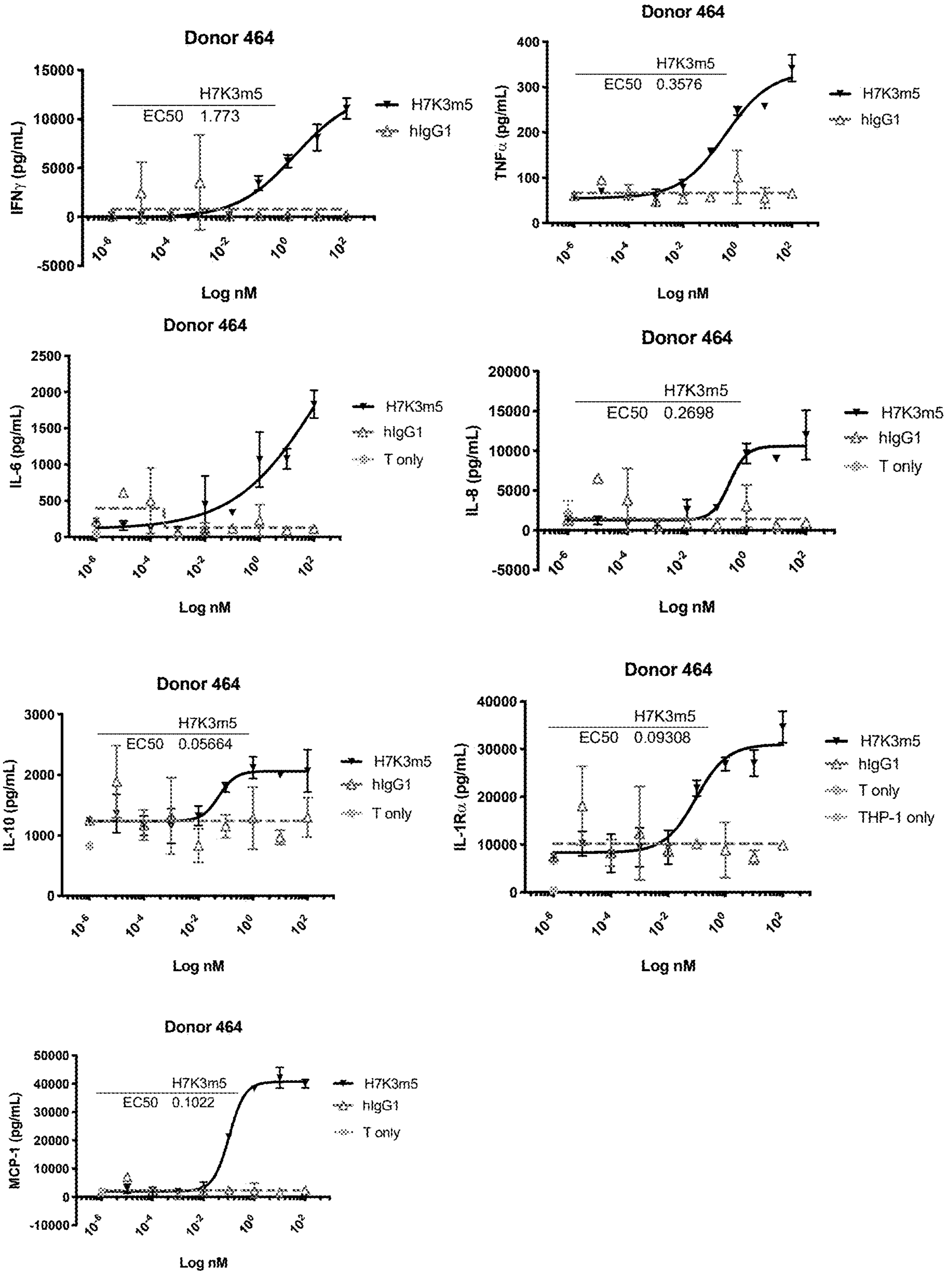
FIG. 19 shows representative cytokine production profile in the supernatant from the in vitro T-cell cytotoxicity assay samples. Anti-LILRB4 induced T-cell cytotoxicity against THP-1 cells is reflected by the elevation of cytokines in the co-culture. The curves are plotted as mean±SD. The $EC_{50}$ values are in nano molar units. An EC50 value cannot be derived for IL-6.

Cytokine measurement by a multiplexing Luminex assay from the supernatant of cytotoxicity assay samples demonstrated a dose-dependent increase of IFNγ and TNFα in H7K3m5 treated samples compared to control samples (FIG. 19). The cytokine profile changes were consistent with increased cell killing activity measured by THP-1 cell quantification (FIG. 18). In addition to increased TNFα and IFNγ levels which are likely produced by activated cytotoxic T cells, a dose-dependent increase of MCP-1 and IL-1Rα known produced by monocytes and macrophages were also observed, which are likely from activated THP-1 cells. IL-6, IL-8, IL-10 levels were also increased in respond to H7K3m5 treatment in comparison to controls. These cytokines are likely from both activated T cells and THP-1 cells.

Figure 20:
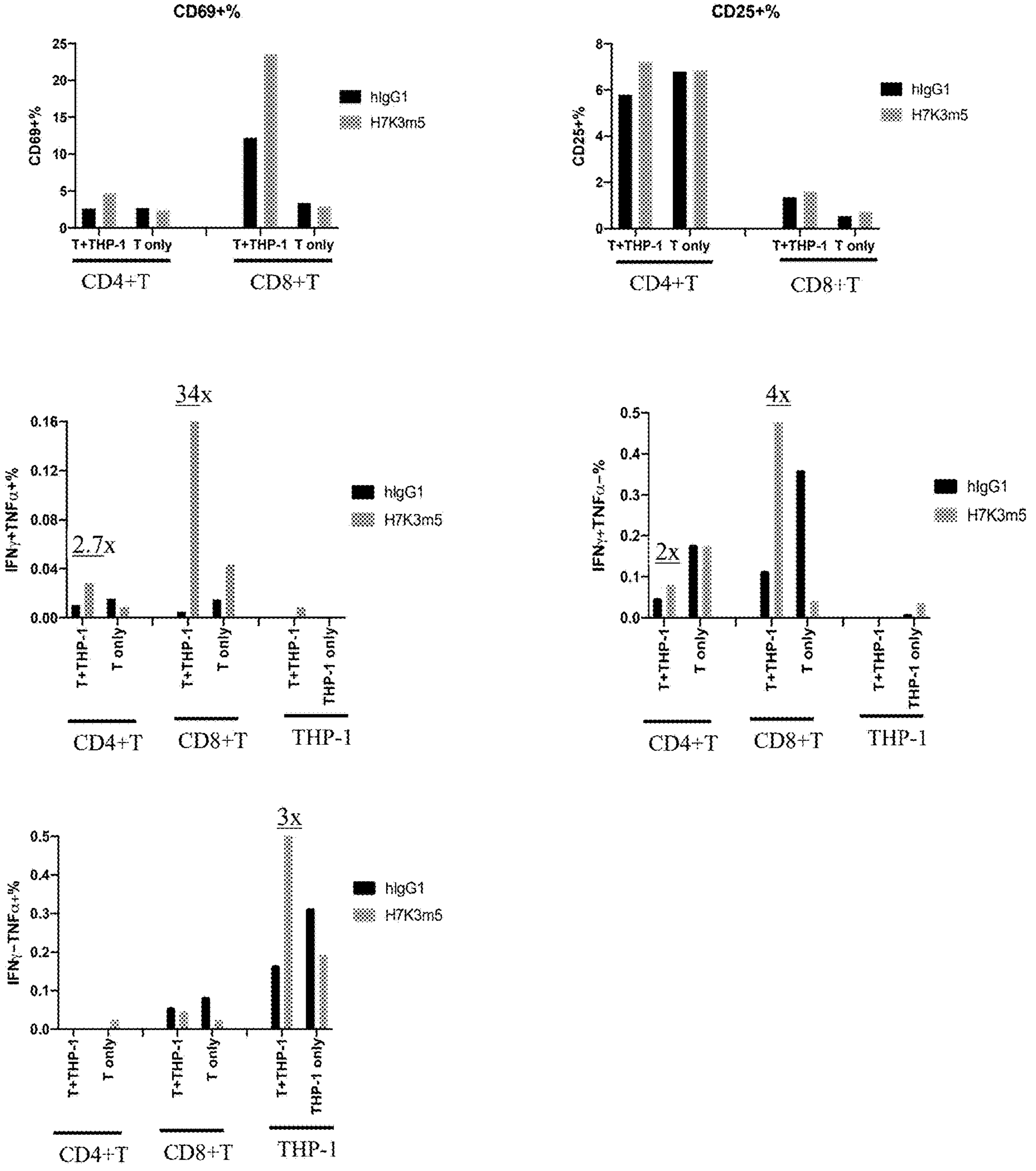
FIG. 20 shows the evaluation of T-cell activation by flow cytometry. A-B: surface staining of T cell activation markers CD69 (A) and CD25 (B). C-E: Intracellular cytokine staining of co-cultured T cells and THP-1 cells by flow cytometry. C: Cells producing both IFNγ and TNFα; D: Cells producing IFNγ but not TNFα; E: Cells producing TNFα but not IFNγ.

T-cell activation markers were assessed by flow cytometry (see FIG. 20). A 2-fold higher percentage of CD69-expressing T cells was observed with H7K3m5 treatment (FIG. 20A). Here, 4.7% of CD4+ T cells and 23.6% of CD8+ T cells treated with H7K3m5 expressed CD69 while only 2.6% of CD4+ T cells and 12.2% of CD8+ T cells treated with isotype control expressed CD69. There was no increase of CD69+ T cells by H7K3m5 treatment when T cells were cultured alone. H7K3m5 had only mild effect on CD25+ T-cell increase (FIG. 20B).

Cytokine production in the co-cultured T cells and THP-1 AML cells was also assessed by intracellular staining for flow cytometry. Compared to isotype control, H7K3m5 treatment increased IFNγ and TNFα producing CD4+ T cells and CD8+ T cells by 2.7-fold and 34-fold, respectively (FIG. 20C). IFNγ-producing CD4+ and CD8+ T cells were increased by 2-fold and 4-fold with H7K3m5 treatment, and IFNγ was not produced by THP-1 cells (FIG. 20D). On the contrary, TNFα-producing THP-1 cells was increased by 3-fold with H7K3m5 treatment when co-cultured with T cells (FIG. 18E). Without T cells, H7K3m5 treatment on THP-1 cells alone did not result in an increase of TNFα-producing THP-1 cells. These data indicated that IFNγ was only produced by activated T cells and TNFα was produced by both activated T cells and THP-1 AML cells.

Taking together, H7K3m5 enhanced antigen presentation of THP-1 cells and activated T cells to produce IFNγ and TNFα.

Figure 21:
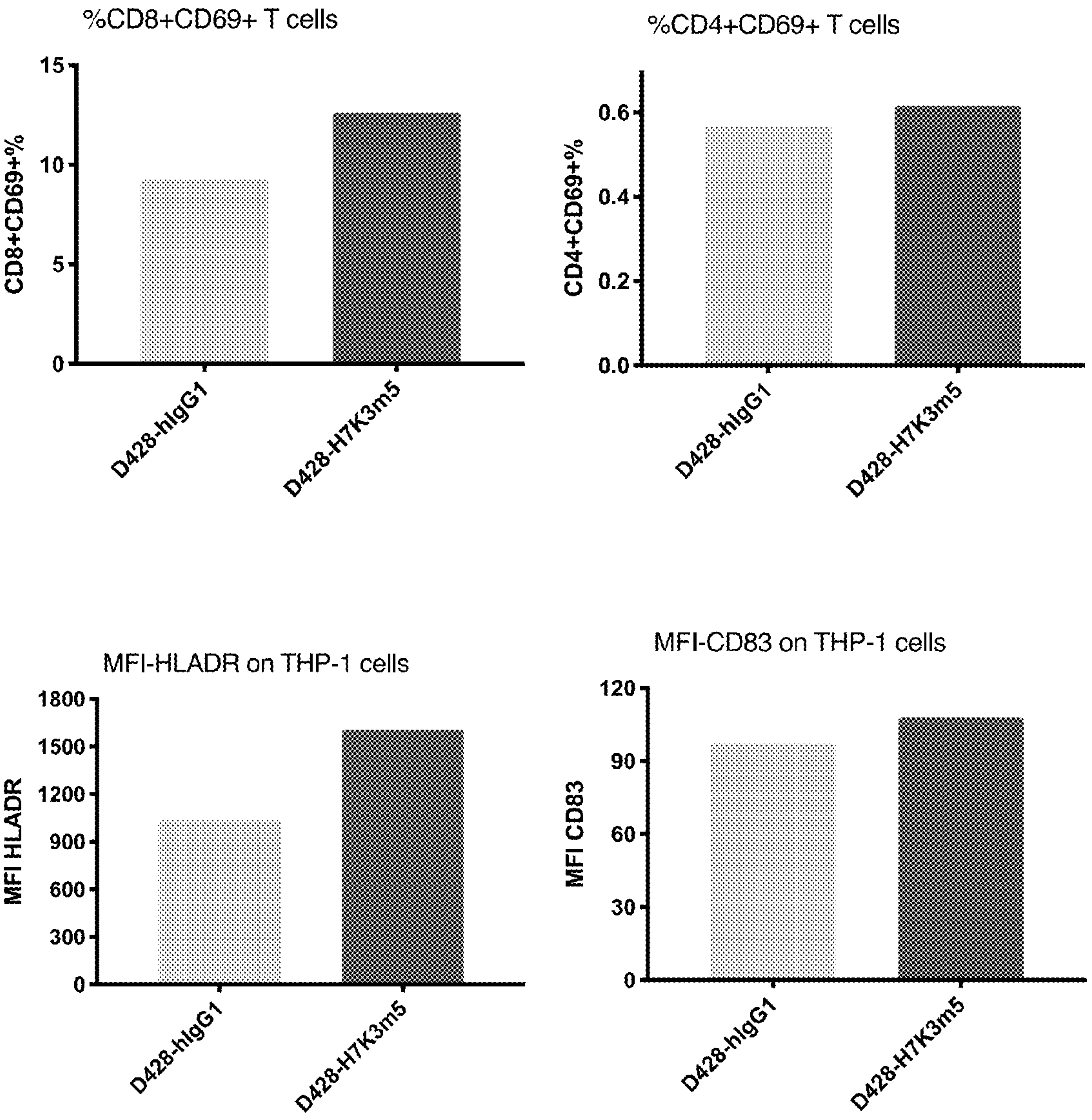
FIG. 21 shows increased T cell activation markers and MHC expression on THP-1 cells upon H7K3m5 treatment. D428=donor 428. MFI=geometric mean fluorescence intensity.

The proposed mechanism of enhancement of T-cell mediated cytotoxicity consists of blockade of LILRB4 inhibitory receptor signaling with the anti-LILRB4 blocking antibody, reduction of arginase production by THP-1 cells, production of cytokines by THP-1 cells (FIGS. 19 and 20) and enhanced antigen presentation ability of THP-1 (FIG. 21). As shown in FIG. 21, THP-1 AML cells and naïve T cells were co-cultured at 37° C. for 48 hrs at E:T ratio of 4:1 in the presence of H7K3m5 or human IgG1 at 1.5 ug/mL (10 nM). T-cell and THP-1 cell activation markers were assessed by flow cytometry (FIG. 21). On THP-1 AML cells, a mild up-regulation of costimulatory molecule CD83 was detected in all experiments. Each experiment used pan T cells from a different donor (n=4). A mild up-regulation of MHC class II molecule HLADR (n=3), MHC class I molecule (n=1), and another costimulatory molecule CD86 (n=2) was also detected on THP-1 cells. These data indicate that H7K3m5 treatment enhances antigen-presentation activity of THP-1. T-cell activation marker CD69 was induced by H7K3m5 treatment moderately (n=1), consistent with increased cytotoxic activity. Taking together, the enhanced antigen presentation of THP-1 may trigger T-cell activation and lead to enhanced cytotoxic activity.

Figure 22:
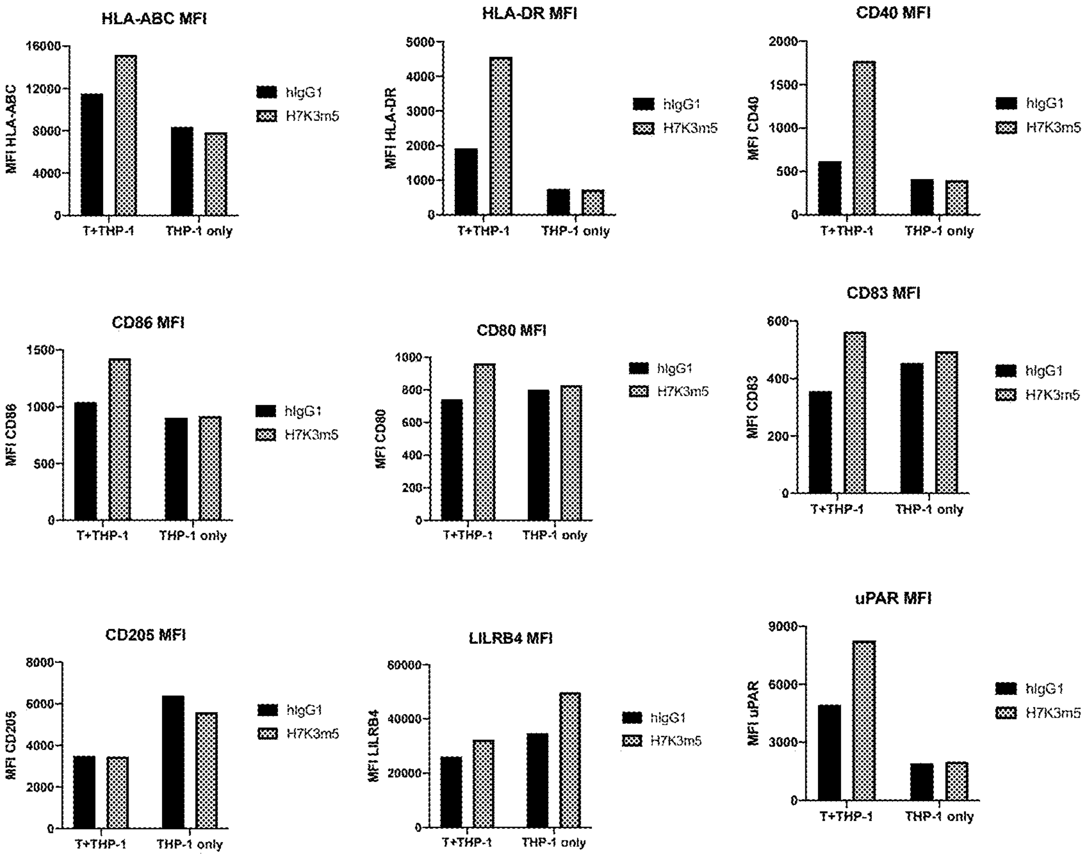
FIG. 22 shows surface expression of activation markers on THP-1 AML cells by flow cytometry. MFI=geometric mean fluorescence intensity.
Figure 23:
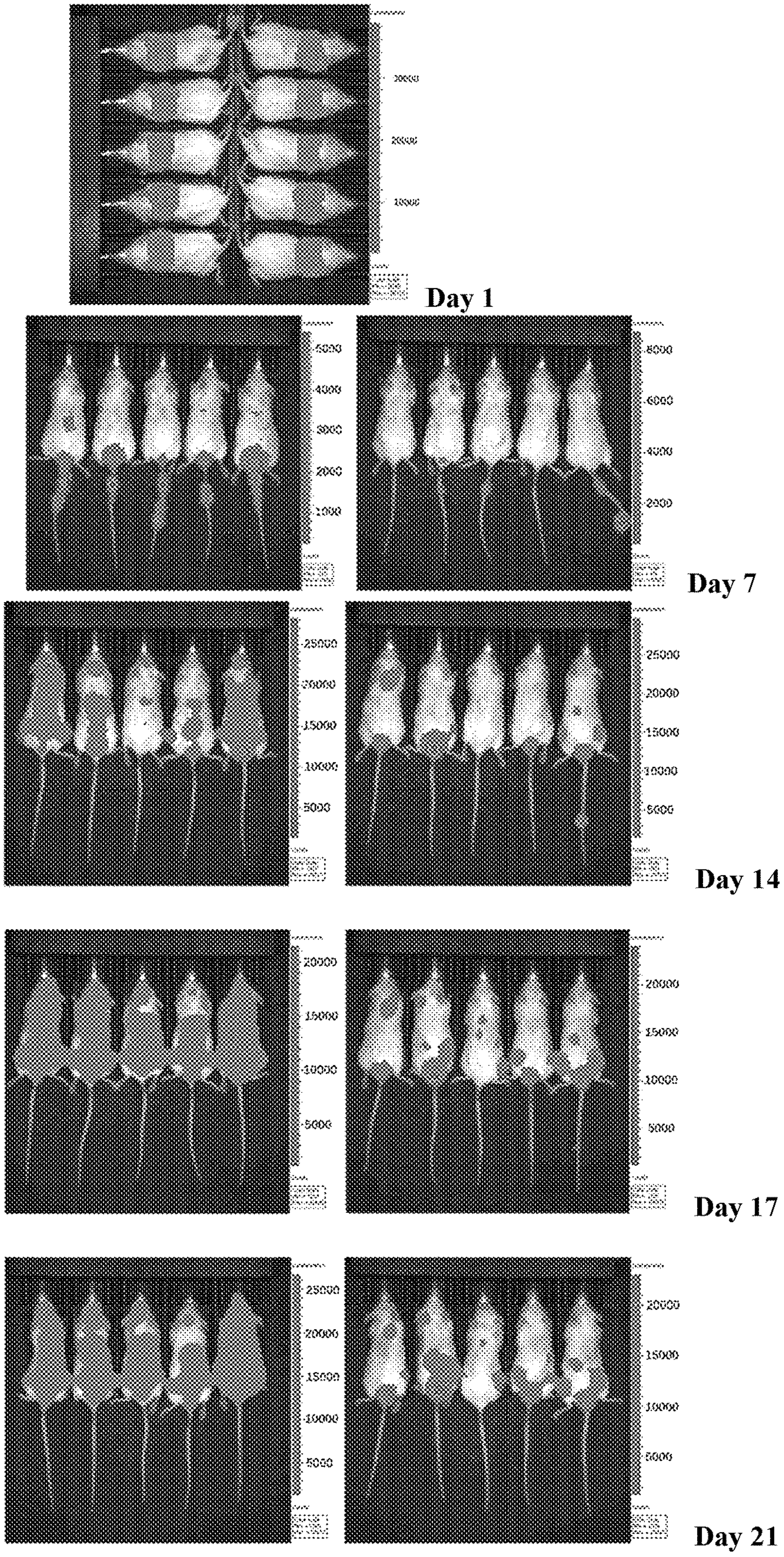
FIG. 23 shows H7K3m5 is efficacious in AML xenograft model. This experiment evaluated the growth kinetics of THP-1.luc cells and determined the efficacy of H7K3m5 in the THP-1.luc human AML xenograft model in female NSG mice using bio-imaging. $1\times10^6$ THP-1.luc cells were intravenously implanted to JAX female NSG mice via tail vein. Whole body bioluminescent imaging was conducted on Day 1 (4-6 hrs after cell injection) prior to animal randomization and single-dose intravenous administration of the vehicle control or H7K3m5 (1 mg/kg). On Days 7, 14, 17 and 21, whole body bioluminescent imaging data were collected for the control and treated animals.

When THP-1 cells are co-cultured with naïve T cells in the presence of H7K3m5, H7K3m5 activates T-cell cytotoxicity against THP-1 (FIG. 20). To further understand the changes to both cell types in this activity, naïve T cells and THP-1 AML cells were co-cultured at 37° C. for 48 hrs at an E:T ratio of 8:1 in the presence of H7K3m5 or human IgG1 at 3 ug/mL (20 nM). THP-1 activation was evaluated by flow cytometry (FIG. 22). Expression of HLA class I (A, B, C) and Class II (HLA-DR), co-stimulatory molecule CD40, CD86, CD80, and CD83 was induced by H7K3m5 treatment, indicating that H7K3m5 enhanced antigen-presentation function of THP-1 cells. On the contrary, expression of inhibitory molecules CD205 and LILRB4 was not reduced by H7K3m5. Interestingly and unexpected, H7K3m5 treatment also increased expression of uPAR, a NF-kB target downstream of LILRB4, which is highly expressed in monocytic AML cells and well known to promote cancer invasion, metastasis, survival and angiogenesis (Deng et al 2018).

When coculturing THP-1 AML cells with naïve T cells, no T-cell activation and cytotoxicity was observed. This is likely due to compromised antigen presentation function of THP-1 AML cells that have high LILRB4 expression. When H7K3m5 was added to co-cultured THP-1 and naïve T cells, enhanced antigen presentation function of THP-1 cells was observed exemplified by increased HLA-DR and CD83 expression. Activation of naïve T cells were correspondingly observed, in particular cytotoxic activation against THP-1 cells. This is corroborated by the increased secretion of cytokines (i.e., TNFα and IFNγ) in tissue culture media. These data demonstrate that H7K3m5 is able to activate T cell cytotoxicity against THP-1 AML cells.

Cytotoxicity of normal monocytes by naïve T cells mediated by H7K3m5 was also evaluated in this in vitro system but no killing of normal monocytes was observed (data not shown). LILRB4 density on normal monocytes is 10-fold lower than that on THP-1 AML cells, more importantly, the antigen presentation capacity of normal monocytes is expected to be significantly lower than that of tumor AML cells due to lack of tumor associated antigens. Although the inventors found that patient AML cells may express LILRB4 at the similar or high levels as that on normal monocytes, it is plausible that AML blasts may be phenotypically more like THP-1 cells and can be killed by activated T cells when treated with H7K3m5.

Figure 24:
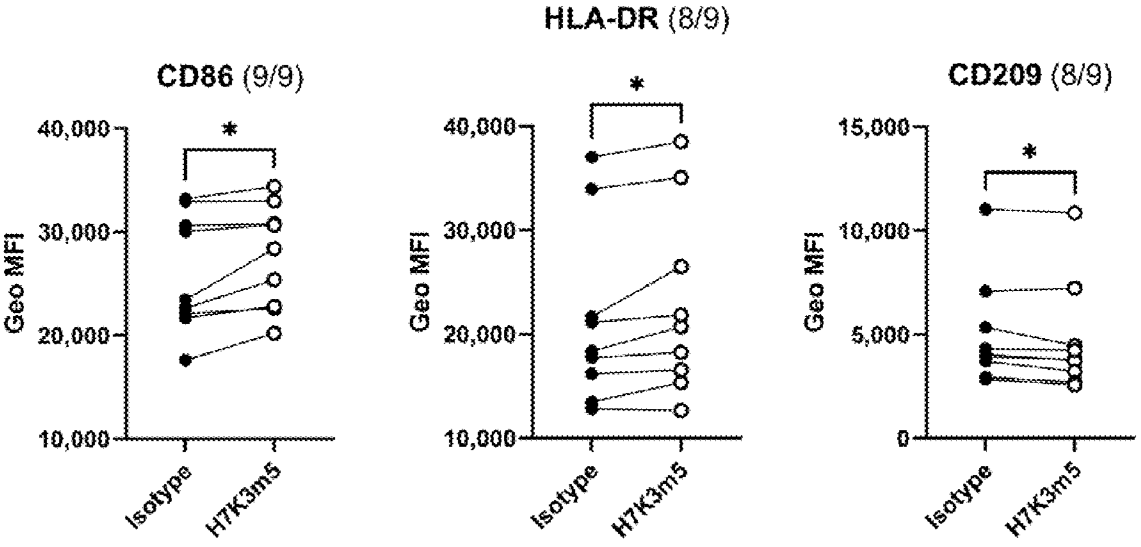
FIG. 24 illustrates the flow cytometric data showing that H7K3m5 potentiates maturation/activation of monocyte-derived dendritic cells (Mo-DC) in response to Toll-Like Receptor (TLR) signaling. H7K3m5 enhanced the expression of activation markers (CD86, HLA-DR) while decreasing the expression of the tolerogenic marker CD209. Each line represents result from a different healthy donor. The fraction of donors in which H7K3m5 produced the desired pro-inflammatory effect is indicated in parentheses. *$p<0.05$ (paired t test).
Figure 25:
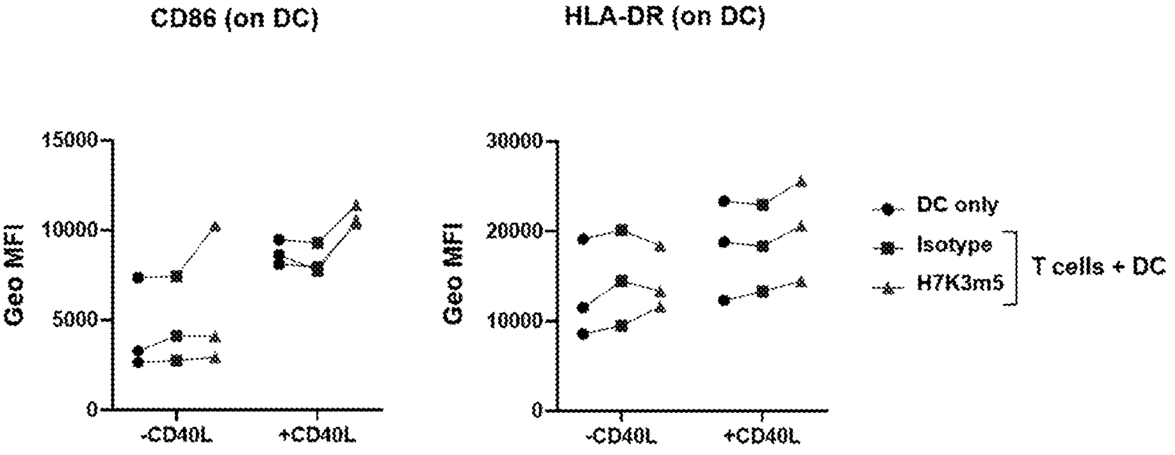
FIG. 25 illustrates the flow cytometry data showing that H7K3m5 enhances the expression of activation markers (CD86 and HLA-DR) on the surface of mature monocyte-derived DC (Mo-DC) upon a mixed leukocyte reaction with allogeneic T cells. The effect of H7K3m5 was evaluated in the absence (−CD40L) or presence (+CD40L) of CD40 ligand to study the effect of H7K3m5 on immature and mature Mo-DC, respectively. Each line represents the result from a different healthy donor (n=3 donors).
Figure 26:
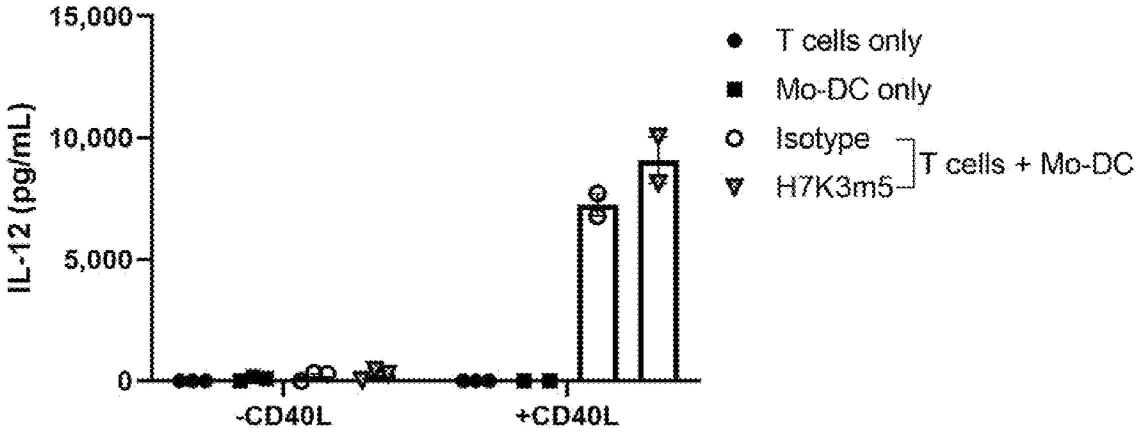
FIG. 26 illustrates the ELISA data showing that H7K3m5 enhances IL-12 production in an allogeneic mixed leukocyte reaction of T cells and mature monocyte-derived DC (Mo-DC). The effect of H7K3m5 was evaluated in the absence (−CD40L) or presence (+CD40L) of CD40 ligand to study the effect of H7K3m5 on immature and mature Mo-DC, respectively. Data are presented as mean±SEM and data for each donor is also shown as individual data points (n=2-3 donors).
Figure 27:
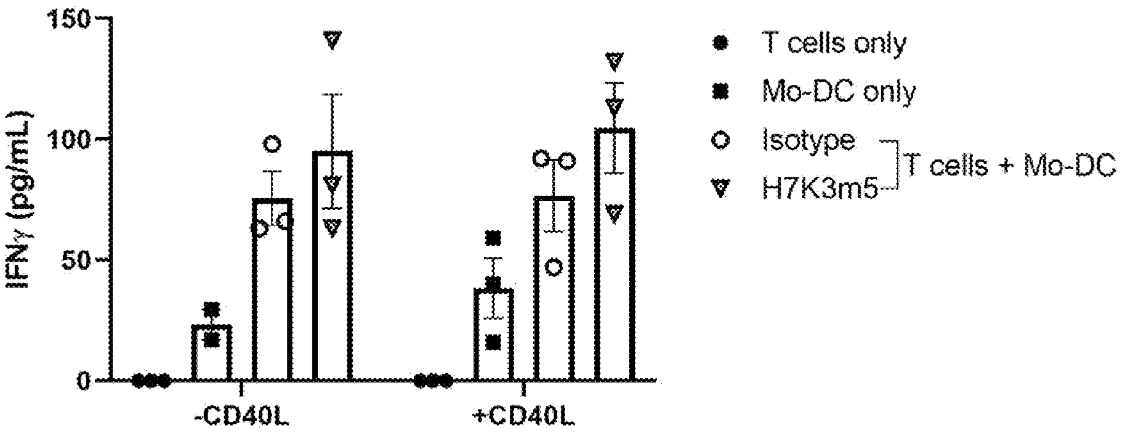
FIG. 27 illustrates the ELISA data showing that H7K3m5 enhances IFN-γ production in an allogeneic mixed leukocyte reaction of T cells and monocyte-derived DC (Mo-DC). The effect of H7K3m5 was evaluated in the absence (−CD40L) or presence (+CD40L) of CD40 ligand to study the effect of H7K3m5 on immature and mature Mo-DC, respectively. Data are presented as mean±SEM and data for each donor is also shown as individual data points (n=3 donors).

The inventors then tested the effect of H7K3m5 on the dendritic cells differentiated from monocytes (Mo-DC). Classical monocytes were isolated from healthy donor PBMC and differentiated into immature dendritic cells with DC media (StemXVivo, 50 g/mL gentamycin, 50 ng/mL GM-CSF and 35 ng/mL IL-4) for 6 days. The immature monocyte-derived dendritic cells (Mo-DC) were then incubated with antibodies (100 nM) in the presence of 100 ng/mL LPS (TLR4 agonist) to induce dendritic cell maturation and activation. After 2 days, the cells were analyzed by flow cytometry for expression of cell surface markers. As shown in FIG. 24, the increased expression of HLA-DR and of the co-stimulatory molecule CD86 and the decreased expression of the tolerogenic marker CD209 indicate that H7K3m5 enhances the antigen-presentation and pro-inflammatory capacity of Mo-DC in response to TLR signaling.

Immature dendritic cells were differentiated from monocytes (Mo-DC) isolated from PBMC of healthy donors with DC media (StemXVivo, 50 μg/mL gentamycin, 100 ng/mL GM-CSF and 35 ng/mL IL-4) for 5 days. On day 5, Mo-DC were supplemented with fresh DC media and treated with 30 μg/mL H7K3m5 or its isotype control in the absence or presence of g/mL CD40 ligand for an additional 2 days. On day 7, T cells were isolated from PBMC of healthy, unrelated donors and suspended in fresh media containing the cytokine cocktail and g/mL H7K3m5. Cultures of T cells only and Mo-DC only were included as controls. At the end of 4 days, IFN-γ and IL-12 levels in media supernatant were measured by ELISA, whereas the cell surface phenotype of Mo-DC was analyzed by flow cytometry. The results of the experiments illustrated in FIGS. 24-27 show that the pro-inflammatory effect of H7K3m5 on Mo-DC is more pronounced if the latter have been matured with CD40 ligand.

Example 5

This example illustrates the generation of LILRB4/CD3 bispecific antibodies based on the heavy and light chain variable domain sequences of H7K3m5 and the antibodies disclosed in WO2019057099. Heavy chain heterodimerization was controlled by knob and hole mutations (Merchant et al *Nature Biotech* 1998, 16, 677-681) stabilized by engineered disulfide bonds (Carter *J Immunol Methods* 2001, 248, 7-15). Correct light chain pairing was controlled by replacing light chain Ckappa or heavy chain CH1 with human T-cell receptor alpha (TRAC) and beta (TRBC) constant domains as described previously (WO2019057122A1). Mutations were also introduced into the human IgG1 constant domains to reduce effector function, improve stability, and increase productivity in CHO (Alegre et al *Transplantation* 1994, 57 1537-43 and Hu et al *Biotechnol Prog* 2017, 33, 786-794).

Expression and Purification of LILRB4/CD3 Bispecific Antibodies

FIG. 28A shows the schematic representation of 6 first generation LILRB4/CD3 bispecific antibodies in 1+1 or 2+1 configurations. The bispecific antibodies in the 1+1 configurations (4-3ab and 4ab-3) were engineered to bind to a single copy of CD3 epsilon and LILRB4. The bispecific antibodies in the 2+1 (44-4ab, 4ab4ab-3, 43ab-4, and 4ab3-4ab) configurations were engineered to bind to a single copy of CD3 epsilon and 2 copies of LILRB4. The 44-3ab and 4ab4ab-3 configurations have both LTLRB4 binding moieties in tandem on one arm of the bispecific. The 43ab-4 and 4ab3-4ab configurations have LILRB4 binding moieties on both arms of the bispecific. The polypeptide chains for each first-generation bispecific antibodies and the amino acid sequences thereof are listed in Table 9.

TABLE 9

Sequences for first-generation LILRB4/CD3 bispecific antibodies

| Antibody No. | Bispecific Name | Polypeptide Names | Configuration | SEQ ID NO. |
|---|---|---|---|---|
| 1 | 4-3ab | 2 | $V_H$(CD3)-TCRβ-$C_H$2-$C_H$3(KiHa) | 92 |
| | | 3 | $V_H$(LILRB4)-$C_H$1-$C_H$2-$C_H$3(KiHb) | 94 |
| | | 10 | $V_L$(CD3)-TCRα | 101 |
| | | 11 | $V_L$(LILRB4)-$C_L$ | 103 |
| 2 | 4ab-3 | 1 | $V_H$(CD3)-$C_H$1-$C_H$2-$C_H$3(KiHa) | 91 |
| | | 5 | $V_H$(LILRB4)-TCRβ-$C_H$2-$C_H$3(KiHb) | 96 |
| | | 9 | $V_L$(CD3)-$C_L$ | 100 |
| | | 12 | $V_L$(LILRB4)-TCRα | 104 |
| 3 | 44-3ab | 2 | $V_H$(CD3)-TCRβ-$C_H$2-$C_H$3(KiHa) | 92 |
| | | 4 | $V_H$(LILRB4)-$C_H$1-L-$V_H$(LILRB4)-$C_H$1-$C_H$2-$C_H$3(KiHb) | 95 |
| | | 10 | $V_L$(CD3)-TCRα | 101 |
| | | 11 | $V_L$(LILRB4)-$C_L$ | 103 |
| 4 | 4ab4ab-3 | 1 | $V_H$(CD3)-$C_H$1-$C_H$2-$C_H$3(KiHa) | 91 |
| | | 6 | $V_H$(LILRB4)-TCRβ-L-$V_H$(LILRB4)-TCRβ-$C_H$2-$C_H$3(KiHb) | 97 |
| | | 9 | $V_L$(CD3)-$C_L$ | 100 |
| | | 12 | $V_L$(LILRB4)-TCRα | 104 |
| 5 | 43ab-4 | 8 | $V_H$(LILRB4)-$C_H$1-L-$V_H$(CD3)-TCRβ-$C_H$2-$C_H$3(KiHa) | 99 |
| | | 3 | $V_H$(LILRB4)-$C_H$1-$C_H$2-$C_H$3(KiHb) | 94 |
| | | 10 | $V_L$(CD3)-TCRα | 101 |
| | | 11 | $V_L$(LILRB4)-$C_L$ | 103 |
| 6 | 4ab3-4ab | 7 | $V_H$(LILRB4)-TCRβ-L-$V_H$(CD3)-$C_H$1-$C_H$2-$C_H$3(KiHa) | 98 |
| | | 5 | $V_H$(LILRB4)-TCRβ-$C_H$2-$C_H$3(KiHb) | 96 |
| | | 9 | $V_L$(CD3)-$C_L$ | 100 |
| | | 12 | $V_L$(LILRB4)-TCRα | 104 |

To generate the first generation the bispecific antibodies, DNA encoding the first-generation bispecific antibodies were cloned into mammalian expression vectors after gene synthesis. Bispecific antibodies were then expressed by transiently transfecting appropriate mix of vectors into Expi293 cells and expressing in 100 mL scale. All samples were first purified from supernatants by protein A affinity chromatography. Bispecific antibodies No. 1-3 were further purified by size-exclusion chromatography (SEC) while bispecific antibodies 4-6 were purified by anion exchange chromatography (AEX). All samples were analyzed by SDS-PAGE and analytical SEC for purity. The results are shown in Table 10. Aliquots were deglycosylated with PNGase F (MEDNA Bio M3103) and were characterized by mass spectrometry using a Water Acquity UPLC coupled to a Xevo G2-XS QTOF using an Acquity UPLC protein BEH SEC column. The results are shown in Table 11.

TABLE 10

Yields and purities of first-generation bispecific antibodies

| Bispecific Antibody | Yield from 100 mL Expi239 (mg) | Purity (SEC) |
|---|---|---|
| 4-3ab | 11.4 | 99.5% |
| 4ab-3 | 6.1 | 100% |
| 44-3ab | 5.8 | 96.5% |
| 4ab4ab-3 | 5.1 | 96.0% |
| 43ab-4 | 2.8 | 98.4% |
| 4ab3-4ab | 2.2 | 97.8% |

TABLE 11

Mass spectrometry data for first generation bispecific antibodies

| Bispecific Antibody | Molecular Weight Calculated (Da) | Molecular Weight Measured (Da) | Significant impurities |
|---|---|---|---|
| 4-3ab | 148,640 | 148,626 | Hole-hole homodimer, O-glycan (+948), LC mispairing, pyro-Q (−17) |
| 4ab-3 | 148,640 | 148,266 | Hole-hole homodimer, O-glycan (+948), pyro-Q (−17) |
| 4ab4ab-3 | 199,311 | 199,298 | O-glycan (+948) |
| 4ab3-4ab | 199,227 | 199,230 | None |
| 44-3ab | 196,423 | 196,410 | Pyro-Q (−17) |
| 43ab-4 | 196,423 | 196,427 | None |

Second generation bispecific antibodies were designed to improve homogeneity and manufacturability. Specifically, this was done by mutating S91A in the TCRα domain to remove O-glycan modification or making a Q1E mutation to prevent N-terminal pyro-Q formation. The polypeptide chains for each first-generation bispecific antibodies and the amino acid sequences thereof are listed in Table 12. DNA encoding the second-generation bispecific antibodies and controls were cloned into mammalian expression vectors after gene synthesis or standard molecular biology protocols starting from first-generation bispecific antibodies. Bispecific antibodies were then expressed using appropriate vectors transiently transfected into CHO-K1 cells and expressed at 1 L scale for 14 days using a fed-batch protocol. Bispecific antibodies were purified from supernatant from all samples using by a protein A column and polished by SEC. All samples were analyzed by SDS-PAGE and analytical SEC for purity. The results are shown in Table 13. Aliquots of samples were deglycosylated and were characterized by mass spectrometry, which showed that the samples lacked impurities of first-generation bispecific antibodies (see Table 14).

In Vitro Cytotoxicity Assay

A FACS based approach was used to determine the ability of the LILRB4/CD3 bispecific antibodies to mediate target cell killing by T cells. In vitro cytotoxicity of THP-1 and MV4-11 cells: Human AML cell line THP-1 and MV-4-11 cells were engineered to express green fluorescent protein (GFP). Human buffy coats were obtained from heathy donors collected by Stanford Blood Center. Human peripheral blood mononuclear cells (PBMC) were isolated from buffy coats by Ficoll Paque Plus (GE Healthcare Catalog No. 17-1440-03) density gradient cell separation. Pan T cells were further isolated from PBMCs using a human Pan T cell isolation kit (Miltenyi Biotec Catalog No. 130-096-535). $5\times10^5$ freshly isolated human pan T cells were used as effector cells and $1\times10^5$ THP-1-GFP were used as target cells in a 5:1 ratio. In the MV4-11 cell killing assay, $9\times10^5$ freshly isolated human pan T cells were used as effector cells and $1\times10^5$ MV4-11-GFP were used as target cells in a 9:1 ratio. Human pan T cells, THP-1-GFP or MV4-11-GFP cells, and increasing concentrations of IO-202 or isotype control human IgG1 (BioXcell Catalog No. BE0297) were mixed in 200 μL total in RPMI 1640 (Gibco Catalog No. 61870-036)+10% heat-inactivated fetal bovine serum (FBS; Gibco Catalog No. 10082-147) in U-shaped 96-well plate and incubated for 48 hrs at 37° C. At the end of incubation, 7-aminoactinomycin D (7-AAD; BD Pharmingen Catalog No. 559925) was added to cells and 100 uL of cells was acquired by FACS Celesta and the percentage of GFP-positive cells were measured. Flow cytometry data were analyzed using Flowjo software (Flowjo LLC) and cell cytotoxicity was calculated as: percent of cytotoxicity=100−([T/NT]×100), where T and NT are the percentages of $GFP^+$ cells treated with or without test antibodies, respectively.

Autologous killing of human normal monocytes: PBMCs at $1\times10^6$ and increased concentrations of LILRB4/CD3 bispecific antibodies or controls were mixed in 200 μL total in RPMI+10% heat-inactivated FBS and 50 ng/ml of IL-2 (R&D systems Catalog No. 202-IL/CF) in a U-shaped 96-well plate and incubated for 48 hours at 37° C. PBMCs incubated with increasing concentrations of rituximab (Biogen/Genentech) were used as assay controls. At the end of incubation, cells were washed and incubated with 5 μL of Fc receptor blocker (human immunoglobulin G [IgG] at 10 mg/mL, Sigma Aldrich Catalog No. 14506) at room temperature for 10 minutes, followed by incubation on ice for 30 minutes with 100 μL of fluorescent conjugated CD14 (Clone

TABLE 12

Sequences for Second Generation LILRB4/CD3 Bispecific antibodies

| Name | Description | Polypeptide | Configuration | SEQ ID NO. |
|---|---|---|---|---|
| 4ab3-4ab | Bispecific 1 | 7 | $V_H$(LILRB4)-TCRβ-L-$V_H$(CD3)-$C_H1$-$C_H2$-$C_H3$(KiHa) | 98 |
| | | 5 | $V_H$(LILRB4)-TCRβ-$C_H2$-$C_H3$(KiHb) | 96 |
| | | 9 | $V_L$(CD3)-$C_L$ | 100 |
| | | 12 S91A | $V_L$(LILRB4)-TCRα(S91A) | 105 |
| 4-3ab Q1E S91A | Bispecific 2 | 2 Q1E | $V_H$(CD3)-TCRβ-$C_H2$-$C_H3$(KiHa) (Q1E) | 93 |
| | | 3 | $V_H$(LILRB4)-$C_H1$-$C_H2$-$C_H3$(KiHb) | 94 |
| | | 10 S91A | $V_L$(CD3)-TCRα(S91A) | 102 |
| | | 11 | $V_L$(LILRB4)-$C_L$ | 103 |
| anti-LILRB4 IgG1 LALA | Control 1 | 13 LALA | $V_H$(LILRB4)-$C_H1$-$C_H2$-$C_H3$ | 106 |
| | | 11 | $V_L$(LILRB4)-$C_L$ | 103 |
| anti-CD3 IgG1 LALA | Control 2 | 1 | $V_H$(CD3)-$C_H1$-$C_H2$-$C_H3$(KiHa) | 91 |
| | | 9 | $V_L$(CD3)-$C_L$ | 100 |
| | | 14 | $C_H2$-$C_H3$(KiHb) | 107 |

TABLE 13

Yields and purities of second-generation bispecific antibodies

| Name | Yield from 1 L CHO-K1 (mg) | Purity (SEC) |
|---|---|---|
| 4ab3-4ab S91A | 164.82 | 98.6% |
| 4-3ab Q1E S91A | 205.56 | 98.4% |
| anti-LILRB4 IgG1 LALA | 416.50 | 99.6% |
| anti-CD3 IgG1 LALA | 38.52 | 99.6% |

TABLE 14

Mass spectrometry data for second generation bispecific antibodies

| Name | Calculated (Da) | Measured (Da) | Significant impurities |
|---|---|---|---|
| 4ab3-4ab S91A | 199192.82 | 199190.7 | None |
| 4-3ab Q1E S91A | 148623.13 | 148621.8 | None |
| anti-LILRB4 IgG1 LALA | 145027.37 | 145027.8 | None |
| anti-CD3 IgG1 LALA | 98523.88 | 98529.8 | Pyro-Q |

M5E2, Catalog No. 555397) and CD19 (Clone HIB19, Catalog No. 555415) from BD Biosciences. Monocytes were identified as CD14-positive cells, while B cells were identified as CD19-positive cells.

Figure 29A:
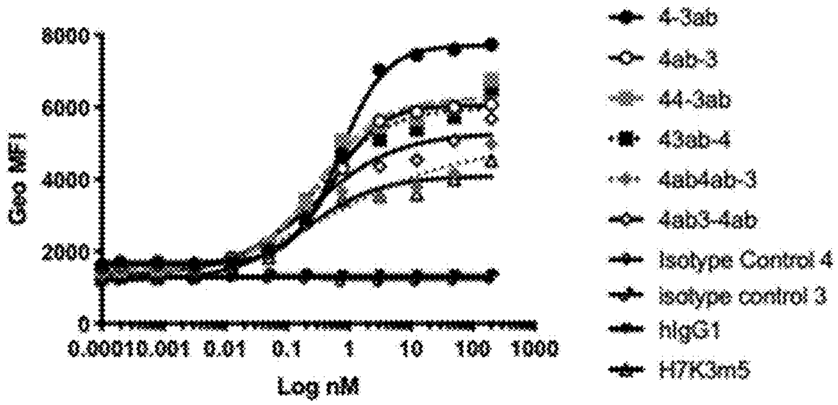
FIGS. 29A and 29B show the binding to normal monocytes and AML cell line THP-1 by CD3 and LILRB4 bispecific antibodies as measured by FACS. Similar binding affinity trends were observed across different anti-LILRB4 mono-specific and bispecific antibodies between monocytes and THP-1.
Figure 29B:
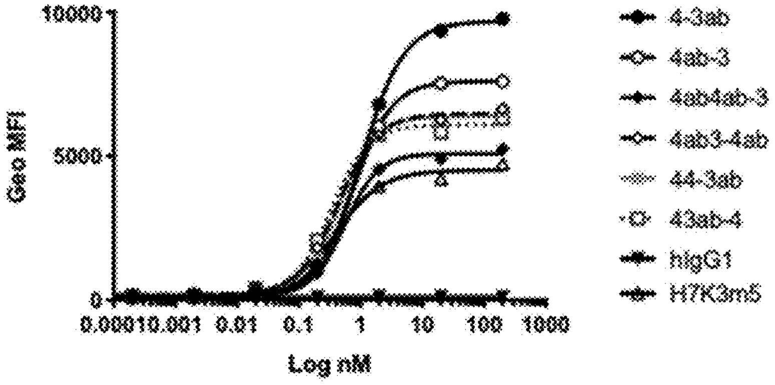
Figure 30A:
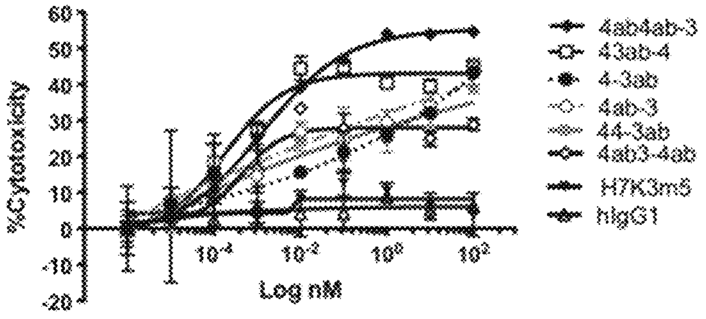
FIGS. 30A and 30B show T cell-mediated cytotoxicity of bispecific CD3/LILRB4 antibodies on monocytes (FIG. 22A) and THP-1-luc-GFP cells (FIG. 22B).
Figure 30B:
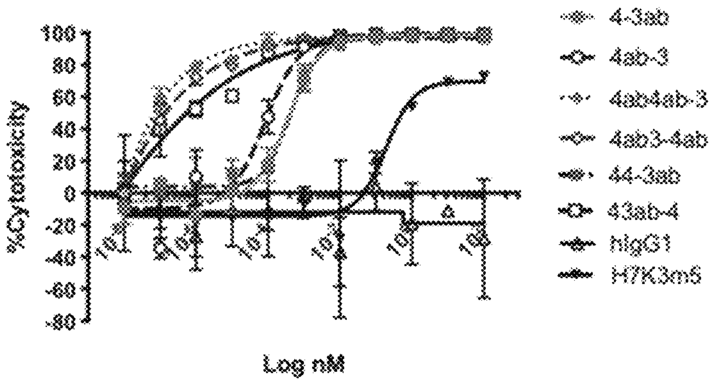
Figure 31A:
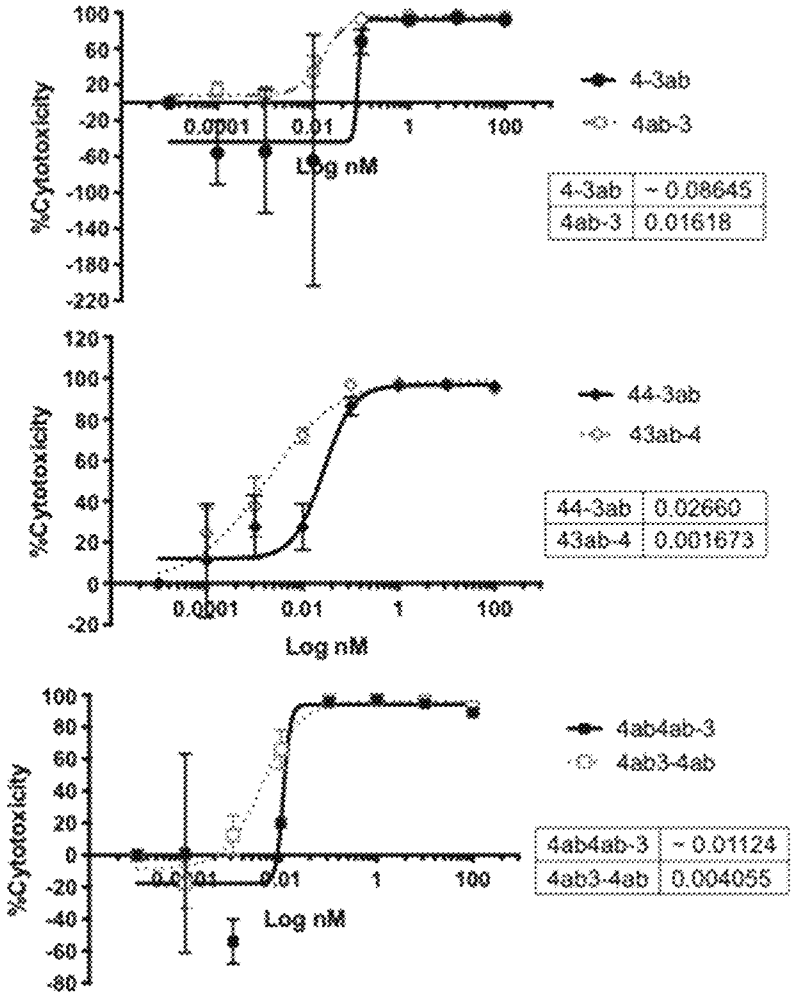
FIGS. 31A and 31B show the autologous killing of monocytes by LILRB4xCD3 bi-specifics (FIG. 31A) and autologous killing of B cells by Rituxan as a control (FIG. 31B).
Figure 31B:
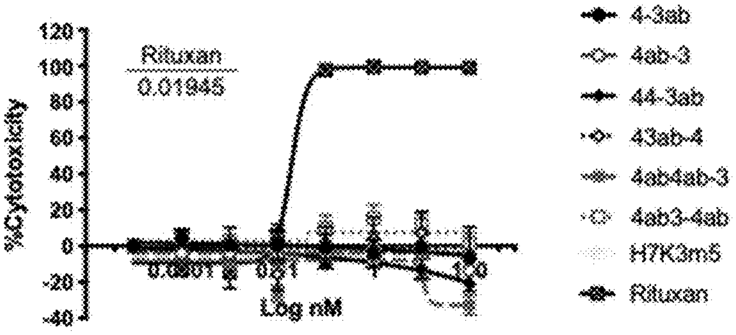

As shown in FIGS. 29A-29B, similar binding affinity trends were observed across different anti-LILRB4 monospecific and bispecific antibodies between monocytes and THP-1. As shown in FIGS. 30A-30B, T cell-mediated cytotoxicity of bispecific LILRB4/CD3 antibodies on monocytes and THP-1-luc-GFP cells are observed. As shown in FIGS. 31A-31B, autologous killing of monocytes by LILRB4/CD3 bi-specifics (FIG. 31A) and autologous killing of B cells by Rituxan as a control (FIG. 31B) were observed.

Cell killing curve generation and $EC_{50}$ calculation was performed by Prism GraphPad software using non-linear sigmoidal dose-response curve fit. The average±SD were calculated by Excel. Results are reported in Tables 15 and 16.

TABLE 15

T-cell cytotoxicity of first generation bispecifics

| Name | THP-1 $EC_{50}$ (nM) | THP-1 (max %) | Monocyte $EC_{50}$ (nM) Donor 1 | Donor 2 | Donor 3 | Monocyte (max %) Donor 1 | Donor 2 | Donor 3 |
|---|---|---|---|---|---|---|---|---|
| 4-3ab | 0.00036 | 98 | n/a ** | 0.0094 | no activity | 43 | 41 | 13 |
| 4ab-3 | 0.000084 | 98.6 | n/a ** | 0.029 | 0.00925 | 43 | 34 | 32.5 |
| 44-3ab | 0.00043 | 96.4 | n/a ** | 0.0034 | no activity | 39 | 30 | 0 |
| 4ab4ab-3 | <0.00001* | 98.3 | 0.0013 | 0.00032 | 0.0029 | 55 | 59 | 54.5 |
| 43ab-4 | <0.00001* | 98.7 | 0.00019 | no activity | 0.000084 | 45 | 0 | 42 |
| 4ab3-4ab | <0.00001* | 98.1 | 0.00043 | 0.00093 | 0.0016 | 29 | 44 | 44 |

*estimated $EC_{50}$

** EC50 cannot be measured accurately; 4-3ab, 4ab-3, and 44-3ab have weaker potency than 4ab4ab-3, 43ab-4, and 4ab3-4ab

TABLE 16

T-cell cytotoxicity of second-generation bispecific antibodies

| Name | THP-1 $EC_{50}$ (nM) | MV4-11 $EC_{50}$ (nM) | Monocyte $EC_{50}$ (nM) | B-cell $EC_{50}$ (nM) |
|---|---|---|---|---|
| 4ab3-4ab | 0.00050 | 0.000034 | 0.0059 | no activity |
| 4-3ab | 0.0043 | 0.0025 | 0.026 | no activity |
| anti-LILRB4 IgG1 LALA | no activity | no activity | no activity | no activity |
| anti-CD3 IgG1 LALA | not tested | no activity | no activity | no activity |
| Rituxan | not tested | not tested | no activity | 0.043 |

Surface Plasmon Resonance (Biacore)

Binding affinities of first-generation bispecific antibodies to recombinant CD3e-CD3d heterodimer protein (Acro Biosystems) or LILRB4 recombinant protein (Sino Biological) were measured by surface plasmon resonance using a Biacore 8K instrument. Briefly, CD3e-CD3d or LILRB4 protein was immobilized on a CM5 chip with EDC and NHS according to standard protocols. Bispecific antibody analytes were then injected at 6 concentration (1.25, 2.5, 5, 10, 20, and 40 nM) or 7 concentrations (20, 2.5, 5, 10, 20, 40, and 80 nM) in 1×HBX-EP+(10 mM HEPES, 150 mM NaCl, 3 mM EDTA, 0.05% Tween 20, pH 7.4), for LILRB4 and CD3e-CD3d, respectively. The chip was regenerated using 10 mM glycine pH 1.5 as the regeneration buffer. The sensorgrams for reference channel Fc1 and buffer channel were subtracted from the test sensorgrams and the experimental data was fitted by 1:1 binding model. See Table 17 for affinities.

TABLE 17

Affinities of first generation bispecifics to recombinant protein and cells

| Bispecific | Biacore affinity to CD3e-CD3d ($K_D$, n M) | Biacore Affinity to LILRB4 ($K_D$, nM) | FACS $EC_{50}$ to CD3+ Jurkat cells | FACS $EC_{50}$ to LILRB4+ THP-1 cells |
|---|---|---|---|---|
| 4-3ab | 49.6 | 0.19 | NC | 1.3 |
| 4ab-3 | 33.4 | 0.27 | NC | 0.77 |
| 44-3ab | 42.1 | 0.23 | NC | 0.45 |
| 4ab4ab-3 | 26.8 | 0.26 | NC | 0.55 |

TABLE 17-continued

Affinities of first generation bispecifics to recombinant protein and cells

| Bispecific | Biacore affinity to CD3e-CD3d ($K_D$, n M) | Biacore Affinity to LILRB4 ($K_D$, nM) | FACS $EC_{50}$ to CD3+ Jurkat cells | FACS $EC_{50}$ to LILRB4+ THP-1 cells |
|---|---|---|---|---|
| 43ab-4 | 47.0 | 0.29 | NC | 0.33 |
| 4ab3-4ab | 57.3 | 0.26 | NC | 0.43 |

Bio-Layer Interferometry (Gator Bio)

Binding affinities of second-generation bispecific antibodies were measured to recombinant human CD3e (Acro, cat #CDE-H5223), cyno CD3e (Acro, cat #CDE-C5226), human LILRB4 (Sino Biological, cat #16742-H08H), and cyno LILRB4 (Acro, cat #CDK-C5227) by Bio-Layer Interferometry (BLI) using an instrument from Gator Bio. Bispecific antibodies were captured using an immobilized anti-human Fc antibody (HFC) probe (Gator Bio, cat #PL168-160003) at 5 ug/mL load. Binding affinities were measured using 6 concentrations (0.6 to 159 nM, 0.7 to 164 nM, 0.8 to 200 nM, and 2.5 to 595 nM), for human CD3e, cyno CD3e, human LILRB4, and cyno LILRB4, respectively. Binding affinity constants were determined using a 1:1 fitting model (Global Fit) with Gator's data analysis software 1.6.1.1203, and the KD was calculated using the ratio Kdis/Kon. See Table 18 for affinities.

TABLE 18

Affinities of second-generation bispecific antibodies to recombinant proteins and cells

| Bispecific | FACS $EC_{50}$ to CD3 + Jurkat cells (estimated, nM) | Affinity to human CD3e (KD, nM) | Affinity to cyno CD3e (KD, nM) | FACS $EC_{50}$ to LILRB4 + THP-1 cells (nM) | Affinity to human LILRB4 (KD, nM) | Affinity to cyno LILRB4 (KD, nM) |
|---|---|---|---|---|---|---|
| 4ab3-4ab S91A | 256.7 | 0.07 | 0.26 | 0.7 | 0.89 | 8.82 |
| 4-3ab Q1E/S91A | 853.6 | 0.10 | 0.07 | 1.3 | 0.84 | 9.53 |

Flow Cytometry

Binding of first and second generation bispecifics to CD3 or LILRB4 was measured by FACS on Jurkat cells or THP-1 cells. To measure binding of bispecifics to THP-1 cells, THP-1 cells were first incubated with human Fc blocker (BD Pharmingen Catalog No. 564220) at 10 ug per one million cells at room temperature for 10 minutes, followed by incubated with serially diluted bispecifics for 30 minutes on ice. Cells were washed twice with BSA staining buffer (BD Pharmingen Catalog No. 554657) and incubated with secondary Alexa 647 conjugated anti-human IgG Fc monoclonal antibody (Biolegend Catalog No. 409306) at 5 ug/mL for 30 minutes on ice. After final wash, 7-AAD was applied to exclude dead cells. To measure binding of first generation bispecifics to Jurkat cells, each bispecific was diluted in buffer including 1% BSA (5-fold dilution series, 400 nM highest concentration) and incubated with cells for 30 minutes at 4° C. Then bispecifics were stained with Alexa 647 anti-human IgG Fc at 5 ug/mL at 4° C. for 0.5 hours before analysis. Binding for CD3 was clearly observed on the cells compared to an isotype control, but the EC50 could not be calculated or only estimated since the binding curve did not reach a plateau. See Tables 17 and 18 for EC50 values.

Example 6

This example illustrates the generation of CAR-T cells that express a CAR protein based on the heavy chain and light chain variable region sequences of H7K3m5.

Figure 32:
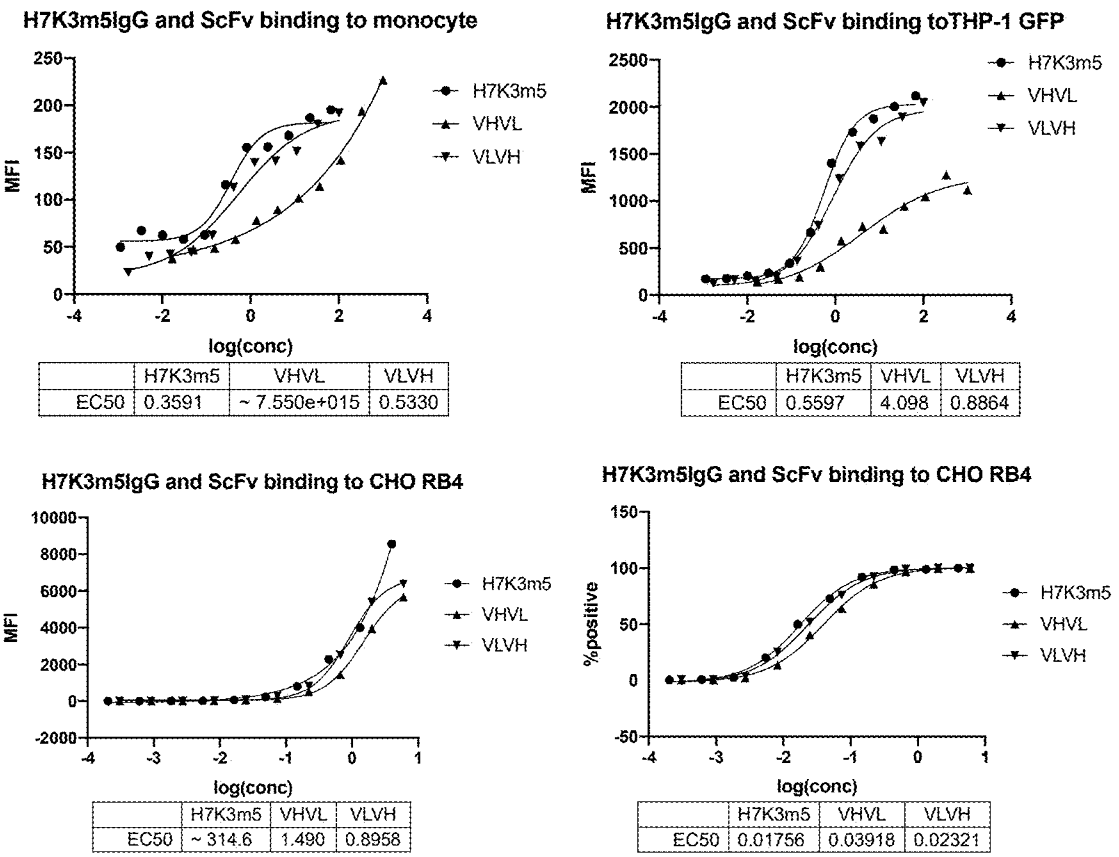
FIG. 32 shows the binding affinity comparison using H7K3m5 full-length IgG and ScFv proteins in flow cytometry assays against human primary monocytes and human leukemia cell line THP-1.

Two different configurations of single chain Fv (scFv) derived from anti-LILRB4 monoclonal antibody H7K3m5 were tested for binding to human primary monocytes and human leukemia cell THP-1 using flow cytometry. As shown in FIG. 32, the VlVh configuration maintains the binding affinity as H7K3m5 whereas the VhVl configuration lost some binding affinity. Therefore, VlVh is selected for the CAR constructs.

Figure 33:
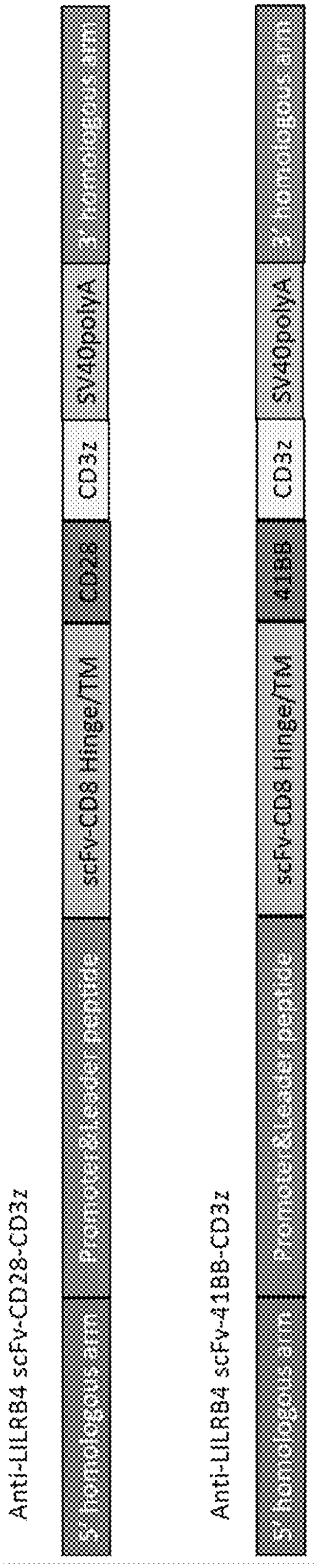
FIG. 33 shows the schematic representation of the DNA construct for expressing the anti-LILRB4 CAR proteins. The DNA construct was based on $2^{nd}$ generation CAR constructs containing CD28 or 4-1BB costimulatory domain with CD3zeta activation domain. The scFv was derived from anti-LILRB4 monoclonal antibody H7K3m5. The 5' and 3' homologous arms are homologous sequences upstream and downstream of the Cas9 DNA cleavage site in the TRAC gene (based on gRNA design). Promoter and leader peptide are elements for gene expression and extracellular translocation. SV40 poly-A tail was included for improving transcript stability and translation.

As illustrated in FIG. 33, the DNA construct for expressing the anti-LILRB4 CAR proteins is a $2^{nd}$ generation CAR constructs containing CD28 or 4-1BB costimulatory domains with CD3zeta activation domain. The scFv is derived from anti-LILRB4 monoclonal antibody H7K3m5. The 5' and 3' homologous arms are homologous sequences upstream and downstream of the Cas9 DNA cleavage site in TRAC gene (based on gRNA design). Promoter and leader peptide are necessary elements for gene expression and extracellular translocation. Here the inventors used JeT promoter to control the expression of scFv (Eyquem J et al. *Nature* (2017) 543:113-117). SV40 poly-A tail is included for improving transcript stability and translation.

Figure 34:
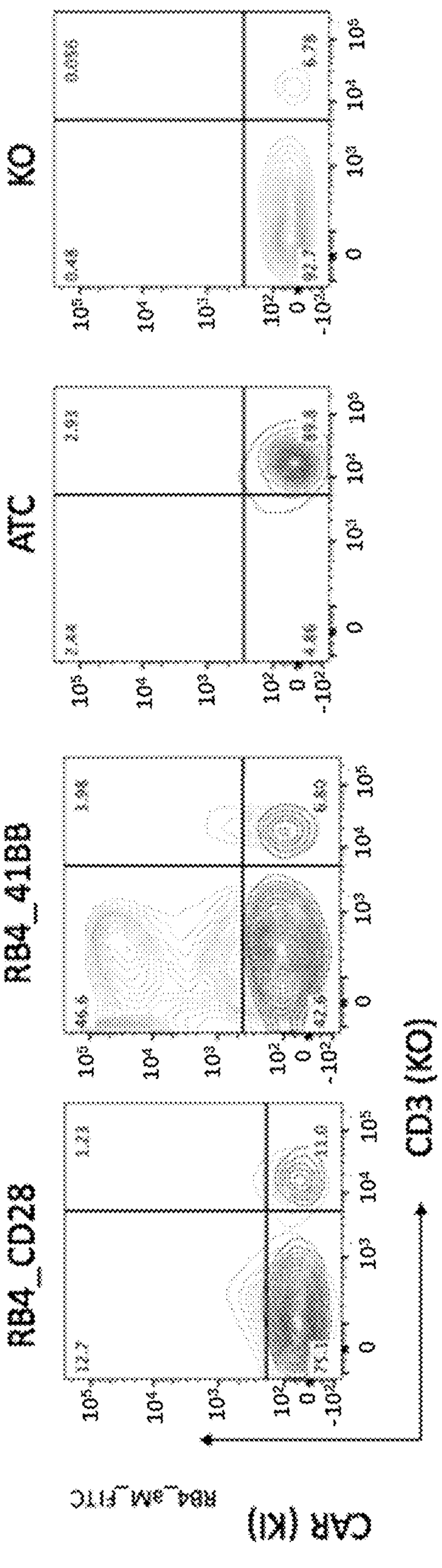
FIG. 34 shows the efficient generation of LILRB4 CAR-T cells using CRISPR knock-out and knock-in method. Human primary T cells were transfected with CRISPR-Cas9 RNP complexes designed to inactivate the TCR alpha (TRAC) locus, with or without DNA template for homologous recombination-based knock in. Following transfection, cells were expanded in culture for 2 weeks. Anti-LILRB4 CAR-T cells were identified by binding to LILRB4-Fc fusion protein (ACRObiosystems CDK-H5259) and anti-Fc antibody (Biolegend B278652, negative control). Successful TCR alpha (TRAC) inactivation (Knock-Out or KO) was measured by anti-CD3 staining (anti-CD3 PE, BD 555333). ATC, activated T cells; KO, TCR alpha (TRAC) inactivated T cells; RB4_CD28, T cells expressing anti-LILRB4 CAR with a CD28 costimulatory domain; RB4_41BB, T cells expressing anti-LTLRB4 CAR with a 4-1BB costimulatory domain.

Human primary T cells were transfected with CRISPR-Cas9 RNP complexes including a guide RNA targeting the 5' end of the first exon of TRAC and supplied with the DNA construct for homologous recombination-based knock in. After knocking out TCRalpha, the cells were grown in complete Optimizer medium with IL-2 300 IU/ml and without anti-CD3/28 added. Following transfection, cells were expanded in culture for 2 weeks. Anti-LILRB4 CAR-T cells were identified by binding to LILRB4-Fc fusion protein (ACRObiosystems CDK-H5259) and anti-Fc antibody (Biolegend B278652). Success in knock-out of the endogenous TCR alpha (TRAC) locus (KO) was measured by anti-CD3 staining (anti-CD3 PE, BD 555333). As shown in FIG. 34, efficient generation of anti-LILRB4 CAR-T cells was confirmed.

Figure 35:
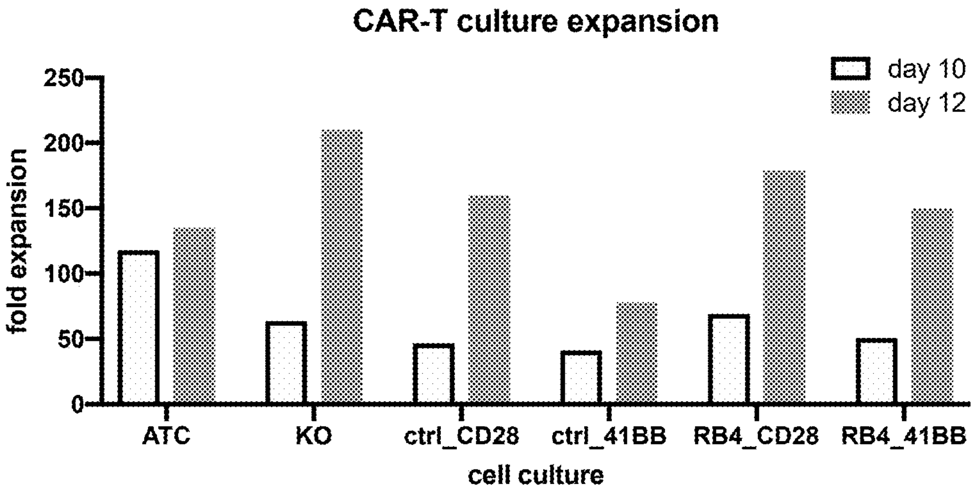
FIG. 35 shows the proliferation of the TCR alpha (TRAC) inactivated T cells (KO) and anti-LTLRB4 CAR (or control CAR) knocked-in T cells. After knocking out TCRalpha, the cells were grown in complete Optimizer medium with IL-2 300 IU/ml and without anti-CD3/28 added. Fold expansion was plotted by dividing the total T cell number on days (as indicated) with the starting culture number. Anti-LILRB4 CAR-T cells had significantly higher fold of expansion in comparison to the control CAR-T cells. ATC, activated T cells; KO, TCR alpha (TRAC) inactivated T cells; ctrl_CD28, T cells expressing a control CAR with a CD28 costimulatory domain; ctrl_41BB, T cells expressing a control CAR with a 4-1BB costimulatory domain; RB4_CD28, T cells expressing Anti-LTLRB4 CAR with a CD28 costimulatory domain; RB4_41BB, T cells expressing Anti-LILRB4 CAR with a 4-1BB costimulatory domain.
Figure 36A:
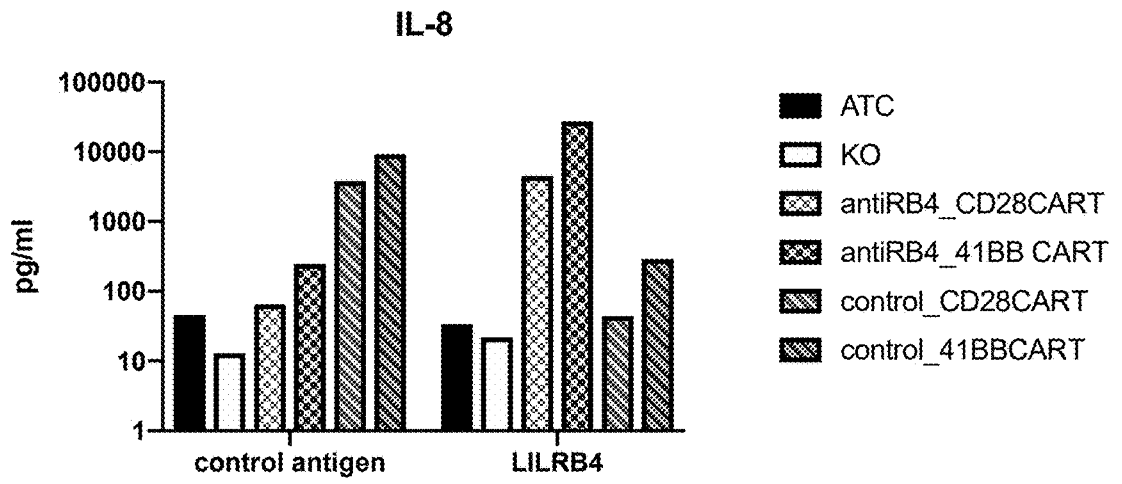
FIGS. 36A-36H show the antigen-dependent activation of CAR-T culture. 1 ug/ml recombinant control antigen or LILRB4 antigen were coated on 96 well plates overnight in PBS buffer. Plates were washed twice with PBS buffer. $1\times10^5$ CAR-T cells in culture media (without any cytokine added) were added to each well and incubated for 72 hours. Cell culture supernatant was collected for cytokine release measurement by Luminex assay. ATC, activated T cells; KO, TCR alpha (TRAC) inactivated T cells; antiRB4_CD28CART, T cells expressing Anti-LILRB4 CAR with a CD28 costimulatory domain; antiRB4_41BB CART, T cells expressing anti-LTLRB4 CAR with a 4-1BB costimulatory domain; control_CD28CART, T cells expressing a control CAR with a CD28 costimulatory domain; control_41BBCART, T cells expressing a control CAR with a 4-1BB costimulatory domain.
Figure 36B:
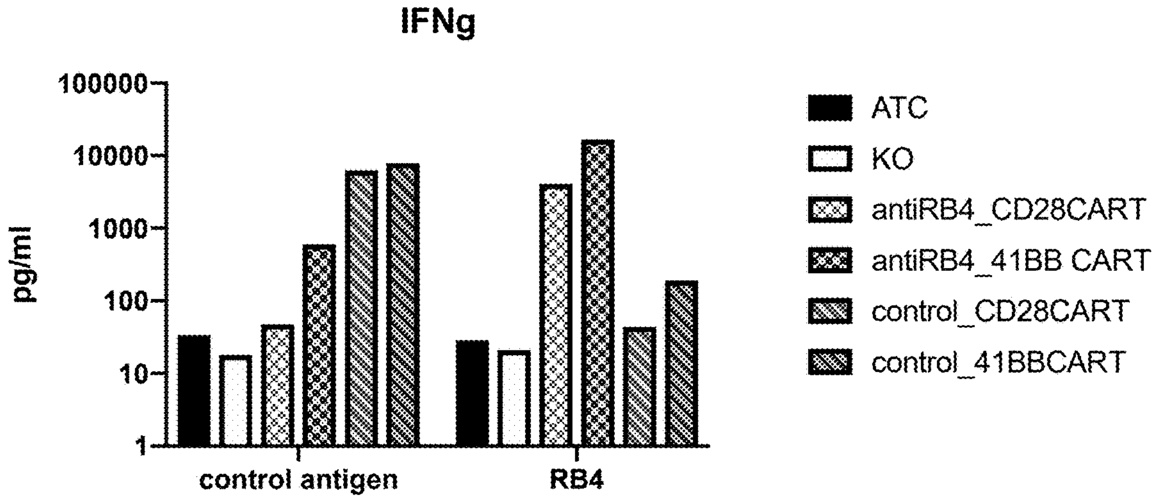
Figure 36C:
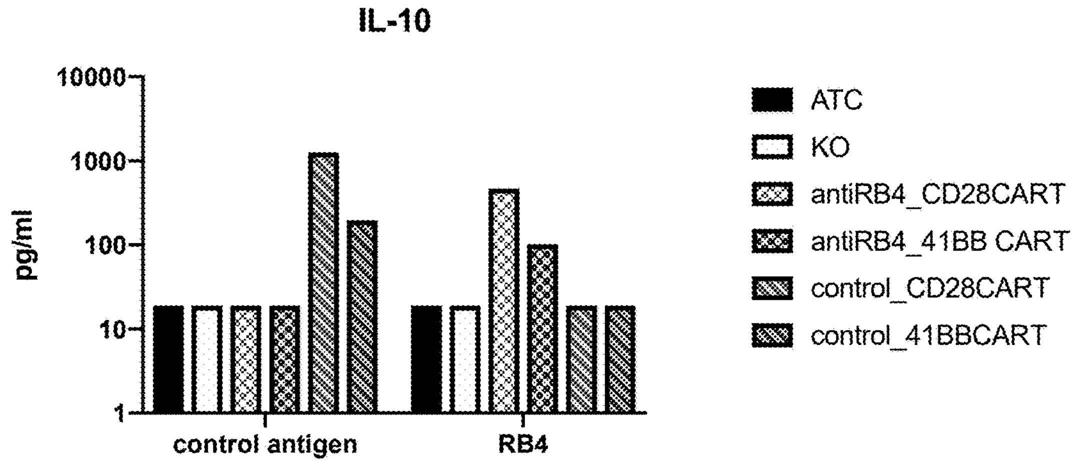
Figure 36D:
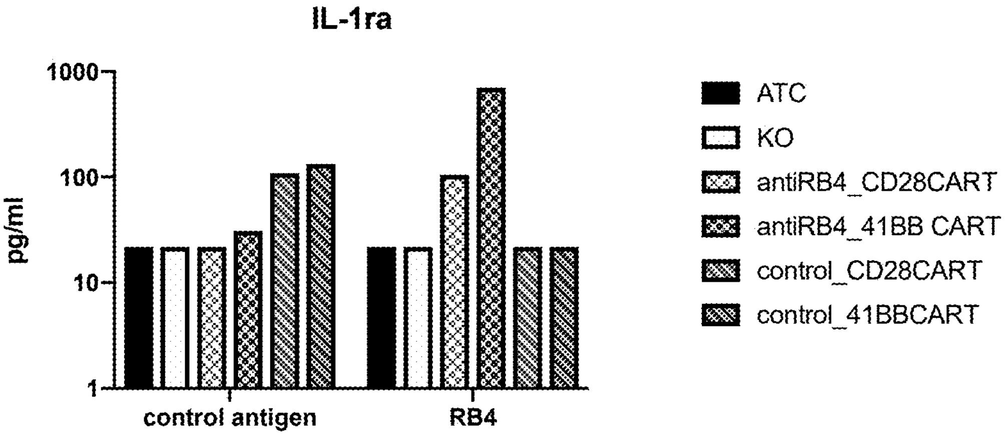
Figure 36E:
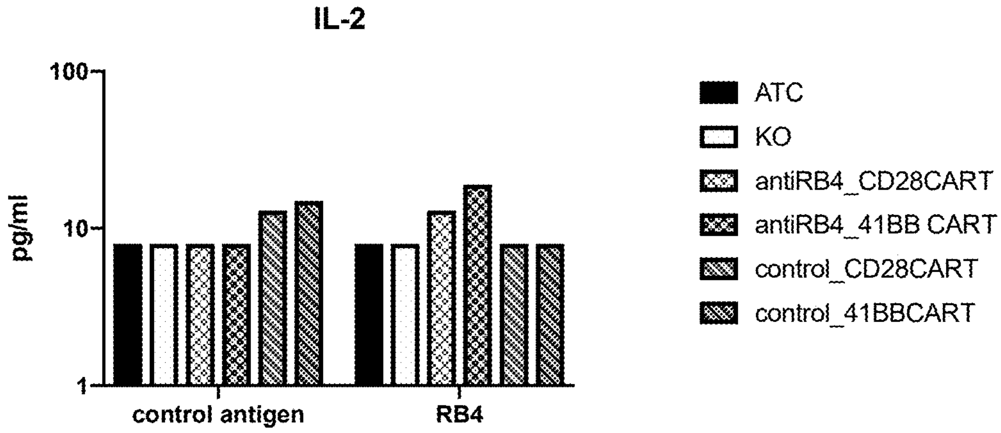
Figure 36F:
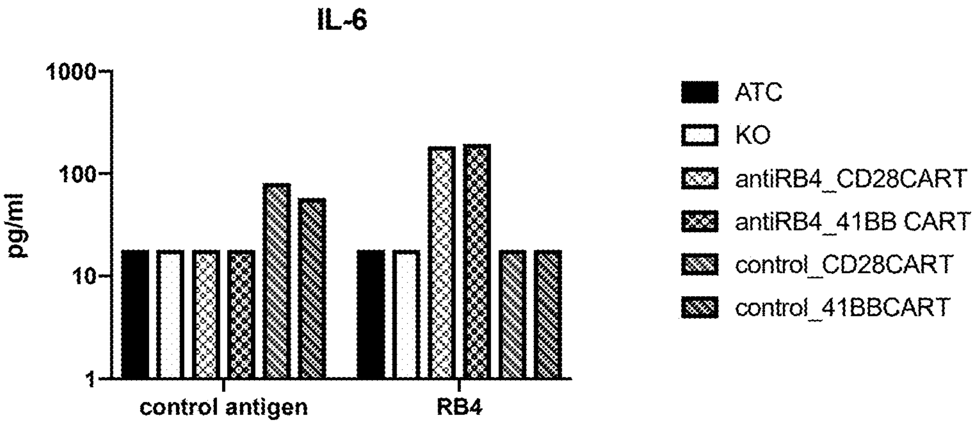
Figure 36G:
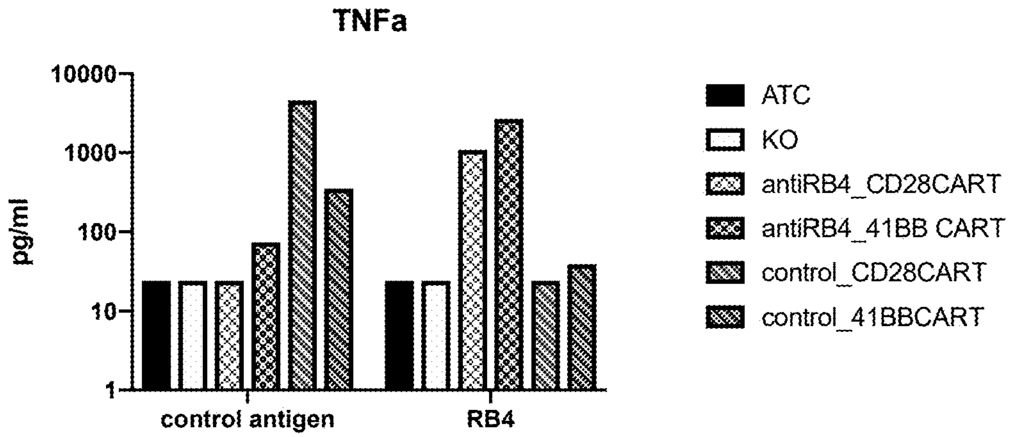
Figure 36H:
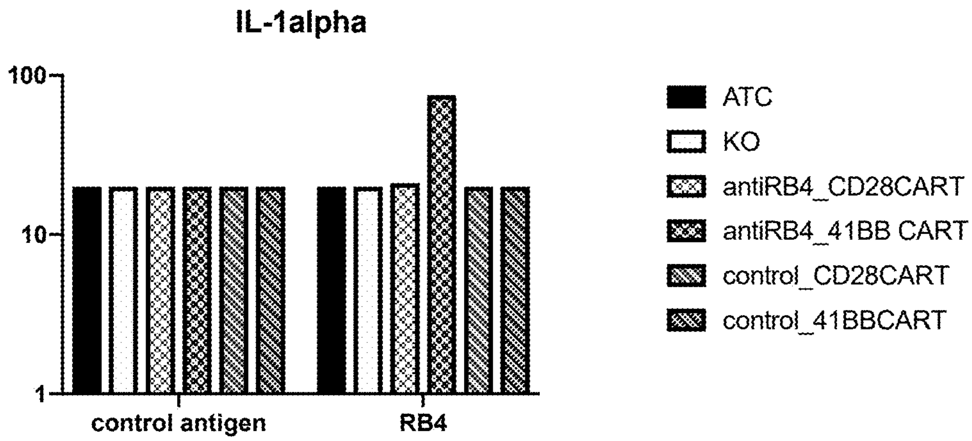

As shown in FIG. 35, the TCR alpha (TRAC) inactivated T cells (KO) and anti-LILRB4 CAR (or control CAR) knocked-in T cells undergo cell proliferation and expansion in vitro. Anti-LILRB4 CAR-T cells had significantly higher fold of expansion in comparison to the control CAR-T cells.

To test the antigen-dependent activation of CAR-T culture, 1 ug/ml recombinant control antigen or LILRB4 antigen were coated on 96 well plate overnight in PBS buffer. Plates were washed twice with PBS buffer. $1\times10^5$ CAR-T cells in culture media (without any cytokine added) were added to each well and incubated for 72 hours. Cell culture supernatant were collected for cytokine release measurement by Luminex assay. As shown in FIGS. 36A-36H, the release of cytokine IL-8, IFNγ, IL-10, IL-1ra, IL-2, IL-6, TNFα and IL1alpha by the anti-LILRB4 CAR-T cells depends on the presence of LILRB4.

Figure 37A:
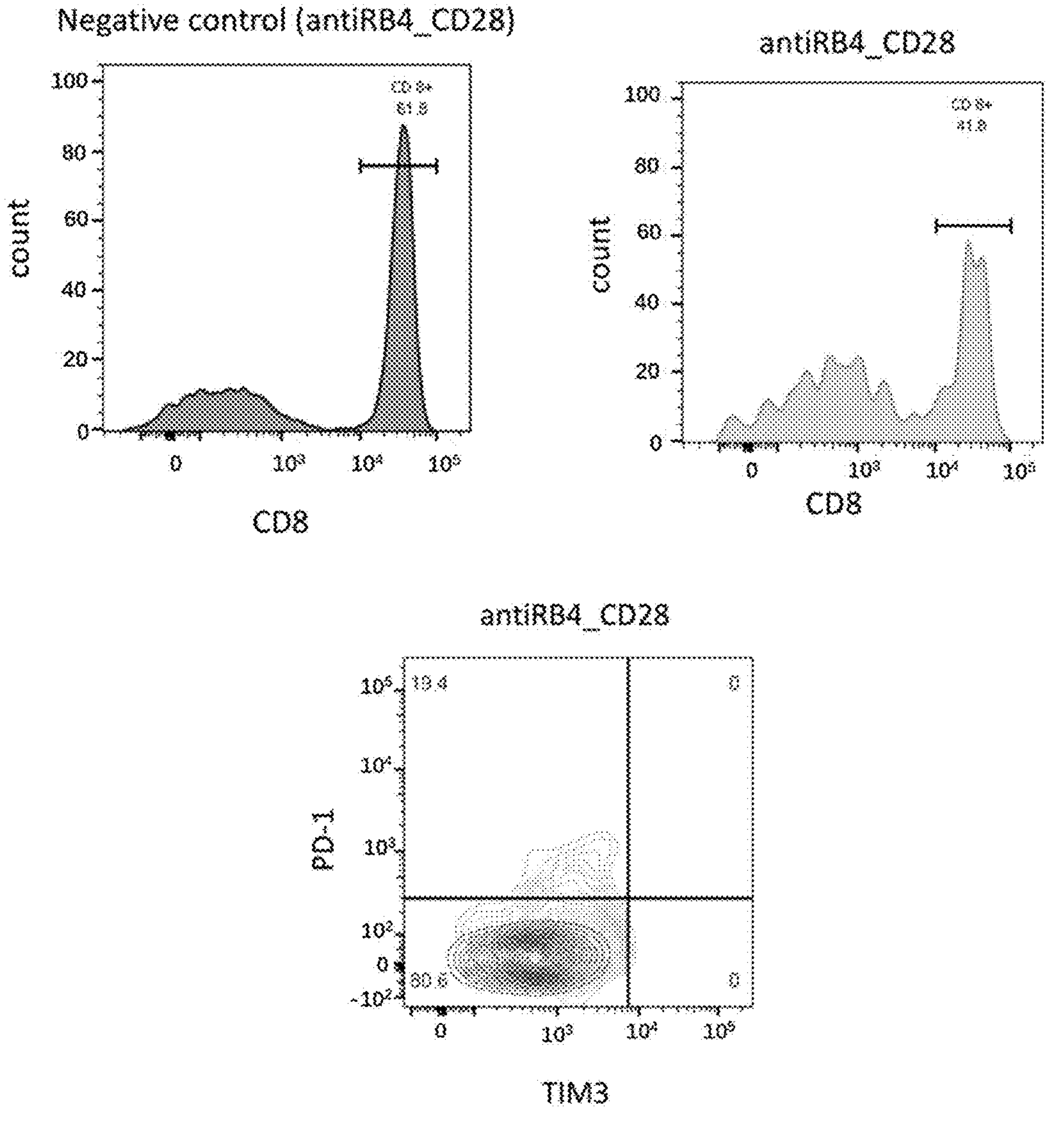
FIGS. 37A-37C show the characterization of CAR-T cells after 2 weeks expansion. Frozen CAR-T cells in liquid nitrogen storage were thawed and kept in culture for 2-3 days before flow cytometry analysis. Antibodies used were anti-CD8 APC Cy7 (BD561945), anti-PD1 PE (BD560908) and anti-TIM3 BV421 (BD565562). Anti-LILRB4 CAR-T cells were identified by binding to LILRB4-Fc fusion protein (ACRObiosystems CDK-H5259) and anti-Fc antibody (Biolegend B278652).
Figure 37B:
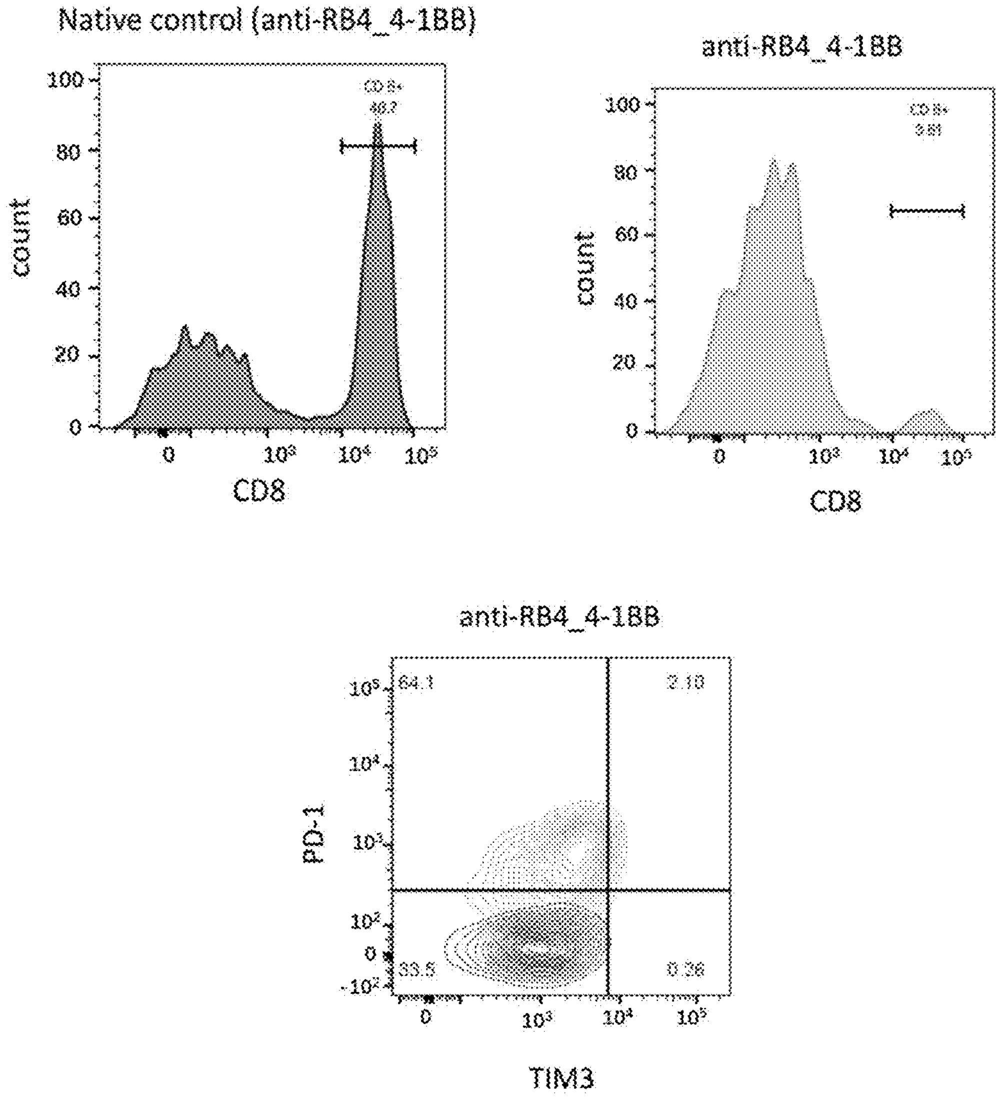
Figure 37C:
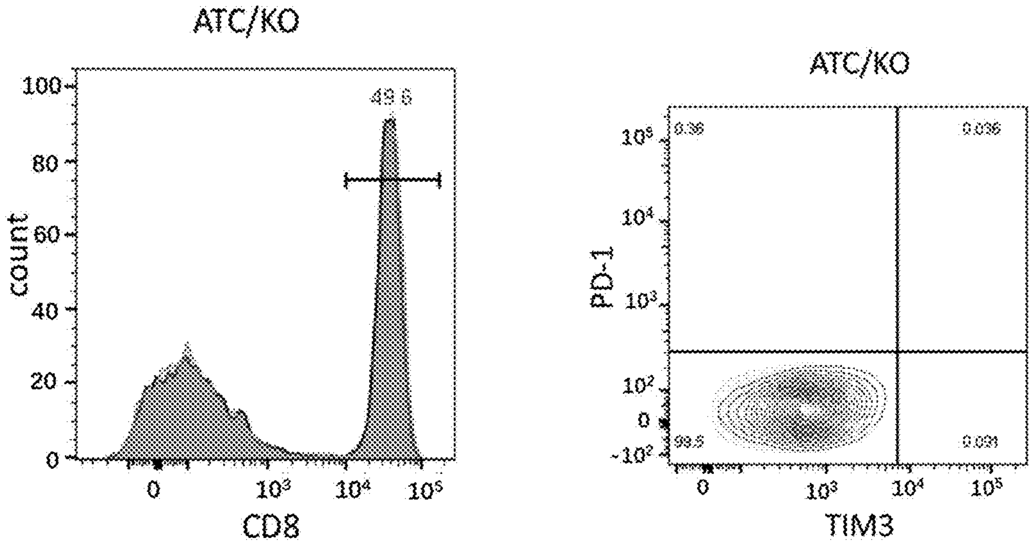

FIGS. 37A-37C show the characterization of CAR-T cells after 2 weeks expansion. Frozen CAR-T cells in liquid nitrogen storage were thawed and kept in culture for 2-3 days before flow cytometry analysis. Antibodies used were anti-CD8 APC Cy7 (BD561945), anti-PD1 PE (BD560908) anti-TIM3 BV421 (BD565562). LILRB4 CAR-T cells were identified by binding to LILRB4-Fc fusion protein (ACRObiosystems CDK-H5259) and anti-Fc antibody (Biolegend B278652). As shown in FIG. 37A, expressing anti-LILRB4_CD28 slightly decreased the percentage of CD8+ T cells (from 61.8% to 41.8%) and did not substantially change the expression of PD-1 and TIM3 on the cells. As shown in FIG. 37B, expressing anti-LILRB4_4-1BB decreased the percentage of CD8+ T cells from 48.7% to 3.61% and increased the expression of PD-1. As shown in FIG. 37C, knock-out (KO) TCR alpha expression at TRAC locus, where the CAR construct was inserted, did not substantially change the percentage of CD8+ T cells or the expression of PD-1 or TIM3.

Figure 38:
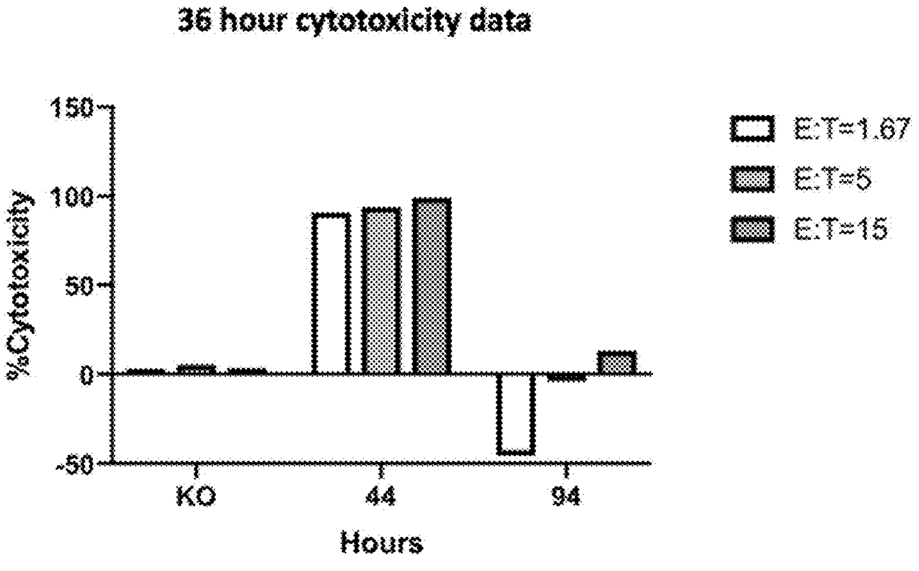
FIG. 38 shows the cytotoxicity of anti-LILRB4 CAR-T cells. CHO K1 RB4 cells were seeded at different density ($6\times10^4$, $2\times10^4$ or $7\times10^3$) for 12 hours, $1\times10^5$ CAR-T cells were added and cytotoxicity were measured by removing the supernatant CAR-T cells and wash the plate 2 times with PBS. Total viable adherent CHO K1 RB4 cells were measured by Promega CTG2.0 luminescence kit. And the % cytotoxicity were calculated by dividing the Luminescent signal of each condition with the same E:T ratio activated T cell control.

To test the cytotoxicity of the anti-LILRB4 CAR-T cells, CHO K1 RB4 cells were seeded at different density ($6\times10^4$, $2\times10^4$ or $7\times10^3$) for 12 hours, $1\times10^5$ CAR-T cells were added and cytotoxicity were measured by removing the supernatant CAR-T cells and wash the plate 2 times with PBS. Total viable adherent CHO K1 RB4 cells were measured by Promega CTG2.0 luminescence kit, and the % cytotoxicity were calculated by dividing the Luminescent signal of each condition with the same E:T ratio activated T cell control. As shown in FIG. 38, anti-LILRB4 CAR-T cells (44) but not anti-CD19 CAR-T cells (94) killed CHO K1 RB4 cells.

Example 7

This example illustrates the design of phase 1 First-in-Human trial.

Figure 39A:
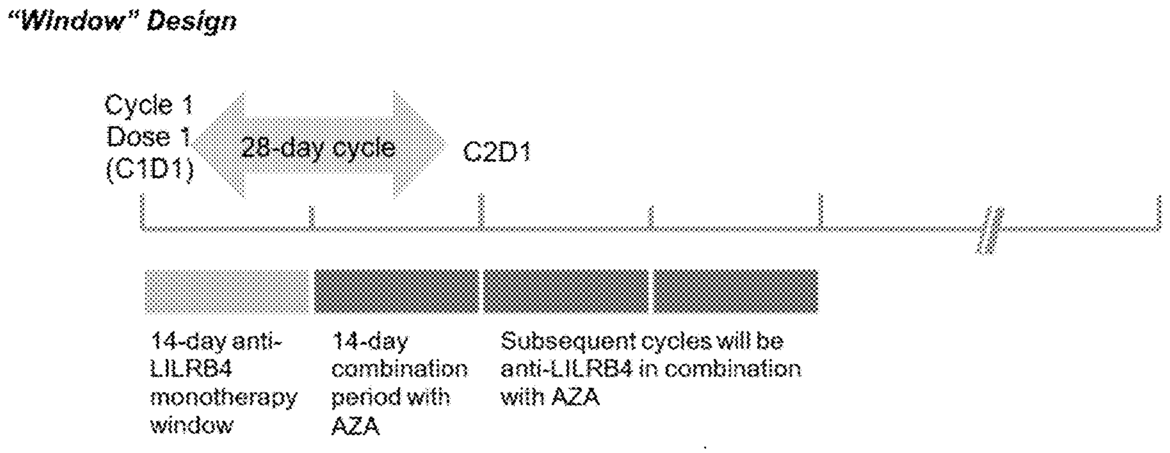
FIGS. 39A-39B show the schematics of a phase 1 first-in-human clinical trial.

As shown in FIG. 39A, a "window" design comprising of a 2-week monotherapy lead-in ("window") of anti-LILRB4 enables the studying of the effects of a monoclonal antibody that specifically targets LTLRB4 as monotherapy.

During the Part 1A monotherapy escalation phase (single dose on Day 1) patients will be enrolled into sequential cohorts of increasing doses of anti-LILRB4 monotherapy. The goal of Part 1A is to determine the MTD of anti-LILRB4 monotherapy (MTD1). DLTs for MTD1 will be evaluated during the first 14 days of treatment (prior to the first dose of anti-LILRB4 in combination with azacytidine/azacitidine), i.e., the first dose-interval for anti-LTLRB4. The initial dose-escalation begins with an accelerated titration design followed by a standard escalation phase that will use a 3+3 design. Part 1 will include both relapsed and/or refractory myelomonocytic (M4) and monocytic/monoblastic (M5) AML patients and chronic myelomonocytic leukemia (CMML) patients.

During Part 1B (starting on Day 15), patients without DLTs during Part 1A will receive the same dose of anti-LILRB4 that was administered in Part 1A in combination with a standard dose of azacytidine/azacitidine (75 mg/$m^2$ subcutaneously for 7 days every 28 days). The MTD of anti-LILRB4 in combination with azacytidine/azacitidine (MTD2) will be determined in the 28-day DLT window, consisting of the 14 days of monotherapy and 14 days of the combination treatment.

The overall DLT period of Part 1 (Part 1A and Part 1B combined) is 28 days. This could also be easily changed to 42 days, with the first 14 days for monotherapy DLT and the last 28 days (with addition of azacytidine/azacitidine) for combotherapy DLT.

Subsequent cycles will be anti-LILRB4 in combination with azacytidine/azacitidine.

Figure 39B:
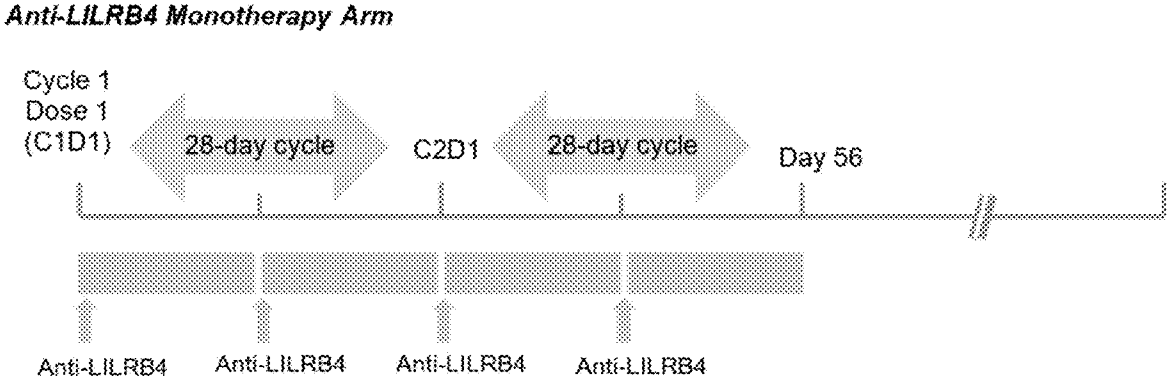
Figure 39C:
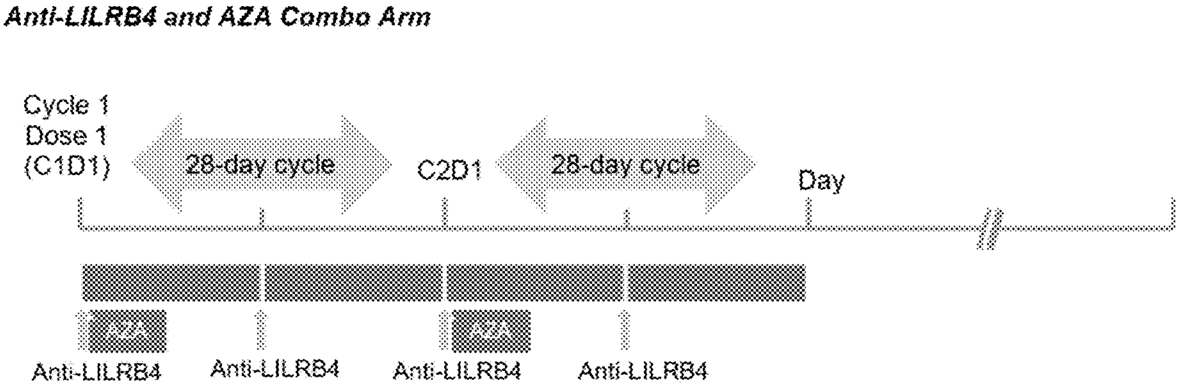
FIGS. 39C-39D are the schematics of potential combination studies of anti-LILRB4 antibody with azacytidine and/or venetoclax. Other potential combinations with anti-LILRB4 would follow the same or a similar schema. AZA, azacytidine; VEN, venetoclax; C1D1, Cycle 1 Day 1; Cycle 2 Day 1; DLT, dose limiting toxicity; MTD1, maximum tolerated dose of anti-LILRB4 monotherapy; MTD2, maximum tolerated dose of anti-LILRB4 in combination with azacytidine. Anti-LILRB4 is administered as monotherapy or in combination with other agents every 14 days until progression of disease or death.

As shown in FIG. 39B and FIG. 39C, once the MTD and/or RP2D for the anti-LILRB4+azacytidine/azacitidine combination has been identified and approval given by the Safety Review Committee (SRC), enrollment in one of two expansion arms (FIG. 39B and FIG. 39C) will commence in relapsed and/or refractory monoblastic/monocytic leukemia patients.

As shown in FIG. 39B, this study will enroll a monotherapy cohort anti-LTLRB4 in patients with relapsed/refractory AML with monocytic differentiation. FIG. 39B can also be the design for a First-in-Human phase 1 trial in case the "window" designed is not accepted.

As shown in FIG. 39C, this study will enroll a combination cohort of anti-LTLRB4+azacytidine/azacitidine in patients with relapsed/refractory AML with monocytic differentiation.

Figure 39D:
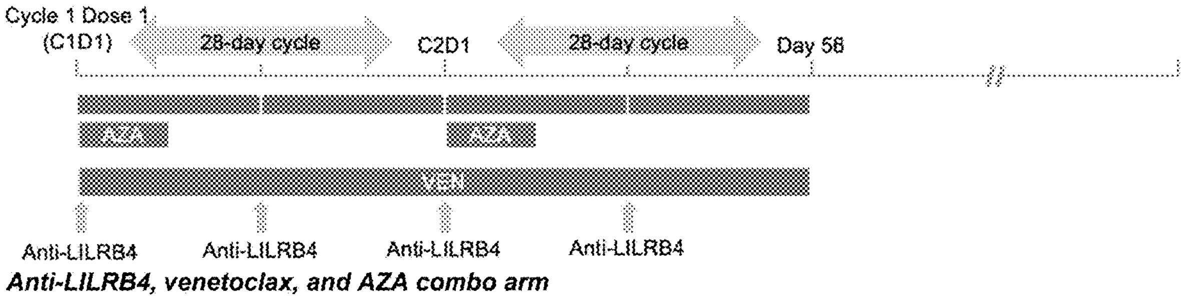

As shown in FIG. 39D, this study will enroll a combination cohort of anti-LTLRB4+azacytidine/azacitidine+venetoclax in patients with relapsed/refractory AML with monocytic differentiation and in patients with newly diagnosed AML with monocytic differentiation.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. An isolated anti-Leukocyte Immunoglobulin-like subfamily B member 4 (anti-LILRB4) antibody or an antigen-binding fragment thereof, comprising:
   a) a heavy chain variable region comprising a heavy chain complementarity determining region (HC-CDR) 1 having an amino acid sequence of SEQ ID NO: 5, an HC-CDR2 having an amino acid sequence of SEQ ID NO: 6 and an HC-CDR3 having an amino acid sequence of SEQ ID NO: 7; and
   b) a light chain variable region comprising a light chain complementarity determining region (LC-CDR) 1 having an amino acid sequence of SEQ ID NO: 8 with a mutation at amino acid residues NS, an LC-CDR2 having an amino acid sequence of SEQ ID NO: 9 and an LC-CDR3 having an amino acid sequence of SEQ ID NO: 10.

2. The antibody or antigen-binding fragment thereof of claim 1, wherein the LC-CDR1 has the amino acid sequence of SEQ ID NO: 28.

3. The antibody or antigen-binding fragment thereof of claim 1, wherein the heavy chain variable region has the amino acid sequence of SEQ ID NO: 1; and wherein the light chain variable region has the amino acid sequence of SEQ ID NO: 27.

4. The antibody or antigen-binding fragment thereof of claim 1, further comprising an immunoglobulin constant region, optionally a constant region of Ig, or optionally a constant region of human IgG.

5. The antibody or antigen-binding fragment thereof of claim 1, which is humanized.

6. The antibody or antigen-binding fragment thereof of claim 1, which is a camelized single domain antibody, a diabody, a scFv, a scFv dimer, a BsFv, a dsFv, a $(dsFv)_2$, a dsFv-dsFv', an Fv fragment, a Fab, a Fab', a $F(ab')_2$, a bispecific antibody, a ds diabody, a nanobody, a domain antibody, or a bivalent antibody, wherein the bispecific antibody is an antibody against LILRB4 and CD3.

7. The antibody or antigen-binding fragment thereof of claim 1 linked to one or more conjugate moieties, wherein the conjugate moiety comprises a clearance-modifying agent, a toxin, a detectable label, a chemotherapeutic agent, a cytokine, or a purification moiety.

8. A pharmaceutical composition comprising the antibody or antigen-binding fragment thereof of claim 1, and a pharmaceutically acceptable carrier.

9. An isolated polynucleotide encoding the antibody or antigen-binding fragment thereof of claim 1.

10. A vector comprising the isolated polynucleotide of claim 9.

11. A host cell comprising the vector of claim 10.

12. A method of expressing the antibody or antigen-binding fragment thereof, comprising culturing the host cell of claim 11 under the condition at which the vector is expressed.

13. A chimeric antigen receptor (CAR) protein, comprising:

a) a heavy chain variable region comprising an HC-CDR1 having an amino acid sequence of SEQ ID NO: 5, an HC-CDR2 having an amino acid sequence of SEQ ID NO: 6 and an HC-CDR3 having an amino acid sequence of SEQ ID NO: SEQ ID NO: 7; and b) a light chain variable region comprising an LC-CDR1 having an amino acid sequence of SEQ ID NO: 8 with a mutation at amino acid residues NS, an LC-CDR2 having an amino acid sequence of SEQ ID NO: 9 and an LC-CDR3 having an amino acid sequence of SEQ ID NO: 10.

14. The CAR protein of claim 13, wherein the LC-CDR1 has the amino acid sequence of SEQ ID NO: 28.

15. The CAR protein of claim 13, wherein the heavy chain variable region has an amino acid sequence of SEQ ID NO: 1; and wherein the light chain variable region has an amino acid sequence of SEQ ID NO: 27.

16. The CAR protein of claim 13, comprising a single-chain variable fragment (scFv) having an amino acid sequence identical to SEQ ID NOS: 66 or 68.

17. The CAR protein of claim 13, further comprising a CD8a transmembrane domain or a CD28 transmembrane domain.

18. The CAR protein of claim 13, further comprising a 4-1BB intracellular co-stimulatory signaling domain, a CD28 intracellular co-stimulatory signaling domain or a CD3ζ intracellular T cell signaling domain.

19. A polynucleotide molecule encoding a CAR protein according to claim 13.

20. An engineered cell comprising the polynucleotide molecule of claim 19, wherein the cell is a T cell, an NK cell or a macrophage.

* * * * *